US007692011B2

(12) United States Patent
Barnham et al.

(10) Patent No.: US 7,692,011 B2
(45) Date of Patent: Apr. 6, 2010

(54) 8-HYDROXY AND 8-MERCAPTO QUINAZOLINONES

(75) Inventors: Kevin Jeffrey Barnham, Coburg (AU); Elisabeth Colette Louise Gautier, Bentleigh (AU); Gaik Beng Kok, North Carlton (AU); Brenda Kwan Yi Leung, Balwyn (AU)

(73) Assignee: Prana Biotechnology Limited, Parkville, Victoria (AU)

( * ) Notice: Subject to any disclaimer, the term of this patent is extended or adjusted under 35 U.S.C. 154(b) by 978 days.

(21) Appl. No.: 10/530,137

(22) PCT Filed: Oct. 3, 2003

(86) PCT No.: PCT/AU03/01303

§ 371 (c)(1),
(2), (4) Date: Oct. 3, 2005

(87) PCT Pub. No.: WO2004/031161

PCT Pub. Date: Apr. 15, 2004

(65) Prior Publication Data

US 2006/0167000 A1    Jul. 27, 2006

(30) Foreign Application Priority Data

| Oct. 4, 2002 | (AU) | ............................. 2002951864 |
| Oct. 4, 2002 | (AU) | ............................. 2002951865 |
| Oct. 4, 2002 | (AU) | ............................. 2002951866 |
| Oct. 4, 2002 | (AU) | ............................. 2002951868 |

(51) Int. Cl.
*C07D 239/70* (2006.01)
(52) U.S. Cl. ..................................................... 544/253
(58) Field of Classification Search ........................ None
See application file for complete search history.

(56) References Cited

U.S. PATENT DOCUMENTS

| 5,902,810 | A | 5/1999 | Pfleiderer et al. |
| 6,337,332 | B1 | 1/2002 | Carpino |
| 6,369,058 | B1 | 4/2002 | Hussein et al. |
| 2002/0025944 | A1 | 2/2002 | Bush et al. |
| 2008/0119470 | A1 * | 5/2008 | Kok et al. ................. 514/234.5 |

FOREIGN PATENT DOCUMENTS

| EP | 0 290 819 B1 | 11/1988 |
| EP | 1 477 482 | 11/2004 |
| WO | WO 95/12417 A1 | 5/1995 |
| WO | WO 95/24379 | 9/1995 |
| WO | WO 96/22990 A1 | 8/1996 |
| WO | WO 98/06403 | 2/1998 |
| WO | WO 98/33802 | 8/1998 |
| WO | WO 98/47969 A1 | 10/1998 |
| WO | WO 99/01441 | 1/1999 |
| WO | WO 01/16114 | 3/2001 |
| WO | WO 02/85908 A1 | 2/2002 |
| WO | WO 02/48117 | 6/2002 |
| WO | WO 02/50065 | 6/2002 |
| WO | WO 03/010146 A1 | 2/2003 |
| WO | WO 03/016309 A1 | 2/2003 |
| WO | WO 03/076418 | 9/2003 |

OTHER PUBLICATIONS

Vippagunta et. al. Advanced Drug Delivery Reviews 48 (2001) 3-26.*
Dorwald F. A. Side Reactions in Organic Synthesis, 2005, Wiley: VCH, Weinheim p. IX of Preface.*
Banker, et. al., Modern Pharmaceuticals, p. 596-7.*
Wolff et. al., "Burger's Medicinal Chemistry and Drug Discovery," 5th Ed. Part 1, pp. 575-977 (1995).*
Lauenstein, et. al., Biochimica et Biophysica Acta (1956), 21, 587-8.*
Iyer, et. al., Journal of Scientific & Industrial Research (1956), 15C, 1-7.*
Nowak, et. al., Journal Arzneimittel-Forschung (1966), 16(3), 407-11.*
Borisy, et. al., Proceedings of the National Academy of Sciences of the United States of America, 100(13) 7977-7982.*
Malesani, et. al., Atti—Istituto Veneto di Scienze, Lettere ed Arti, Classe di Scienze Matematiche e Naturali (1973), vol. Date 1972, 131, 9-16.*
Banker, et. al., Modern Pharmaceuticals, (1996) p. 596-7.*
Borisy, et. al., Proceedings of the National Academy of Sciences of the United States of America, (2003) 100(13) 7977-7982.*
Chemical Abstract 45:48030 (& Yakugaku Zasshi (1945), 65, 69 ; Chem Abs RN410543-30-5.
Chemical Abstract 111:194704 (& Tetrahedron Letters (1989), 30 (12), 1529-39).
Chemical Abstract 24:53157 (& Journal of the American Chemical Society, 1930, 52, 3974.7).
Chemical Abstract 48:46261 (& Journal of the Chemical Society, Abstracts, 1952, 5985-5993).
Koshimuro K. et al. "The Role of 6R-tetrhydrobiopterin in the nervous system", Progress in Neurobiology 61 (2000), 415-438.
Constantino et al. "Modeling of Poly(ADP-ribose)polymerase (PARP) inhibitors. Docking of ligands and Quantitative Structure-Activity Relationship Analysis", *J. Med. Chem.*, 44:23, 3786-3794 (2001).

* cited by examiner

*Primary Examiner*—James O Wilson
*Assistant Examiner*—Jeffrey H Murray
(74) *Attorney, Agent, or Firm*—Scully, Scott, Murphy & Presser, P.C.

(57) ABSTRACT

The present invention relates to neurologically active 8-hydroxy- or 8-mercapto-quinazolinones. Also disclosed are processes for the preparation of these compounds and their use as pharmaceutical or veterinary agents, in particular for the treatment of neurological conditions, more specifically neurodegenerative conditions, such as Alzheimer's disease.

11 Claims, 5 Drawing Sheets

8-HYDROXY AND 8-MERCAPTO QUINAZOLINONES

The present invention relates to neurologically-active compounds, processes for their preparation and their use as pharmaceutical or veterinary agents, in particular for the treatment of neurological conditions, more specifically neurodegenerative conditions such as Alzheimer's disease.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

The life span is thought to be biologically fixed for each species, and the length of the human life span is uncertain, but may be up to 120 years. Since life expectancy has risen significantly in this century, the elderly are an increasing segment of our population, and their health care needs will continue to grow for decades.

Although normal aging is characterized by modest reductions in the mass and volume of the human brain, which may be due to the atrophy and/or death of brain cells, these changes are far more profound in the brains of patients who succumb to a neurodegenerative condition. Most of these conditions are sporadic (i.e., not due to genetic mutations) and of unknown cause, but hundreds of different mutations in many genes have been shown to cause familial (inherited) variants of several neurodegenerative conditions. Many of the dozen or more genes that harbor these mutations were discovered in the quest to determine the genetic basis of neurodegenerative conditions just in the last ten years. Neurodegenerative conditions evolve gradually after a long period of normal brain function, due to progressive degeneration (i.e., nerve cell dysfunction and death) of specific brain regions. Since symptomatic expression of disease occurs when nerve cell loss exceeds a "threshold" for the continuing function (e.g., memory, movement) performed by the affected brain region, the actual onset of brain degeneration may precede clinical expression by many years.

Intellectual and higher integrative cognitive faculties become progressively impaired and interfere with activities of daily living in neurological conditions resulting in dementia. The precise prevalence of dementia in the elderly population is unknown, but may be 15% of people over 65 years old with 5% severely and 10% mildly to moderately demented. The prevalence of severe dementia increases from 1% at 65 years to 45% at 85 years. There are many causes of dementia, but Alzheimer's Disease (AD) accounts for 50% of demented patients over 65 years of age.

AD is a primary degenerative disease of the brain. It is characterized by progressive decline of cognitive functions such as memory, thinking, comprehension, calculation, language, learning capacity and judgement. Dementia is diagnosed when these declines are sufficient to impair personal activities of daily living. AD shows an insidious onset with slow deterioration. This disease needs to be clearly differentiated from age-related normal decline of cognitive functions. The normal decline is much less, much more gradual and leads to milder disabilities. The onset of AD is usually after 65 years of age, although earlier onset is not uncommon. As age advances, the incidence increases rapidly (it roughly doubles every 5 years). This has obvious implications for the total number of individuals living with this disorder as life expectancy increases in the population.

The aetiology of dementia of AD is unclear. There is considerable evidence of a heritable predisposition for some forms of AD (reviewed in St George-Hyslop, 2000), and the expression of certain isoforms of ApoE has also been linked to a higher risk of AD (Corder et al, 1993; Czech et al 1994). The toxic accumulation of aluminium has been suggested as a causative agent in AD, although this hypothesis has now been largely superseded. The brains of AD patients display abnormal deposits which include β-amyloid protein (Aβ).

Aβ is known to be present in the brains of individuals with certain neurodegenerative diseases, but it is not known whether it is symptomatic of an underlying disease process, or is actually involved in the aetiology of the disease. For example, some authors believe that the Aβ deposits may be indicative of a normal brain defence mechanism, in which the brain attempts to sequester the Aβ; such deposits can be present in the brains of normal individuals. There is a mutation of tau protein in which neurofibrillary tangles, but no amyloid plaques are present in the brain; this condition is known as tauopathy.

One proposed approach to AD therapy is to inhibit production of Aβ in the brain. Proteolytic cleavage of APP by BACE1 and γ-secretase generates the full-length Aβ, which is then released from cells (Nunan and Small, 2000). Therefore inhibitors of either BACE1 or γ-secretase may be of therapeutic value. Alternatively, a number of studies have shown that cholesterol can influence Aβ release (Simons et al., 1998; Hartmann, 2001; Fassbender et al., 2001; Frears et al., 1999; Friedhoff et al., 2001). However, there is some disagreement in the art as to the value of lowering cholesterol levels, and some workers consider that cholesterol is actually beneficial. For example, Ji et al, (2002) have suggested that the binding of Aβ to cholesterol might prevent Aβ toxicity by inhibiting its oligomerization.

In an alternative approach, it has been proposed that by unravelling the proteolytic processing of the amyloid precursor protein (APP), which generates the Aβ amyloid monomer, a number of possible therapeutic targets may be possible (Shearman et al., 2000; Sinha et al., 1999), and this approach is in an early stage of clinical development. Attempts to promote the clearance of Aβ from the brain through immunization with Aβ, while efficacious in a transgenic mouse model for AD (Schenk et al 1999), have been found to have significant adverse effects (Brower, 2002).

It has also been suggested that deposition of amyloid-like fibrils may also be important in other neurodegenerative diseases. These include Parkinson's disease, dementia with Lewy body formation, multiple system atrophy, Hallerboden-Spatz disease, and diffuse Lewy body disease.

One of the competing theories of the aetiology of AD is that the causative step(s) lies within the pathway of the intracerebral biogenesis and accumulation of the Aβ amyloid protein (see recent reviews by Selkoe, 2001; Beyreuther et al., 2001; Bush, 2001). However, to date no drugs or agents which target this pathway have been demonstrated to have a lasting effect on modifying the clinical expression of the disease or in preventing or ameliorating the decline in cognitive function associated with neurodegenerative disorders, including Alzheimer's disease.

A further hypothesis is that AD is caused by the toxic accumulation of Aβ amyloid, due in part to excess binding of copper and zinc, metal ions which are abundant in the regions most affected. Moreover, it has been suggested that when $Zn^{2+}$ and $Cu^{2+}$ ions interact with Aβ, aggregation of Aβ into fibrils and plaques occurs (Atwood et al., 1998); confirmed by recent data from animals deficient in synaptic $Zn^{2+}$ (Lee et al., 2002). It has also been suggested that redox-active $Cu^{2+}$-Aβ interactions can generate $H_2O_2$ from $O_2$ (Huang et al., 1999). Both Cu 2+ and $Zn^{2+}$ have been shown to affect Aβ-lipid membrane interactions (Curtain et al., 2001).

The brain is an organ that concentrates metal ions and recent evidence suggests that a breakdown in metal homeostasis plays a critical role in a variety of age-related neurodegenerative diseases. Common features of these diseases include the deposition of misfolded protein (each disease has its own specific amyloid protein) and substantial cellular damage as a result of oxidative stress. Indeed data is now rapidly accumulating that metallochemical reactions could emerge as the common denominator underlying amyloidogenic neurological disorders such as Alzheimer's disease, amylotrophic lateral sclerosis (ALS), prion diseases—including Creutzfeldt-Jakob Disease (CJD), transmissible spongioform encephalopathies (TSE), cataracts, mitochondrial disorders, Parkinson's disease and Huntington's disease. In these instances, the pathological aggregation of a specific protein is promoted by abnormal redox activity in a physiological environment typified by the presence of transition metals and available reducing agents. [Bush, 2000 (Curr Opin Chem Biol. 2000 April; 4(2):184-91)].

A method of treatment of AD using iodochlorohydroxyquinoline an antibiotic [also known as clioquinol (CQ)], is disclosed and claimed in U.S. Pat. Nos. 5,994,323 and 6,001,852 by P. N. Geromylatos S. A. and in U.S. patent application Ser. No. 09/972,913 by Bush et al. CQ was withdrawn as an antibiotic in 1970, because of its association with an uncommon neurological syndrome, subacute myelo-optic neuropathy (SMON), which was observed only in Japan in the 1960s, in patients thought to have received the drug over long periods and probably at doses higher than those recommended at the time (Shiraki, 1975). However, recent evidence suggests that SMON was caused by an overuse-related vitamin B12 deficiency in an exceptionally vulnerable population, and therefore could be rehabilitated for study in a clinical setting (Yassin et al., 2000; Bush and Masters, 2001).

However, no in vivo results in animal models or in humans are provided in the Geromylatos and Bush patents. U.S. Pat. No. 5,994,323 discloses a composition comprising CQ and Vitamin B12, and its use for the treatment of "diseases or disorders responsive to CQ administration while inhibiting detrimental side effects" of CQ. These diseases include AD. U.S. Pat. No. 6,001,852 discloses a method of treatment of AD using CQ, preferably together with Vitamin B12. Both U.S. Pat. No. 5,994,323 and U.S. Pat. No. 6,001,852 suggest a dosage of 10-750 mg per day; U.S. Pat. No. 5,994,323 recommends that if treatment is over a long period CQ should be given intermittently, for up to 3 weeks at a time followed by a "wash-out" period of 1-4 weeks.

In U.S. application Ser. No. 09/972,913 CQ is exclusively referred to in terms of its ability to disaggregate Aβ deposits. No other mechanism of neurotoxicity is discussed. PCT/US99/05291 by General Hospital Corporation discloses the use of CQ in combination with specific copper and zinc chelators to promote dissolution of amyloid plaques and inhibition of amyloid plaque formation and/or the production of ROS by Aβ.

U.S. Pat. No. 6,001,852 also suggests that a composition comprising CQ and Vitamin B12 could be used in the treatment of Parkinson's disease; however, in this context it is suggested that CQ acts primarily via clearing iron from the substantia *nigra*.

The efficacy of CQ in the treatment of AD rests upon its ability to enter the CNS and then sequester the transition metals Cu, Zn and Fe from various Aβ entities thereby reducing Aβ toxicity and liberating it for clearance. The effectiveness of CQ is restricted by its poor aqueous solubility which limits its oral bioavailability. CQ is also known to undergo considerable conjugative metabolism and has a history of toxicity as discussed above. The fact that CQ is a bidentate metal ligand makes necessary the commitment of at least two molecules for every metal ion captured.

SUMMARY OF THE INVENTION

The present invention provides a means of treating neurological conditions including those characterised by the abnormal reaction between proteins and metals.

We have now developed heterocyclic compounds having two fused 6-membered rings with a nitrogen atom at position 1 and a hydroxy or mercapto group at position 8 with at least one ring being aromatic through the collective optimization of one or more of the following properties:
  (a) metal chelation (as hereinafter defined);
  (b) aqueous solubility;
  (c) reduced cell toxicity;
  (d) amyloid dispersion properties;
  (e) membrane permeability appropriate for CNS penetration; and
  (f) metabolic stability.

These compounds include examples of therapeutics which are concentrated in the CNS through active transport, contain antioxidant activity in addition to their metal chelation properties which in some cases leads to enhanced metal chelation properties and demonstrate a prodrug strategy which masks the 8-hydroxy or 8-mercapto moiety to favour CNS penetration and make use of the known esterase activity which resides on the inner surface of the blood brain barrier (BBB).

According to the present invention there is provided a method for the treatment, amelioration and/or prophylaxis of a neurological condition which comprises the administration of an effective amount of a compound of formula I:

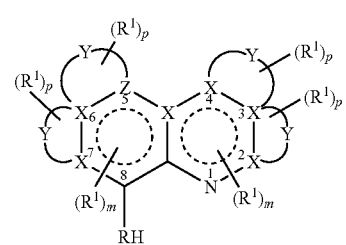

in which
  R is O or S;
  $R^1$ is independently selected from H, optionally substituted alkyl, optionally substituted alkenyl; optionally substituted alkynyl; optionally substituted aryl; optionally substituted heterocyclyl; an antioxidant; a targeting moiety; CN; halo; $CF_3$; $SO_3H$; and $OR^2$, $SR^2$, $SOR^2$, $SO_2R^2$, $NR^2R^3$, $(CH_2)_n$ $NR^2R^3$, $HCNOR^2$, $HCNNR^2R^3$, $CONR^2R^3$, $CSNR^2R^3$, NCOR², NCSR², COR², CO₂R², CSR² or SO₂NR²R³ in which R² and R³ are independently selected from H, optionally substituted alkyl, optionally substituted alkenyl, optionally substituted alkynyl, optionally substituted aryl, optionally substituted heterocyclyl, an antioxidant or a targeting moiety and n is an integer of 1 to 10;

X is independently selected from CH, CO, N and NH;

Z is independently selected from CH, CO, N, NH and O;

Y is absent or together with the ring to which it is attached forms a 5- or 6-membered optionally substituted aryl or a 5- or 6-membered optionally substituted heterocyclyl;

m is an integer from 1 to 3; and p is an integer from 1 to 4, salts, hydrates, solvates, derivatives, pro-drugs, tautomers and/or isomers thereof to a subject in need thereof, with the provisos that:

(i) at least one of X and Z is other than CH;

(ii) phanquinone or tautomers thereof are excluded i.e., when R is O, R¹ at position 7 is OH, X is CH and Y is absent, then Z is not

(iii) when R is O, Y is absent, Z is CH, X is CH other than at position 3 where X is N, m is 2 and R¹ is

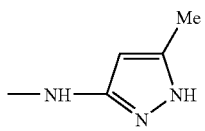

at position 3, then R¹ at position 2 is not

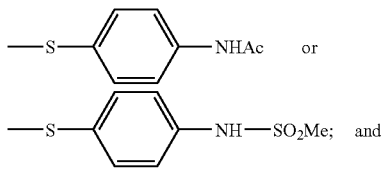

(iv) clioquinol i.e, when R is O, Y is absent, Z and X are CH and m is 2, then R¹ at position 5 is not chloro and R¹ at position 7 is not iodo.

Further according to the present invention there is provided use of the compound of formula I in the manufacture of a medicament for the treatment, amelioration and/or prophylaxis of a neurological condition.

The invention also provides use of the compound of formula I for the treatment, amelioration and/or prophylaxis of a neurological condition.

The invention further provides the compound of formula I for use in the treatment, amelioration and/or prophylaxis of a neurological condition.

The invention still further provides use of the compound of formula I as a pharmaceutical, preferably a neurotherapeutic or neuroprotective agent, more preferably an antiamyloidogenic agent. Preferably, the neurological condition is a neurodegenerative condition, more preferably neurodegenerative amyloidosis such as Alzheimer's disease or Parkinson's disease.

R is preferably O.

R¹ is preferably halo, optionally substituted aryl, optionally substituted heterocyclyl, optionally substituted alkyl, OR², SR², (CH₂)ₙNR²R³, CONR²R³ and NCOR² in which n, R² and R³ are as defined above. More preferably R¹ is fluoro; iodo; chloro; optionally substituted phenyl such as 4-halophenyl, for example, 4-fluorophenyl or 4-chlorophenyl; an optionally substituted unsaturated 3 to 6-membered heteromonocyclic group containing 1 to 4 nitrogen atoms such as imidazolyl or pyridinyl; an optionally substituted saturated 3 to 6-membered heteromonocyclic group containing 1 to 4 nitrogen atoms such as imidazolidinyl or piperazinyl; an optionally substituted saturated 3 to 6-membered heteromonocyclic group containing 1 to 2 oxygen atoms and 1 to 3 nitrogen atoms such as morpholinyl; optionally substituted C₁₋₄ alkyl such as methyl or ethyl; optionally substituted C₂₋₆ cycloalkyl such as cyclopropyl; optionally substituted C₁₋₆ alkoxy; optionally substituted thio; CH₂NR⁴R⁵ in which R⁴ and R⁵ are independently selected from H and C₁₋₄ alkyl; or CONH(CH₂)₂R⁶ in which R⁶ is optionally substituted heterocyclyl.

Y is preferably an optionally substituted phenyl; an optionally substituted unsaturated 5- or 6-membered heteromonocyclic group containing 1 to 4 nitrogen atoms such as imidazolyl or pyridinyl; or an optionally substituted saturated 5 or 6-membered heteromonocyclic group containing 1 to 2 oxygen atoms and 1 to 3 nitrogen atoms such as morpholinyl.

While not wishing to be bound by theory, it is believed that substituent R¹ has a limited effect, electronically or sterically, in the chelating properties of the compounds of the present invention. Substitution can therefore be used to modulate other parameters such as cytotoxicity and physicochemical properties including the number of hydrogen bond donors and acceptors, lipophilicity (ClogP, ElogP and LogD), solubility and polar surface area. Modulation of these parameters contribute to the optimisation of the pharmacokinetic profile of the compounds. It is also postulated that when substituent R¹ is located at positions 2 and/or 7 in addition to modulating cytotoxicity and physicochemical properties could also affect activity if the substituent provides chelating properties.

Illustrative classes of compounds of formula I are as follows:

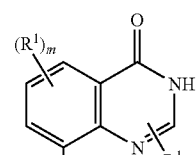
8-hydroxy-4(3H)-quinazolinones

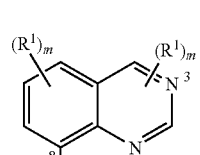
8-hydroxy-quinazoline

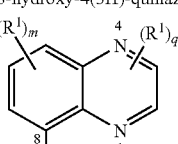
8-hydroxy-quinoxaline

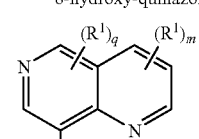
[1,6]naphthyridin-8-ol

-continued 9-hydroxypyrimido[1,6-a]pyrimidin-4-one 8-hydroxy-cinnoline 6-hydroxy-phenazine 4-hydroxy-acridine 4,7(4,10)-phenanthrolin-5-ol 9-hydroxypyrido[1,2-a]pyrimidin-4-one pyrido[3,2-d]pyrimidin-4-ol pyrido[2-3-d]pyridazin-8-ol -continued

[1,7]naphthyridin-8-ol

[1,5]naphthyridine-4,8-diol

[1,5]naphthyridine-8-ol pyrido[3,4-b]pyrazin-8-ol pyrido[3,4-b]pyrazin-5-ol pyrido[4,3-d]pyrimidin-8-ol 4-hydroxy-4a,8a-dihydro-pyrano[3,2,b]pyridin-2-one 8-hydroxy-6H-[1,6]naphthyridin-5-one 8-hydroxy-6H-[1,6]naphthyrin-5-one dibenzo[a,g]quinolizin-8-one

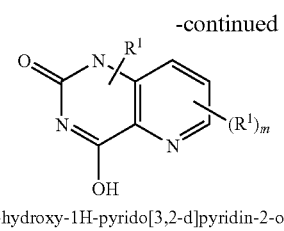

4-hydroxy-1H-pyrido[3,2-d]pyridin-2-one in which $R^1$, m, n and p are as defined above and q is an integer of 1 or 2.

The 8-hydroxyl or 8-mercapto group on the compounds of formula I may be blocked to form a prodrug, in particular an ester prodrug. The 8-hydroxy or 8-mercapto represents a principal site of metabolism for the compound of formula I: conjugation with glucuronic acid or sulphate gives a hydrophilic species ready to be excreted. Such conjugates probably do not pass the blood brain barrier. The ester prodrug may protect the compound of formula I from conjugation. Esterases integral to the blood brain barrier may then release the C8-hydroxy or mercapto on passage through that barrier activating the compound for its role in the CNS.

A preferred compound of formula I is a compound of formula IA

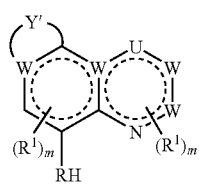

IA in which
R, $R^1$ and m are as defined above;
W is CH, N or NH;
U is CH, CO or N; and
Y' is absent or together with the ring to which it is attached forms a 6 membered N-containing optionally substituted heterocyclyl.
Preferred compounds of formula IA are as follows:
(i) Formula Ia

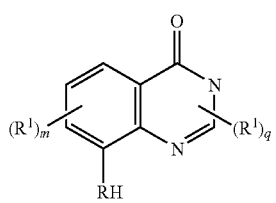

Ia in which R, $R^1$, m and q are as defined above.
Preferably $R^1$ is located at positions 2, 3, 5 and/or 7 and is selected from halo, optionally substituted aryl, optionally substituted heterocyclyl, optionally substituted alkyl and $(CH_2)_n NR^2R^3$ in which n, $R^2$ and $R^3$ are as defined above. More preferably $R^1$ is chloro, optionally substituted phenyl, $C_{3-6}$ cycloalkyl, $CH_2NR^4R^5$ in which $R^4$ and $R^5$ are independently selected from H and $C_{1-4}$ alkyl or optionally substituted pyridinyl.

Particularly preferred examples are shown below.

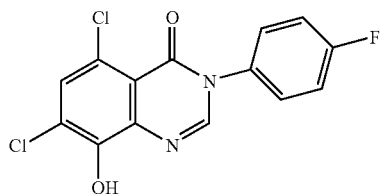

1055

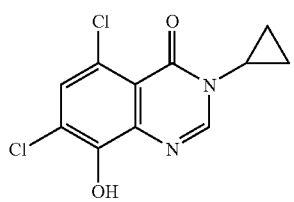

1061

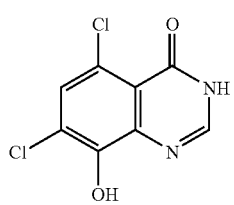

1067

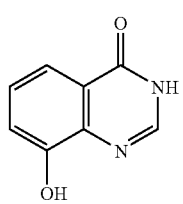

1049

(ii) Formula Ib

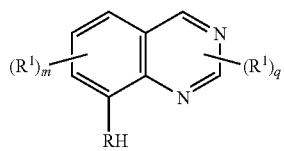

Ib in which R, $R^1$, m and q are as defined above.
Preferably $R^1$ is located at positions 2, 4, 5 and/or 7 and is selected from halo and optionally substituted heterocyclyl. More preferably, $R^1$ is chloro and/or morpholinyl.
Preferred examples are shown below.

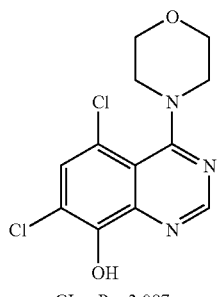

CLogP = 3.087

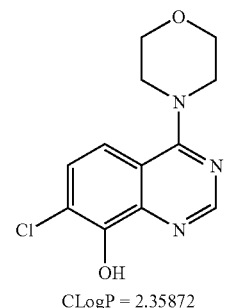

CLogP = 2.35872

-continued

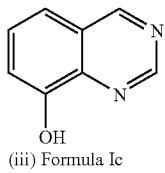
(iii) Formula Ic

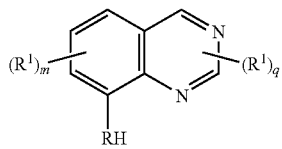

in which R, R¹, m and q are as defined above.

Preferably R¹ is located at positions 2, 5 and/or 7 and is selected from halo and $CH_2NR^4R^5$ in which $R^4$ and $R^5$ are independently selected from H and $C_{1-4}$ alkyl.

Preferred examples are shown below.

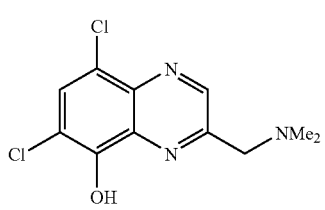
1066

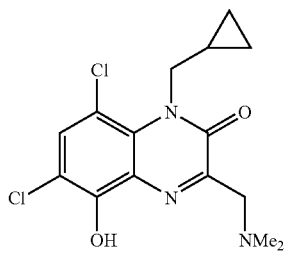
CLogP = 2.57029
1064

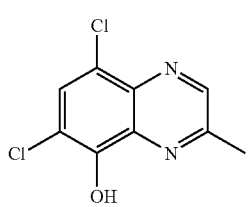
1065

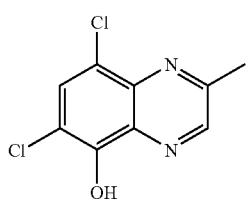

(iv) Formula Id

-continued

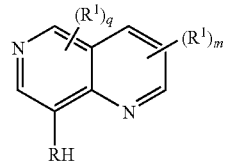
Ic in which R, R¹, m and q are as defined above.

Preferably R¹ is located at positions 2 and/or 7 and is selected from optionally substituted heterocyclyl, $CO_2R^2$, $(CH_2)_nNR^2R^3$ and $CONR^2R^3$ in which n, $R^2$ and $R^3$ are as defined above.

Preferred examples are shown below.

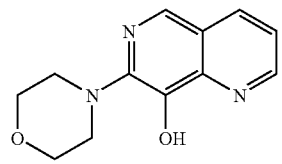
1053

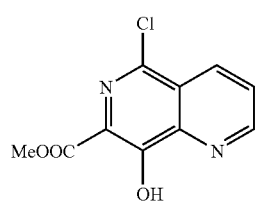
1045

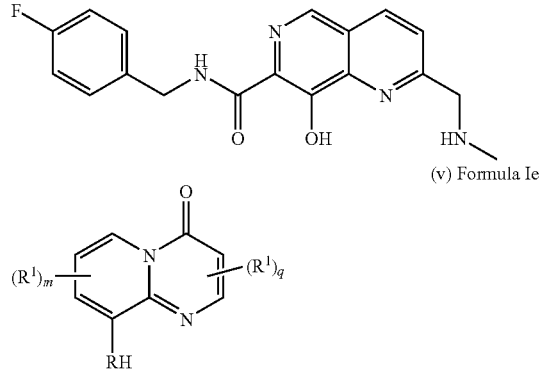
1070

(v) Formula Ie

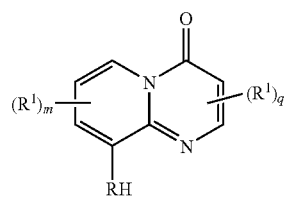

in which R, R¹, m and q are as defined above.

Preferably R¹ is located at positions 2, 3, 6 and/or 7 and is selected from halo, optionally substituted aryl and $(CH_2)_n NR^2R^3$ in which n, $R^2$ and $R^3$ are as defined above.

Preferred examples are shown below.

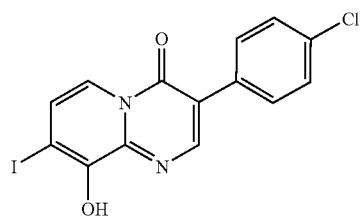
1063

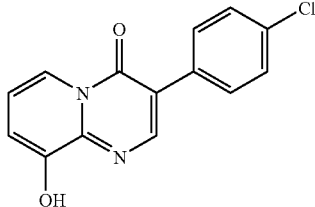

1069

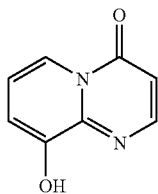

1048

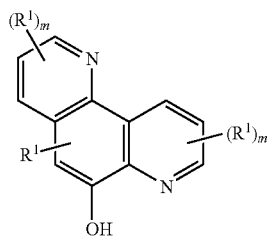

(vi) Formula If in which R¹ and m are as defined above.

Preferably R¹ is located at positions 2 and/or 6 and is selected from halo and $(CH_2)_nNR^2R^3$ in which n, $R^2$ and $R^3$ are as defined above.

Preferred examples are shown below.

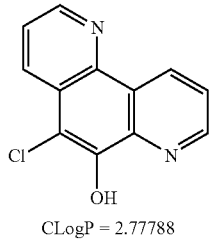

CLogP = 2.77788

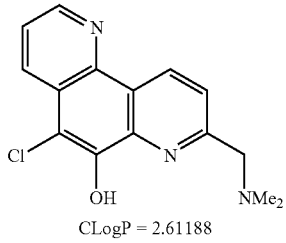

CLogP = 2.61188

1026

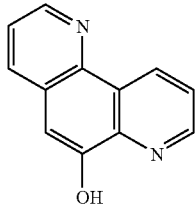

In a further aspect, the invention provides a pharmaceutical or veterinary composition comprising the compound of formula I as defined above, together with a pharmaceutically or veterinarily acceptable carrier.

Some of the compounds of formula I are novel per se.

Accordingly, the invention provides a compound of formula II which is a compound of formula I with the provisos that at least one R¹ is other than H.

Preferred compounds of formula II are compounds of the formula IA, more preferably compounds of the formulae Ia, Ib, Ic, Id and Ie defined above, most preferably 1045, 1061, 1066, 1053, 1063, 1064, 1065, 1067, 1069 and 1070.

The compound of formula II defined above may be prepared using the processes described in detail hereinafter.

DETAILED DESCRIPTION OF THE INVENTION

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

The term "alkyl" used either alone or in compound words such as "optionally substituted alkyl" or "alkylamino" refers to straight chain, branched chain or cyclic hydrocarbon groups having from 1 to 10 carbon atoms, preferably 1 to 6 carbon atoms, more preferably 1 to 4 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl. Preferred alkyl groups are $C_{1-4}$ alkyl such as methyl or ethyl and $C_{2-6}$ cycloalkyl such as cyclopropyl.

The term "alkenyl" used either alone or in compound words such as "optionally substituted alkenyl", denotes linear, branched or mono- or poly-cyclic radicals having at least one carbon-carbon double bond of 2 to 20 carbon atoms, preferably 2 to 14 carbon atoms, more preferably 2 to 6 carbon atoms. Examples of alkenyl radicals include allyl, ethenyl, propenyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" used either alone or in compound words such as "optionally substituted alkynyl" refers to straight chain or branched chain radicals having at least one carbon-carbon triple bond of 2 to 20 carbon atoms, preferably 2 to 14 carbon atoms, more preferably 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "heterocyclyl group" used either alone or in compound words such as "optionally substituted heterocyclyl" refers to monocyclic or polycyclic heterocyclic groups containing at least one heteroatom atom selected from nitrogen, sulphur and oxygen.

Suitable heterocyclic groups include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyridinyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

Preferably the heterocyclyl is an unsaturated 5 or 6-membered heteromonocyclic group containing 1 to 3 nitrogen atoms such as imidazolyl or pyridinyl; a saturated 5 or 6-membered heteromonocyclic group containing 1 to 4 nitrogen atoms such as imidazolidinyl or piperazinyl; or a saturated 5 or 6-membered heteromonocyclic group containing 1 to 2 oxygen atoms and 1 to 3 nitrogen atoms such as morpholinyl.

The term "aryl" used either alone or in compound words such as "optionally substituted aryl" denotes a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Preferably, the aryl is optionally substituted phenyl such as 4-halophenyl, more preferably 4-fluorophenyl or 4-chlorophenyl.

The term "halo" refers to fluorine, chlorine, bromine or iodine, preferably fluorine, iodine or chlorine.

The term "alkoxy" refers to straight chain or branched oxy-containing radicals preferably each having alkyl portions of 1 to about 6 carbon atoms. Examples of alkoxy include methoxy, ethoxy, propoxy, butoxy and tert-butoxy.

The term "optionally substituted thio" refers to optional substituents such as radicals containing a linear or branched alkyl of 1 to 10 carbon atoms, preferably 1 to 6 carbon atoms, more preferably 1 to 4 carbon atoms, attached to a divalent sulphur atom. Examples of alkylthio radicals include methylthio, ethylthio, propylthio, butylthio and hexylthio.

The term "optionally substituted" refers to a group which may or may not be further substituted with one or more groups selected from alkyl, alkenyl, alkynyl, aryl, aldehyde, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. Preferably, the optional substituent is $C_{1-6}$ alkyl, more preferably $C_{1-4}$ alkyl; $CF_3$; fluorine; chlorine; iodine; cyano; $C_{1-6}$ alkoxy, more preferably $C_{1-4}$ alkoxy; aryl; heterocyclyl; amino; or alkylamino.

The term "antioxidant" is used herein in its broadest sense and refers to a group which has the capacity to react with a reactive oxygen species such as a hydroxyl radical in such a way as to generate a non toxic product. Examples include phenols such as 3,4,5-trimethoxyphenyl and 3,5-di-t-butyl-4-hydroxyphenyl, indole amines such as melatonin and flavonoids. Other examples may be found the literature (Wright, 2001; Karbownik, 2001; Gilgun-Sherki, 2001).

The term "targeting moiety" is used herein in its broadest sense and refers to a group which will facilitate the brain delivery of the drug by way of an active transport mechanism. The targeting moiety is recognised by specific transporter enzymes integral to the blood brain barrier and these transporter enzymes then provide a mechanism for the drug to be imported into the brain. Typically such transporters are sodium dependant and their substrates contain carboxylic acids such as ascorbic acid and L-glutamate. Conjugation of the targeting moiety to the drug is enacted so as to retain the acid moiety. Examples can be found in the literature (Manfredini, 2002, Sakaedu, 2001).

The term "metal chelator" is used herein in its broadest sense and refers to compounds having two or more donor atoms capable of binding to a metal atom, preferably Cu, Zn or Fe wherein at least two of the donor atoms are capable of simultaneous binding to the metal atom and the resultant metal complex has a thermodynamic stability greater than or equal to that of the metal ion: biological ligand complex. The use of metal chelators as treatments for neurological disorders in the present invention is distinguished from the previously known concept of "chelation therapy". "Chelation therapy" is a term associated clinically with the removal of bulk metals such as in Wilson's disease, β-thallesemia and haemochromatosis. The break down in metal homeostasis in these diseases can be described as a catastrophic event much like a dam bursting leading to overwhelming flooding of the problem metal. The mechanism of action of such compounds is that bulk metal is sequestered by the chelators and cleared by excretion. By way of comparison the breakdown in metal homeostasis associated with neurological conditions of the present invention is more akin to the constant drip of a leaky tap, which if left long enough will eventually cause local damage over a long period of time. The intention of the "metal chelator" of the present invention is to disrupt an abnormal metal-protein interaction to achieve a subtle repartitioning of metals and a subsequent normalization of metal distribution with the aim that once the toxic cycle is short-circuited, endogenous clearance processes can cope more effectively with the accumulating amyloidogenic protein.

The salts of the compound of Formula I or II are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the invention.

By "pharmaceutically acceptable derivative" is meant any pharmaceutically acceptable salt, hydrate, ester, amide, active metabolite, analogue, residue or any other compound which is not biologically or otherwise undesirable and induces the desired pharmacological and/or physiological effect.

The term "pro-drug" is used herein in its broadest sense to include those compounds which are converted in vivo to compounds of Formula I or II. Use of the pro-drug strategy optimises the delivery of the drug to its site of action, for example, the brain. In one aspect, the term refers to the presence of a $C_{1-6}$ alkyl or arylester moiety which is designed to resist hydrolysis until the pro-drug has crossed the BBB, where esterases on the inner surface of the BBB act to hydrolyse the ester and liberate the C8 hydroxyl of the compounds of formula I or II. In a second aspect, the term refers to the attachment at position 2 of an antioxidant group, in particular the 3,4,-5trimethoxyphenyl moiety or derivatives thereof. Exposure to the prooxidative environment of the brain will then lead to hydroxylation of the 3,4,5-trimethoxyphenyl group to give a 2-hydroxy-3,4,5-trimethoxyphenyl substituent, the hydroxyl group of which acts to enhance the chelation properties of the compounds of formula I or II.

The term "tautomer" is used herein in its broadest sense to include compounds of Formula I or II which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of Formula I or II may have one or more chiral centres, it is capable of existing in enantiomeric forms.

The compositions of the present invention comprise at least one compound of Formula I or II together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

The term "neurological condition" is used herein in its broadest sense and refers to conditions in which various cell types of the nervous system are degenerated and/or have been damaged as a result of neurodegenerative disorders or injuries or exposures. In particular, compounds of formula I or II can be used for the treatment of resulting conditions, in which damage to cells of the nervous system has occurred due to surgical interventions, infections, exposure to toxic agents, tumours, nutritional deficits or metabolic disorders. In addition, compounds of the formula I or II can be used for the treatment of the sequelae of neurodegenerative disorders, such as Alzheimer's disease, Parkinson's disease, multiple sclerosis, amylotrophic lateral sclerosis, epilepsy, drug abuse or drug addiction (alcohol, cocaine, heroin, amphetamine or the like), spinal cord disorders and/or injuries, dystrophy or degeneration of the neural retina (retinopathies) and peripheral neuropathies, such as diabetic neuropathy and/or the peripheral neuropathies induced by toxins.

The term "neurodegenerative disorder" as used herein refers to an abnormality in which neuronal integrity is threatened. Neuronal integrity can be threatened when neuronal cells display decreased survival or when the neurons can no longer propagate a signal.

Neurological disorders that can be treated with the compounds of the present invention include acute intermittent porphyria; adriamycin-induced cardiomyopathy; AIDS dementia and HIV-1 induced neurotoxicity; Alzheimer's disease; amylotrophic lateral sclerosis; atherosclerosis; cateract; cerebral ischaemia; cerebral palsy; cerebral tumour; chemotherapy-induced organ damage; cisplatin-induced nephrotoxicity; coronary artery bypass surgery; Creutzfeldt-Jacob disease and its new variant associated with "mad cow" disease; diabetic neuropathy; Down's syndrome; drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); haemorrhagic stroke; Halleroboden-Spatz disease; heart attack and reperfusion injury; Huntington's disease; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; peri-natal asphyxia; Pick's disease; progressive supra-nuclear palsy; radiotherapy-induced organ damage; restenosis after angioplasty; retinopathy; senile dementia; schizophrenia; sepsis; septic shock; spongiform encephalopathies; subharrachnoid haemorrage/cerebral vasospasm; subdural haematoma; surgical trauma, including neurosurgery; thalassemia; transient ischaemic attack (TIA); traumatic brain injury (TBI); traumatic spinal injury; transplantation; vascular dementia; viral meningitis; and viral encephalitis.

Additionally, compounds of the present invention may also be used to potentiate the effects of other treatments, for example to potentiate the neuroprotective effects of brain derived nerve growth factor.

The invention is particularly directed to conditions which induce oxidative damage of the central nervous system, including acute and chronic neurological disorders such as traumatic brain injury, spinal cord injury, cerebral ischaemia, stroke (ischaemic and haemorragic), subharrachnoid haemorrage/cerebral vasospasm, cerebral tumour, Alzheimer's disease, Creutzfeldt-Jacob disease and its new variant associated with "mad cow" disease, Huntington's disease, Parkinson's disease, Friedrich's ataxia, cataract, dementia with Lewy body formation, multiple system atrophy, Hallerboden-Spatz disease, diffuse Lewy body disease, amylotrophic lateral sclerosis, motor neuron disease, multiple sclerosis, fatal familial insomnia, Gertsmann Straussler Sheinker disease and hereditary cerebral haemorrhage with amyoidoisis-Dutch type.

More particularly, the invention is directed to the treatment of neurodegenerative amyloidosis. The neurodegenerative amyloidosis may be any condition in which neurological damage results from the deposition of amyloid. The amyloid may be formed from a variety of protein or polypeptide precursors, including but not limited to Aβ, synuclein, huntingtin, or prion protein.

Thus the condition is preferably selected from the group consisting of sporadic or familial Alzheimer's disease, amyotrophic lateral sclerosis, motor neuron disease, cataract, Parkinson's disease, Creutzfeldt-Jacob disease and its new variant associated with "mad cow" disease, Huntington's disease, dementia with Lewy body formation, multiple system atrophy, Hallerboden-Spatz disease, and diffuse Lewy body disease.

More preferably the neurodegenerative amyloidosis is an Aβ-related condition, such as Alzheimer's disease or dementia associated with Down syndrome or one of several forms of autosomal dominant forms of familial Alzheimer's disease (reviewed in St George-Hyslop, 2000). Most preferably the Aβ-related condition is Alzheimer's disease.

In a particularly preferred embodiment of all aspects of the invention, prior to treatment the subject has moderately or severely impaired cognitive function, as assessed by the Alzheimer's Disease Assessment Scale (ADAS)-cog test, for example an ADAS-cog value of 25 or greater.

In addition to slowing or arresting the cognitive decline of a subject, the methods and compounds of the invention may also be suitable for use in the treatment or prevention of neurodegenerative conditions, or may be suitable for use in alleviating the symptoms of neurodegenerative conditions. The compounds may be able to provide at least a partial reversal of the cognitive decline experienced by patients. If administered to a subject who has been identified as having an increased risk of a predisposition to neurodegenerative conditions, or to a subject exhibiting pre-clinical manifestations of cognitive decline, such as Mild Cognitive Impairment or minimal progressive cognitive impairment, these methods and compounds may be able to prevent or delay the onset of clinical symptoms, in addition to the effect of slowing or reducing the rate of cognitive decline.

Currently Alzheimer's disease and other dementias are usually not diagnosed until one or more warning symptoms have appeared. These symptoms constitute a syndrome known as Mild Cognitive Impairment (MCI), which was recently defined by the American Academy of Neurology, and refers to the clinical state of individuals who have memory impairment, but who are otherwise functioning well, and who do not meet clinical criteria for dementia (Petersen et al., 2001). Symptoms of MCI include:

(1) Memory loss which affects job skills
(2) Difficulty performing familiar tasks
(3) Problems with language
(4) Disorientation as to time and place (getting lost)
(5) Poor or decreased judgement
(6) Problems with abstract thinking
(7) Misplacing things
(8) Changes in mood or behaviour
(9) Changes in personality
(10) Loss of initiative MCI can be detected using conventional cognitive screening tests, such as the Mini Mental Status Exam, and the Memory Impairment Screen, and neuropsychological screening batteries.

The term "subject" as used herein refers to any animal having a disease or condition which requires treatment with a pharmaceutically-active agent. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to treat, ameliorate or prevent a neurological condition.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compounds of the present invention may additionally be combined with other medicaments to provide an operative combination. It is intended to include any chemically compatible combination of pharmaceutically-active agents, as long as the combination does not eliminate the activity of the compound of formula I or II. It will be appreciated that the compound of the invention and the other medicament may be administered separately, sequentially or simultaneously.

Other medicaments may include, for example, where the condition is a β-amyloid related condition, particularly Alzheimer's disease, an inhibitor of the acetylcholinesterase active site, for example phenserine, galantamine, or tacrine; an antioxidant, such as Vitamin E or Vitamin C; an anti-inflammatory agent such as flurbiprofen or ibuprofen optionally modified to release nitric oxide (for example NCX-2216, produced by NicOx) or an oestrogenic agent such as 17-β-oestradiol.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

As used herein, a "pharmaceutical carrier" is a pharmaceutically acceptable solvent, suspending agent or vehicle for delivering the compound of formula I or II to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I or II may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, fructose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I or II as well as the pharmaceutically-active agent useful in the method of the invention can be administered, for in vivo application, parenterally by injection or by gradual perfusion over time independently or together. Administration may be intravenously, intraarterially, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The invention includes various pharmaceutical compositions useful for ameliorating disease. The pharmaceutical compositions according to one embodiment of the invention are prepared by bringing a compound of formula I or II, analogues, derivatives or salts thereof, or combinations of compound of formula I or II and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compounds of formula I or II may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula I or II may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Dosage levels of the compound of formula I or II of the present invention are of the order of about 0.5 mg to about 20 mg per kilogram body weight, with a preferred dosage range between about 0.5 mg to about 10 mg per kilogram body weight per day (from about 0.5 gms to about 3 gms per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10-50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

Figure 1:
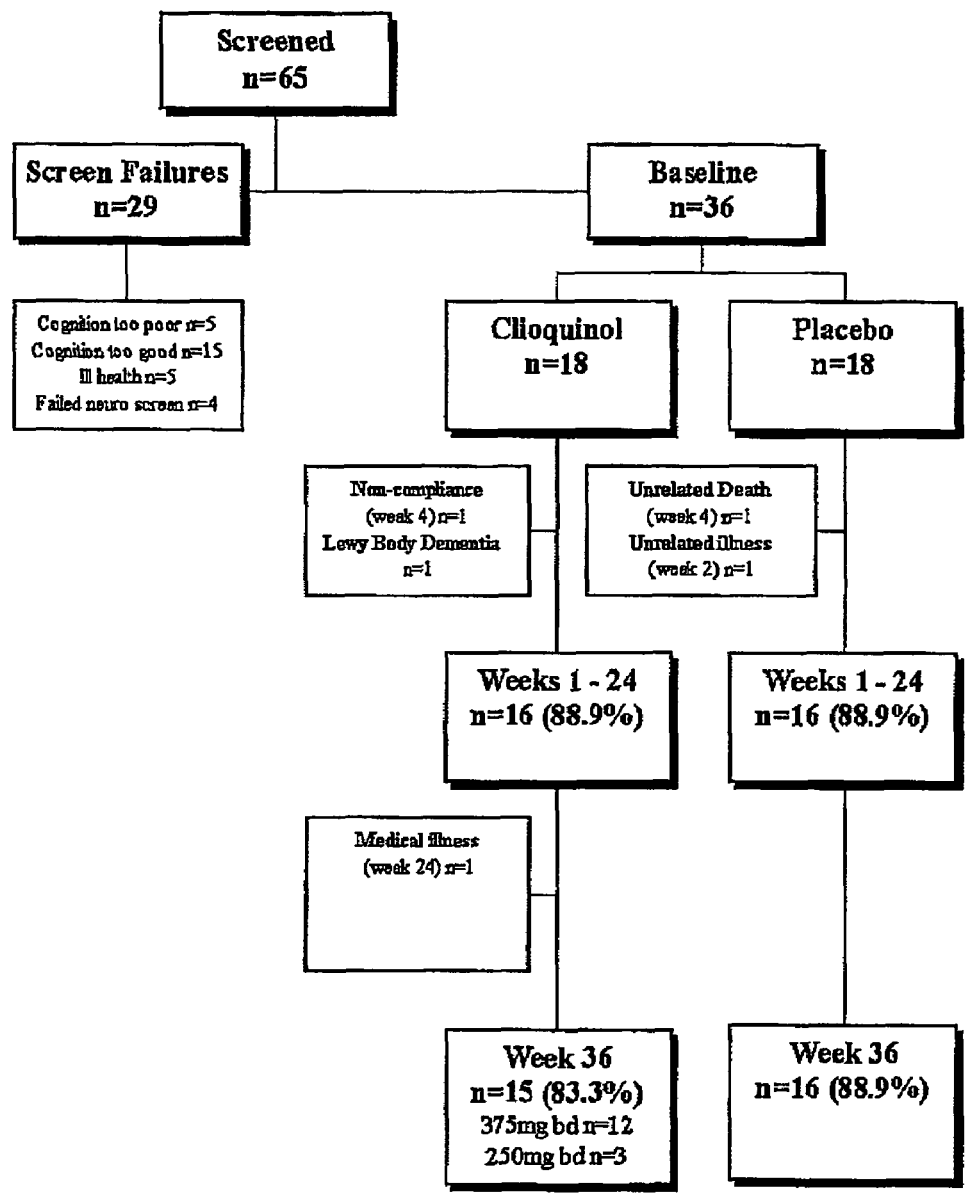
FIG. 1 is a flow chart of subjects studied.

The invention will now be described in detail by way of reference only to the following non-limiting examples.

(1) PREPARATION OF 8-HYDROXY-QUINOXALINES AND 8-HYDROXY-3H-QUINAZOLIN-4-ONES

8-Hydroxy-quinoxalines and 8-hydroxy-3H-quinazolin-4-ones) can be prepared by processes known in the literature. For example, condensation of an appropriately substituted 1,2-phenylenediamine with 1,2-dicarbonyl compounds such as pyruvic aldehyde provides a range of 2- or 3-substituted 8-hydroxyquinoxalines (see for example: Abe and coworkers, *J. Med. Chem.*, 1998, 41, 4062) (Scheme 1). An alternative synthesis of such compounds via condensation of the 1,2-phenylenediamine with epoxides in the presence of Bismuth(0) is shown in Scheme 2 (see Antoniotti and coworkers, *Tetrahedron Letters,* 2002, 4, 3971). Further elaboration of the 2- and/or 3-position(s) can be achieved using known methods.

Scheme 1

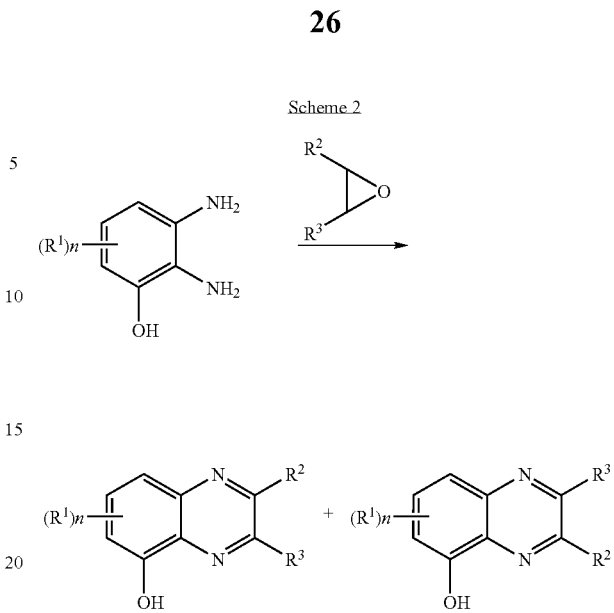

8-Hydroxy-3H-quinazolin-4-one itself was prepared according to a literature procedure (see Iyer and Dhar, *J. Sci. Ind. Res.*, 1956, 15C, 1). Derivatives of 8-hydroxy-3H-quinazolin-4-one can be synthesised by numerous methods known in the literature. One of the most common approaches to 3H-quinazolin-4-one derivatives is via substituted 2-aminobenzamides. The 2-aminobenzamides may be accessed via two different approaches (Scheme 3). For example, a 2-nitrobenzoic acid 3A is first converted into the corresponding anthranilic acid 3B. In the presence of amine and an activating agent such as CDI, 3B gives the 2-aminobenzamide 3C (Path A). Alternatively, 3A and an amine in the presence of CDI can first be converted into the 2-nitrobenzamide 3D. Subsequent reduction of 3D gives 3C (Path B).

The compound, 4,6-dichloro-3-hydroxy-2-nitrobenzoic (4F) (Scheme 4) is a key intermediate used for the provision of a range of 8-hydroxy-3H-quinazolin-4-ones and specifically for the synthesis of 5,7-dichloro-substituted derivatives. Hence, according to Golstein and Schaaf (*Helv. Chim. Acta*, 1957, 57(23), 132), commercially available 2,4-dichlorobenzoic acid (4A) is nitrated to give 2,4-dichloro-5-nitrobenzoic acid (4B). Compound 4B is converted, via the amine 4C and the acetamide 4D, into 3-acetamide-4,6-dichloro-2-nitrobenzoic acid (4E). Subsequent base hydrolysis of 4E gives the 2-nitrobenzoic acid 4F. All steps proceed in high yields (about 90%).

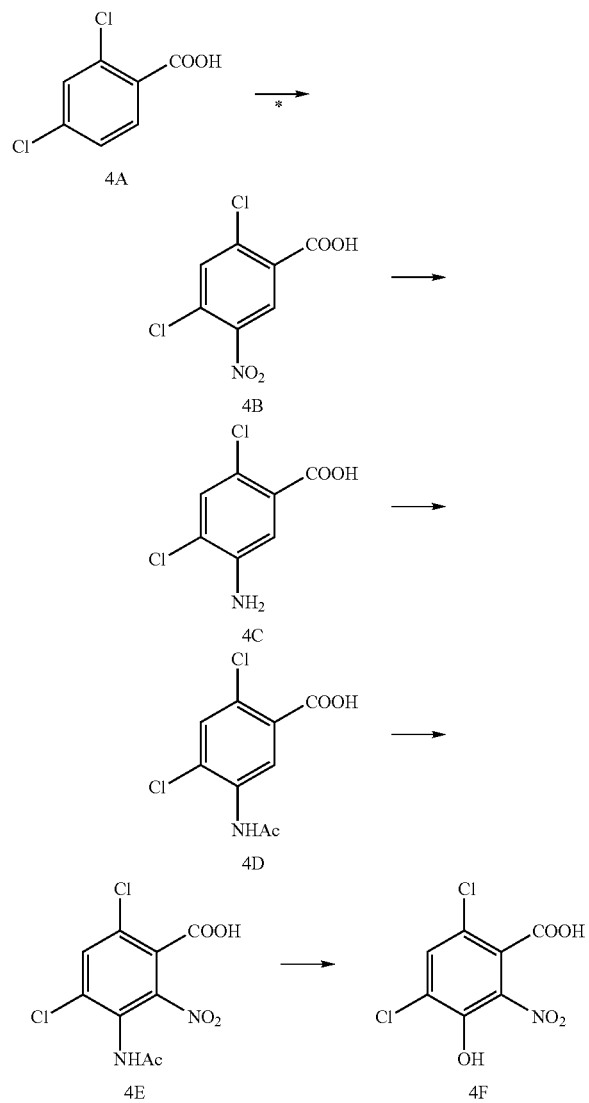

*prepared according to Golstein and Schaaf, Helv. Chim. Acta, 1957, 57(23), 132

The intermediate of formula 4E above is novel and therefore forms part of the present invention. The use of this novel intermediate results in the process of Scheme 4 being high yielding and amenable to scale-up.

The conversion of a 2-nitrobenzoic acid such as compound 4F into 8-hydroxy-3H-quinazolin-4-ones (5C) is shown in Scheme 5. Hence, treatment of 4F with an amine in the presence of CDI produces the N-(substituted) benzamide 5A. Reduction of the nitro group and coupling of the resultant amine 5B with formic acid/CDI provides the desired N-alkylated derivative 5C.

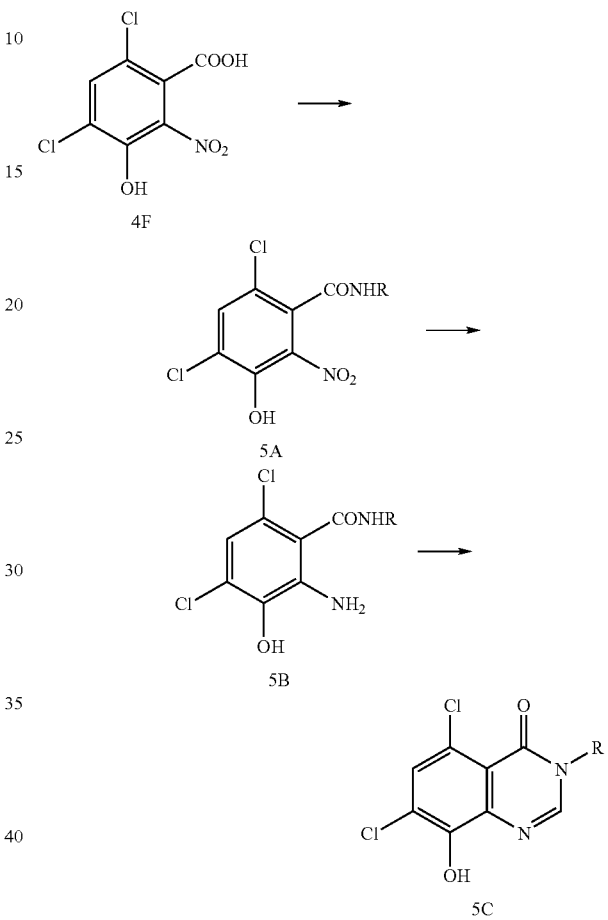

N-alkylated quinazolin-4-ones may also be prepared via the route shown in Scheme 6. Hence, the appropriately substituted 2-nitrobenzoic acid such as 4F is first treated with an amine in the presence of an activating agent such as CDI. This provides the corresponding nitrobenzamide which, under reducing conditions, gives the aminobenzamide. Subsequent treatment of the aminobenzamide with refluxing formamide produces the 3H-quinazolin-4-one. The 3H-quinazolin-4-one is then deprotonated with a base such as NaH and treated with an appropriate alkyl halide.

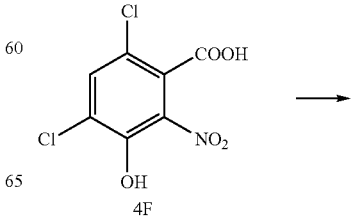

-continued

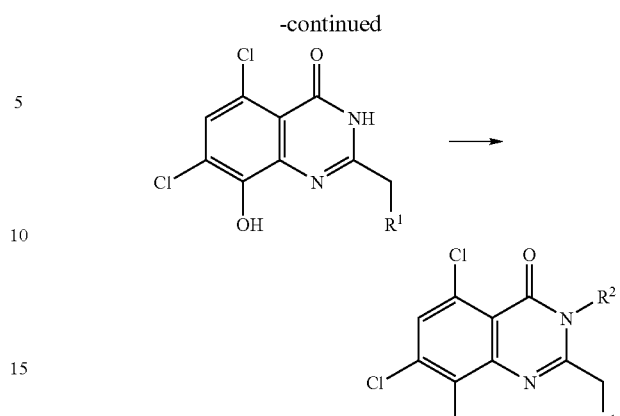

2,3-Disubstituted-8-hydroxy-3H-quinazolin-4-ones may also be synthesised via the route shown in Scheme 8. Hence, a 2-amino-3N-(substituted)benzamide is treated with the appropriate carboxylic acid such as Boc-protected glycine. Subsequent dehydration with sodium methoxide (see Lee and coworkers, *J. Med. Chem.*, 1995, 38, 3547) produces the desired analog.

Scheme 8

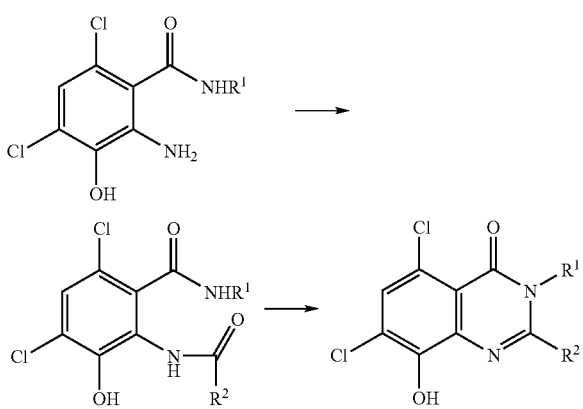

(2) PREPARATION OF 8-METHOXY-4(3H)-QUINAZOLINONE, 8-HYDROXY-CINNOLINE, 5,8-DIHYDROXY-QUINOXALINE, 4,5-DIHYDROXY-PHENAZINE, 4,8-DIHYDROXY-PHENAZINE, 4-HYDROXY-ACRIDINE AND 5-HYDROXY-3-METHYL-2(1H)-QUINOXALINONE

General

The following compounds were prepared by the methods described in the literature: 8-methoxy-4(3H)-quinazolinone (3),[5] 8-hydroxy-cinnoline (C1),[2] 5,8-dihydroxy-quinoxaline (B39),[1] 4,5-dihydroxy-phenazine (F5),[3] 4,8-dihydroxy-phenazine (F2),[3] 4-hydroxy-acridine (E1),[4] and 5-hydroxy-3-methyl-2(1H)-quinoxalinone (B12)[19]. The following compounds were sourced commercially: 8-Hydroxy-quinazoline (A1), 4-hydroxy-phenazine (F1), 4,10-phenanthrolin-5-ol (D2), 4,7-phenanthrolin-5,6-diol (D3) and 8-hydroxy-2-me-

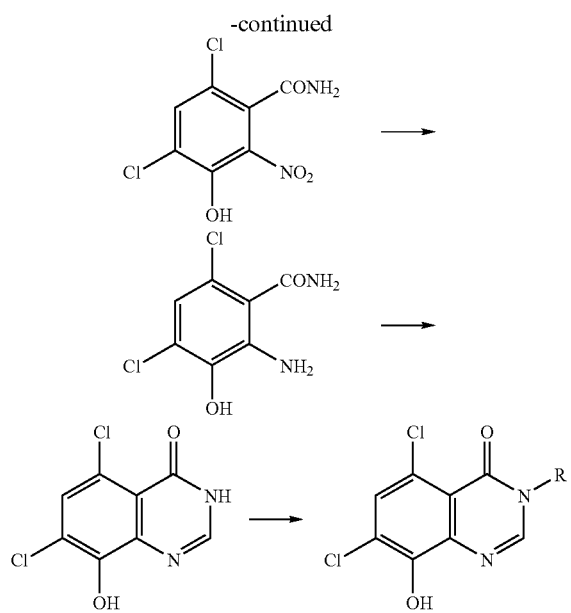

Scheme 7 shows a route to the synthesis of 2-substituted 8-hydroxy-3H-quinazolin-4-ones. Hence, treatment of an anthranilic acid such as 2-amino-4,6-dichloro-3-hydroxy-benzoic acid with thionyl chloride and subsequent reaction of the acid chloride with ammonia gives the corresponding benzamide. This, in turn, is treated with chloroacetyl acetic acid to provide 5,7-dichloro-2-chloromethyl-8-hydroxy-3H-quinazolin-4-one (see for example: Tani and coworkers, *J. Med. Chem.*, 1979, 22, 95). Further elaboration of the 2-chloromethyl derivative into a range of 2-substituted-methyl derivatives, e.g., 2-(methylamino)methyl derivatives, can be achieved using standard literature methods. N-alkylation of these derivatives using the conditions earlier described produces 2,3-disubstituted derivatives.

Scheme 7

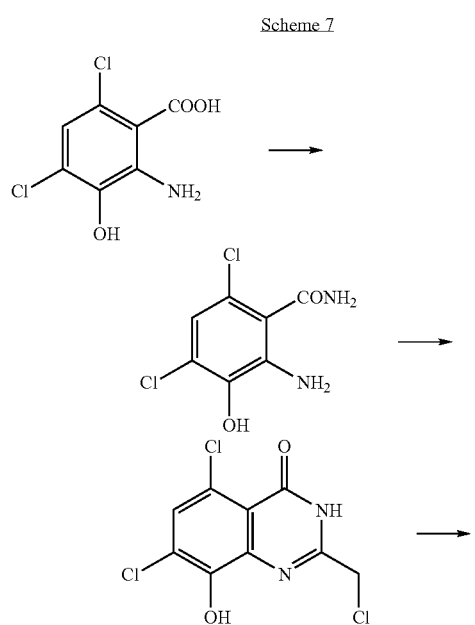

thyl-4(3H)-quinazolinone (1). Amines: ethylamine, histamine, 2-(2-aminoethyl)pyridine, 2-(2-methylaminoethyl)pyridine; aldehydes: 4-imidazolecarboxaldehyde, 2-thiazolecarboxaldehyde and 2-pyridinecarboxaldehyde, azoles: pyrazole, imidazole, methylimidazole and 1H-1,2,3-triazole, boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid and 4-fluorophenylboronic acid; and organozinc reagents: 2-pyridylzinc bromide, 2-(methylthio)phenylzinc iodide, 2-(ethoxycarbonyl)phenylzinc iodide and 6-methylpyridylzinc bromide (0.5 M solution in THF) were commercially available (Aldrich). 3-Pyridylboronic acid was purchased from Frontier Scientific. 2-Aminomethylthiazole was prepared according to the literature.[13] Solvents were analytical grade and used as supplied. THF was distilled from sodium and benzophenone under argon. $^1$H NMR spectra (δ, relative to TMS) were recorded on a Varian Unity 300 spectrometer unless otherwise indicated; J-Values are given in hertz. Mass spectral data were recorded on a Micromass Quattro II mass spectrometer.

The synthesis of derivatives of 6 classes of compounds: 8-hydroxy-quinazoline, 8-hydroxy-quinoxaline, 8-hydroxy-cinnoline, 4,7(4,10)-phenanthrolin-5-ol, 4-hydroxy-acridine and 6-hydroxy-phenazine, is described in Part A, B, C, D, E and F, respectively.

PART A: SYNTHESIS OF 8-HYDROXY-QUINAZOLINE DERIVATIVES A2-A138

The preparation of a series of 8-hydroxy-quinazoline derivatives is summarized in Charts A1-A5.

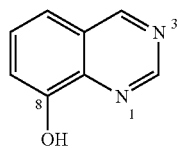

Class A

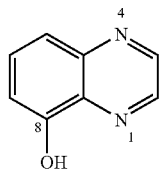

Class B

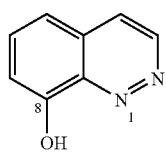

Class C

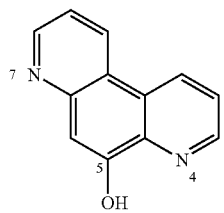

Class D

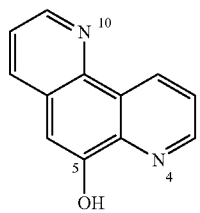

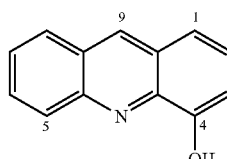

Class E

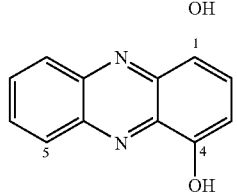

Class F

CHART A1

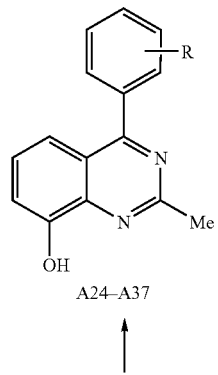

A24–A37

-continued
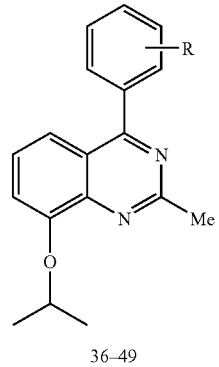
36–49
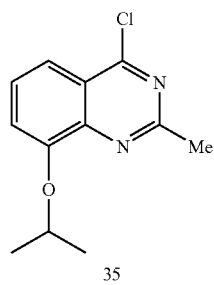
35
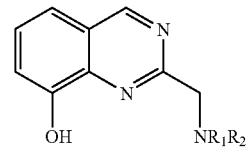
A142–A153
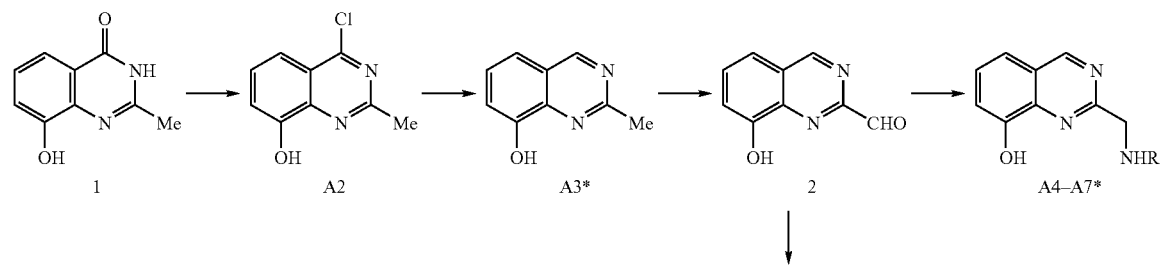
1    A2    A3*    2    A4–A7*
\* - and 5-chloro; 5-chloro-7-iodo;
7-chloro-5-iodo; 5,7-dichloro and
5-bromo derivatives thereof
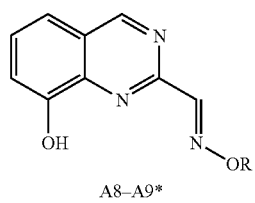
A8–A9*
A10*
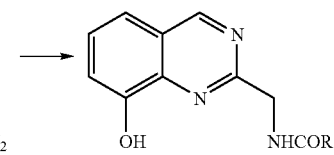
A130*

CHART A2
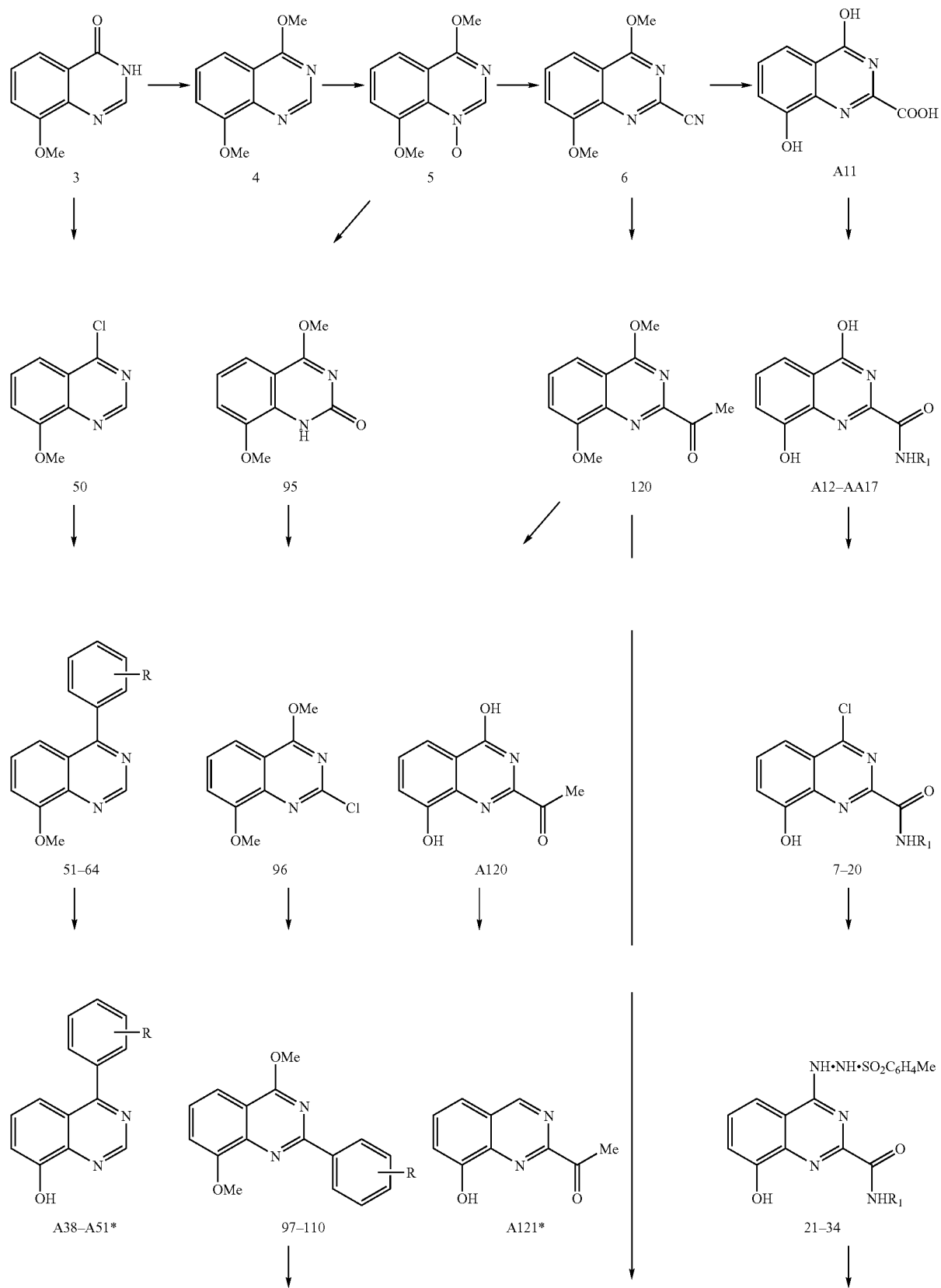

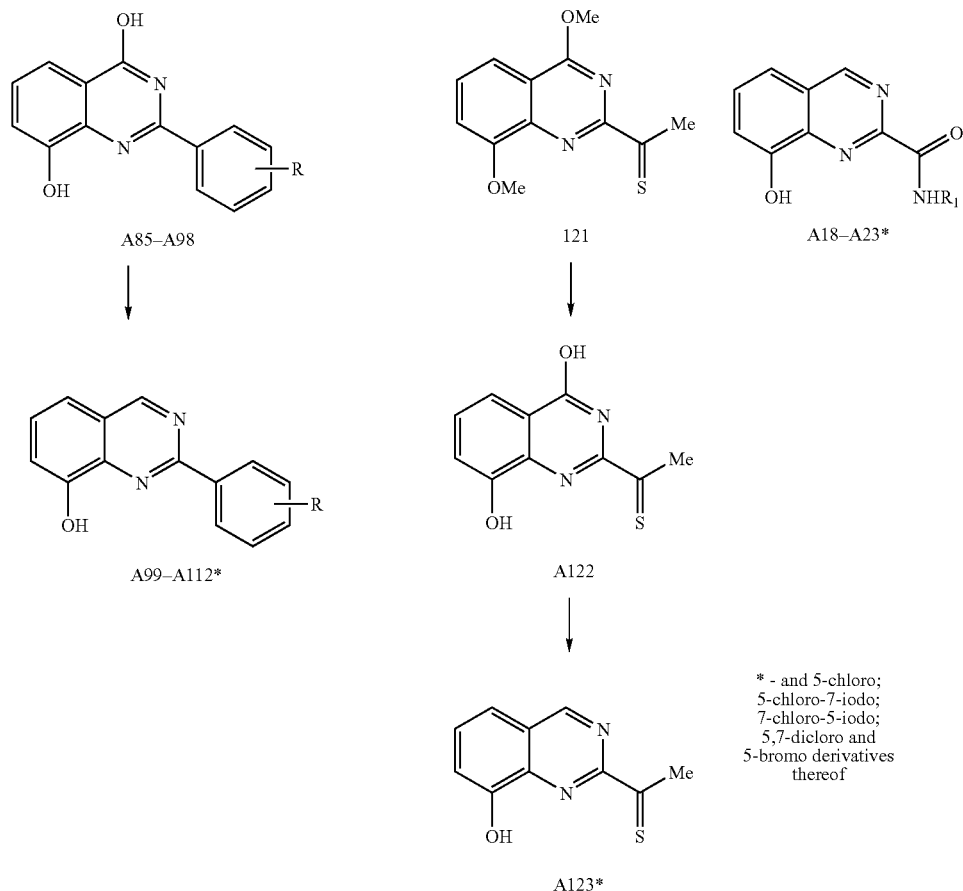
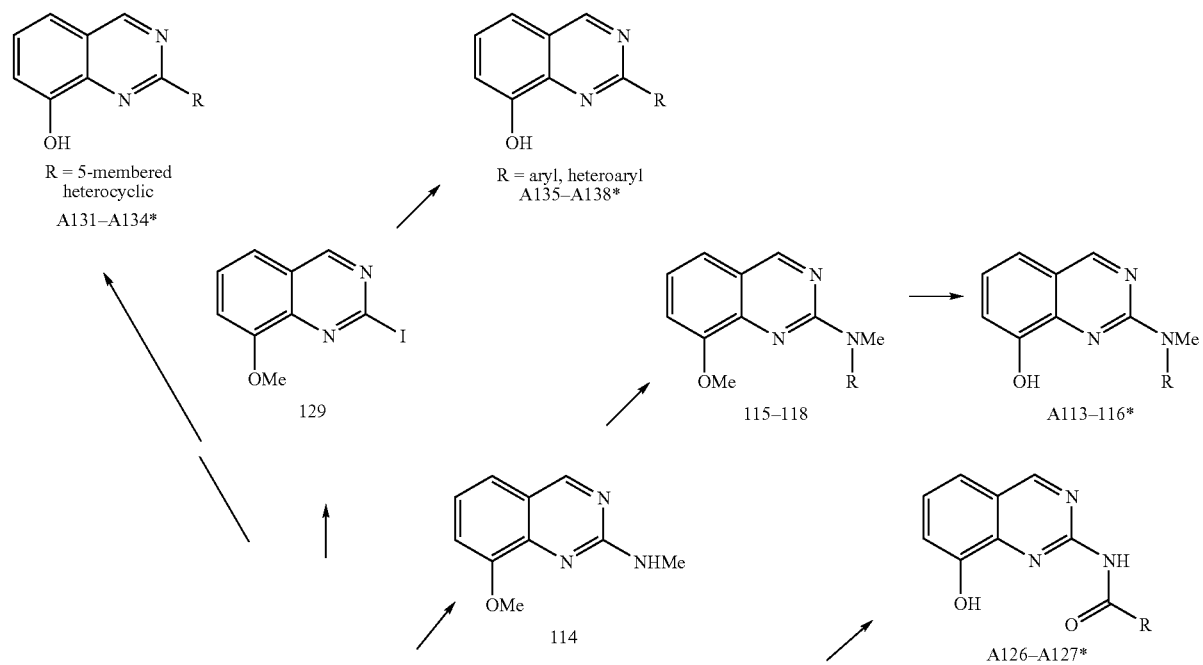
CHART A3
* - and 5-chloro;
5-chloro-7-iodo;
7-chloro-5-iodo;
5,7-dicloro and
5-bromo derivatives
thereof

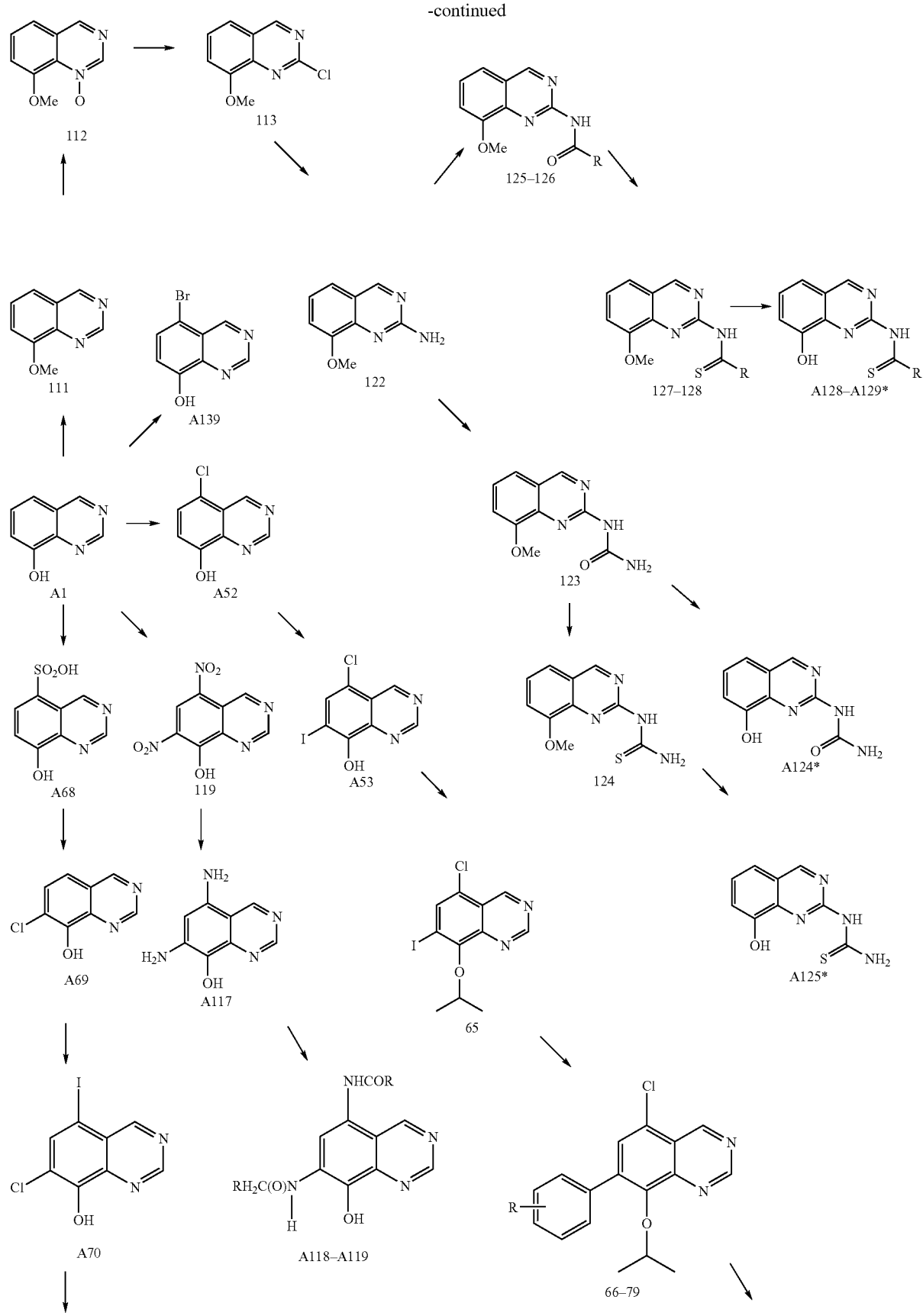

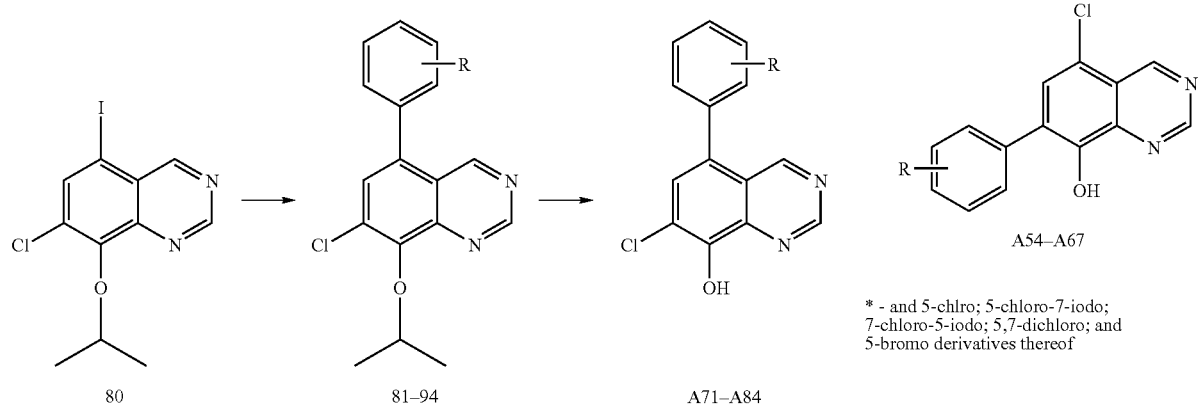
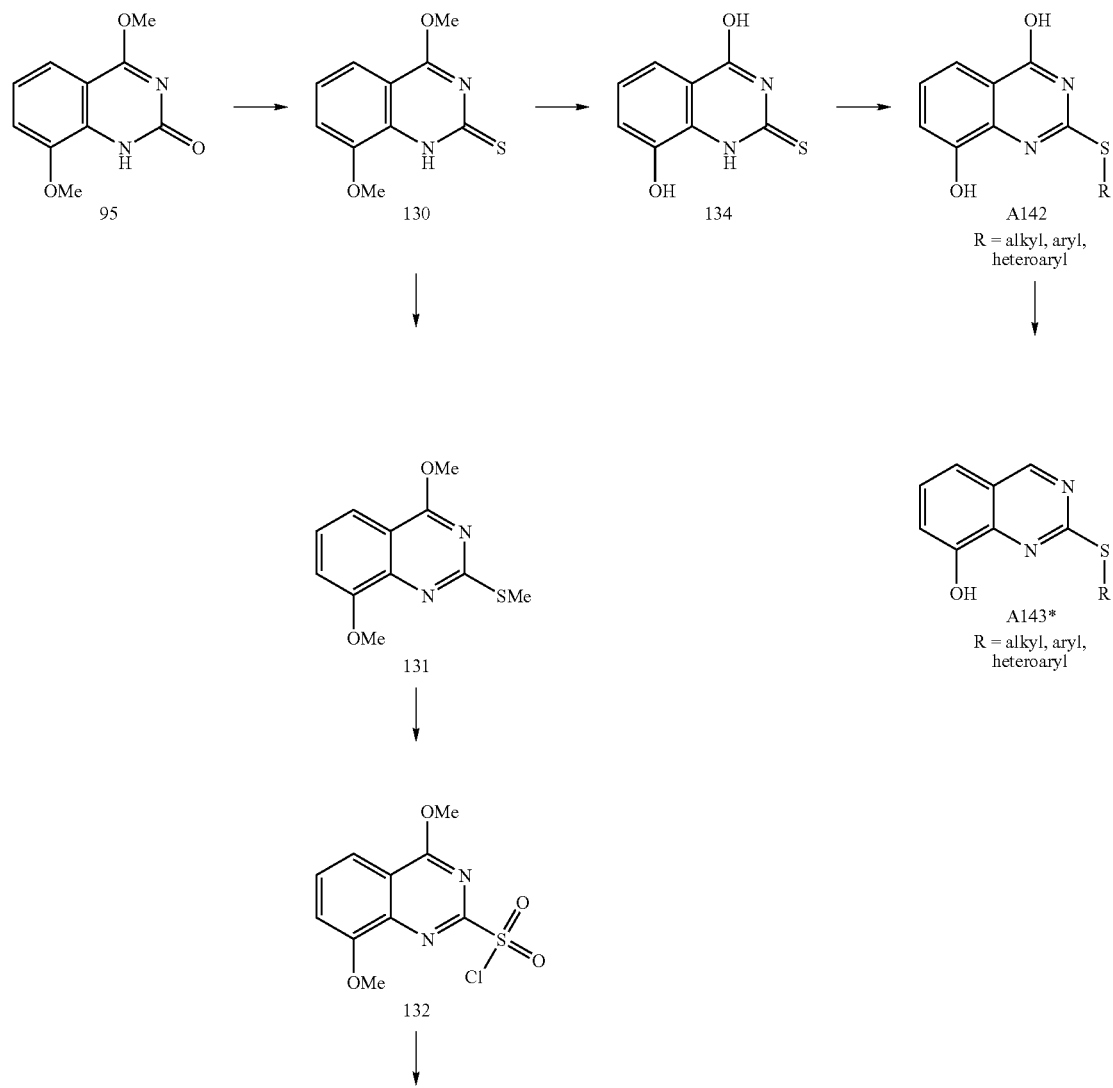
CHART A4

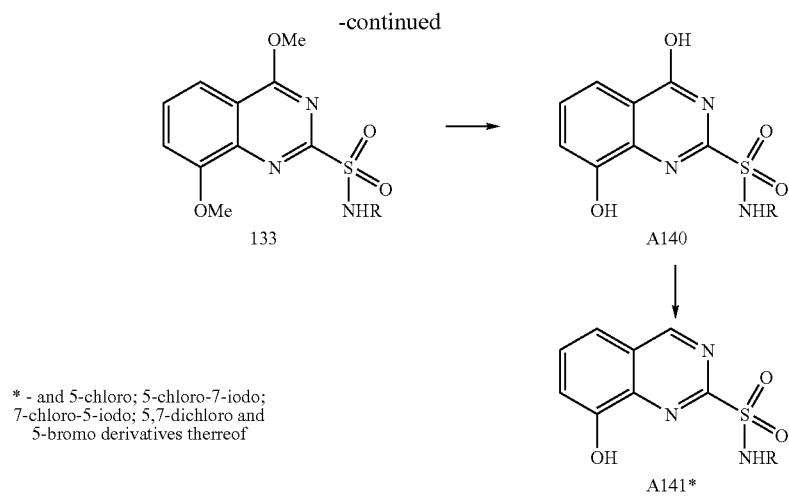
\* - and 5-chloro; 5-chloro-7-iodo; 7-chloro-5-iodo; 5,7-dichloro and 5-bromo derivatives therreof
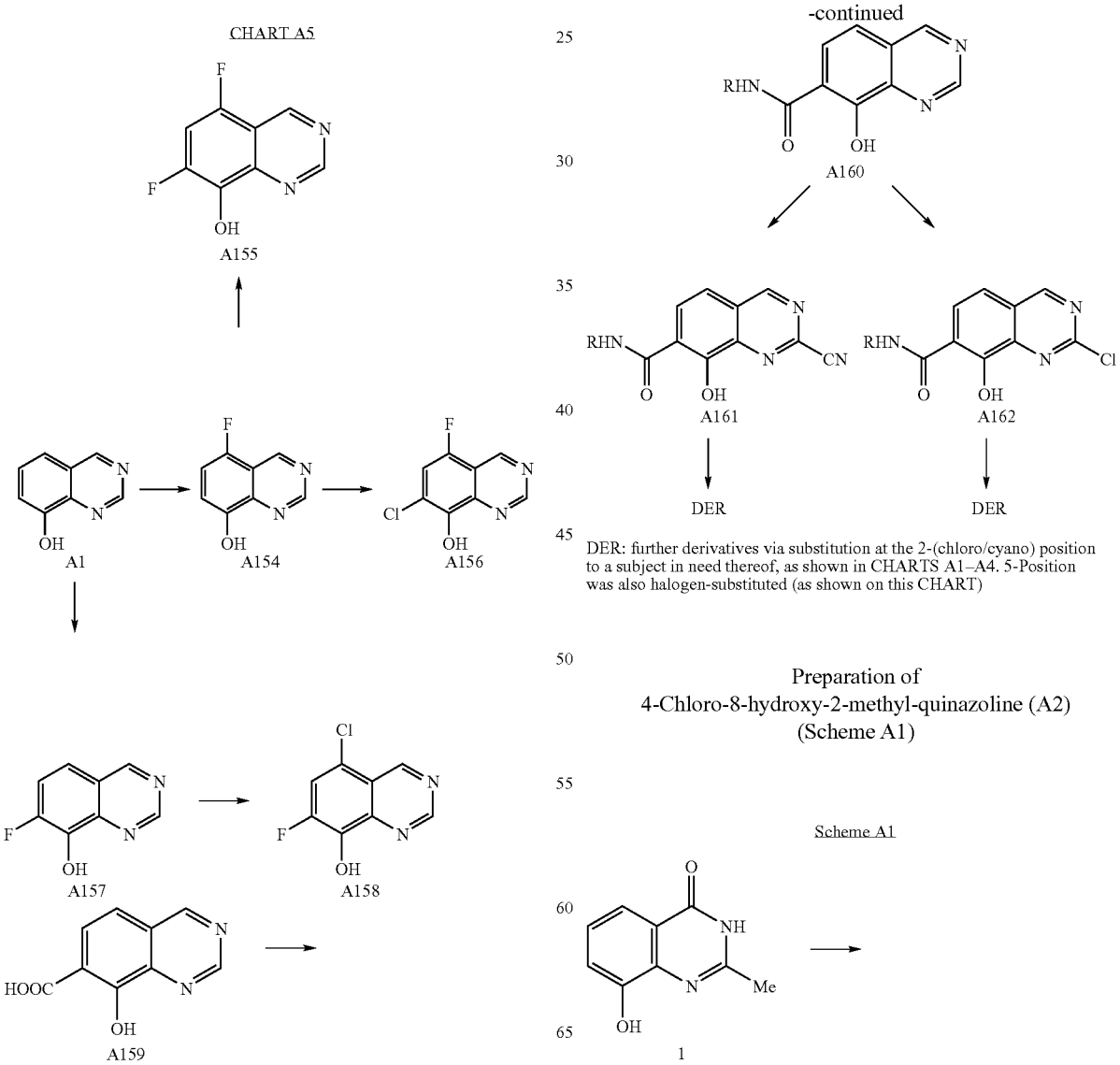
DER: further derivatives via substitution at the 2-(chloro/cyano) position to a subject in need thereof, as shown in CHARTS A1–A4. 5-Position was also halogen-substituted (as shown on this CHART)
Preparation of
4-Chloro-8-hydroxy-2-methyl-quinazoline (A2)
(Scheme A1)

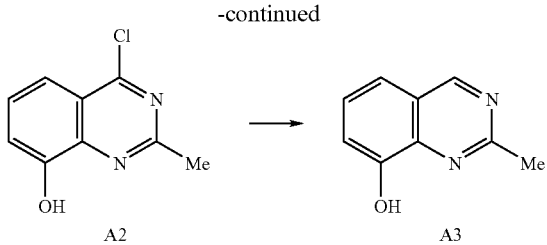

8-Hydroxy-2-methyl-4(3H)-quinazolinone (0.01 mol) and phosphorus oxychloride (10 mL) were heated under reflux for 30 min. The excess phosphorus oxychloride was removed under reduce pressure and the residue was added to a mixture of ice (50 g) and water (50 ml), and the pH adjusted to 6 (aqueous ammonia). 4-Chloro-8-hydroxy-2-methyl-quinazoline (A2) was isolated via filtration.

Preparation of 8-Hydroxy-2-methyl-quinazoline (A3) (Scheme A1)

4-Chloro-8-hydroxy-2-methyl-quinazoline (0.01 mol) was treated with hydriodic acid (100 mL; freshly distilled from red phosphorus) according to the method described[6] in the literature. This provided 8-hydroxy-2-methyl-quinazoline (A3) as a solid.

Preparation of 8-Hydroxy-quinazoline-2-carboxaldehyde (2) (Scheme A2)

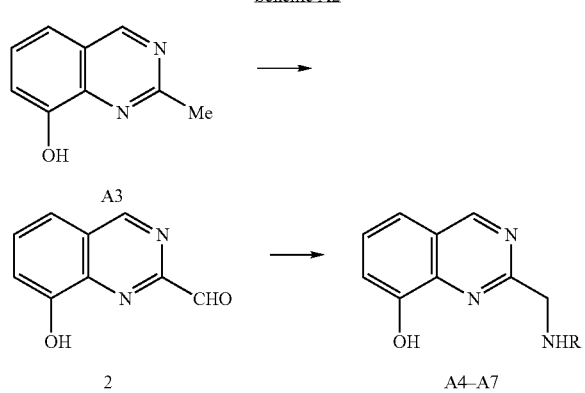

A solution of 8-hydroxy-2-methyl-quinazoline (A3) (5 mmol) in dioxane (10 mL) was added dropwise over 3 h into a stirred mixture of SeO$_2$ (8.8 mmol) in dioxane (30 mL) at 50° C. The resulting mixture was then heated at 80° C. for 16 h, allowed to cool, and the solids filtered off. The filtrate was concentrated and purified via column chromatography on silica (dichloromethane/MeOH, 40:1). This afforded 8-hydroxy-quinazoline-2-carboxaldehyde (2) as a solid.

Preparation of 2-[Alkylamino-methyl]-8-hydroxy-quinoxaline (A4-A7) (Scheme A2)

Sodium triacetoxyborohydride (1 mmol) was added to a stirred solution of 8-hydroxy-quinoxaline-2-carboxaldehyde (1 mmol) and ethylamine (1 mmol) in dichloromethane (10 mL). The mixture was left to stir at RT for 16 h, neutralized (aqueous NaHCO$_3$), and concentrated. The residue, after column chromatography on silica, afforded A4.

In a similar fashion, reductive amination of 2 with amines: histamine gave A5, 2-(2-aminoethyl)pyridine gave A6, 2-(2-methylaminoethyl)pyridine gave A7.

Preparation of 8-hydroxy-quinazoline-2-carboxaldehyde Oximes (A8-A9) (Scheme A3)

Scheme A3

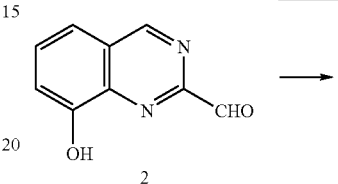

A mixture of 8-hydroxy-quinazoline-2-carboxaldehyde (2) (1 mmol), NaOAc (2 mmol), hydroxylamine hydrochloride (1.5 mmol) and water (10 mL) was heated at 100° C. for 15 min. The precipitate was isolated by filtration. This provided 8-hydroxy-quinazoline-2-carboxaldehyde oxime (A8) as a solid.

The reaction, repeated using 2 with methoxylamine hydrochloride in pyridine, gave A9.

Preparation of 8-Hydroxy-2-methylamino-quinazoline (A10) (Scheme A4)

Scheme A4

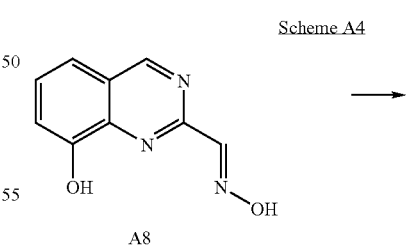

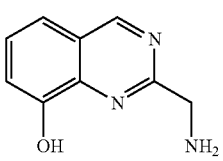

A solution of the 2-carboxylic acid oxime (1 mmol) in MeOH (20 mL) was treated under hydrogenolysis conditions (atmospheric H₂, 10% Pd/C) for 16 h. The solids were filtered off and the filtrate concentrated to provide 8-hydroxy-2-methylamino-quinazoline (A10).

Preparation of
4,8-Dimethoxy-quinazoline-2-carboxylic acid (A11)
(Scheme A5)

in H₂O (100 mL) at 0° C. was added NaCN (90 mmol). After 3 h, the reaction mixture was neutralised (HOAc) and extracted with dichloromethane, the extracts combined and dried. Solvent removal gave the 2-cyano-compound 6.

A mixture of 6 (20 mmol) and NaOH (40 mmol) in H₂O (20 mL) was heated at 100° C. for 4 h, and cooled. The pH of the solution was adjusted to 4 (glacial HOAc) and the mixture extracted with ethyl acetate (50 mL×4). The combined extracts were dried and the volatiles removed. This provided

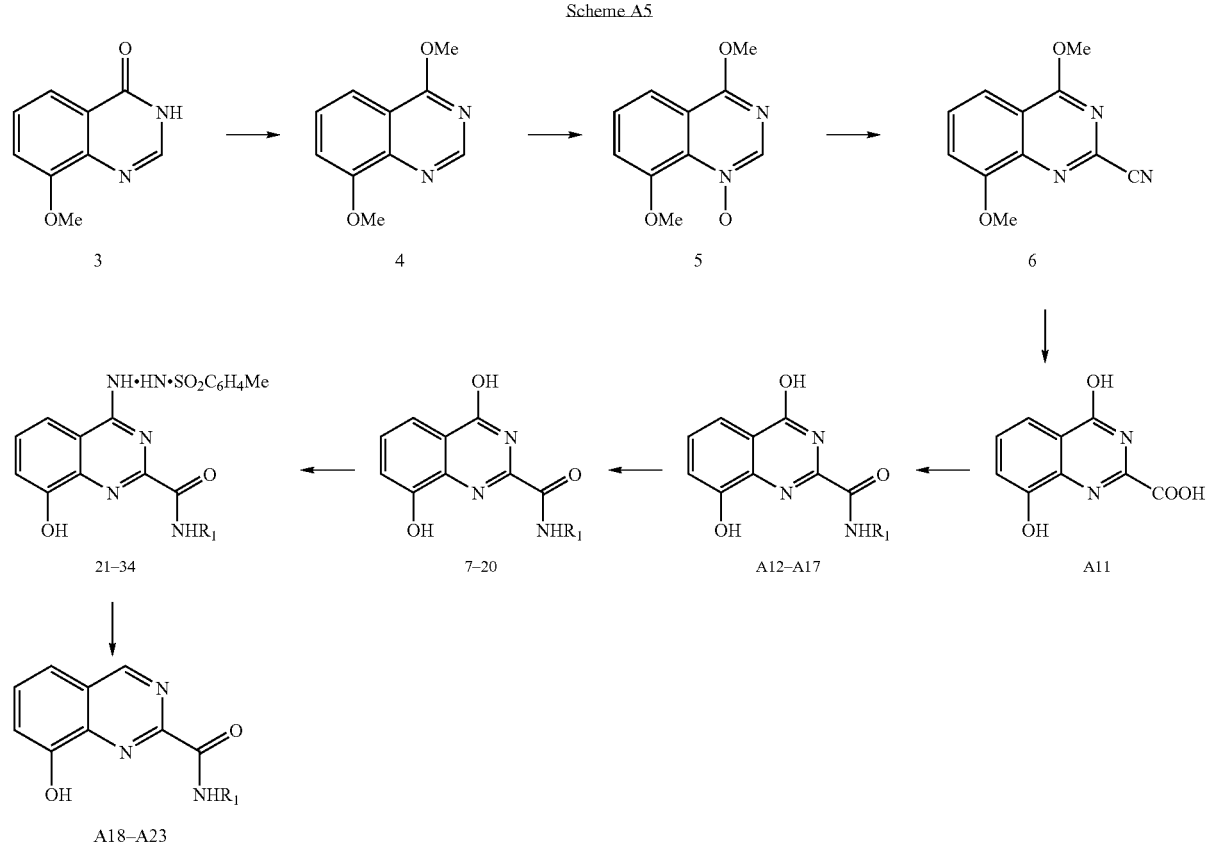

Scheme A5

To a stirring mixture of 8-methoxy-4(3H)-quinazolinone⁵ (3) (0.05 mol) and THF (100 mL) was added iodomethane (0.1 mol), tetrabutylammonium bromide (100 mg) and aqueous NaOH (prepared from 7.55 g of NaOH in 20 mL H₂O). After 16 h at 40° C., the mixture was concentrated and the remaining residue partitioned between H₂O and dichloromethane (1:1, 200 mL). The organic layer was washed with brine, dried and concentrated. Column purification gave 4,8-dimethoxy-quinazoline (4).

To a stirred solution of 4 (40 mmol) in CHCl₃ (200 mL) at 0° C. was added m-chloroperbenzoic acid (44 mmol) portionwise over 10 min. After a further 30 min at 0° C., the mixture was allowed to warm to RT over 30 min and then concentrated to dryness. To the remaining residue was added ethyl acetate and 1 N NaHCO₃ (1:1, 200 mL); the layers were separated and the organic layer was dried (Na₂SO₄), and concentrated. This provided the N-oxide 5.

A mixture of 5 (30 mmol), benzene (80 mL) and dimethyl sulphate (35 mmol) was stirred under reflux for 16 h, allowed to cool, and concentrated in vacuo. To the remaining residue 4,8-dimethoxy-quinazoline-2-carboxylic acid as a solid. Subsequent de-O-methylation with BBr₃ gave 4,8-dihydroxy-quinazoline-2-carboxylic acid (A11).

Preparation of
4,8-dihydroxy-quinazoline-2-carboxylic acid amides
(A12-A17) (Scheme A5)

1,3-Dicyclohexylcarbodiimide (1 mmol) was added to a stirred solution of 1-hydroxybenzotriazole hydrate (1 mmol) and 4,8-dihydroxy-quinazoline-2-carboxylic acid (A11) (1 mmol) in DMF and dichloromethane (1:1, 10 mL). After 30 min, histamine (1 mmol) was added and the mixture stirred at RT for a further 16 h. The volatiles were then removed in vacuo and the remaining residue gave, after purification by column chromatography on silica (ethyl acetate/i-PrOH/2 N NH₄OH, 6:2:1), 4,8-dihydroxy-quinazoline-2-carboxylic acid[2-(1H-imidazol-4-yl)-ethyl-amide (A12).

The above reaction was repeated using amines with A11: 2-(2-aminoethyl)pyridine gave A13, 2-(aminomethyl)pyridine gave A14, 2-aminothiazole gave A15, 2-aminophenol gave A16, 1,2-phenylenediamine gave A17.

Preparation of 8-Hydroxy-quinazoline-2-carboxylic acid amides (A18-A23) (Scheme 5)

The 4-hydroxy-compound (A12) (1.2 mmol) and phosphorus oxychloride (4 mL) were heated under reflux for 15 min and allowed to cool. Ice (50 g) was added and the mixture basified with aqueous ammonia. The mixture was extracted with dichloromethane (20 mL×3), the extracts combined, dried, and concentrated. This provided the corresponding 4-chloro-compound 7.

To a stirred mixture of p-toluenesulfonhydrazide (Aldrich, 2 mmol) in CHCl$_3$ (10 mL) at 50° C. was added portionwise over 10 min, the 4-chloro-compound 7 (1 mmol). After 16 h, the solid was isolated via filtration, washed with H$_2$O, and dried. This provided the 4-N-(p-toluenesulfonhydrazino)-compound 21.

The 4-N-(p-toluenesulfonhydrazino)-compound 21 (0.8 mmol) was added to Na$_2$CO$_3$ (10 mmol) and H$_2$O (10 mL) at 95° C., and the mixture heated under reflux for 15 min, cooled, filtered, and the filtrate extracted with CHCl$_3$. The extracts were combined and dried. Subsequent removal of volatiles afforded the 8-hydroxy-quinazoline-2-carboxylic acid amide (A18).

In a similar fashion, the remaining 4(3H)-quinazolinones A13-A17 were converted into 8-hydroxy-quinazoline-2-carboxylic acid amides (A19-A23).

Preparation of 4-Aryl(or heterocyclic)-8-hydroxy-2-methyl-quinoxaline (A24-A37) (Scheme A6)

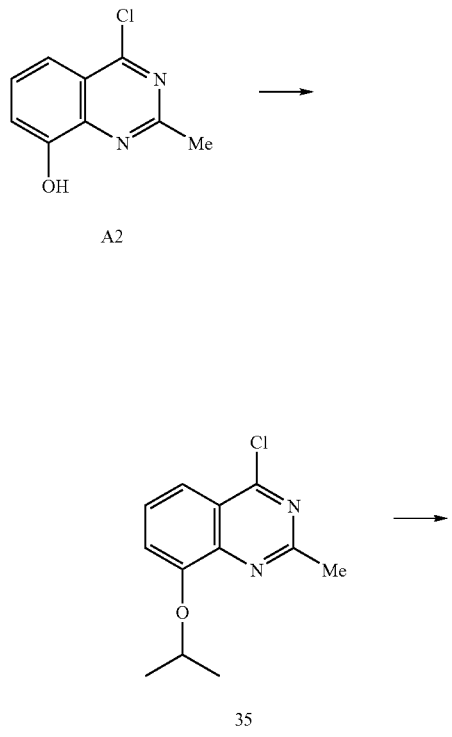

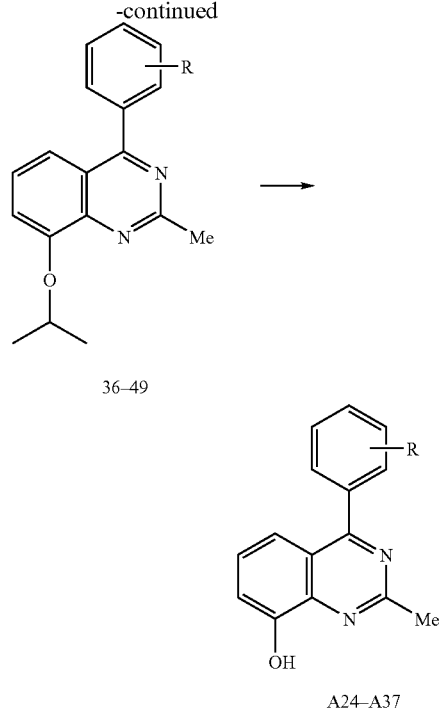

2-Bromopropane (9 mmol) was added to a stirred mixture of 4-chloro-8-hydroxy-2-methyl-quinazoline (A2) (6 mmol), K$_2$CO$_3$ (24 mmol) and DMSO (20 mL). After 16 h at RT, saturated NH$_4$Cl (20 mL) was added and the mixture extracted with dichloromethane (20 mL×3). The extracts were combined and concentrated. Diethyl ether (100 mL) was added to the residue and the resulting mixture washed successively with 2 N NaOH, H$_2$O and brine, and dried (Na$_2$SO$_4$). Solvent removal afforded 4-chloro-8-isopropoxy-2-methyl-quinazoline (35) as a solid.

To a stirred mixture of 4-chloro-8-isopropoxy-2-methyl-quinazoline (35) (0.58 mmol), phenylboronic acid (0.62 mmol), 2 N Na$_2$CO$_3$ (7.2 mL), EtOH (1.2 mL) and benzene (6 mL) was added, under a blanket of argon, Pd(PPh$_3$)$_4$ (20 mg). The mixture was stirred under reflux for 16 h, cooled, and concentrated. Subsequent column chromatography (ethyl acetate/hexane) provided 8-isopropoxy-2-methyl-4-phenyl-quinazoline (36) as a solid.

To a stirred solution of 8-isopropoxy-2-methyl-4-phenyl-quinazoline (36) (0.34 mmol) in dichloromethane (2 mL) at −78° C. was added BCl$_3$ (1.36 mL of a 1 M solution in dichloromethane, 1.36 mmol). The reaction mixture was allowed to warm to RT (over 2 h) and stirred for a further 2 h. MeOH (5 mL) was added and the mixture was concentrated to dryness. The process was repeated four times. Further washing of the remaining residue with diethyl ether (2 mL×3) provided 8-hydroxy-2-methyl-4-phenyl-quinazoline (A24).

In a similar fashion, treatment of 4-chloro-8-isopropoxy-2-methyl-quinazoline (35) with boronic acids: 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid, 4-fluorophenylboronic acid and 3-pyridylboronic acid; and isopropoxy cleavage with BCl₃ gave 4-aryl(or heterocyclic)-8-hydroxy-2-methyl-quinazolines (A25-A37).

Preparation of 4-Aryl(or heterocyclic)-8-hydroxy-quinazoline (A38-A51) (Scheme A7)

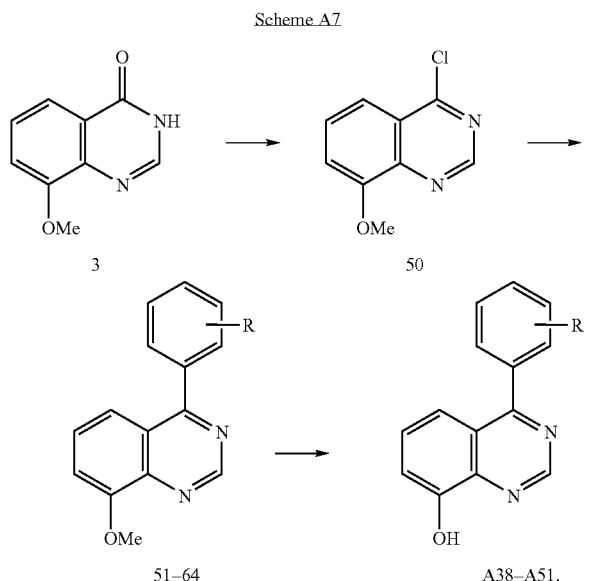

Using the procedure as previously described in Example 9, 8-methoxy-4(3H)-quinazolone⁵ (3) (10 mmol) and phosphorus oxychloride provided 4-chloro-8-methoxy-quinazoline 50. Treatment of the 4-chloride 50 with phenylboronic acid as described in Example 9 gave, after de-O-methylation with BBr₃, the 4-phenyl derivative A38. The coupling reaction of 50 was repeated using a range of boronic acids: 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid, 4-fluorophenylboronic acid and 3-pyridylboronic acid gave 51-64; and subsequent cleavage of the methyl ether with BBr₃ gave the 4-aryl(or heterocyclic)-8-hydroxy-quinazolines A39-A51.

Preparation of 5-Chloro-8-hydroxy-quinazoline (A52) (Scheme A8)

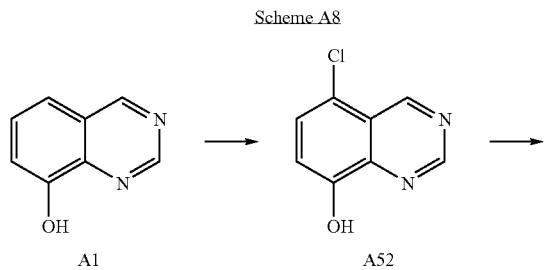

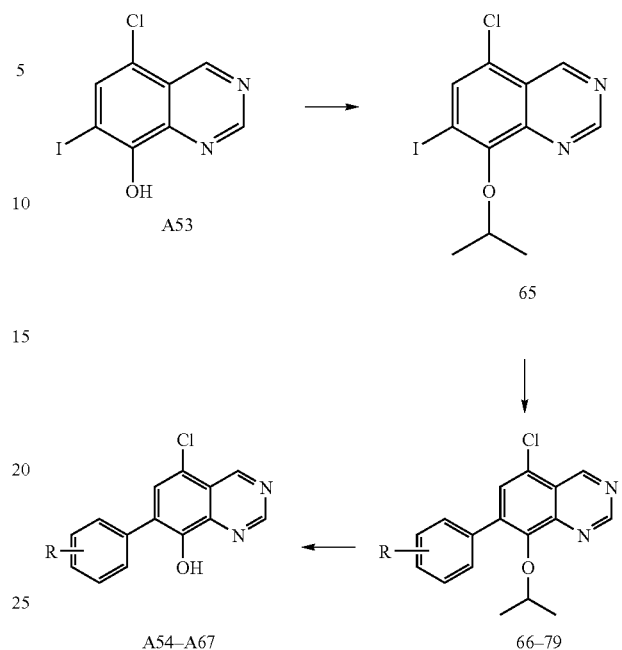

Chlorine (12 mmol) was added into a stirred solution of 8-hydroxy-quinazoline (A1) (10 mmol) in 93% H₂SO₄ following a previously published⁷ procedure. After 3 h, ice (100 g) and H₂O (100 mL) was added, the mixture basified with aqueous ammonia, extracted with dichloromethane, and the extracts dried. Solvent removal gave the 5-chloro-compound A52.

Preparation of 5-Chloro-8-hydroxy-7-iodo-quinazoline (A53) (Scheme A8)

5-Chloro-8-hydroxy-quinazoline (10 mmol) was added to a stirred solution of ICl (12 mmol) in concentrated HCl (10 mL).⁸ After 5 min, the precipitate was isolated via filtration, washed successively with H₂O, saturated sodium thiosulfate and H₂O, and dried. This provided 5-chloro-8-hydroxy-7-iodo-quinazoline (A53) as a solid.

Preparation of 7-Aryl(or heterocyclic)-5-chloro-8-hydroxy-quinazolines (A54-A67) (Scheme A8)

The 8-hydroxy-compound A53 was converted into the corresponding isopropyl ether 65 using 2-bromopropane according to the method as described in Example 9.

Treatment of 5-chloro-7-iodo-8-isopropoxy-quinazoline (65), according to the method described in Example 9, with a range of boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid, 4-fluorophenylboronic acid and 3-pyridylboronic acid gave 66-79; and subsequent cleavage of the 8-isopropoxy group with BCl₃, gave A54-A79.

Preparation of 7-Chloro-8-hydroxy-quinazoline (A69) (Scheme A9)

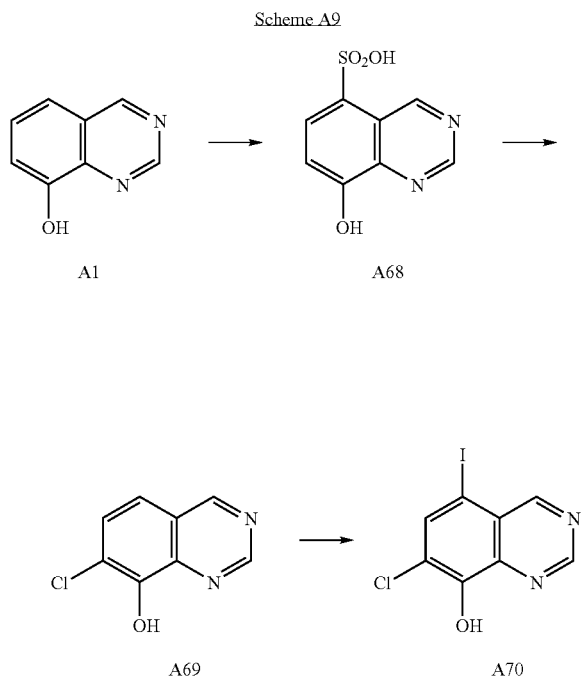

8-Hydroxy-quinazoline (A1) (0.1 mol) and concentrated sulfuric acid (50 mL) were heated at 100° C. for 5 h, and allowed to cool. The solution was then carefully added to 300 mL of cold H₂O. The resulting precipitate was isolated via filtration, washed with H₂O, and dried. This provided the 5-sulfonic acid A68 as a solid.

To a stirred mixture of 5-sulfonic acid A68 (0.09 mol) and H₂O (225 mL) was added KOH (0.25 mol) and NaOCl (230 mL of a solution containing 10-13% available chlorine).⁹ After 1.5 h at RT, the solution was passed through a column of Amberlite IR-120(H⁺) resin. The effluent concentrated to 20 mL. Acetone (20 mL) was then added and the precipitate isolated by filtration. Subsequent washing with acetone and drying gave 7-chloro-8-hydroxy-quinazoline (A69).

Preparation of 7-Chloro-8-hydroxy-5-iodo-quinazoline (A70) (Scheme A9)

To a solution of 7-chloro-8-hydroxy-quinazoline (A69) (0.1 mol) and potassium acetate (0.15 mol) in MeOH and H₂O (19:1, 250 mL) was added, over 30 min, a solution of iodine (0.095 mol) in MeOH and H₂O (19:1, 350 mL). The mixture was then heated under reflux for 15 min, cooled and H₂O (400 mL) was added. The precipitate was isolated by filtration, washed with saturated sodium thiosulfate and H₂O, and dried. This provided 7-chloro-8-hydroxy-5-iodo-quinazoline (A70) as a solid.

Preparation of 4-Aryl(or heterocyclic)-7-chloro-8-hydroxy-quinazolines (A71-A84) (Scheme A10)

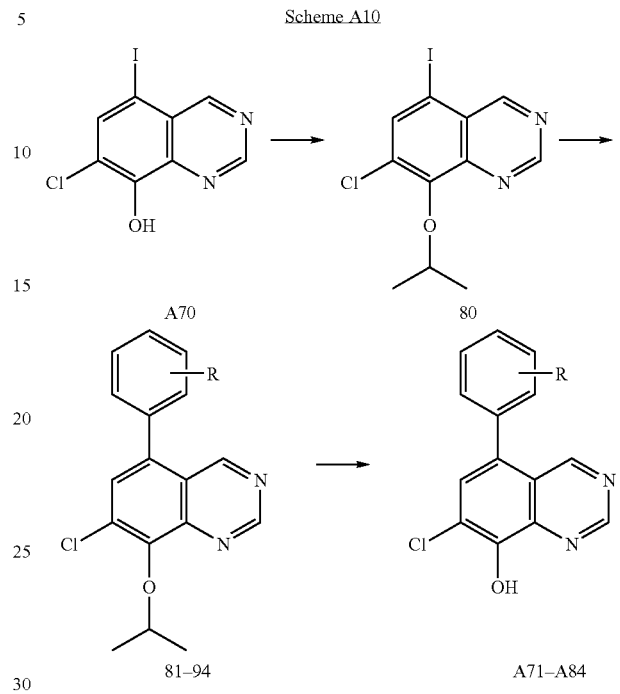

According to the method described in Example 9, treatment of 5-chloro-7-iodo-8-isopropoxy-quinazoline (80), with a range of boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid, 4-fluorophenylboronic acid and 3-pyridylboronic acid gave 81-94; and subsequent cleavage of the 8-isopropoxy group with BCl₃, gave A71-A84.

Preparation of 2-Chloro-4,8-dimethoxy-quinoxaline (96) (Scheme A11)

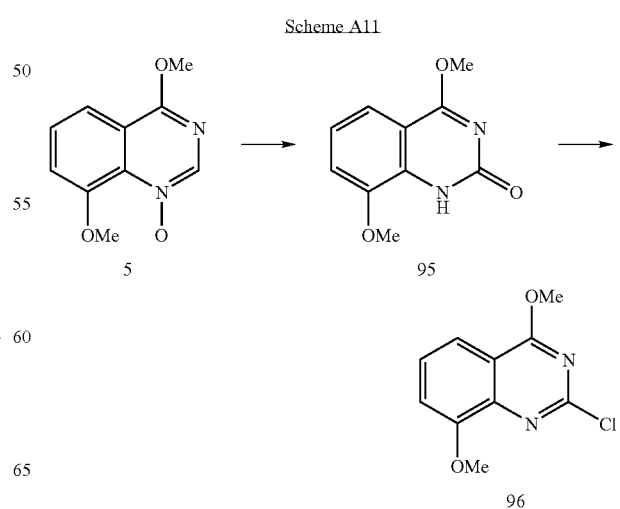

Ac₂O (6 mL) was added to a stirred mixture of the N-oxide 5 (10 mmol) and dichloromethane (10 mL). The solvent was then removed in vacuo and the resulting solution heated under reflux for 1 h, cooled, and concentrated. The remaining residue was washed with diethyl ether (10 mL×2). This provided 4,8-dimethoxy-2(1H)-quinazolinone (95) as a solid.

Treatment of 4,8-dimethoxy-2(1H)-quinazolinone (95) (5 mmol) with phosphorus oxychloride (20 mL) and standard workup according to Example 8 provided the 2-chloride 96.

Preparation of 2-Aryl(or heterocyclic)-4,8-dihydroxy-quinazolines (A85-A98) (Scheme A12)

Scheme A12

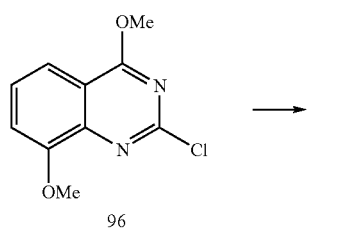

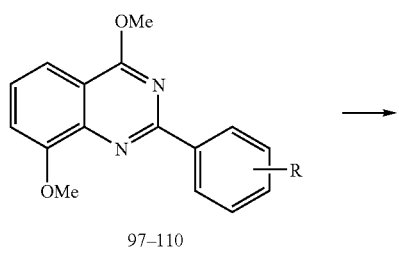

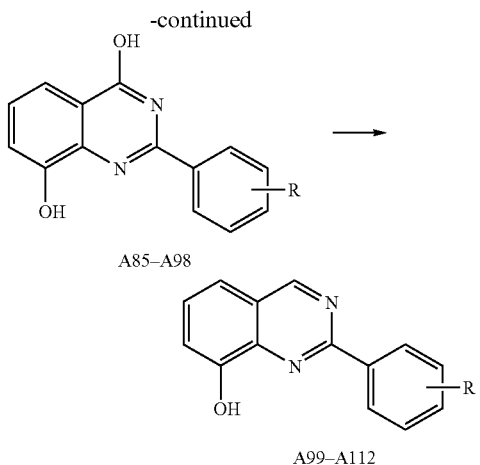

According to the procedure previously described in Example 9, coupling of the 2-chloride 96 (0.1 mmol) with boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid, 4-fluorophenylboronic acid and 3-pyridylboronic acid gave 97-110; and subsequent cleavage of the 8-O-methyl ether with BBr₃, gave A85-A98.

Preparation of 2-Aryl(or heterocyclic)-8-hydroxy-quinazoline (Scheme A12)

Sequential treatment of the 4-hydroxy-compounds A85-A98 with phosphorus oxychloride, p-toluenesulfonhydrazide and Na₂CO₃, according to the method previously described in Example 6, provided the 2-aryl(or heterocyclic)-8-hydroxy-quinazolines A99-A112.

Preparation of 2-Chloro-8-methoxy-quinazoline (113) (Scheme A13)

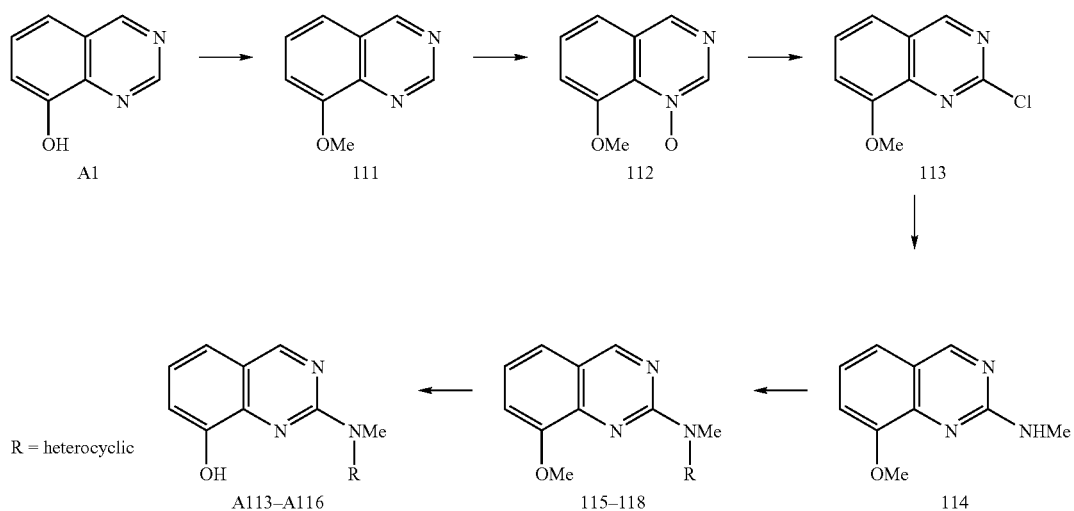

According to the procedure previously described in Example 6, 8-hydroxy-quinazoline (A1) (20 mmol) and iodomethane gave 8-methoxy-quinazoline (111). 8-Methoxy-quinazoline (111) (10 mmol) was then treated with m-chloroperbenzoic acid which gave the N-oxide 112. Subsequent treatment of the N-oxide 112 with Ac$_2$O and phosphorus oxychloride according to Example 14 afforded 2-chloro-8-methoxy-quinazoline (113).

Preparation of 2-[(N'-methyl)-heterocyclic]-8-hydroxy-quinazolines (A113-A116) (Scheme A13)

A solution of 2-chloro-8-methoxy-quinazoline (113) (10 mmol) in pyridine (10 mL) was added methylamine hydrochloride (Aldrich, 15 mmol). After 16 h at RT, the mixture was concentrated in vacuo. Subsequent column purification of the residue gave the 2-(N'-methyl)-compound 114.

Amination of 114 (1 mmol) with 2-bromopyridine (1.2 mmol) in the presence of [Pd$_2$(dba)$_3$] and DPPP according to the method described[11] in the literature, provided 8-methoxy-2-[(N'-pyridyl)methyl]-quinazoline (115). Subsequent treatment of 115 with BBr$_3$ (Example 6) afforded the 8-hydroxy-quinazoline derivative A113.

Amination of 114 was repeated using a range of 2-bromo-substituted heterocyclics: 2-bromothiazole, 4-bromo-1H-imidazole and 4-bromo-1-methylimidazole which provided 116-118; and subsequent cleavage of the O-methyl ether with BBr$_3$, gave A114-A116.

Preparation of 5,7-Diamino-8-hydroxy-quinazoline (A117) (Scheme A14)

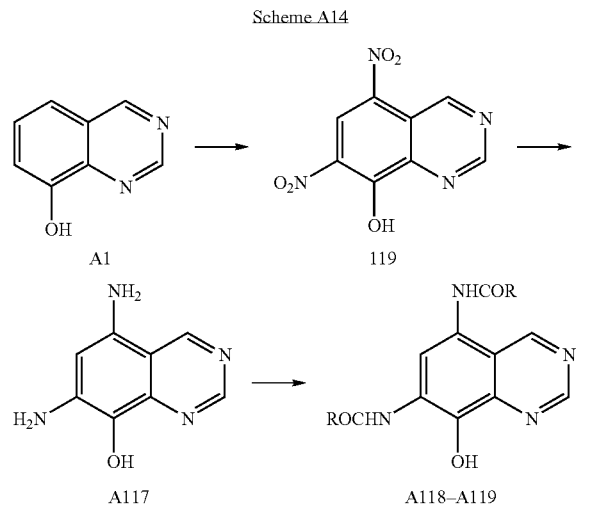

Scheme A14

To a solution of 8-hydroxy-quinazoline (A1) (0.05 mol) in acetic acid (175 mL) was added a solution of nitric acid (0.16 mol) in acetic acid (25 mL), keeping the temperature below 30° C. After 2 h, the 5,7-dinitro-compound 119 was isolated by filtration, washed with H$_2$O, and dried.

Hydrogenolysis of the 5,7-dinitro-compound 119 (0.045 mol) in MeOH (200 mL) in the presence of platinum oxide gave, after filtration to remove solids and concentration, 5,7-diamino-8-hydroxy-quinazoline (A117).

Preparation of 5,7-Diacylamino-8-hydroxy-quinazolines (A118-A119) (Scheme A14)

Acetic acid (2 mmol) and CDI (2.2 mmol) were heated under reflux in dry THF (10 mL) for 1 h. 5,7-Diamino-8-hydroxy-quinazoline (A117) (2 mmol) was added and the mixture heated under reflux for 16 h. Removal of volatiles in vacuo and subsequent column chromatography of the resulting residue provided 5,7-desacetamido-8-hydroxy-quinazoline (A118).

In a similar fashion, treatment of 5,7-diamino-8-hydroxy-quinazoline (A117) with benzoic acid provided 5,7-dibenzoylamido-8-hydroxy-quinazoline (A119).

Preparation of 2-Acetyl-4,8-dihydroxy-quinazoline (A120) (Scheme A15)

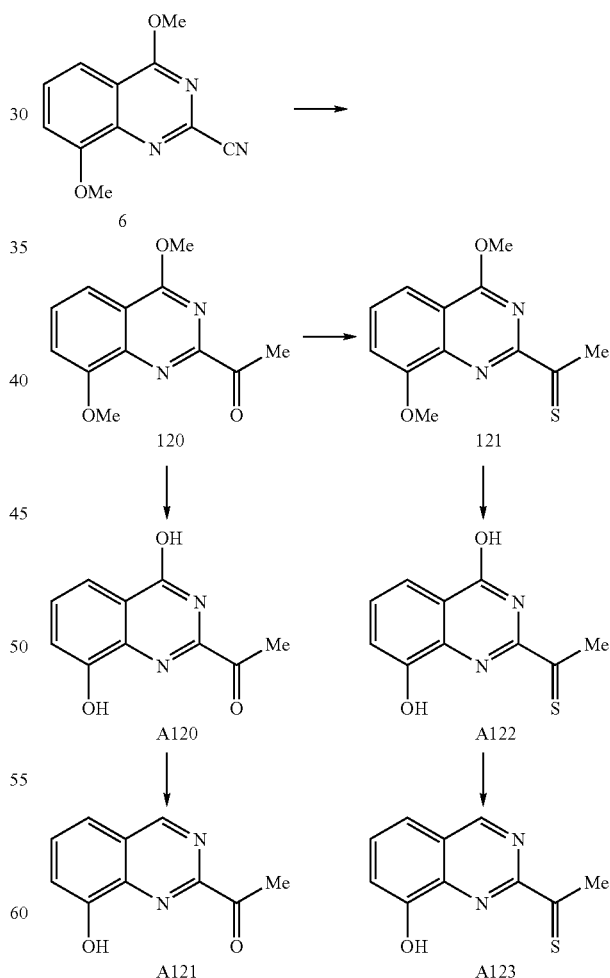

Methylmagnesium bromide (1.2 mL of a 3 M solution in diethyl ether, 3.5 mmol) was added dropwise into a stirred solution of 6 (0.6 mmol) in diethyl ether (10 µL) at −15° C.

The resulting solution was allowed to warm to RT over 2 h and stirred at RT for a further 4 h. The reaction mixture was then quenched with saturated NH$_4$Cl and extracted with ethyl acetate (10 mL×3), the extracts combined, dried and concentrated to provide 120.

Treatment of 120 with BBr$_3$ (Example 6) gave A120.

Preparation of 2-Acetyl-8-hydroxy-quinazoline (A121) (Scheme A15)

Successive treatment of A120 with phosphorus oxychloride, p-toluenesulphonhydrazide and Na$_2$CO$_3$ (Example 6) gave A121.

Preparation of 2-S-Acetyl-4,8-dihydroxy-quinazoline (A122) (Scheme A15)

A solution of 120 (1 mmol) and Lawesson's reagent (0.7 mmol) in THF (10 mL) was heated under reflux for 16 h and allowed to cool. Concentration and subsequent column chromatography of the residue gave 121. Treatment of 121 with BBr$_3$ (Example 6) gave A122.

Preparation of 2-S-Acetyl-8-hydroxy-quinazoline (A123) (Scheme A15)

Successive treatment of A122 with phosphorus oxychloride, p-toluenesulphonhydrazide and Na$_2$CO$_3$ (Example 6) gave A123.

Preparation of 8-Hydroxy-quinazoline-2-urea (A124) (Scheme A16)

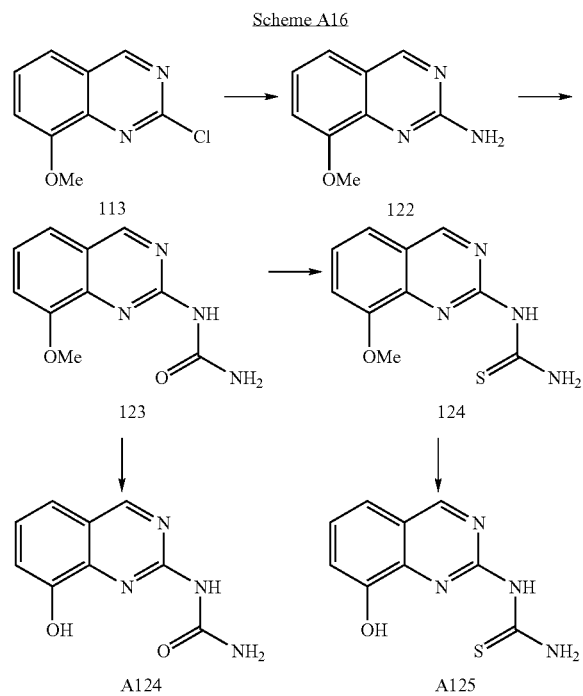

The 2-chloride 113 was converted into the amine 122 according to standard Chichibabin reaction conditions. The 2-amine 122 (1 mmol) and isocyanate (1 mmol) in dry CHCl$_3$ (10 mL) were then heated under reflux for 16 h. This gave, after filtration, the urea derivative 123. Treatment of 123 with BBr$_3$ gave A124.

Preparation of 8-Hydroxy-quinazoline-2-thiourea (A125) (Scheme A16)

The 2-urea derivative 123 (1 mmol) and Lawesson's reagent (0.7 mmol) in THF (10 mL) was heated under reflux for 16 h, allowed to cool and concentrated. Subsequent column purification on silica gave 124. Treatment of 124 with BBr$_3$, according to Example 6, then provided A125.

Preparation of 2-Acylamido-8-hydroxy-quinazolines (A126-A127) (Scheme A17)

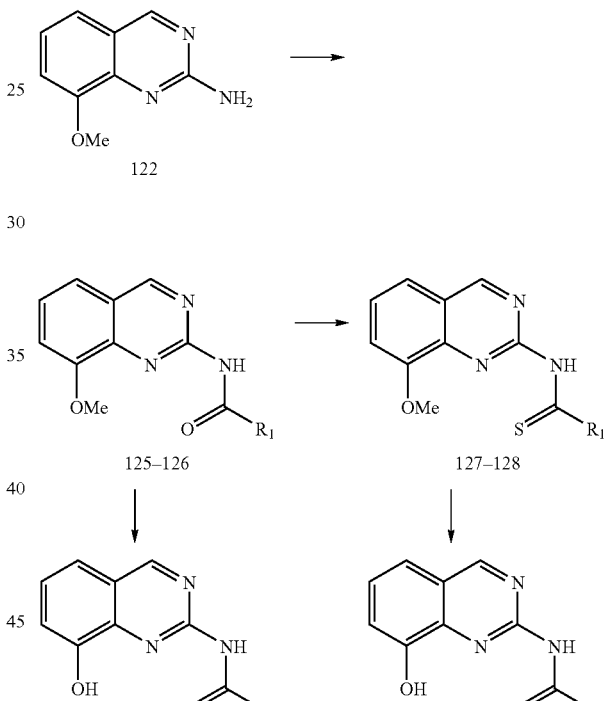

The 2-amine 122 was acylated under standard conditions: Ac$_2$O gave 125; benzoic anhydride gave 126. Respective treatment of 125 and 126 with BBr$_3$ (Example 6) provided A126 and A127.

Preparation of 2-Thioacylamido-8-hydroxy-quinaxolines (A128-A129) (Scheme A17)

The acylamido compounds 125 and 126 were individually treated with Lawesson's reagent according to conditions previously described (Example 21), which furnished, after standard workup, 127 and 128. Subsequent O-methyl ether cleavage with BBr$_3$ then gave A128 and A129, respectively.

Preparation of 2-(acylamido)-methyl-8-hydroxy-quinazolines (A130) (Scheme A18)

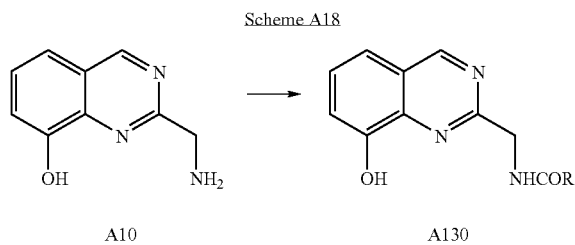

Standard acylation of the amine A10 using a range of acid anhydrides provided, after column purification, the 2-(acylamido)-methyl derivatives A130.

Preparation of 2-(Azole)-8-hydroxy-quinazolines (A131-A134) (Scheme A19)

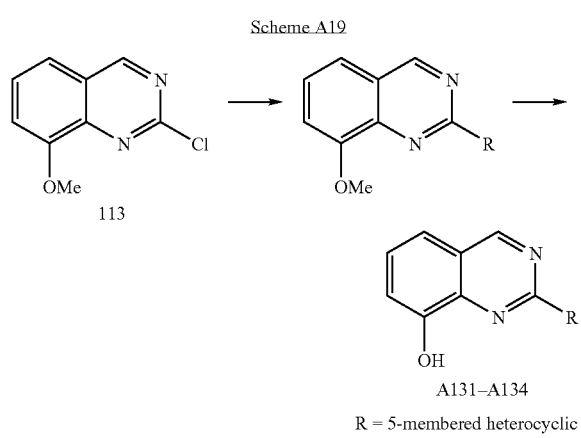

R = 5-membered heterocyclic

A mixture of the 2-chloride 113 (0.5 mmol) and pyrazole (2.5 mmol) was heated at 175° C. in a steel autoclave for 48 h. The crude product was then treated with BBr$_3$ according to the procedure described in Example 6. Subsequent purification by column chromatography gave 2-pyrazol-1-yl-quinazolin-8-ol (A131).

The above procedure was repeated using imidazole, 2-methylimidazole and 1H-1,2,3-triazole to give A132-A134.

Preparation of 2-Aryl(or heterocyclic)-8-hydroxy-quinazolines (A135-A138) (Scheme A20)

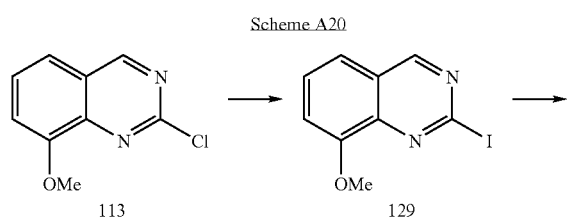

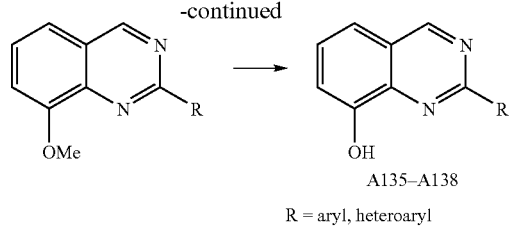

R = aryl, heteroaryl

According to a literature[12] procedure, the 2-chloride 113 (5 mmol) was treated with acetyl chloride and sodium iodide in AcCN. Standard workup followed by column chromatography on silica furnished the 2-iodo-compound 129.

To a stirred solution of 129 (0.1 mmol) and PdCl$_2$(PPh$_3$)$_2$ (5 mg) in THF (2.5 mL) under an argon atmosphere at RT was added over 5 min 2-pyridylzinc bromide (0.37 mL of a 0.5 M solution in THF, 0.185 mmol). After 2 h, saturated NH$_4$Cl (5 mL) was added and the mixture extracted with dichloromethane (10 mL×3). The combined extracts were washed with H$_2$O and brine, dried and concentrated. Subsequent column chromatography on silica gave 8-methoxy-2-pyrid-2-yl-quinazoline. The 8-O-methyl ether was cleaved according to the procedure of Example 6, to give 2-(pyrid-2-yl)-8-hydroxy-quinazoline (A135).

The reaction was repeated using: 2-(methylthio)phenylzinc iodide, 2-(ethoxycarbonyl)phenylzinc iodide and 6-methylpyridylzinc bromide to give A136-A138.

Preparation of 5-Bromo-8-hydroxy-quinazoline (A139) (Scheme A21)

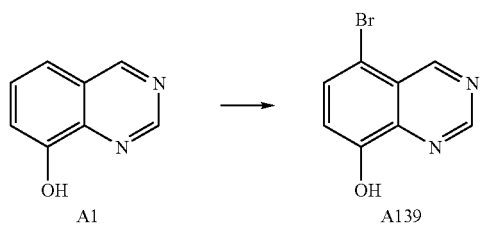

Bromination of 8-hydroxy-quinazoline (A1) with N-bromosuccimide, according to the method previously described by Gerson and McNeil,[15] gave 5-bromo-8-hydroxy-quinazoline (A139).

Preparation of 8-Hydroxy-quinazoline-2-sulfonic acid (2-pyridin-2-yl-ethyl)-amide (A140 and A141) (Scheme A22)

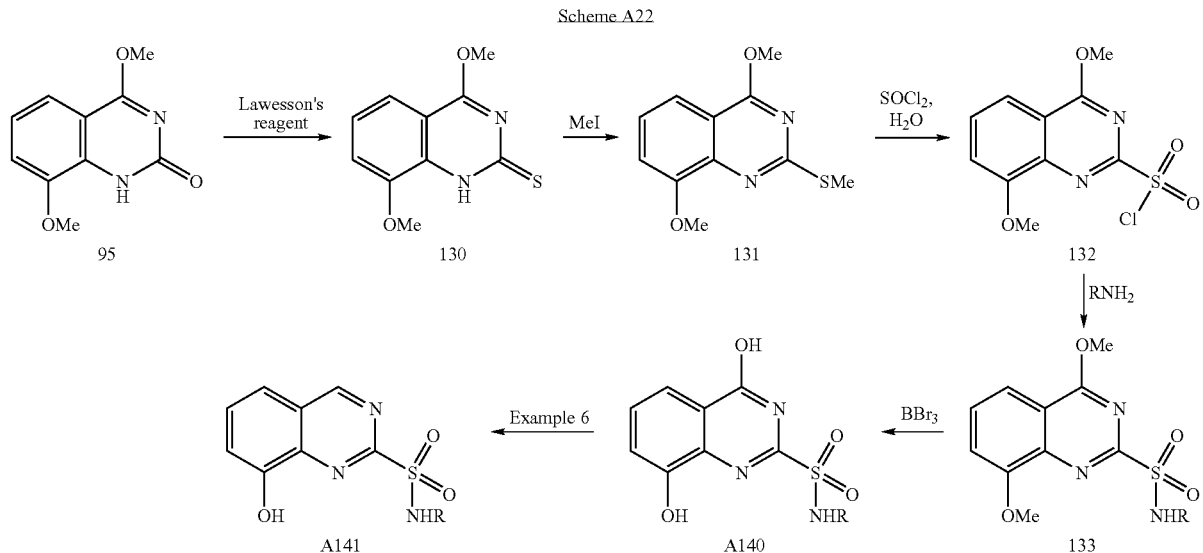

RNH$_2$: preferably, ethylamine, histamine, 2-(2-aminoethyl)pyridine, 2-(2-methylaminoethyl)pyridine Preparation of 2-Alkyl(or aryl or heterocyclic)sulfanyl-8-hydroxy-quinazoline (A142 and A143) (Scheme A23)

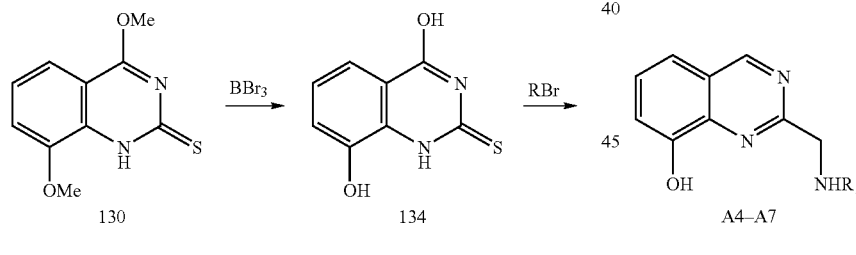

RBr: preferably, 2-bromopyridine, 2-bromothiazole, 4-bromo-1H-imidazole, 4-bromo-1-methylimidazole Reductive Amination of Amines (A4-A7) from Example 3 to Give A142-A153 (Scheme A24)

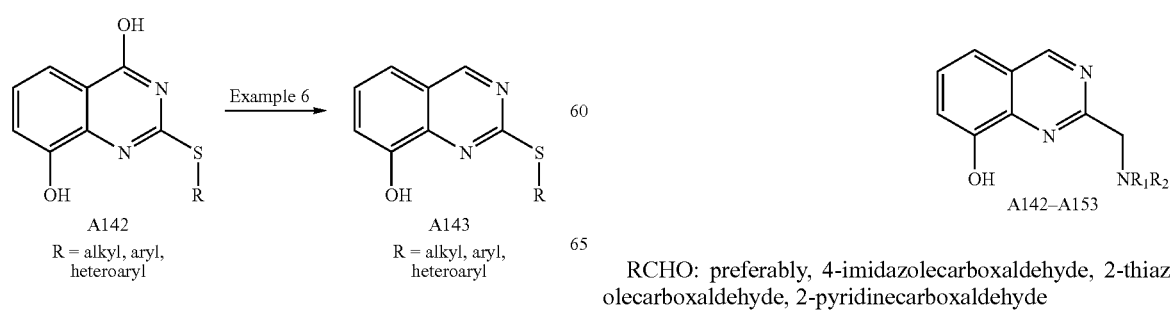

RCHO: preferably, 4-imidazolecarboxaldehyde, 2-thiazolecarboxaldehyde, 2-pyridinecarboxaldehyde Preparation of 5-fluoro-, 7-fluoro, 5,7-difluoro, 5-chloro-7-fluoro and 7-chloro-5-fluoro-quinazolines (A154-A158) (Scheme A25)

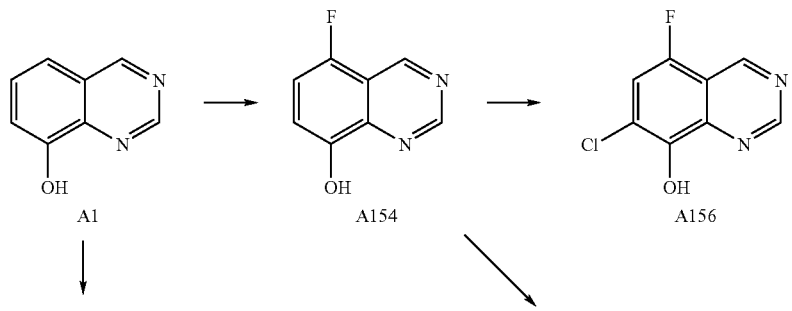

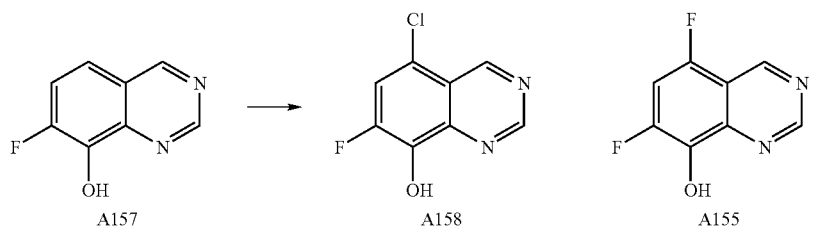

The synthesis of the fluorinated quinazoline derivatives (A154-A158) followed literature methods[18] for 8-hydroxy-quinoline.

Preparation of 8-Hydroxy-quinazoline-7-carboxylic acid amides (A160) (Scheme A26)

Scheme A26

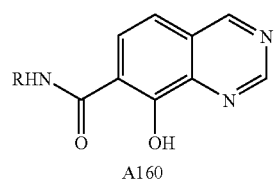

-continued

8-Hydroxy-quinazoline (A1) was converted into 8-hydroxy-quinazoline-2-carboxylic acid (A159) following the literature method[20] for the carboxylation of 8-hydroxy-quinoline. Subsequent conversion of A159 into the amide A160 followed the procedure described in Example 8.

PART B: SYNTHESIS OF 8-HYDROXY-QUINOXALINE DERIVATIVES

Charts B1-B4 show the routes to the 8-hydroxy-quinoxaline derivatives. The synthetic procedures were, unless otherwise indicated, analogous to those previously described in Part A.

CHART B1
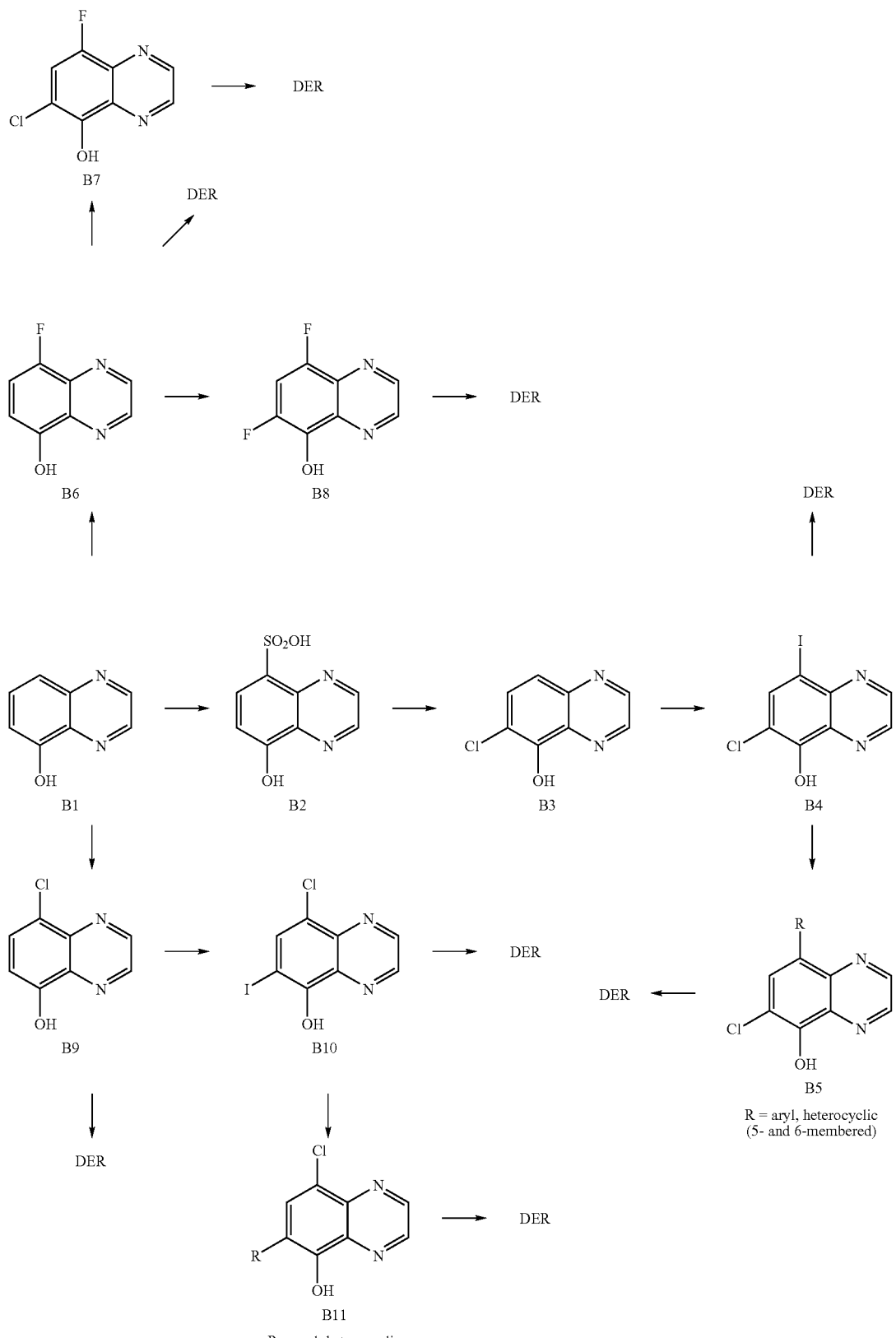
DER: derivatives via substitution of 2- and/or 3-chloro/cyano group(s) to a subject in need thereof
e.g. $NR_1R_2$ ($R_1$ = H, alkyl; $R_2$ = alkyl, aryl, heterocyclic), SR, CONHR, alkylamino CHART B2
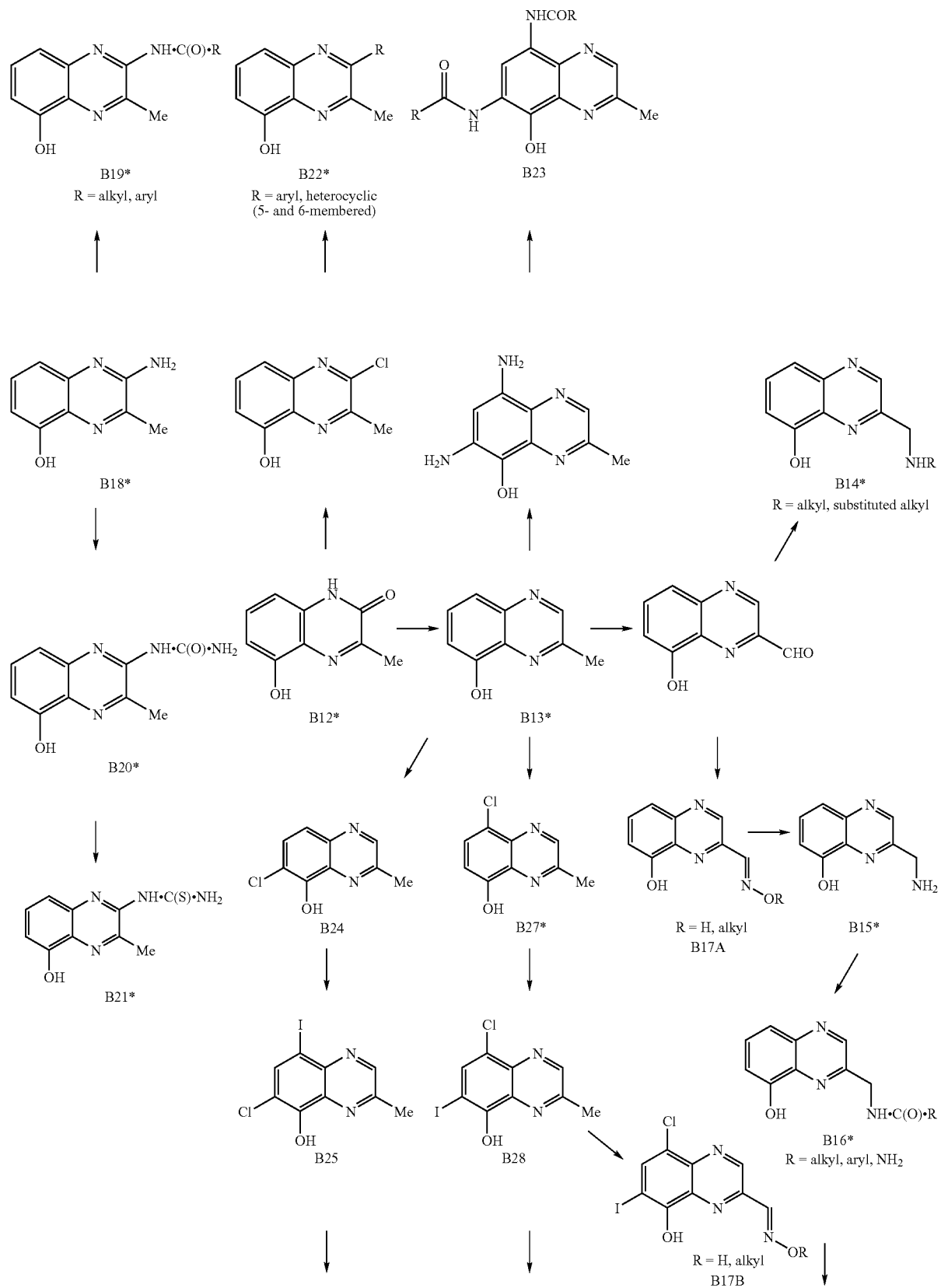

-continued
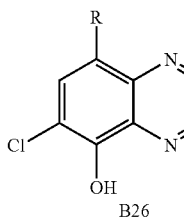
B26
R = aryl, heterocyclic
(5- and 6-membered)
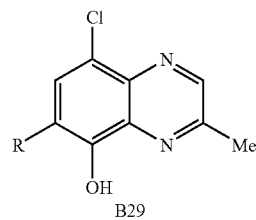
B29
R = aryl, heterocyclic
(5- and 6-membered)
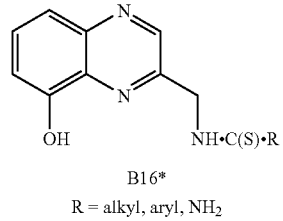
B16*
R = alkyl, aryl, NH$_2$
DER: derivatives via substitution of 3-chloro/cyano group to a subject in need thereof e.g. NR$_1$R$_2$ (R$_1$ = H, alkyl; R$_2$ = alkyl, aryl, heterocyclic), SR, CONHR, alkylamino
\* - and halogen-substitution, preferably at the 5- and/or 7-position(s)
CHART B3
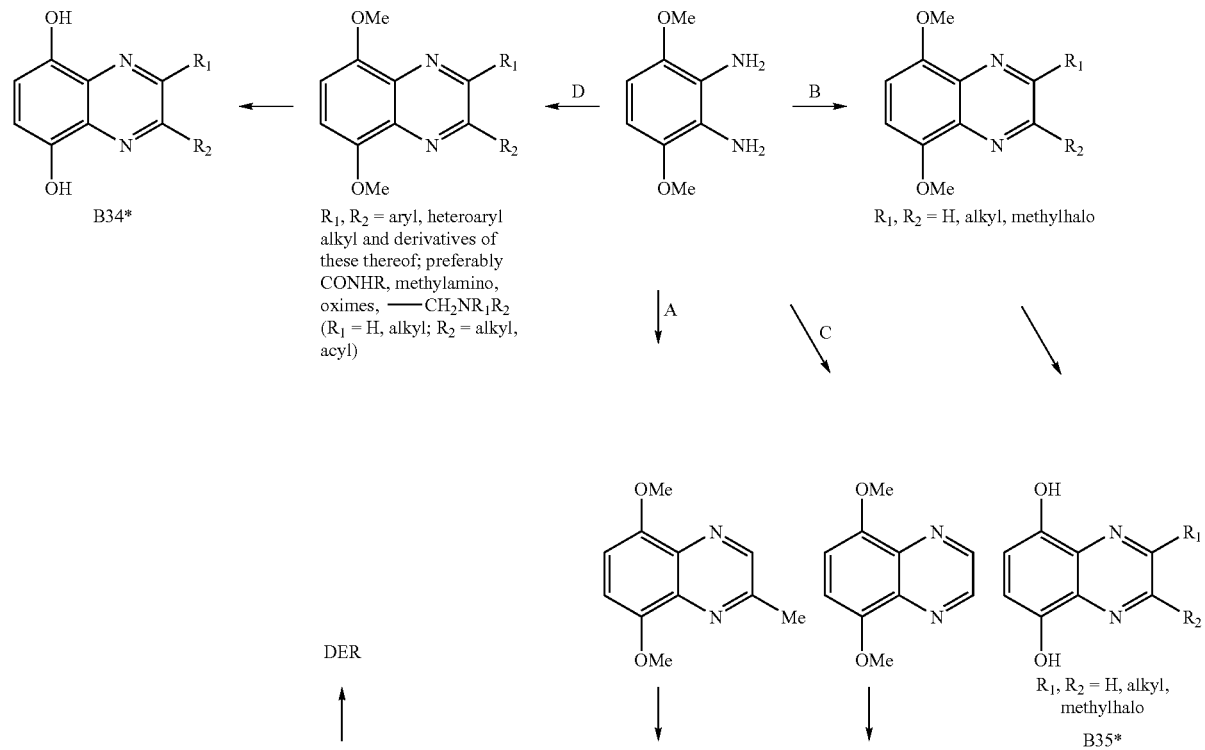
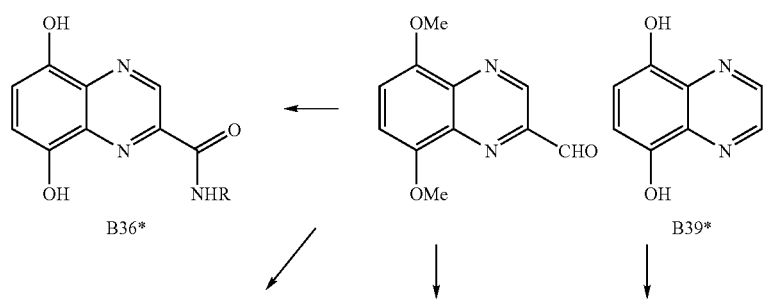

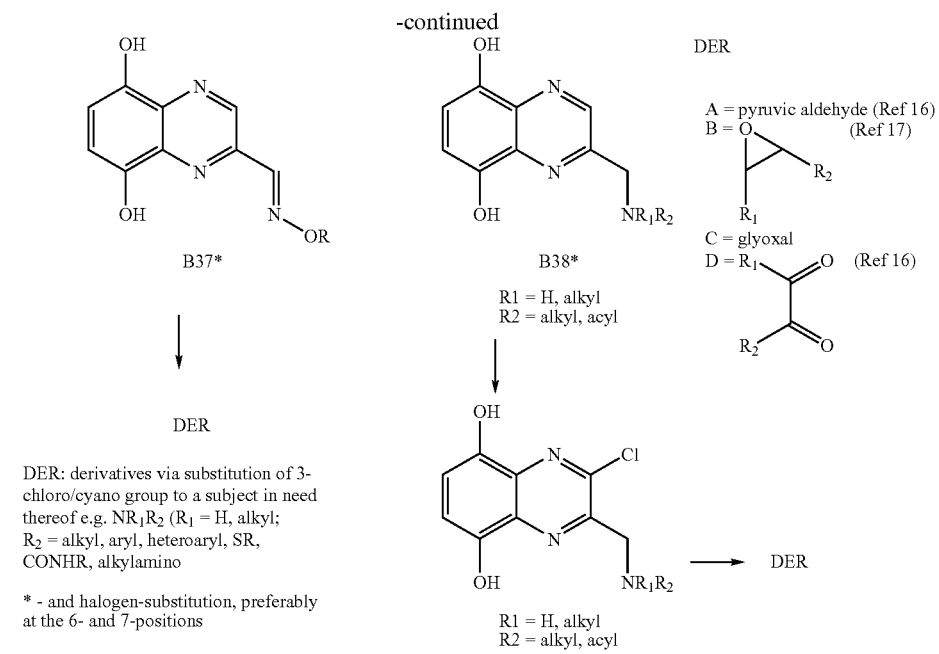
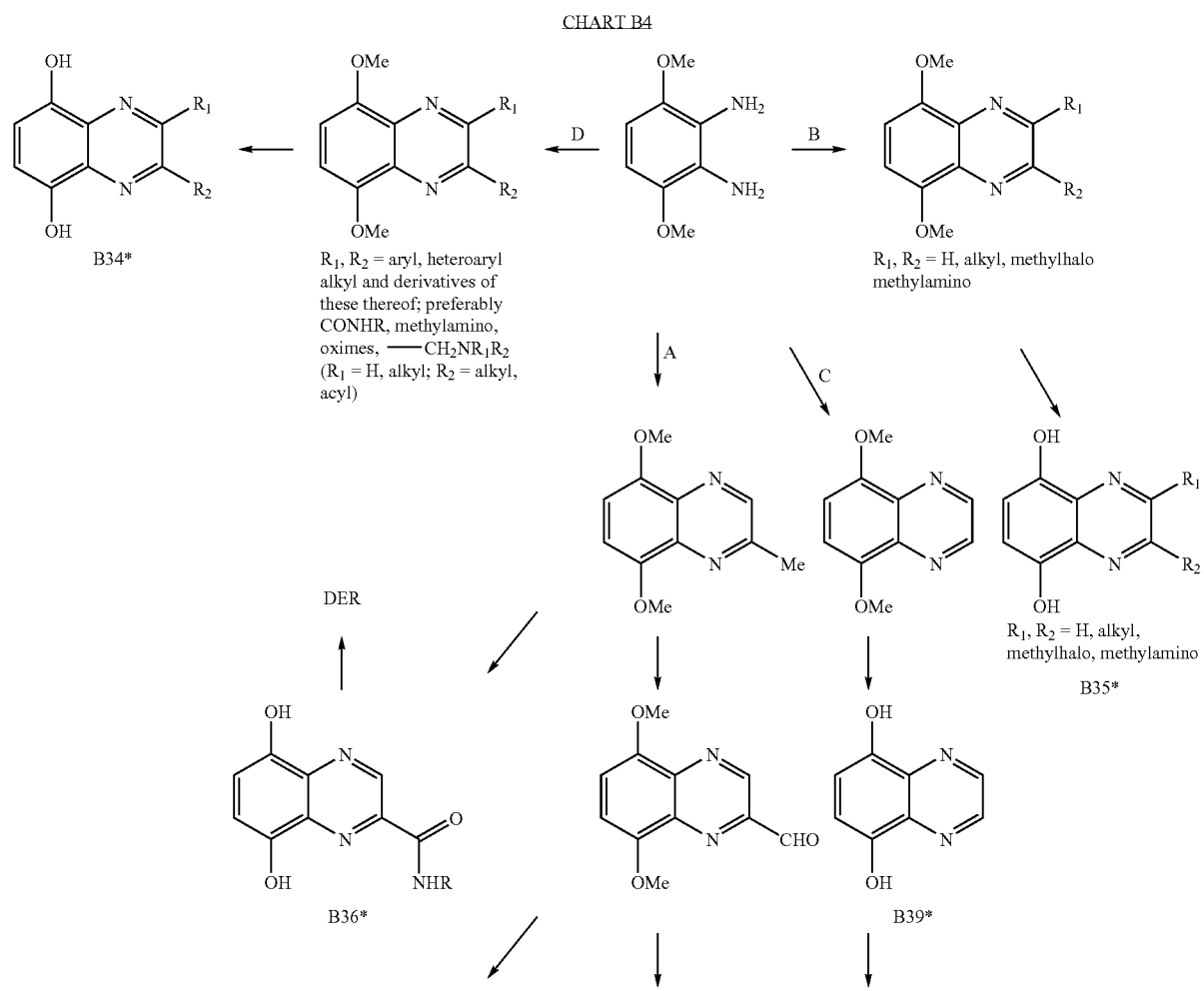
CHART B4

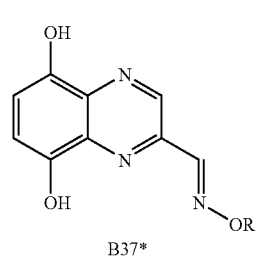

B37*

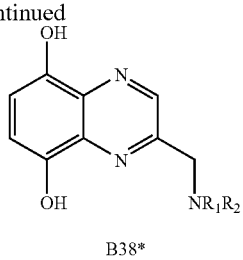

B38*

R1 = H, alkyl
R2 = alkyl, acyl

DER

A = pyruvic aldehyde (Ref 16)
B = (Ref 17)
C = glyoxal
D = (Ref 16)

↓

DER

DER: derivatives via substitution of 3-chloro/cyano group to a subject in need thereof e.g. $NR_1R_2$ ($R_1$ = H, alkyl; $R_2$ = alkyl, aryl, heteroaryl, SR, CONHR, alkylamino

* - and halogen-substitution, preferably at the 6- and 7-positions

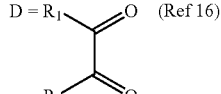

↓

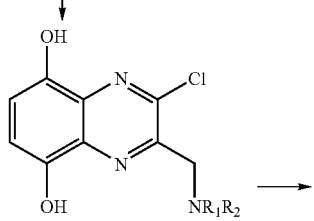

R1 = H, alkyl
R2 = alkyl, acyl

→ DER

PART C: SYNTHESIS OF 8-HYDROXY-CINNOLINE DERIVATIVES

Charts C1 and C2 show the routes to the 8-hydroxy-cinnoline derivatives. The synthetic procedures were, unless otherwise stated, analogous to those previously described in Part A.

CHART C1

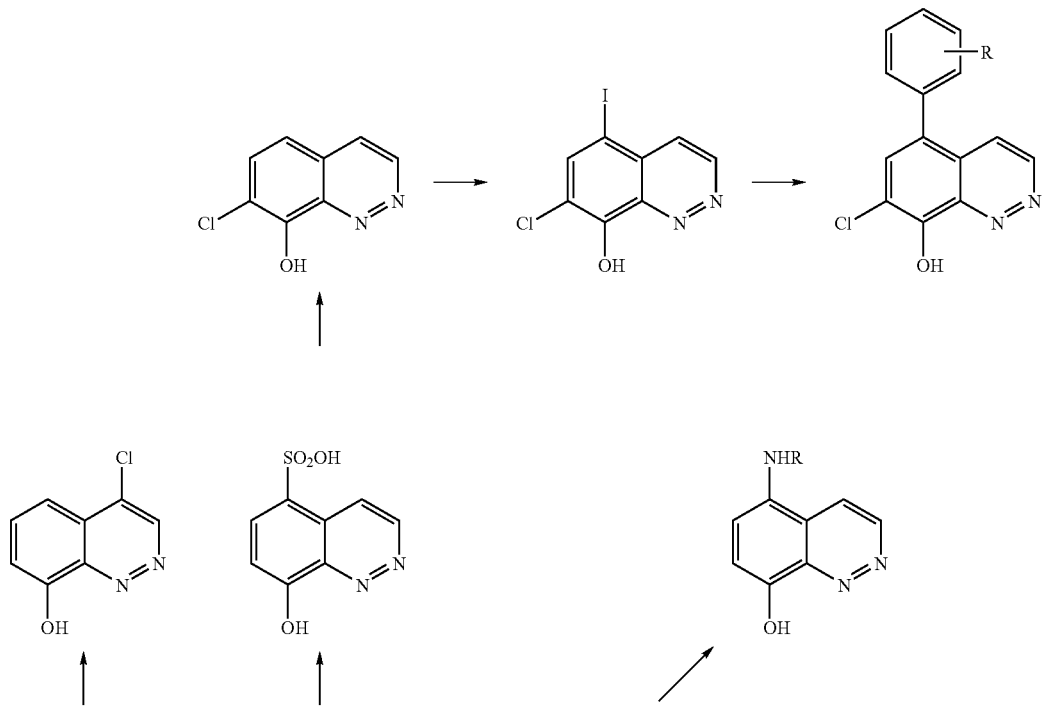

-continued
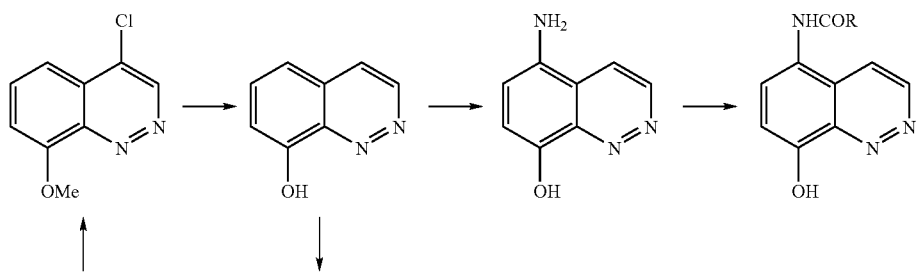
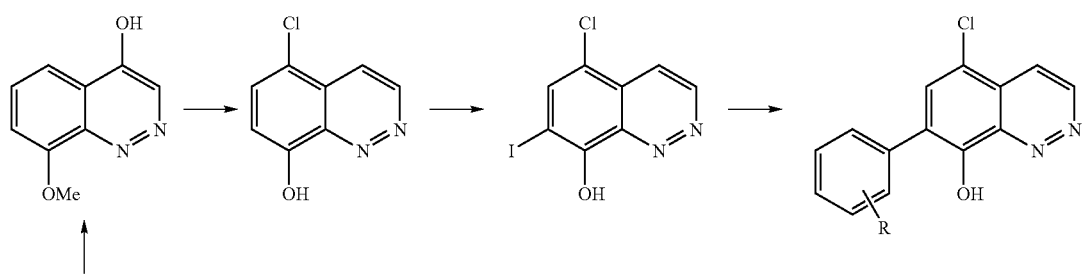
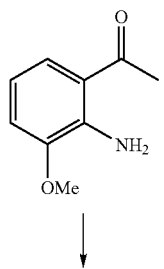
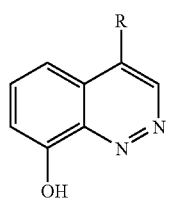
R = alkyl, aryl
CHART C2
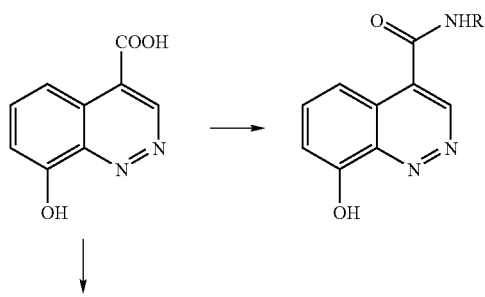

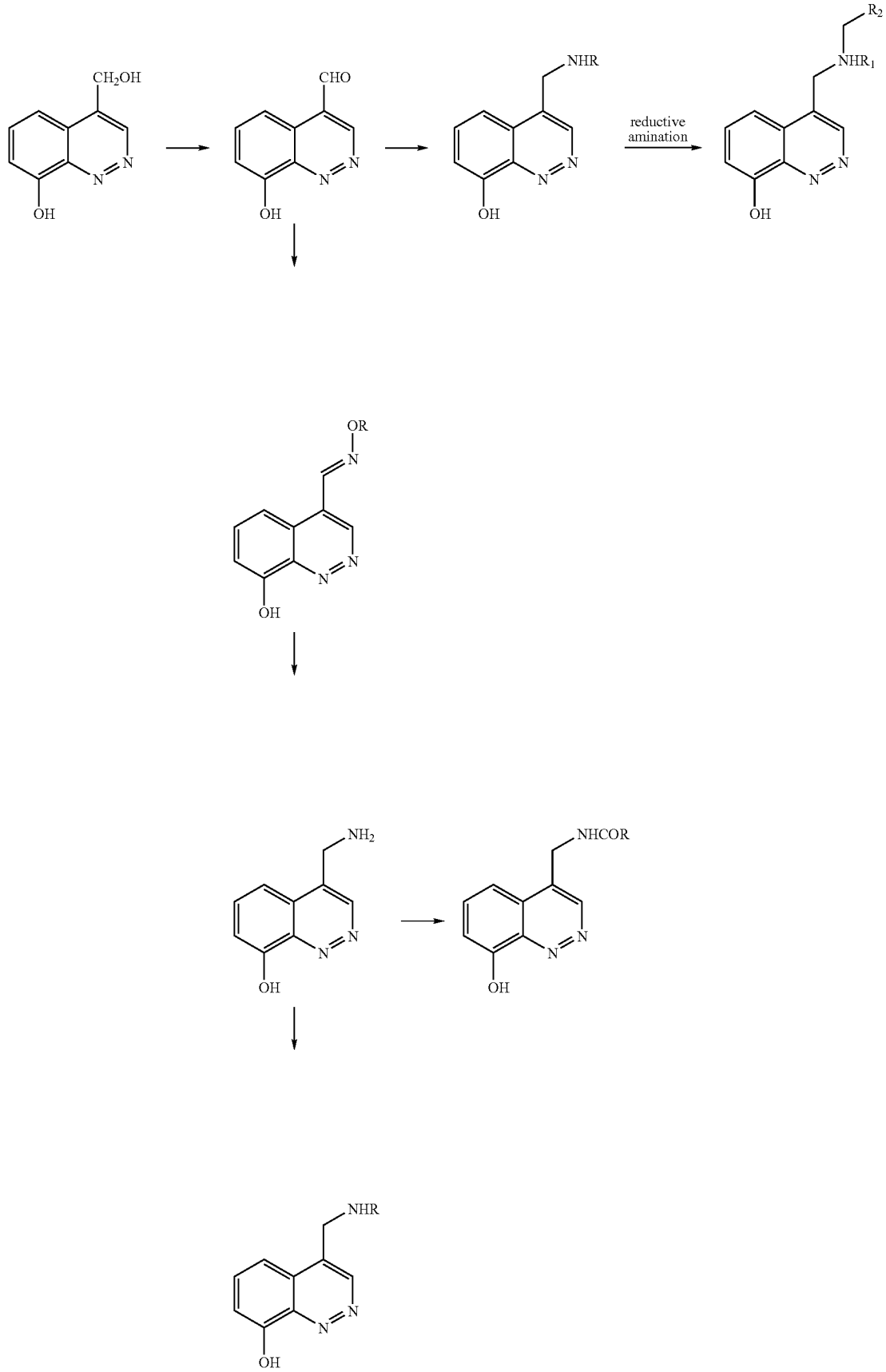

PART D: SYNTHESIS OF 4,7(4,10)-PHENANTHROLIN-5-OL DERIVATIVES
Charts D1-D4 show the routes to the 4,7(4,10)-phenanthrolin-5-ol derivatives. The synthetic procedures were, unless otherwise stated, analogous to those previously described in Part A. The reactions shown in Chart D1 were also repeated using 4,7-phenanthrolin-5,6-diol (D3) instead of 4,7-phenanthrolin-5-ol (D1) as starting material.
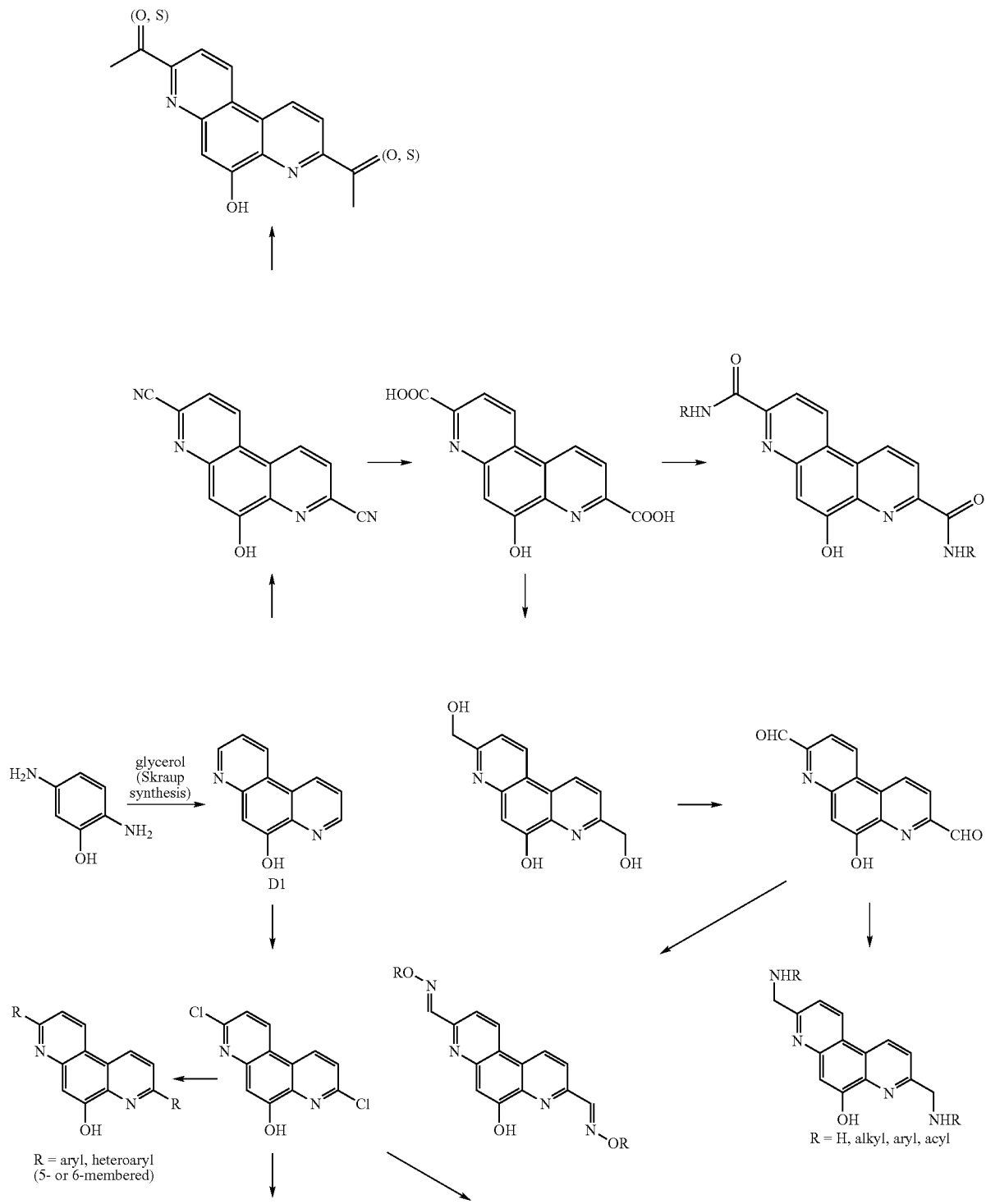
CHART D1

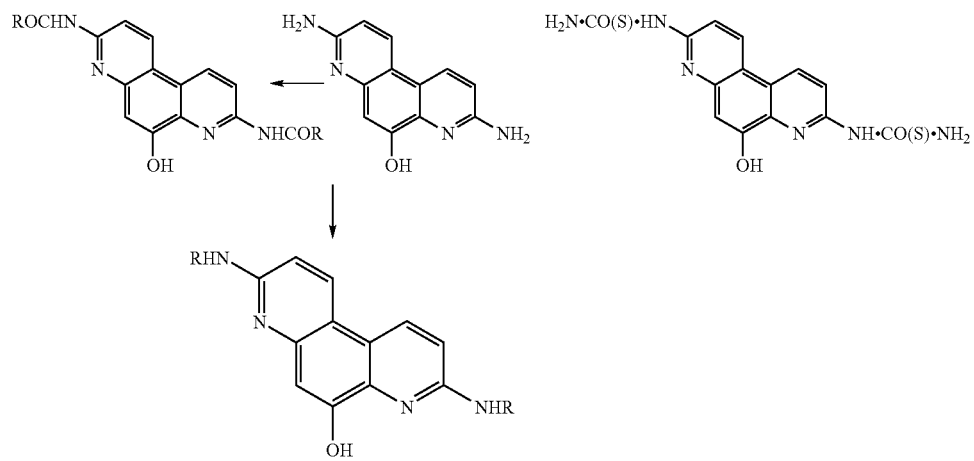
CHART D2
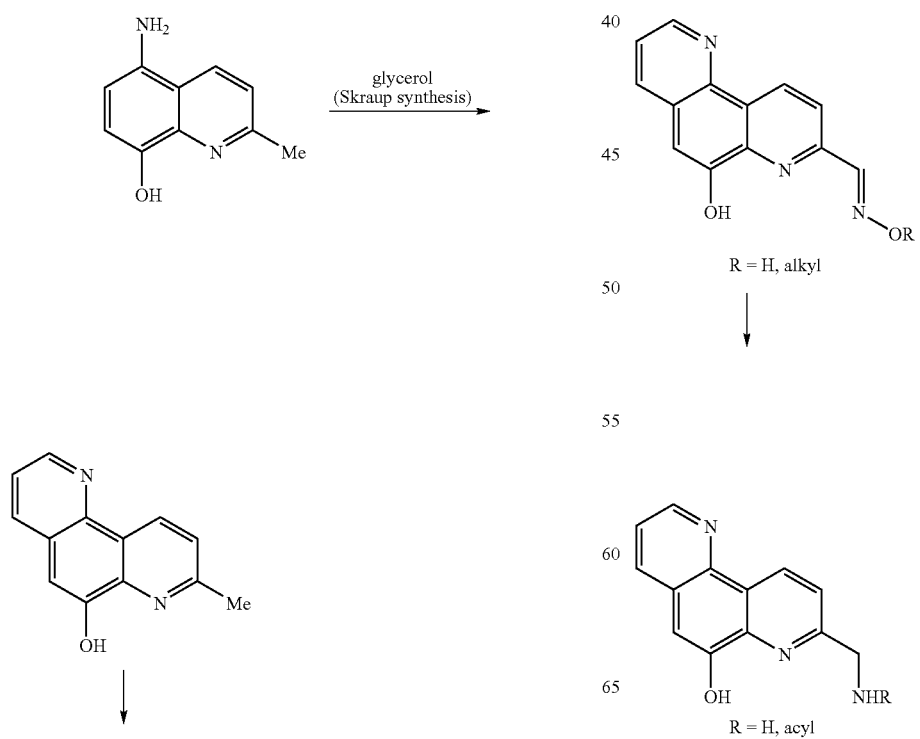
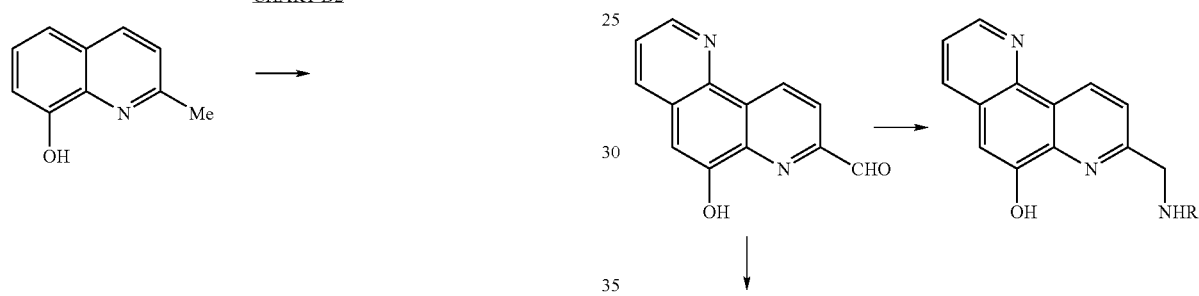
R = H, alkyl
R = H, acyl

CHART D3
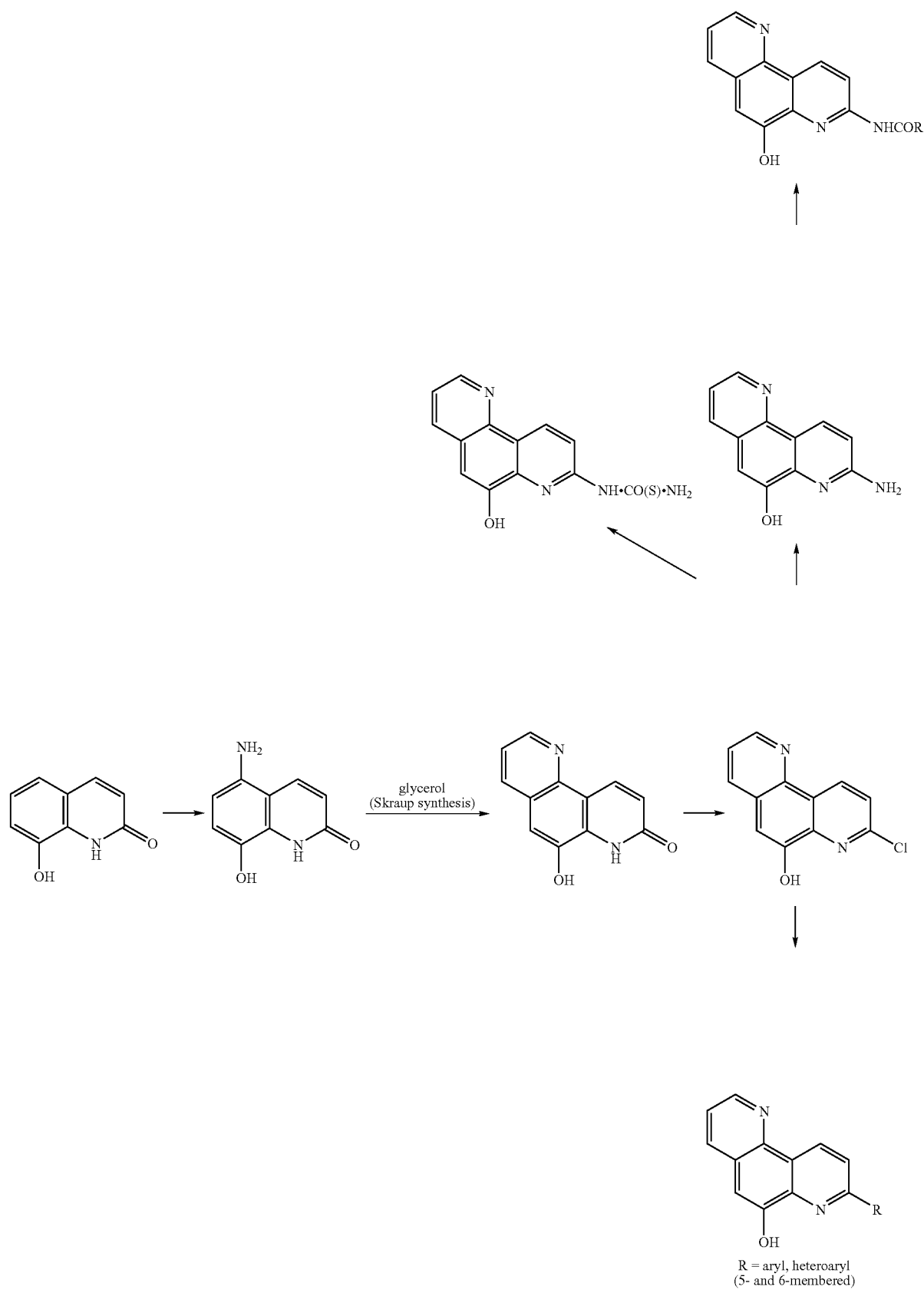
R = aryl, heteroaryl
(5- and 6-membered)

CHART D4

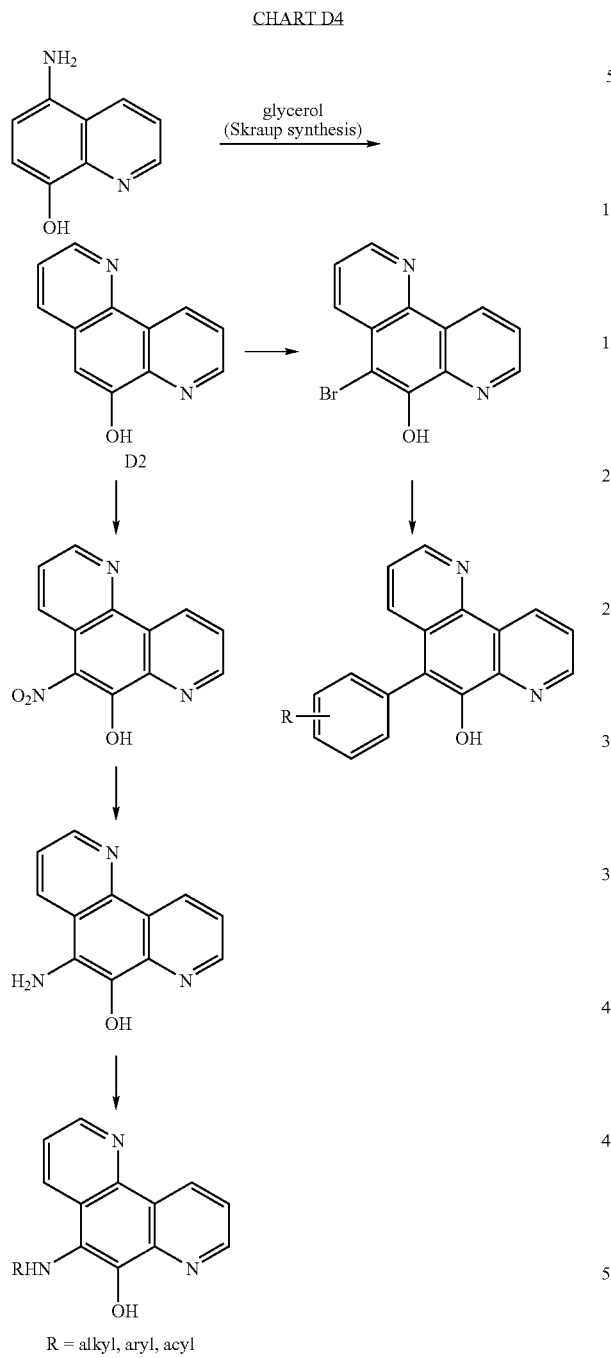

R = alkyl, aryl, acyl

Skraup synthesis of 4,7-Phenanthrolin-5-ol (D1)

A stirring mixture of 3-hydroxy-p-phenylenediamine (0.185 mol), glycerol (1.17 mol), arsenic solution (100 mL; prepared from 123 g of arsenic pentoxide in 100 mL $H_2O$) and diluted sulphuric acid (400 mL; prepared by adding 240 mL of concentrated sulphuric acid to 200 mL $H_2O$) was heated under reflux for 4 h, allowed to cool and then made alkaline with concentrated ammonia. The mixture was extracted with benzene. Removal of the benzene afforded 4,7-Phenanthrolin-5-ol (D1).

PART E: SYNTHESIS OF 4-HYDROXY-ACRIDINE DERIVATIVES

The 4-hydroxy-acridines were prepared via Ullman condensation[4,14] of a substituted 2-halobenzoic acid and a substituted aniline as shown in Chart E1. Hence, condensation of aniline itself with 2-bromo-3-nitro-benzoic acid gave 4-hydroxy-acridine (E1). In an analogous fashion, o-anisidine gave 4-amino-5-hydroxy-acridine and 4,5-dihydroxy-acridine. Further derivatives of these acridines (Chart E2) were prepared using analogous reaction conditions previously described for the synthesis of compounds in Parts A-D.

CHART E1

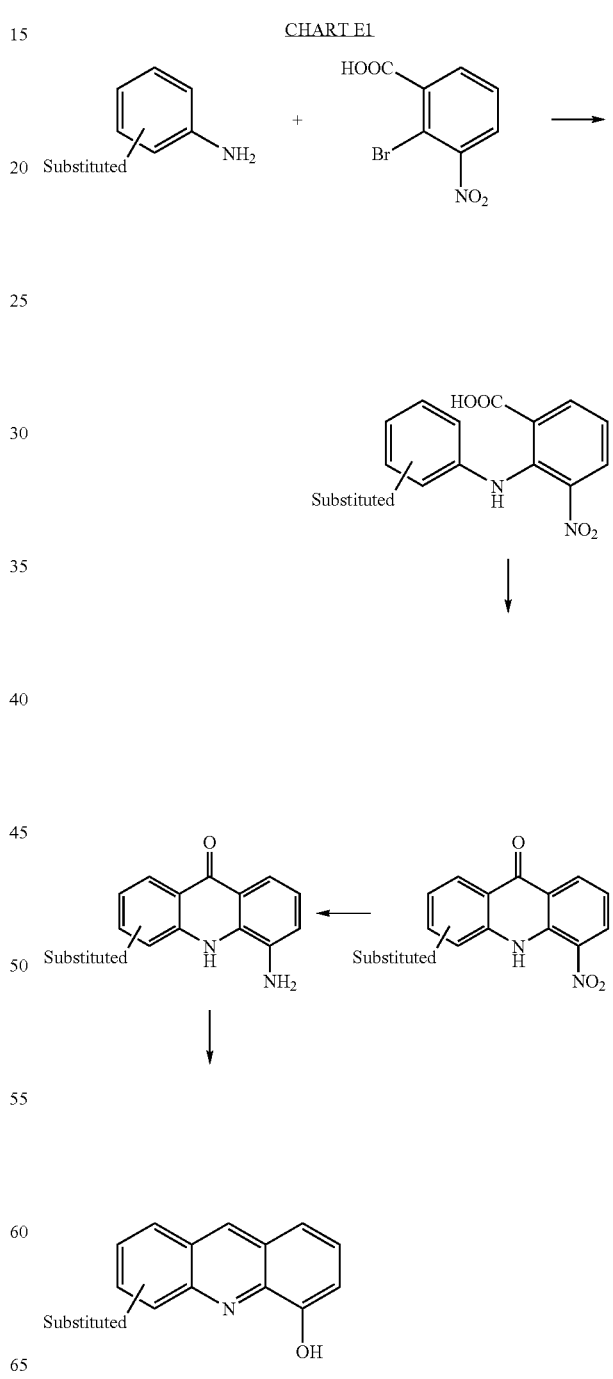

Substituents on aniline include alkyl, methoxy, halogen

CHART E2
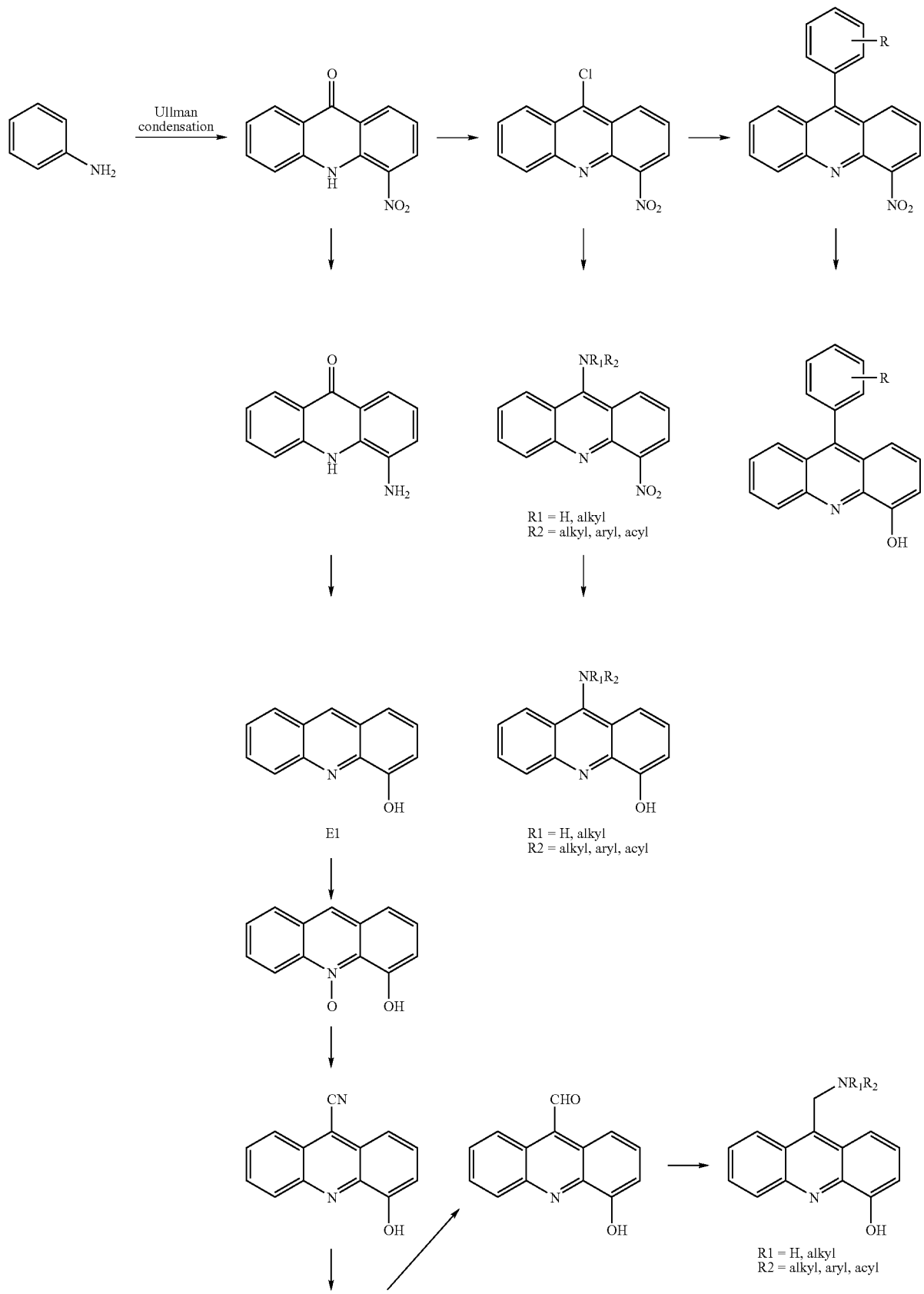

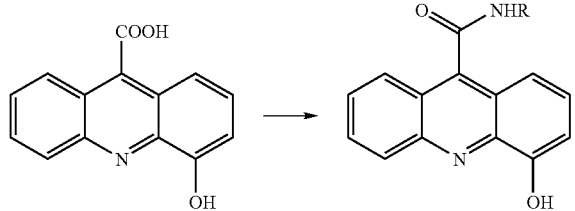
PART F: SYNTHESIS OF 4,5(4,8)-DIHYDROXY-PHENAZINE DERIVATIVES
The compounds, 4,5- and 4,8-dihydroxy-phenazines (F1 and F2), were prepared according to the literature[3] procedure.
The synthesis of derivatives of these compounds, as summarized in Charts F1-F3, unless otherwise stated, followed reaction conditions analogous to those previously described in Parts A-E.
CHART F1
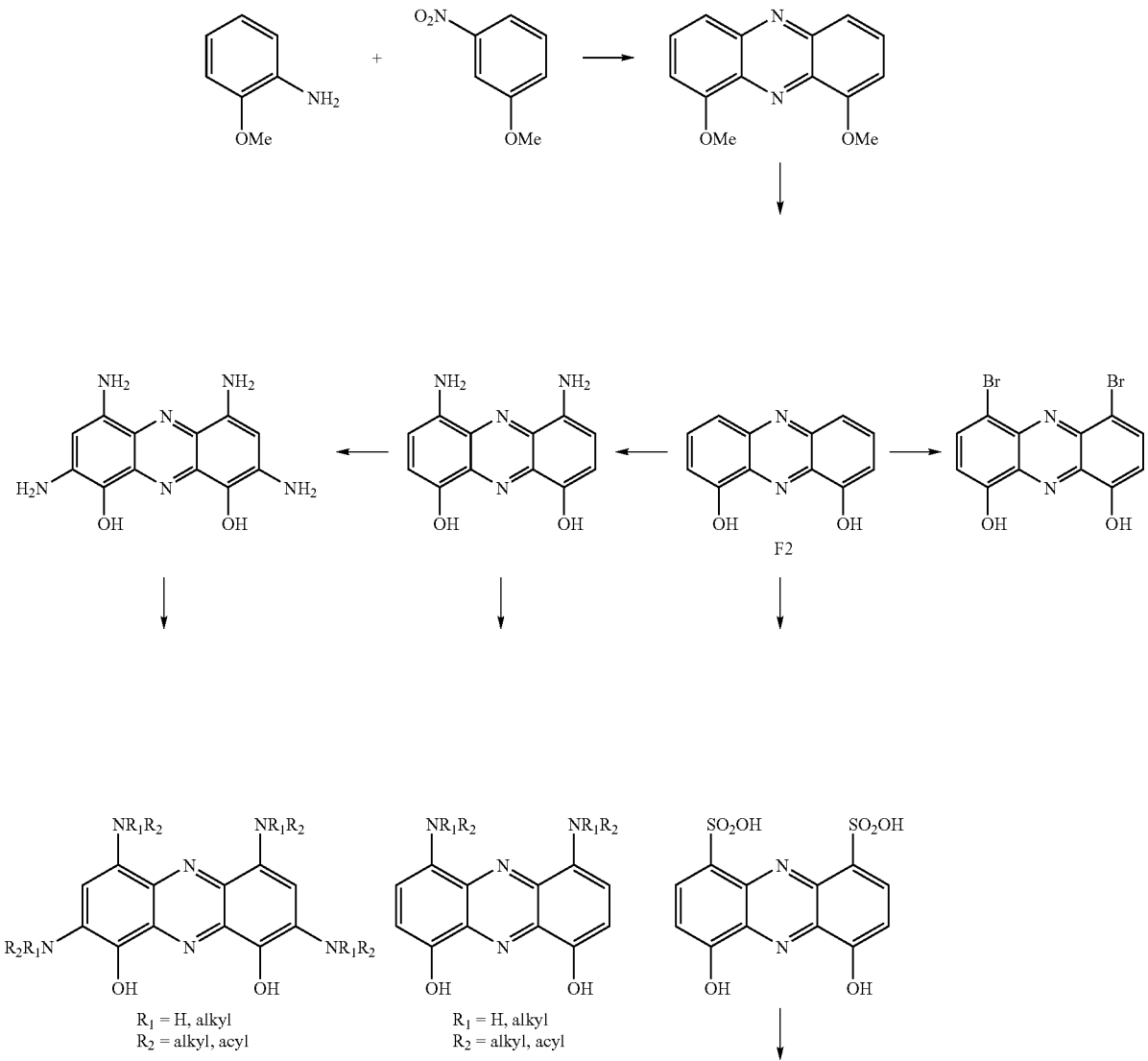

-continued
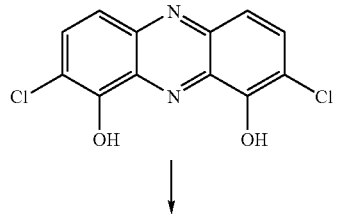
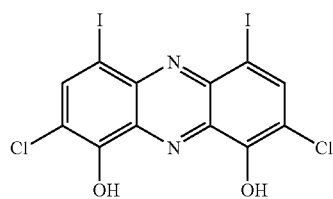
CHART F2
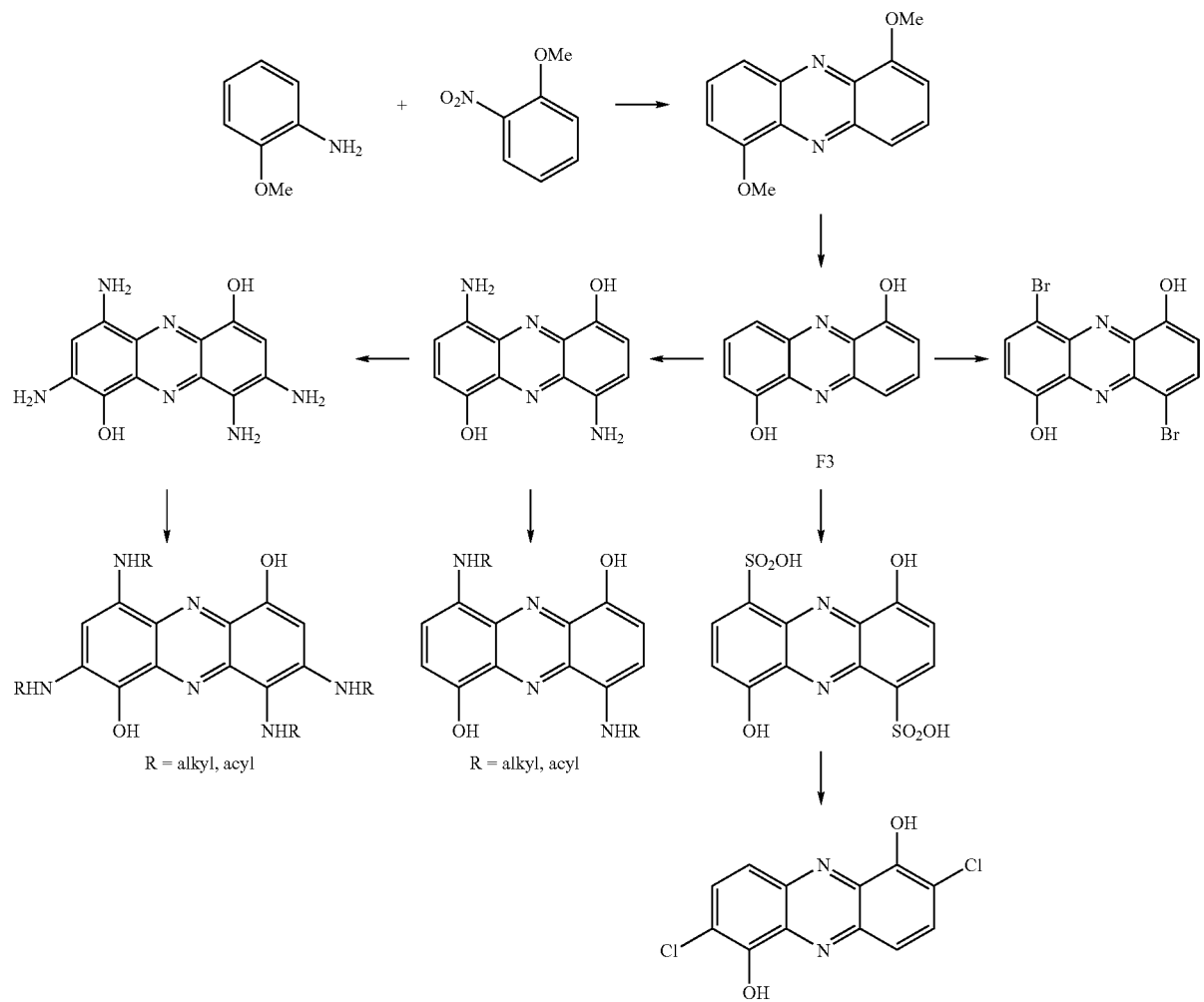
R = alkyl, acyl
R = alkyl, acyl CHART F3
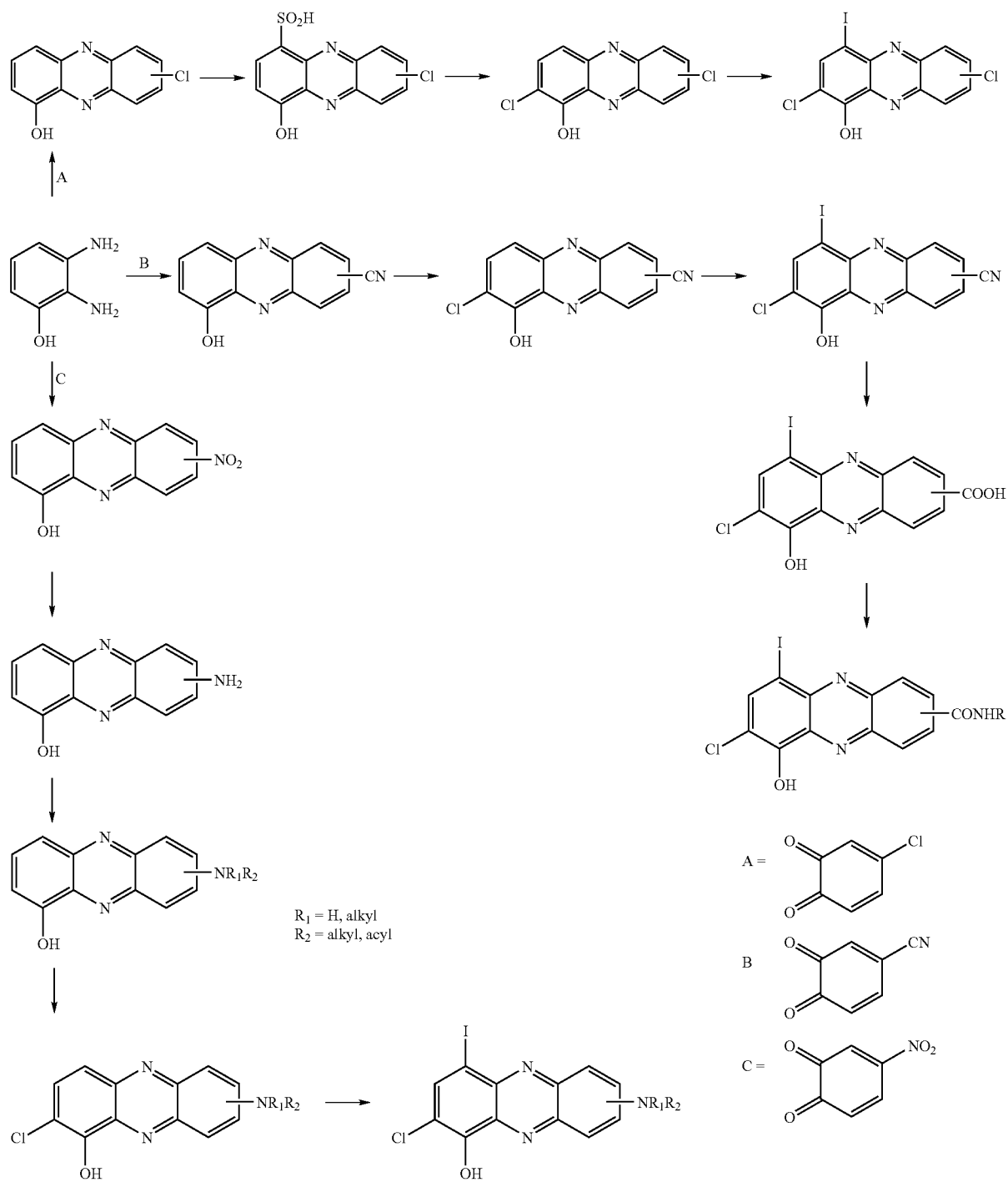
REFERENCES
1. F. E. King, N. G. Clark and P. M. H. Davis, *J.* 1949, 3012-3016.
2. E. J. Alford, H. Irving, H. S. Marsh and K. Schofield, *J.* 1952, 3009-3017.
3. A. Sugimoto, S. Kato, H. Inoue and E. Imoto, *Bull. Chem. Soc. Jpn.*, 1976, 49(1), 337-338.
4. A. Corsini and E. J. Billo, *J. Inorg. Nucl. Chem.*, 1970, 32, 1241-1255.
5. R. N. Iyer, N. Anand and M. L. Dhar, *J. Sci. Ind. Res.*, 1956, 15C, 1-7.
6. A. Albert and A. Hampton, *J.* 1952, 4985-4993.
7. H. Gerson, M. W. McNeil and S. G. Schulman, *J. Org. Chem.*, 1971, 36, 1616-1618.

8. A. Atsushi, N. Kazuo, H. Kinichi and O. Masana, *Radioisotopes,* 1974, 23(1), 6-9.
9. H. Gerson, M. W. McNeil and A. T. Grefig, *J. Org. Chem.,* 1969, 34, 3268-3270.
10. H. Gerson and M. W. McNeil, *J. Org. Chem.,* 1971, 8, 821-824.

then be converted, e.g. under Curtius conditions, into the corresponding 7-amino compound. The amino functionality, in turn, can be further elaborated using known methods. For example, diazotisation in the presence of HCl provides the corresponding chloride. Further elaboration of the chloride can readily be achieved using known methods.

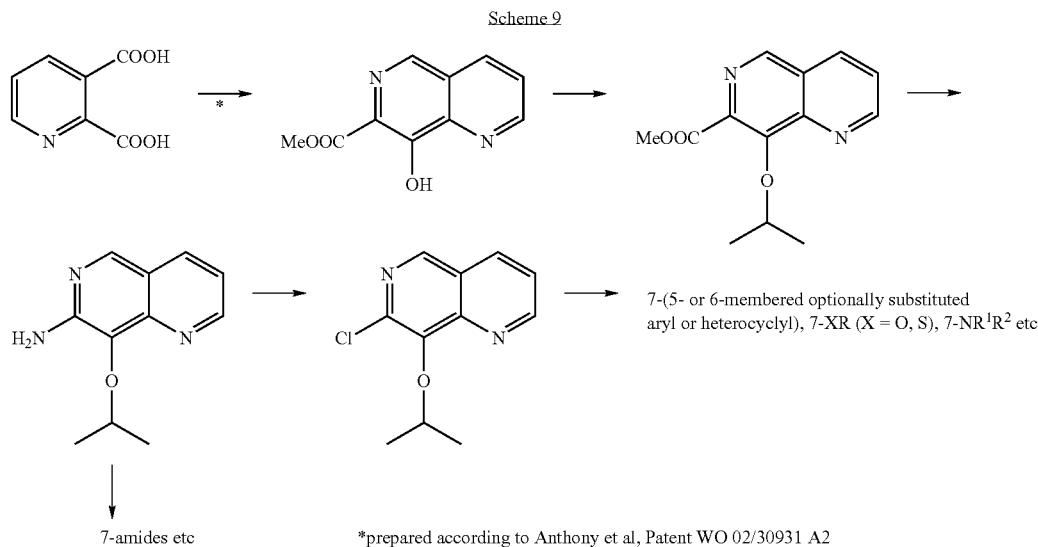

Scheme 9

7-(5- or 6-membered optionally substituted aryl or heterocyclyl), 7-XR (X = O, S), 7-NR¹R² etc 7-amides etc

*prepared according to Anthony et al, Patent WO 02/30931 A2

11. S. Wagaw and S. L. Buchwald, *J. Org. Chem.,* 1996, 61, 7240-7241.
12. R. C. Corcoran and S. H. Bang, *Tetrahedron Lett.,* 1990, 31, 6757-6758.
13. (a) A. Dondoni, G. Fantin, M. Fogagnolo, A. Medici and P. Pedrini, *Synthesis,* 1987, 998-1001. (b) A. Dondoni, F. L. Merchan, P. Merino, I. Rojo and T. Tejero, *Synthesis,* 1996, 641-646.
14. S. Issmaili, G. Boyer and J.-P. Galy, *Synlett,* 1999, 641-643.
15. H. Gerson and M. W. McNeil, *J. Org. Chem.,* 1972, 37, 4078-4082.
16. X.-H. Bu, H. Liu, M. Du, K. M. C. Wong, V. W. W. Yam and M. Shionoya, *Inorg. Chem.,* 2001, 40, 4143-4149.
17. S. Antoniotti and E. Dunach, *Tetrahedron Lett.,* 2002, 43, 3971-3973.
18. H. Gerson, M. W. McNeil, R[5]. Parmegiani and P. K. Godfrey, *J. Med. Chem.,* 1972, 15, 987-989, and references cited therein.
19. I. Y. Postovskii and N. G. Koshel, *Khim. Geterotsikl. Soedin.,* 1970, 7, 981-985.
20. V. V. Ragulin, I. R. Ragulina and L. G. Shakirov, *Zhurnal Prikladnoi Khimii,* 1994, 67(7), 1227-1229.

(3) PREPARATION OF 8-HYDROXY-[1,6]NAPHTHYRIDINES

A range of 7-substituted-8-hydroxy-[1,6]naphthyridines can be prepared using the route shown in Scheme 9 (see for example: Anthony and coworkers, Patent WO 02/30931 A2). Hence, 2,3-pyridinedicarboxylic acid is readily transformed through a series of reactions into 8-hydroxy-[1,6]naphthyridine-2-carboxylic acid methyl ester. The 7-methyl ester can 5,7-Disubstituted-8-hydroxy-[1,6]naphthyridines can be accessed from an advanced intermediate such as 5,8-dihydroxy-[1,6]naphthyridine-7-carboxylic acid methyl ester (prepared according to the procedure of Albert and Hampton, *J. Chem. Soc.,* 1952, 4985; Blanco and coworkers, *J. Heterocyclic Chem.,* 1996, 33, 361). Chlorination of 5,8-dihydroxy-[1,6]naphthyridine-7-carboxylic acid methyl ester with $POCl_3$ or $SOCl_2$ provides 5-chloro-8-hydroxy-[1,6]naphthyridine-7-carboxylic acid methyl ester. Elaboration of the chloride into a range of 5-substituted-8-hydroxy-[1,6]naphthyridines can be achieved using known methods. Further elaboration using literature methods provides a range of 5,7-disubstituted-8-hydroxy-[1,6]naphthyridines.

Derivatives of 8-hydroxy-[1,6]naphthyridine substituted at 2-, 3- and/or 4-positions can be synthesised using an appropriately substituted 2,3-pyridinedicarboxylic acid. For example, the commercially available 6-methyl-2,3-pyridinedicarboxylic acid can be transformed into 8-hydroxy-2-methyl-[1,6]naphthyridine-7-carboxylic acid methyl ester (Scheme 10). Other substituted 2,3-pyridinedicarboxylic acids can readily be prepared using known methods (see for example: Wepplo, U.S. Pat. No. 4,460,776). Further elaboration of the 8-hydroxy-2-methyl-[1,6]naphthyridine provides a range of analogs such as 2-(methylamino)methyl and 2-(alkylamino)methyl derivatives. Various 7-substituted derivatives of these compounds can be prepared from the corresponding 7-methoxycarbonyl, 7-chloro or 7-amino compounds using known methods.

Scheme 10

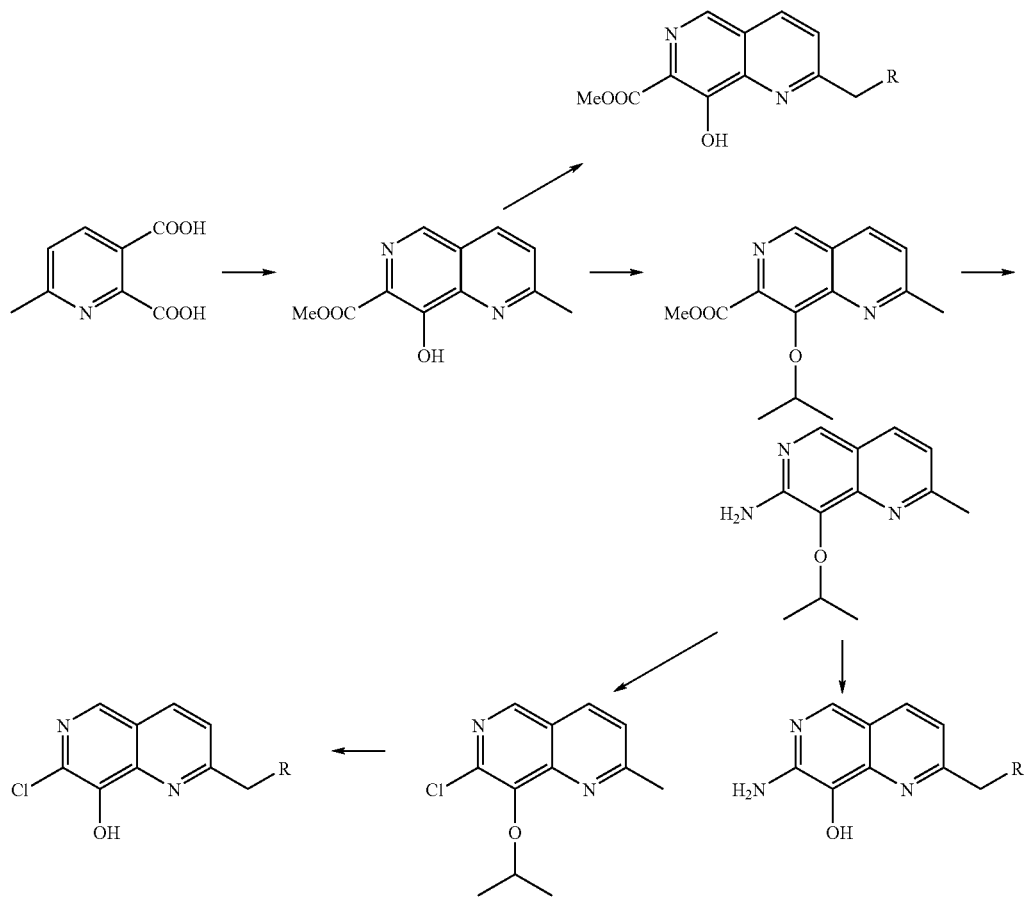

(4) PREPARATION OF PYRIDO[3,2-d]PYRIMI-DIN-4-OL, [1,7]NAPHTHYRIDIN-8-OL, PYRIDO[2,3-d]PYRIDAZIN-8-OL, [1,6]NAPHTHYRIDIN-8-OL, PYRIDO[3,4-b]PYRAZIN-5-OL, PYRIDO[3,4-b]PYRAZIN-8-OL, [1,5]NAPHTHYRIDIN-4,8-DIOL, [1,5]NAPHTHYRIDIN-8-OL AND PYRIDO[4,3-d]PYRIMIDIN-8-OL

General

The following reagents were sourced commercially:—amines: ethylamine, histamine, 2-(2-aminoethyl)pyridine, 2-(2-methylaminoethyl)pyridine; aldehydes: 4-imidazolecarboxaldehyde, 2-thiazolecarboxaldehyde and 2-pyridinecarboxaldehyde, azoles: pyrazole, imidazole, methylimidazole and 1H-1,2,3-triazole, boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid and 4-fluorophenylboronic acid; and organozinc reagents: 2-pyridylzinc bromide, 2-(methylthio)phenylzinc iodide, 2-(ethoxycarbonyl)phenylzinc iodide and 6-methylpyridylzinc bromide (0.5 M solution in THF) (Aldrich). 3-Pyridylboronic acid was purchased from Frontier Scientific and pyrido[3,2-d]pyrimidin-4-ol from Ambinter, France. 2-Aminomethylthiazole was prepared according to the literature.[1] Solvents were analytical grade and used as supplied. THF was distilled from sodium and benzophenone under argon. $^1$H NMR spectra (δ, relative to TMS) were recorded on a Varian Unity 300 spectrometer unless otherwise indicated; J-Values are given in hertz. Mass spectral data were recorded on a Micromass Quattro II mass spectrometer.

The synthesis of derivatives of 8 classes of compounds: pyrido[3,2-d]pyrimidin-4-ol (A), [1,7]naphthyridin-8-ol (B), pyrido[2,3-d]pyridazin-8-ol (C), [1,6]naphthyridin-8-ol (D), pyrido[3,4-b]pyrazin-5-ol (E), pyrido[3,4-b]pyrazin-8-ol (F), and [1,5]naphthyridin-4,8-diol, [1,5]naphthyridin-8-ol (G) and pyrido[4,3-d]pyrimidin-8-ol (H), is described.

A

-continued

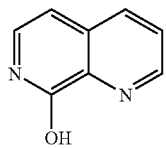
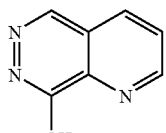
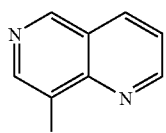
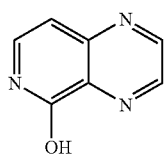
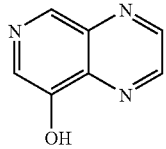
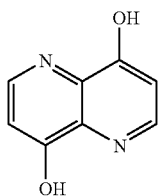
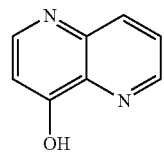

B

C

D

E

F

G

-continued

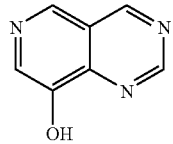

H

Charts A1-A3 summarise the routes used in the synthesis of a series of pyrido[3,2-d]pyrimidin-4-ol derivatives. The preparation of the derivatives of [1,7]naphthyridin-8-ol is described in Charts B1-B2. Compound B1 was prepared following the literature method[2] for the synthesis of a similar compound. The synthesis of the pyrido[2,3-d]pyridazin-8-ol itself and derivatives C1 and C2 followed the method previously described[3] by Brzezinski and coworkers. Further derivatives in this series were prepared following the routes summarised in Charts C1-C4. Charts D1-D2 show the routes to a series of [1,6]naphthyridin-8-ol derivatives. The synthesis of compound D1 used the method[4] of Blanco and coworkers. Other members in this series have been prepared following the routes shown in Charts D1-D2. Chart E1 describes the route to a series of pyrido[3,4-b]pyrazin-5-ol derivatives. Condensation of 1,2,3-triaminopyridine with 2,3-dihydroxy-1,4-dioxan gave pyrido[3,4-b]pyrazin-5-ol (E1), the parent compound in this series; the same reaction employing 2,3,4-triaminopyridine as starting material (Chart F1) gave pyrido[3,4-b]pyrazin-8-ol (F1). Further derivatives in the pyrido[3,4-b]pyrazin-5-ol and pyrido[3,4-b]pyrazin-8-ol classes were prepared using the routes shown in Charts E1 and F1. Charts G1-G2 show the routes employed in the synthesis of a range of [1,5]naphthyridin-4,8-diol and [1,5]naphthyridin-8-ol derivatives. The synthesis of compound G1, the precursor to the parent compound, [1,5]naphthyridin-4,8-diol, followed the route described[5] by Brown and Dewar. Pyrido[4,3-d]pyrimidin-8-ol (H1) was prepared[4] following the route shown in Chart H1, employing 4,5-pyrimidinedicarboxylic acid as starting material. Further derivatives in this class were prepared using routes as shown in Charts H1 and H2.

CHART A1

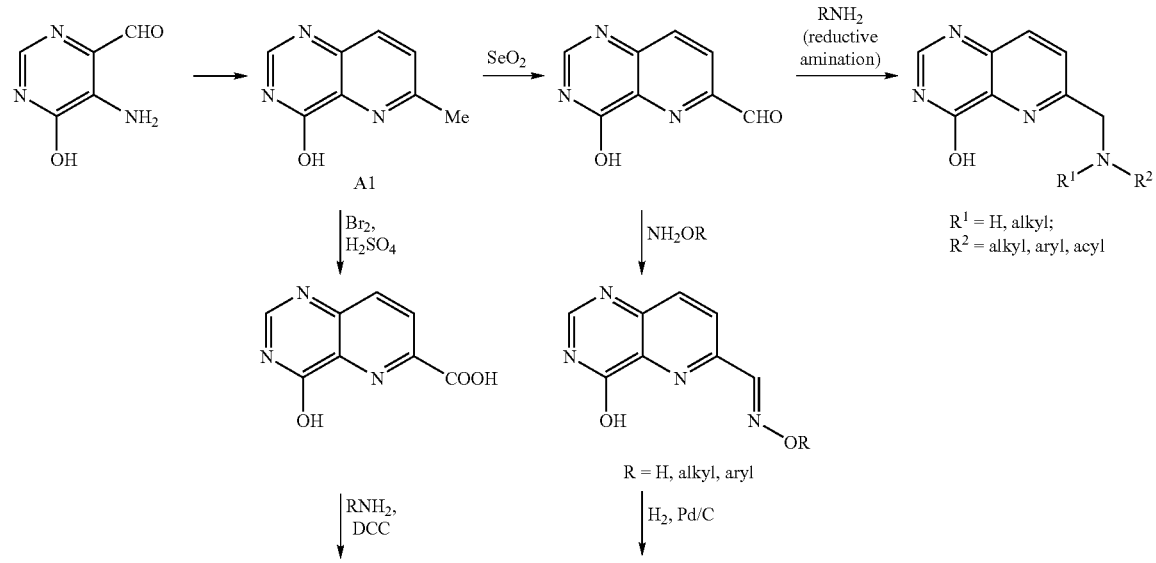

-continued
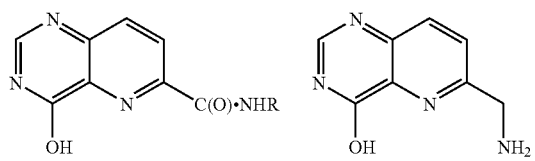
CHART A2
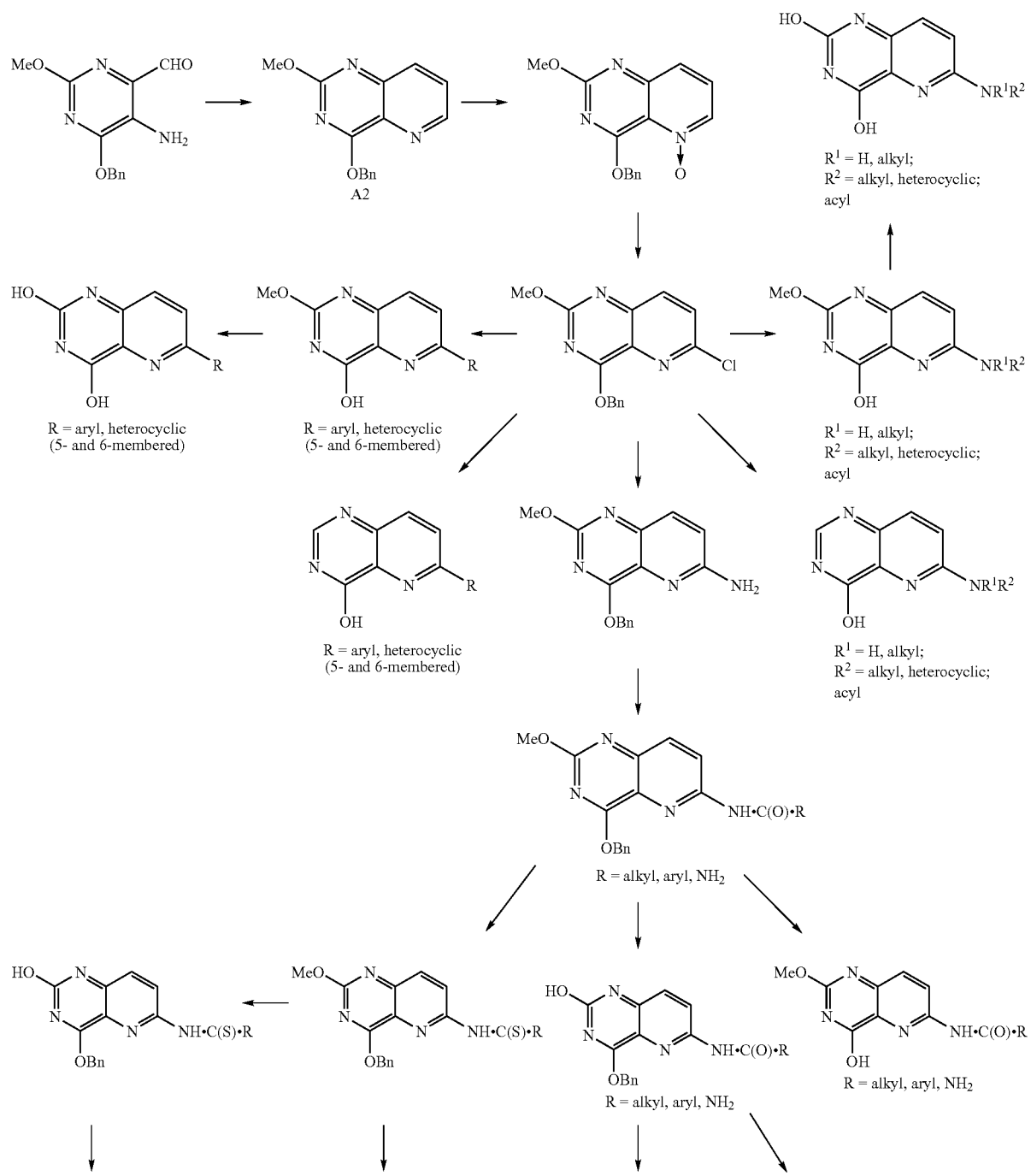

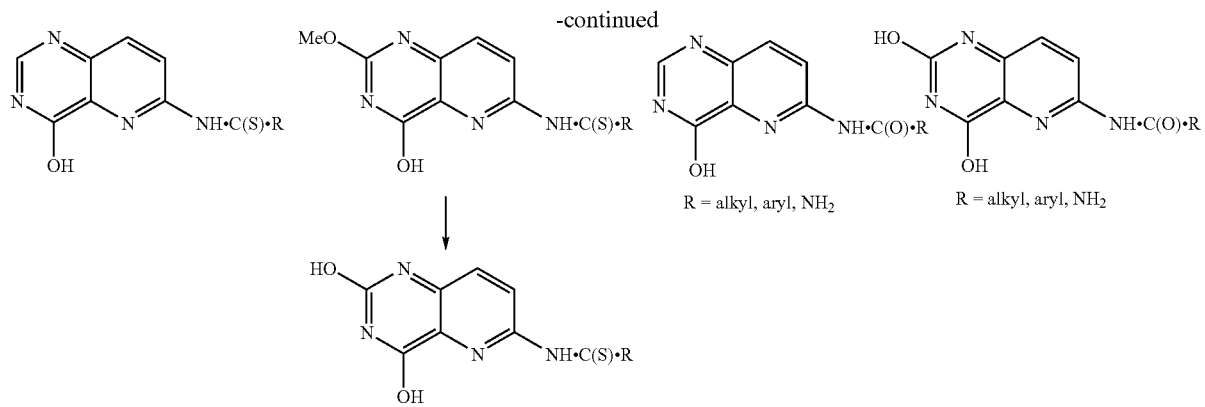
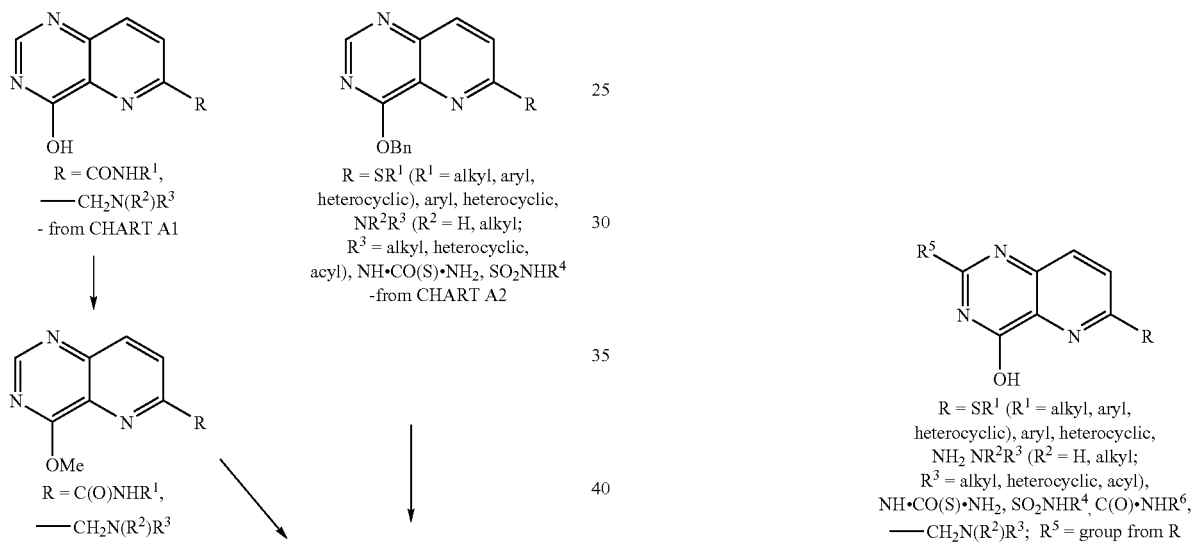
CHART B1
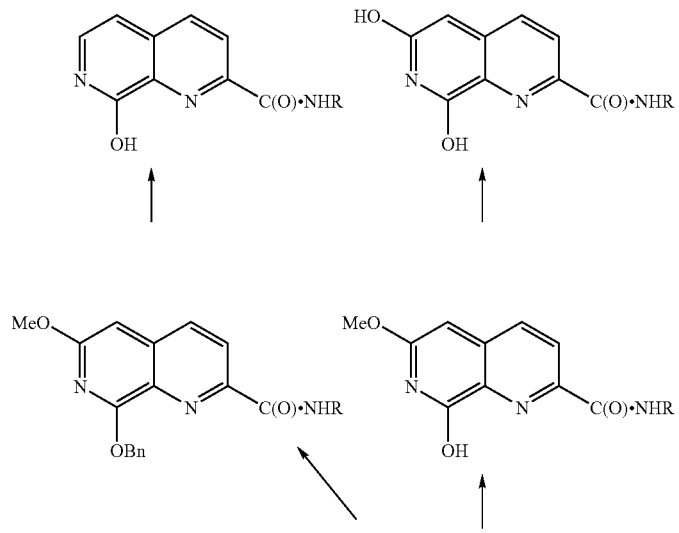

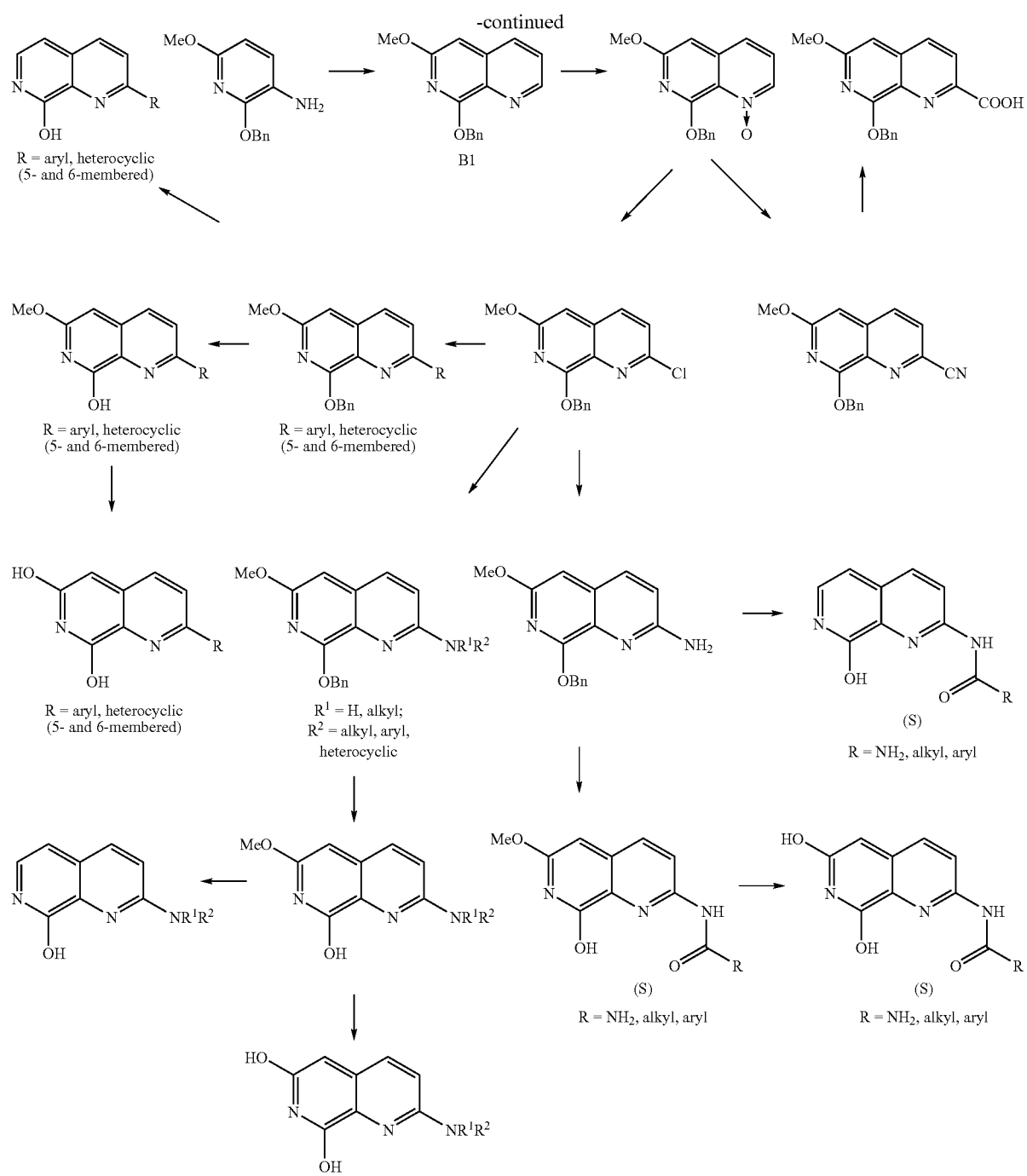
CHART B2
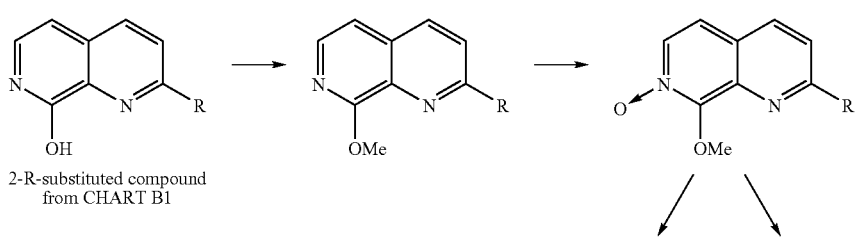

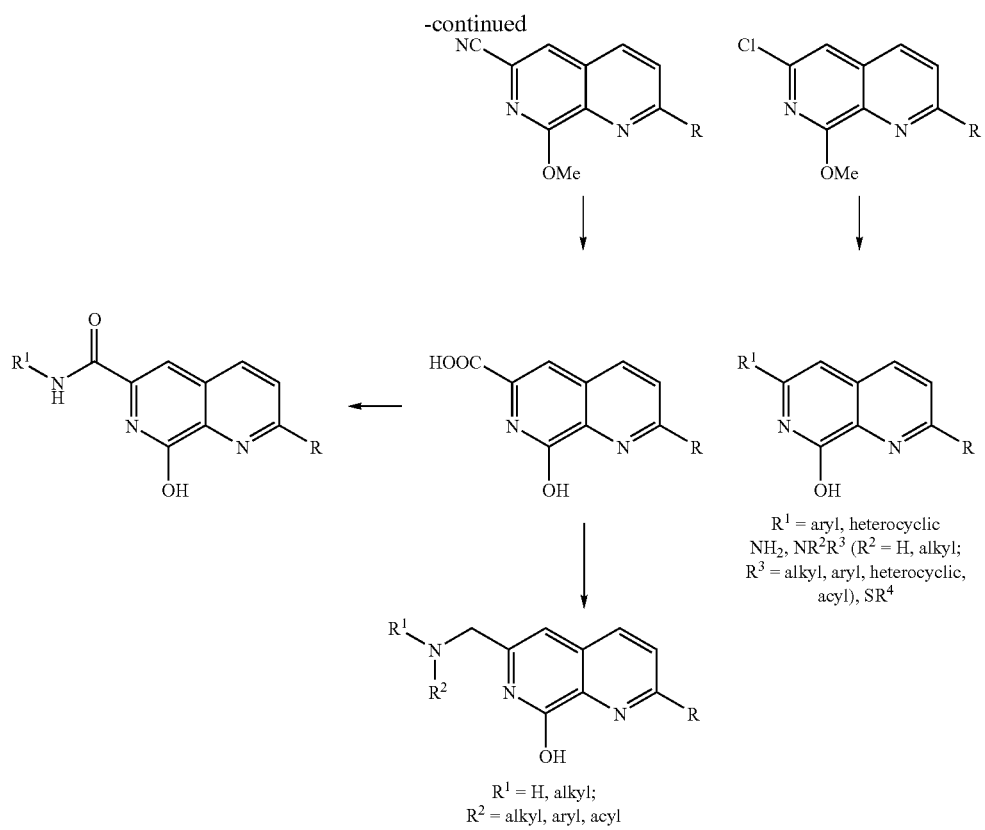
CHART C1
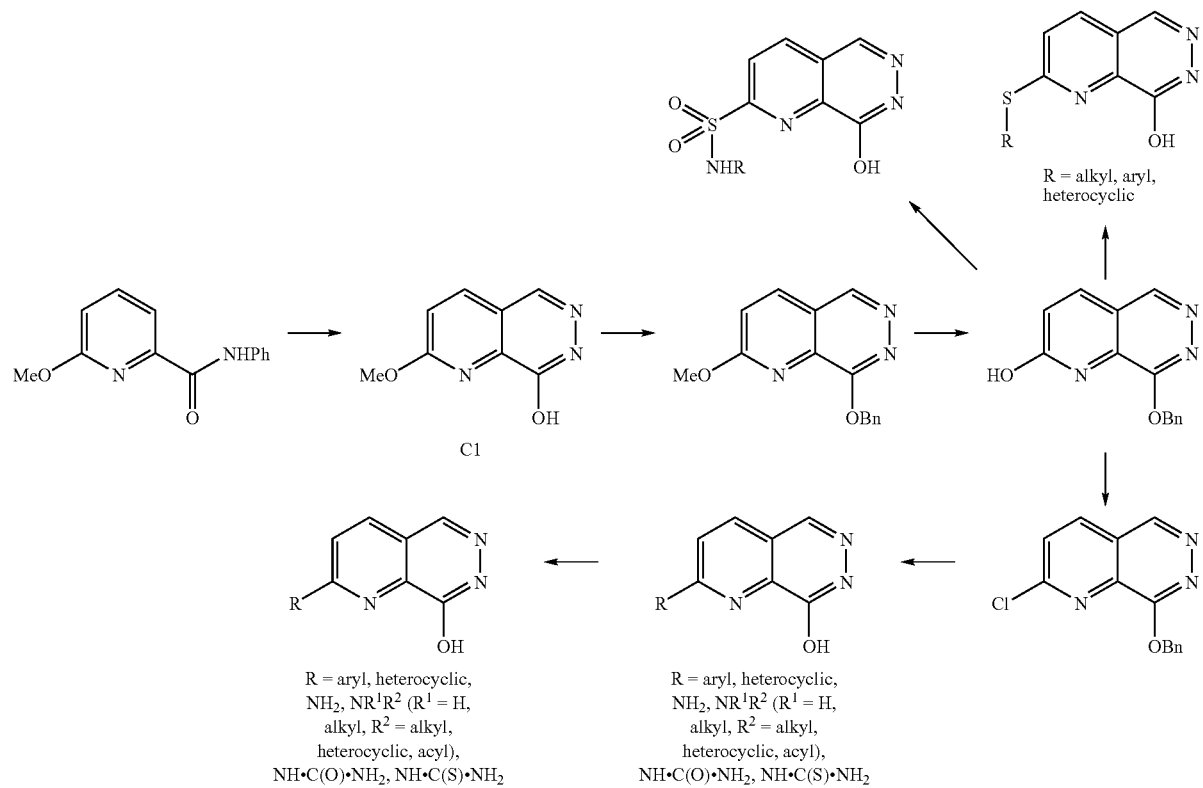

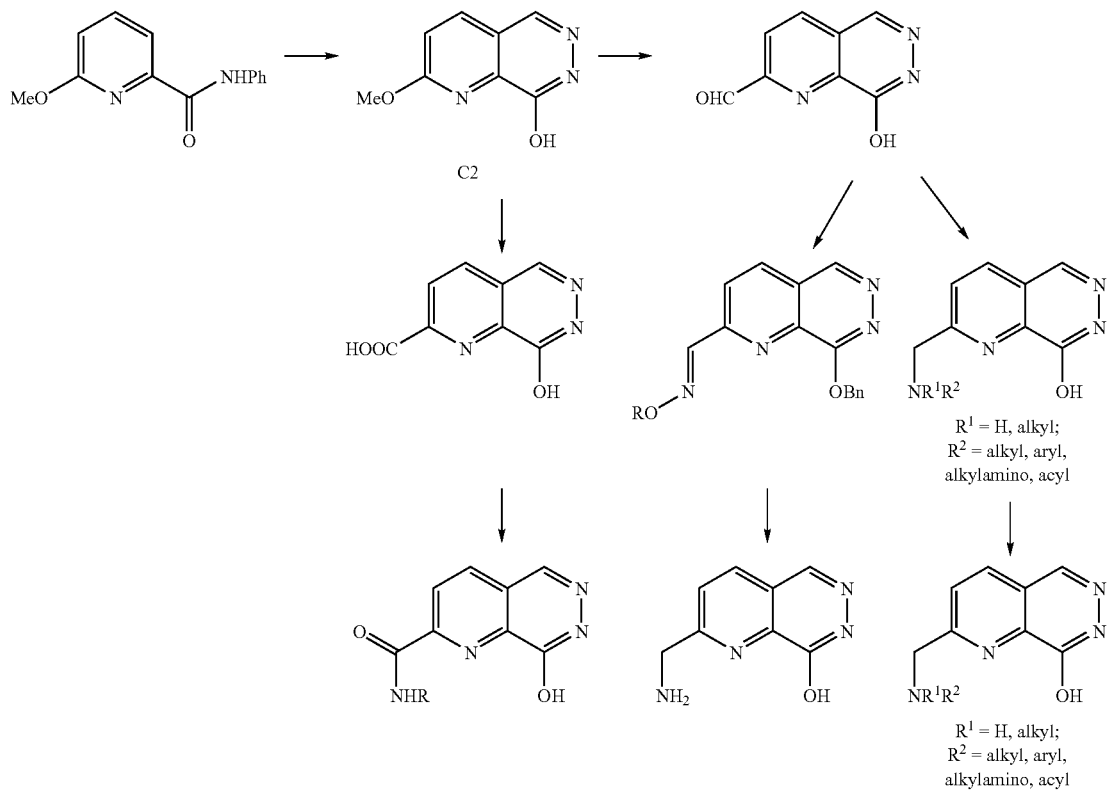
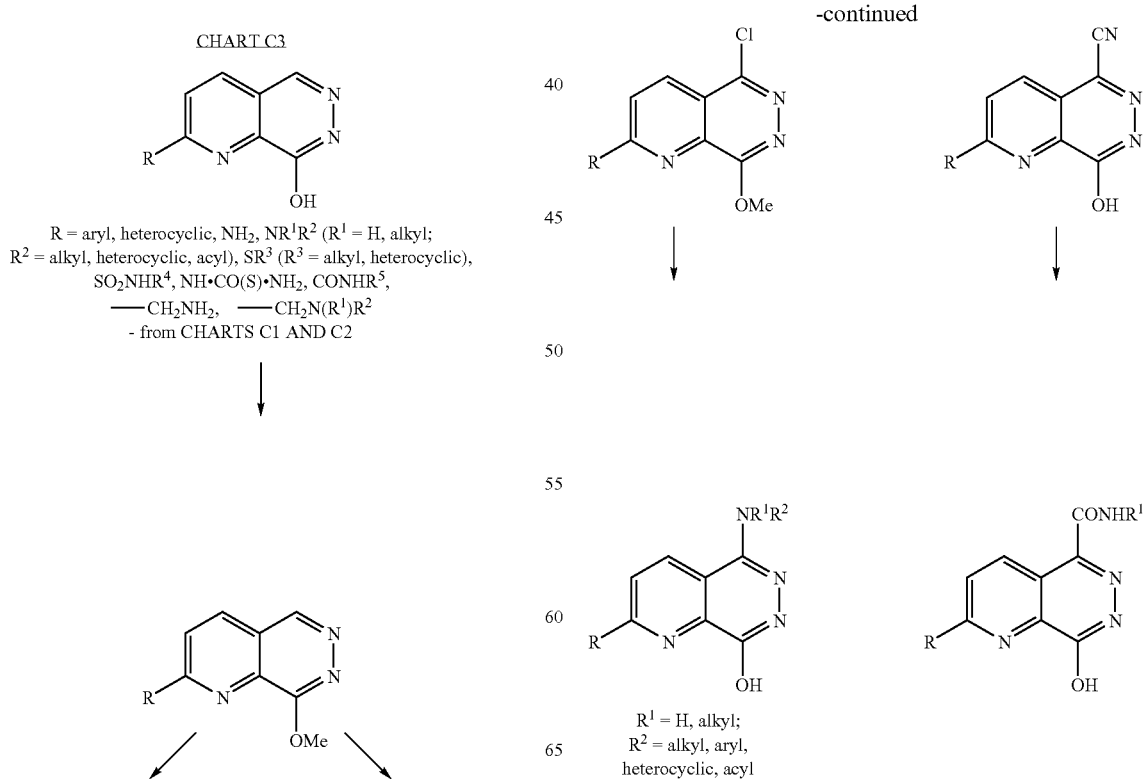

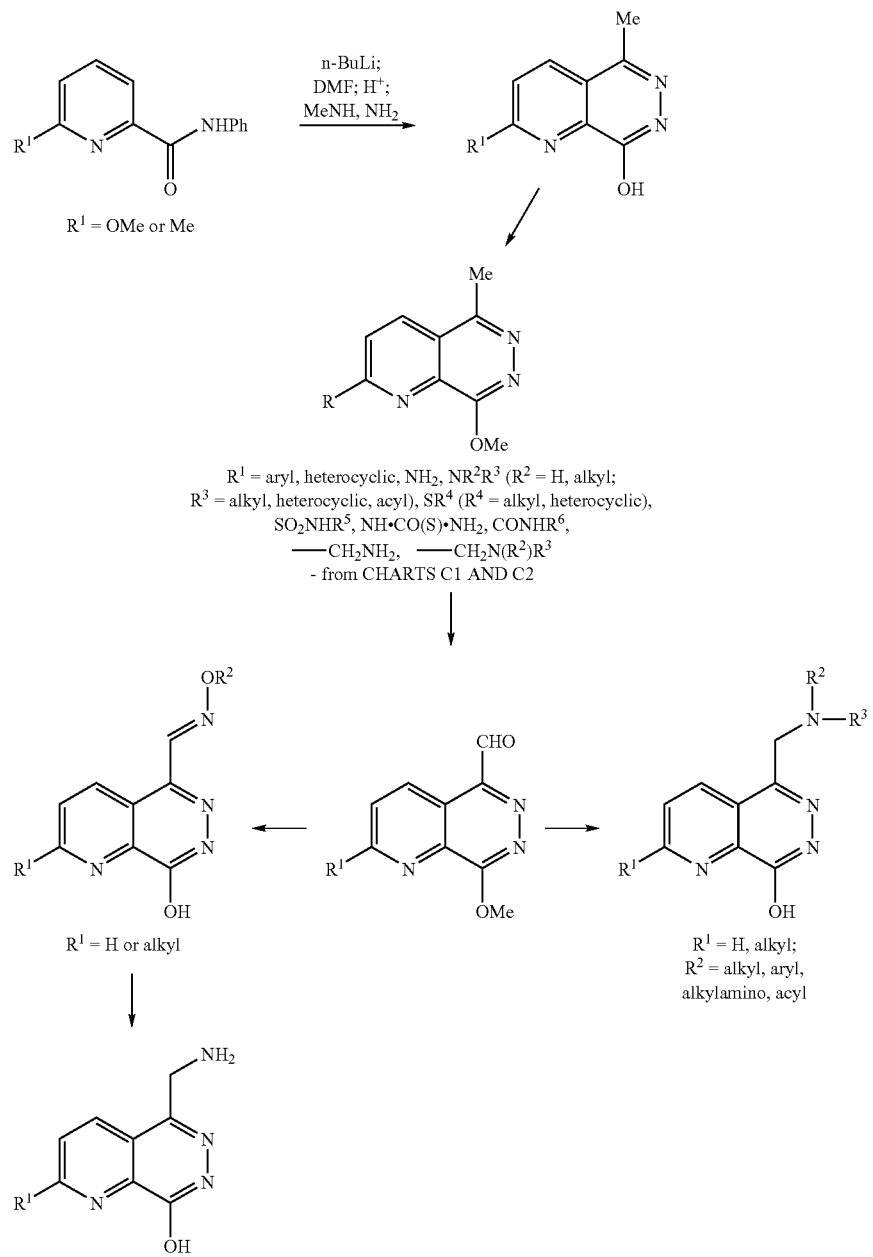
CHART C4
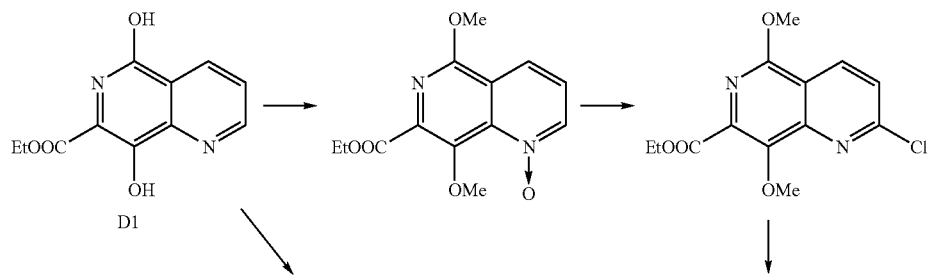
CHART D1

-continued

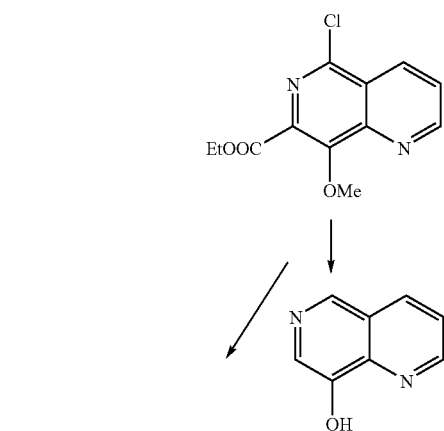

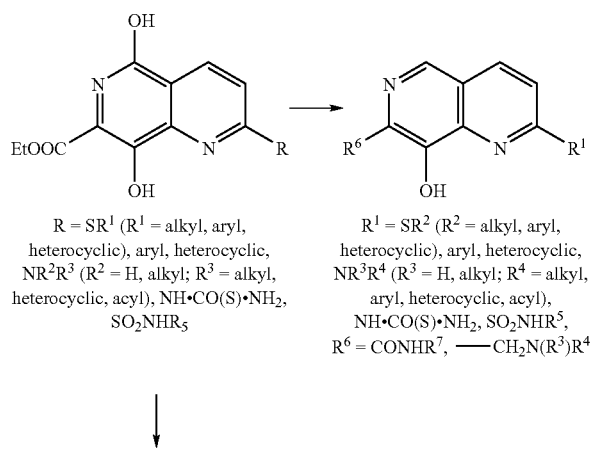

R = SR¹ (R¹ = alkyl, aryl, heterocyclic), aryl, heterocyclic, NR²R³ (R² = H, alkyl; R³ = alkyl, heterocyclic, acyl), NH•CO(S)•NH₂, SO₂NHR₅

R¹ = SR² (R² = alkyl, aryl, heterocyclic), aryl, heterocyclic, NR³R⁴ (R³ = H, alkyl; R⁴ = alkyl, aryl, heterocyclic, acyl), NH•CO(S)•NH₂, SO₂NHR₅, R⁶ = CONHR⁷, —CH₂N(R³)R⁴

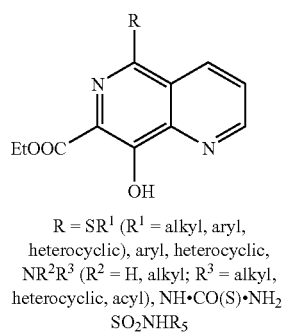

R = SR¹ (R¹ = alkyl, aryl, heterocyclic), aryl, heterocyclic, NR²R³ (R² = H, alkyl; R³ = alkyl, heterocyclic, acyl), NH•CO(S)•NH₂, SO₂NHR₅

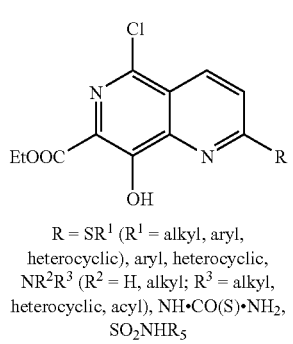

R = SR¹ (R¹ = alkyl, aryl, heterocyclic), aryl, heterocyclic, NR²R³ (R² = H, alkyl; R³ = alkyl, heterocyclic, acyl), NH•CO(S)•NH₂, SO₂NHR₅

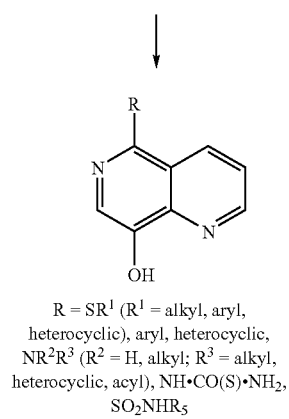

R = SR¹ (R¹ = alkyl, aryl, heterocyclic), aryl, heterocyclic, NR²R³ (R² = H, alkyl; R³ = alkyl, heterocyclic, acyl), NH•CO(S)•NH₂, SO₂NHR₅

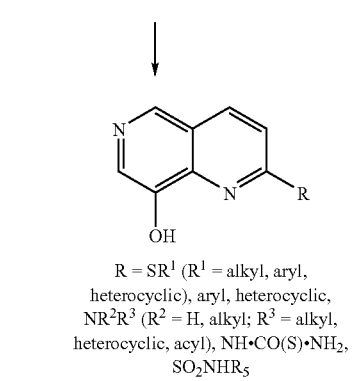

R = SR¹ (R¹ = alkyl, aryl, heterocyclic), aryl, heterocyclic, NR²R³ (R² = H, alkyl; R³ = alkyl, heterocyclic, acyl), NH•CO(S)•NH₂, SO₂NHR₅

CHART D2

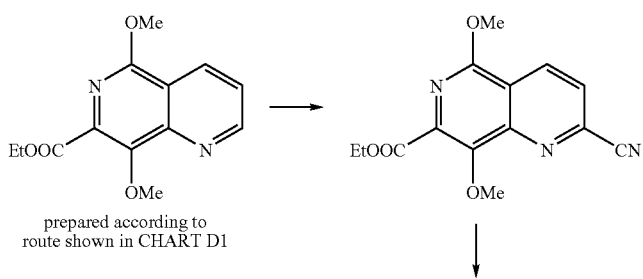

prepared according to route shown in CHART D1

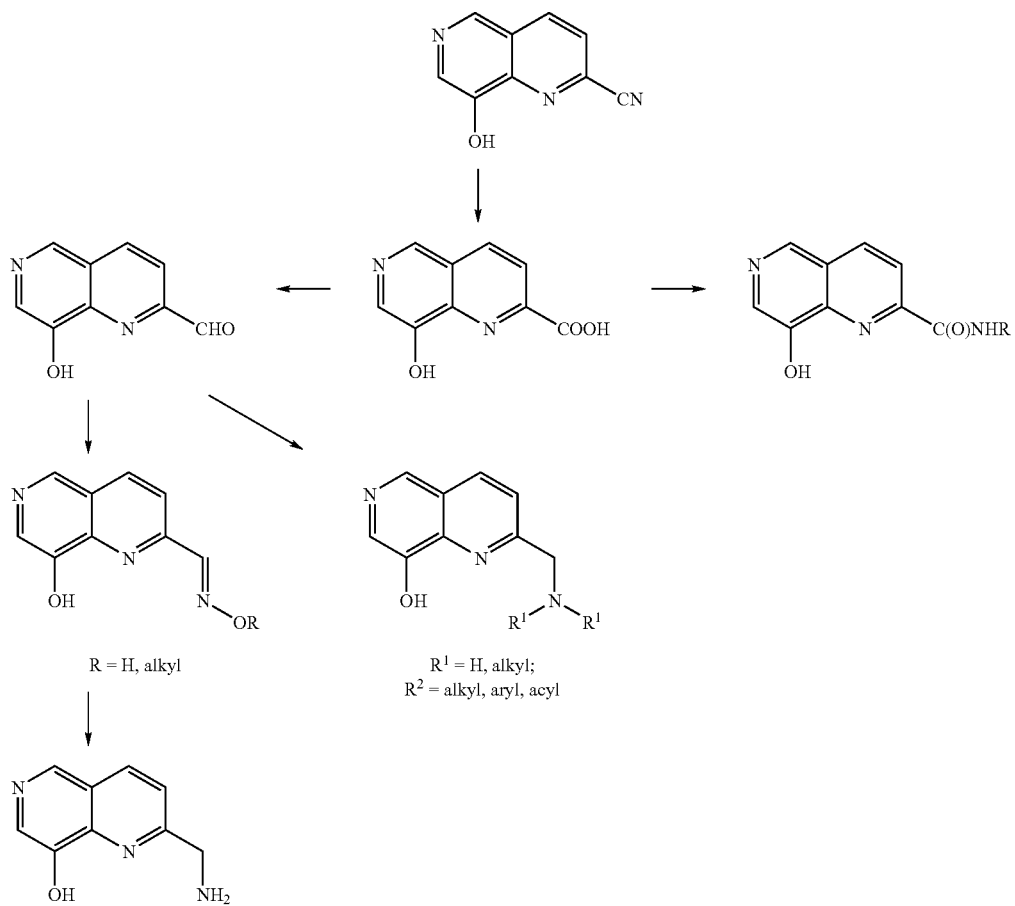
CHART E1
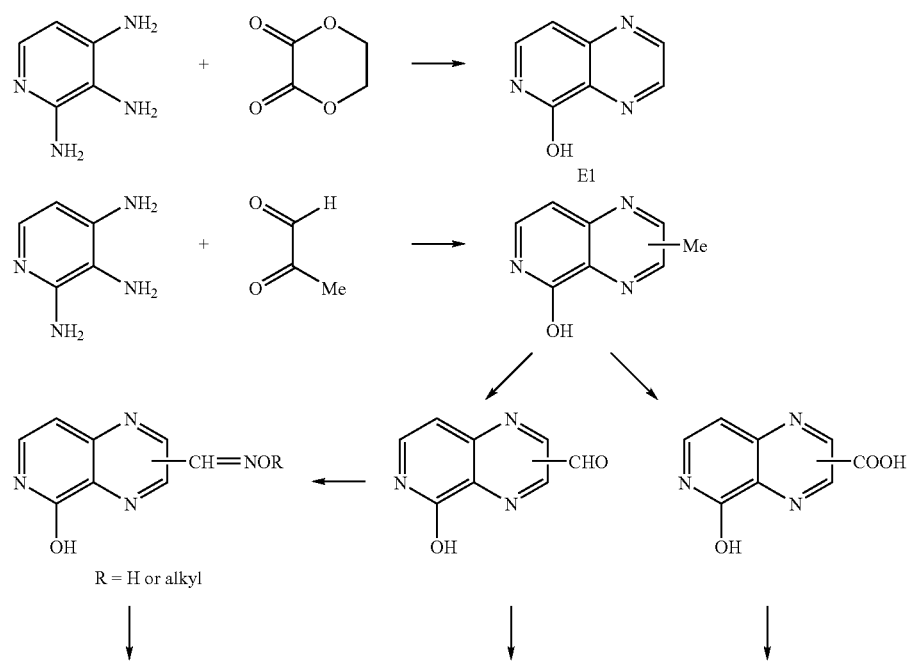

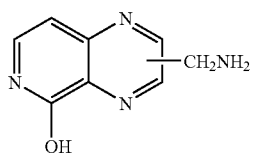
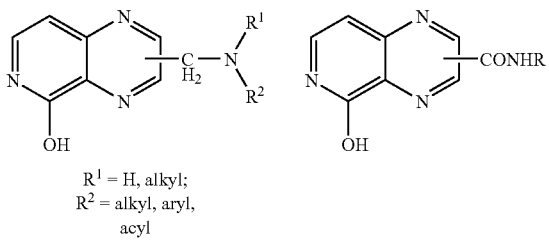
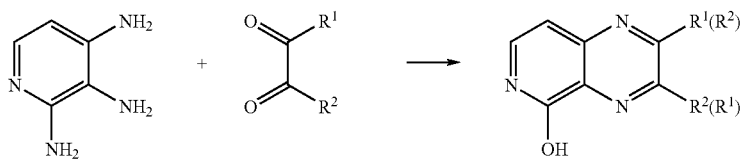
R¹, R² = alkyl, substituted alkyl, aryl, heterocyclic, OH
example:
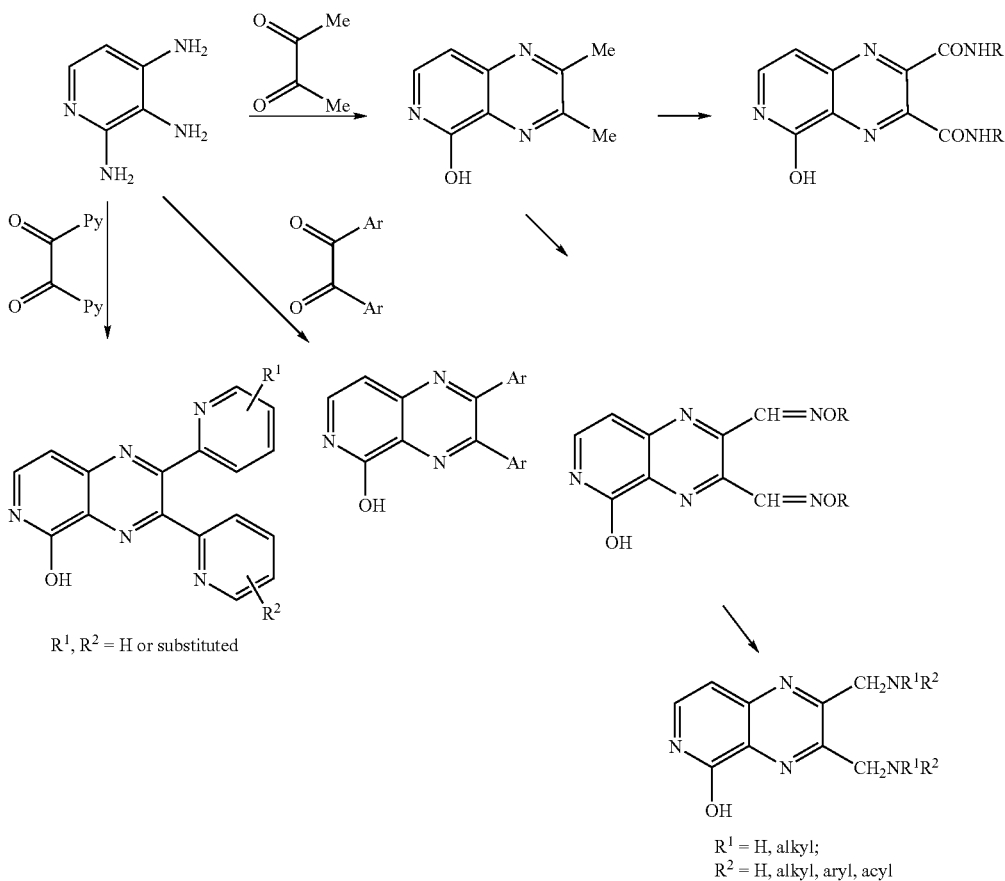
R¹ = H, alkyl;
R² = H, alkyl, aryl, acyl
CHART F1
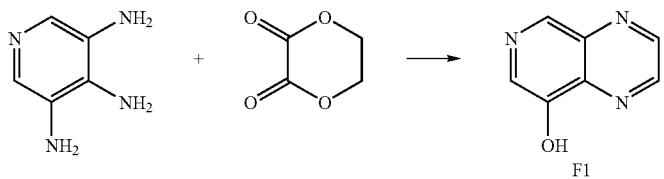

-continued
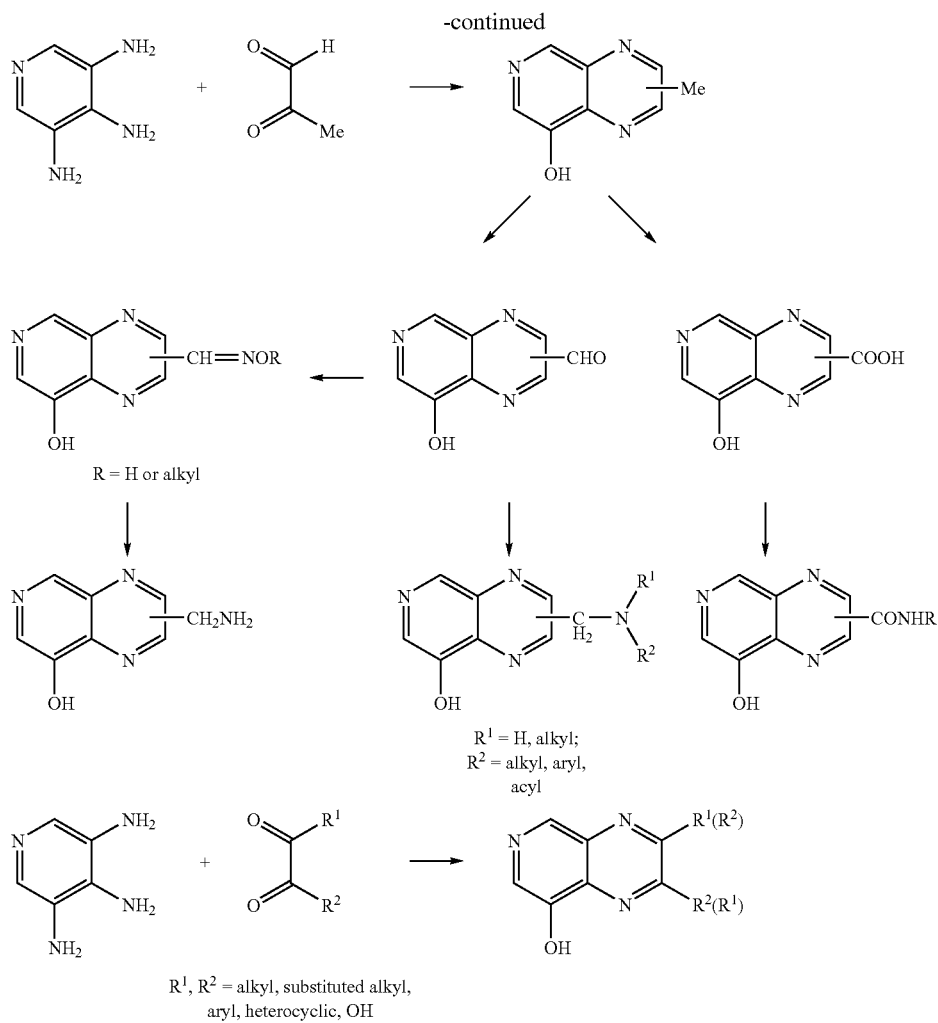
example:
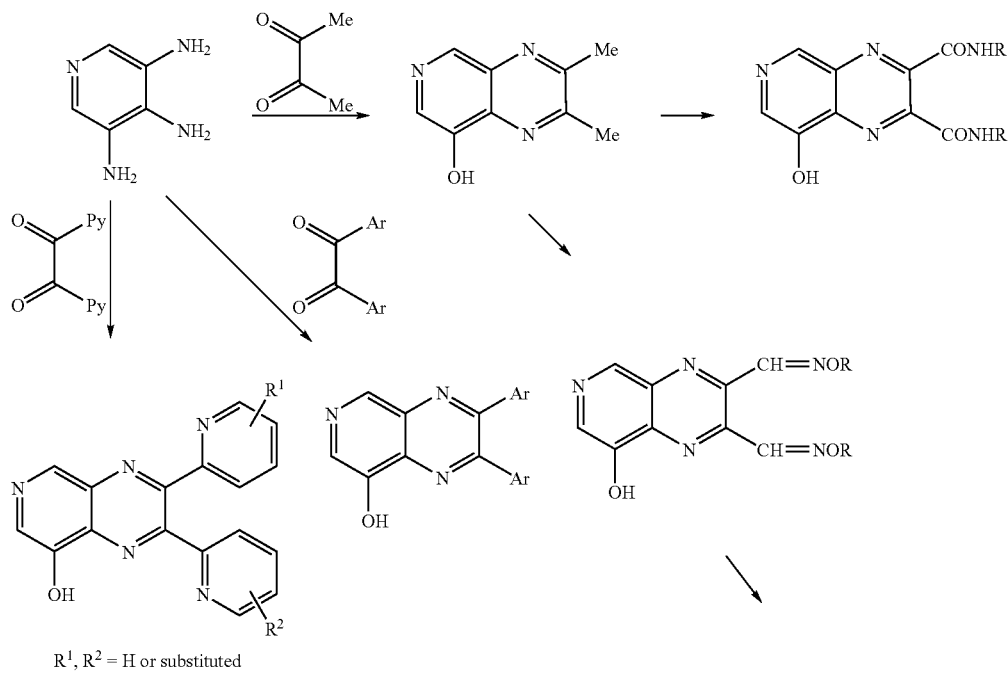

-continued
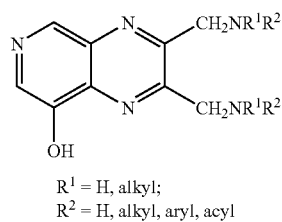
R[1] = H, alkyl;
R[2] = H, alkyl, aryl, acyl
CHART G1
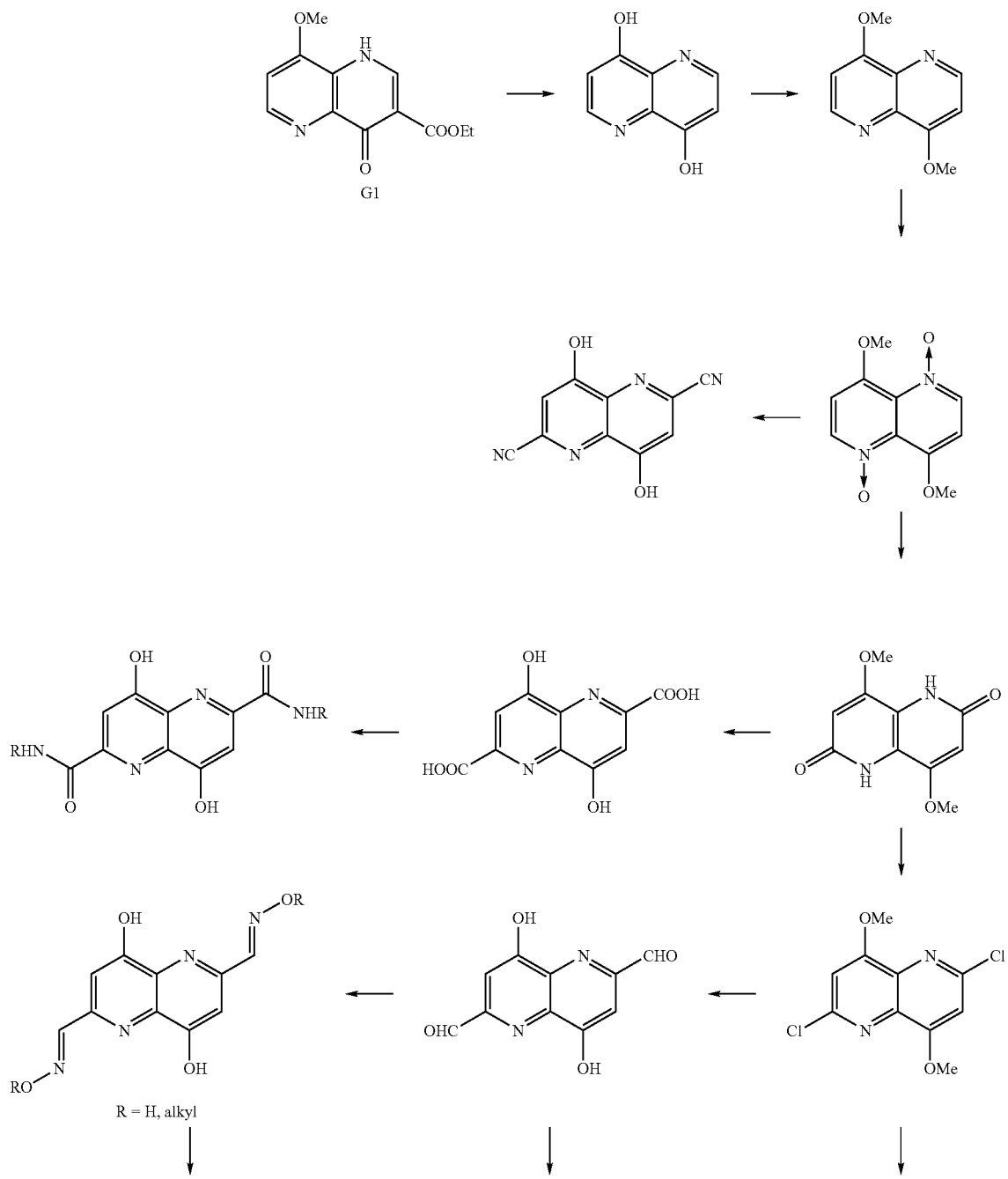
R = H, alkyl

125
126
-continued
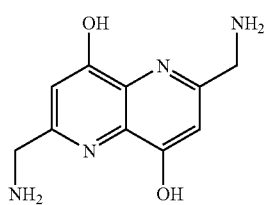
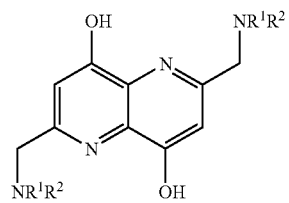
$R^1$ = H, alkyl;
$R^2$ = alkyl, aryl, acyl
R = $NH_2$, $SR^1$ ($R^1$ = alkyl, aryl, heterocyclic), aryl, heterocyclic, $NR^2R^3$ ($R^2$ = H, alkyl; $R^3$ = alkyl, heterocyclic, acyl), NH·CO(S)·$NH_2$, $SO_2NHR_5$
CHART G2
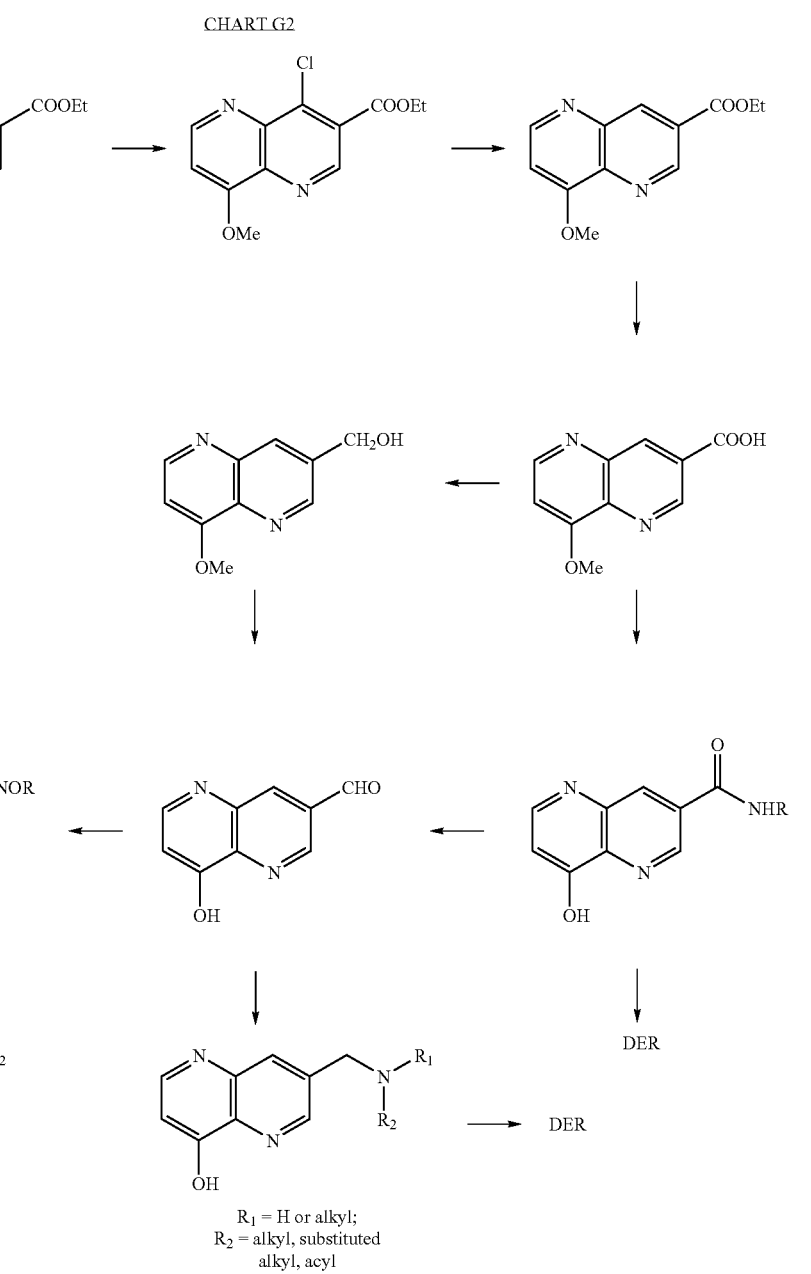
R = H or alkyl
$R_1$ = H or alkyl;
$R_2$ = alkyl, substituted alkyl, acyl

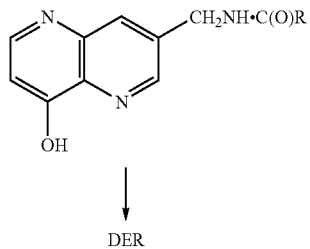

-continued

DER: derivatives with substitutions at 2- and 6-positions as in CHART G1

CHART H1

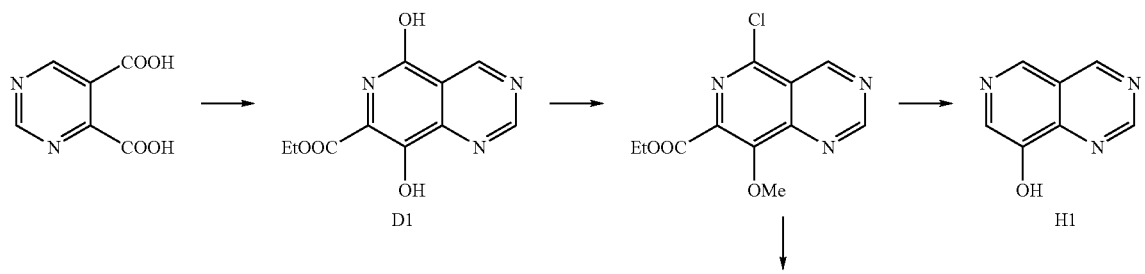

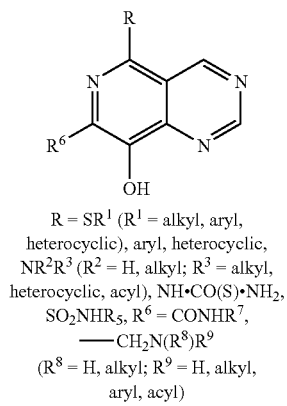

R = SR¹ (R¹ = alkyl, aryl, heterocyclic), aryl, heterocyclic, NR²R³ (R² = H, alkyl; R³ = alkyl, heterocyclic, acyl), NH·CO(S)·NH₂, SO₂NHR₅, R⁶ = CONHR⁷, —CH₂N(R⁸)R⁹
(R⁸ = H, alkyl; R⁹ = H, alkyl, aryl, acyl)

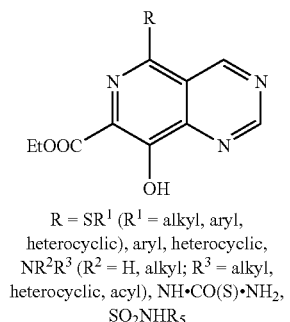

R = SR¹ (R¹ = alkyl, aryl, heterocyclic), aryl, heterocyclic, NR²R³ (R² = H, alkyl; R³ = alkyl, heterocyclic, acyl), NH·CO(S)·NH₂, SO₂NHR₅

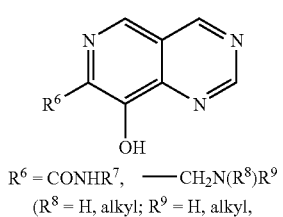

R⁶ = CONHR⁷, —CH₂N(R⁸)R⁹
(R⁸ = H, alkyl; R⁹ = H, alkyl, aryl, acyl)

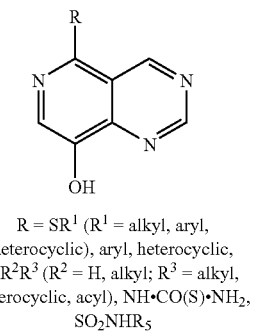

R = SR¹ (R¹ = alkyl, aryl, heterocyclic), aryl, heterocyclic, NR²R³ (R² = H, alkyl; R³ = alkyl, heterocyclic, acyl), NH·CO(S)·NH₂, SO₂NHR₅

CHART H2

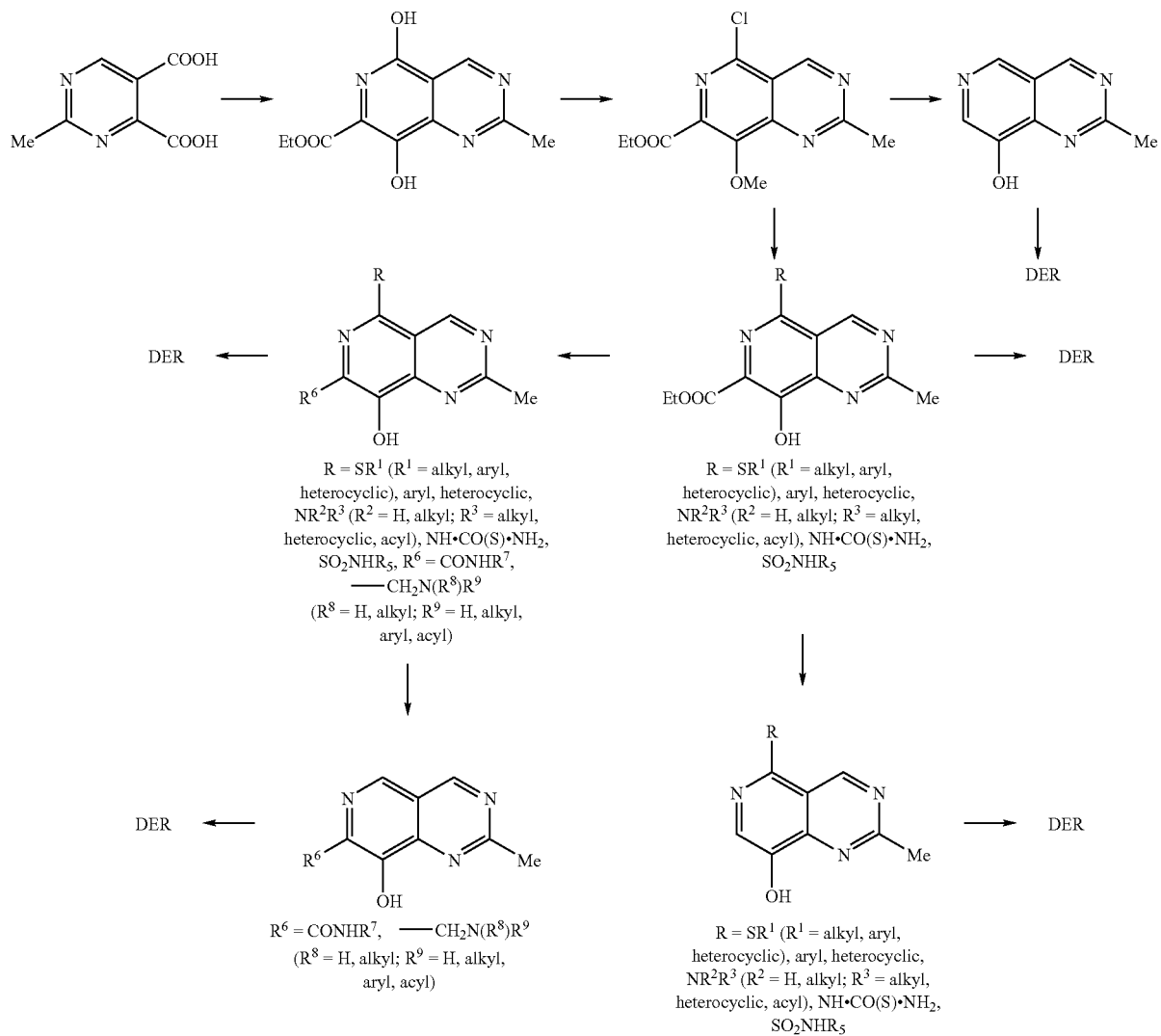

DER: derivatives thereof, prepared via substitution of the 2-methyl group to a subject in need thereof e.g. COOH, CONHR, alkylamino, alkylamido, oxime, alkyloxime

REFERENCES 1. (a) A. Dondoni, G. Fantin, M. Fogagnolo, A. Medici and P. Pedrini, *Synthesis,* 1987, 998-1001. (b) A. Dondoni, F. L. Merchan, P. Merino, I. Rojo and T. Tejero, *Synthesis,* 1996, 641-646.

2. A Albert and A. Hampton, *J.,* 1952, 4985-4993.

3. J. Z. Brzezinski, H. B. Bzowski and J. Epsztajn, *Tetrahedron,* 1996, 52, 3261-3272.

4. M. Blanco, M. G. Lorenzo, I. Perillo and C. B. Schapira, *J. Heterocyclic Chem.,* 1996, 33, 363-366.

5. S. B. Brown and M. J. S. Dewar, *J. Org Chem.,* 1978, 43, 1331-1337.

(5) PREPARATION OF 8-HYDROXY-6H-[1,6]NAPHTHYRIDIN-5-ONE, 4-HYDROXY-4a,8a-DIHYDRO-PYRANO[3,2-b]PYRIDIN-2-ONE, 8-HYDROXY-6H-[1,6]NAPHTHYRIN-5-ONE, DIBENZO[a,g]QUINOLIZIN-8-ONE AND 4-HYDROXY-1H-PYRIDO[3,2-d]PYRIMIDIN-2-ONE

General

The following reagents were sourced commercially:— amines: ethylamine, histamine, 2-(2-aminoethyl)pyridine, 2-(2-methylaminoethyl)pyridine; aldehydes: 4-imidazolecarboxaldehyde, 2-thiazolecarboxaldehyde and 2-pyridinecarboxaldehyde, azoles: pyrazole, imidazole, methylimidazole and 1H-1,2,3-triazole, boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid and 4-fluorophenylboronic acid; and organozinc reagents: 2-pyridylzinc bromide, 2-(methylthio)phenylzinc iodide, 2-(ethoxycarbonyl)phenylzinc iodide and 6-methylpyridylzinc bromide (0.5 M solution in THF) (Aldrich). 3-Pyridylboronic acid was purchased from Frontier Scientific. 2-Aminomethylthiazole was prepared according to the literature.[4] Solvents were analytical grade and used as supplied. THF was distilled from sodium and benzophenone under argon. $^1$H NMR spectra (δ, relative to TMS) were recorded on a Varian Unity 300 spectrometer unless otherwise indicated; J-Values are given in hertz. Mass spectral data were recorded on a Micromass Quattro II mass spectrometer.

The synthesis of derivatives of 5 classes of compounds: 8-hydroxy-6H-[1,6]naphthyridin-5-one (A), 4-hydroxy-4a,8a-dihydro-pyrano[3,2-b]pyridin-2-one (B), 8-hydroxy-6H-[1,6]naphthyrin-5-one (C), dibenzo[a,g]quinolizin-8-one (D) and 4-hydroxy-1H-pyrido[3,2-d]pyrimidin-2-one (E), is described.

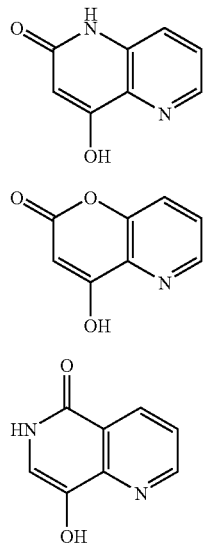

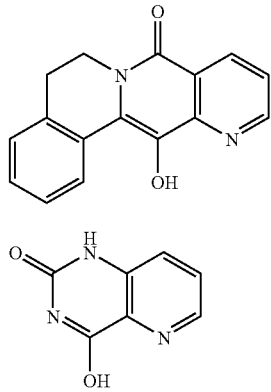

Condensation of ethyl 3-amino-picolin-2-ate with acetic anhydride according to the method of Zhou and coworkers[1] gave 8-hydroxy-6H-[1,6]naphthyridin-5-one (A1). By substituting ethyl 3-amino-picolin-2-ate respectively with ethyl 5-chloro-3-amino-picolin-2-ate and ethyl 6-methyl-3-amino-picolin-2-ate, the corresponding 2-methyl- and 3-chloro-8-hydroxy-6H-[1,6]naphthyridin-5-one derivatives were obtained. Further derivatisation of these systems as shown in Charts A1-A4 gave a series of 8-hydroxy-6H-[1,6]naphthyridin-5-ones. The preparation of a series of 4-hydroxy-4a,8a-dihydro-pyrano[3,2-b]pyridin-2-ones is described in Charts B1-B2. The method of Blanco and coworkers[2] was employed for the synthesis of C2 which upon subsequent acid hydrolysis provided 8-hydroxy-6H-[1,6]naphthyrin-5-one (C1). Further derivatives in this series were prepared following routes shown in Charts C1-C2. Charts D1-D2 show the preparation of a series of dibenzo[a,g]quinolizin-8-ones. The key step, involving the construction of the ring system, followed the method previously described[3] by Colye and coworkers. Chart E1 shows the routes employed in the preparation of a series of 4-hydroxy-1(alkylated)-pyrido[3,2-d]pyrimidin-2-one derivatives.

CHART A1

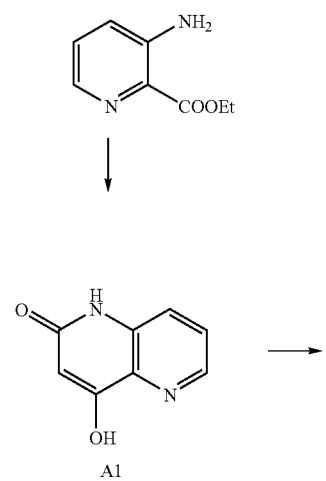

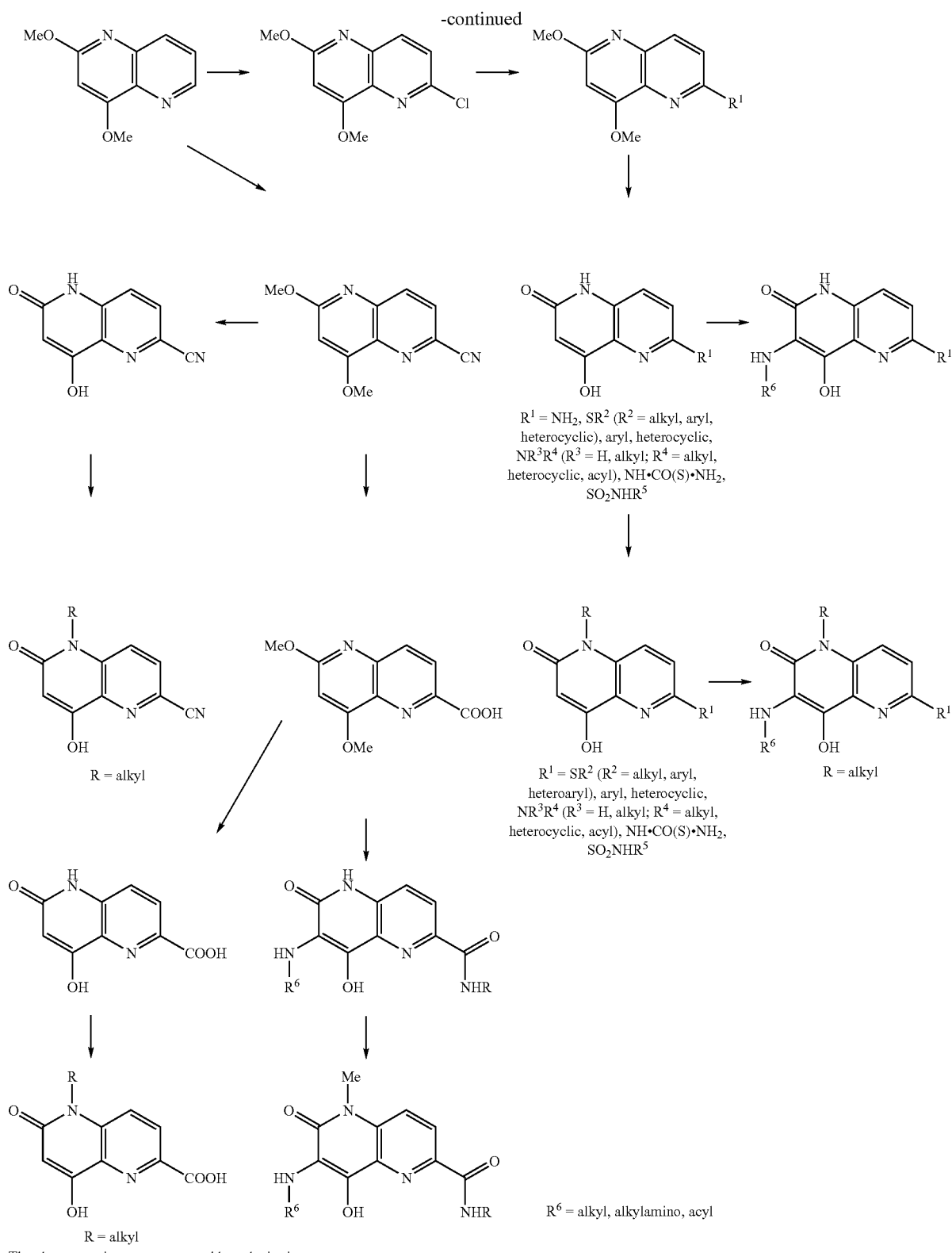
R⁶ = alkyl, alkylamino, acyl
R = alkyl
The above reactions were repeated by substituting CHART A2
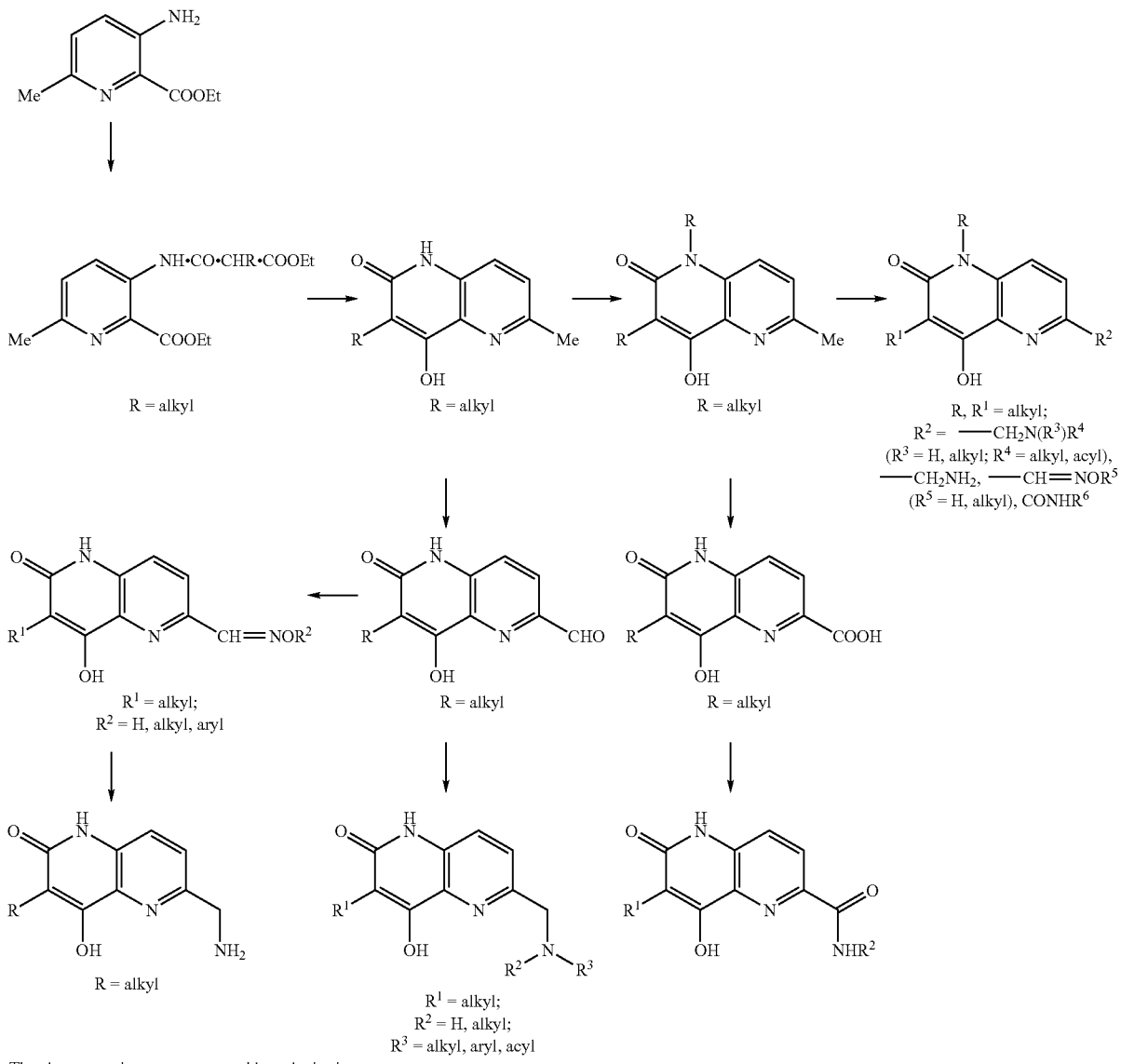
The above reactions were repeated by substituting
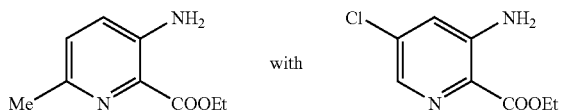 with
CHART A3
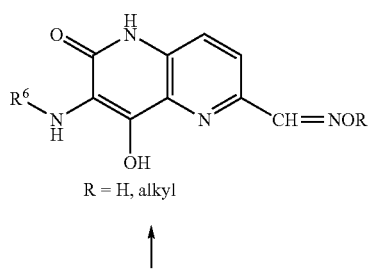
R = H, alkyl

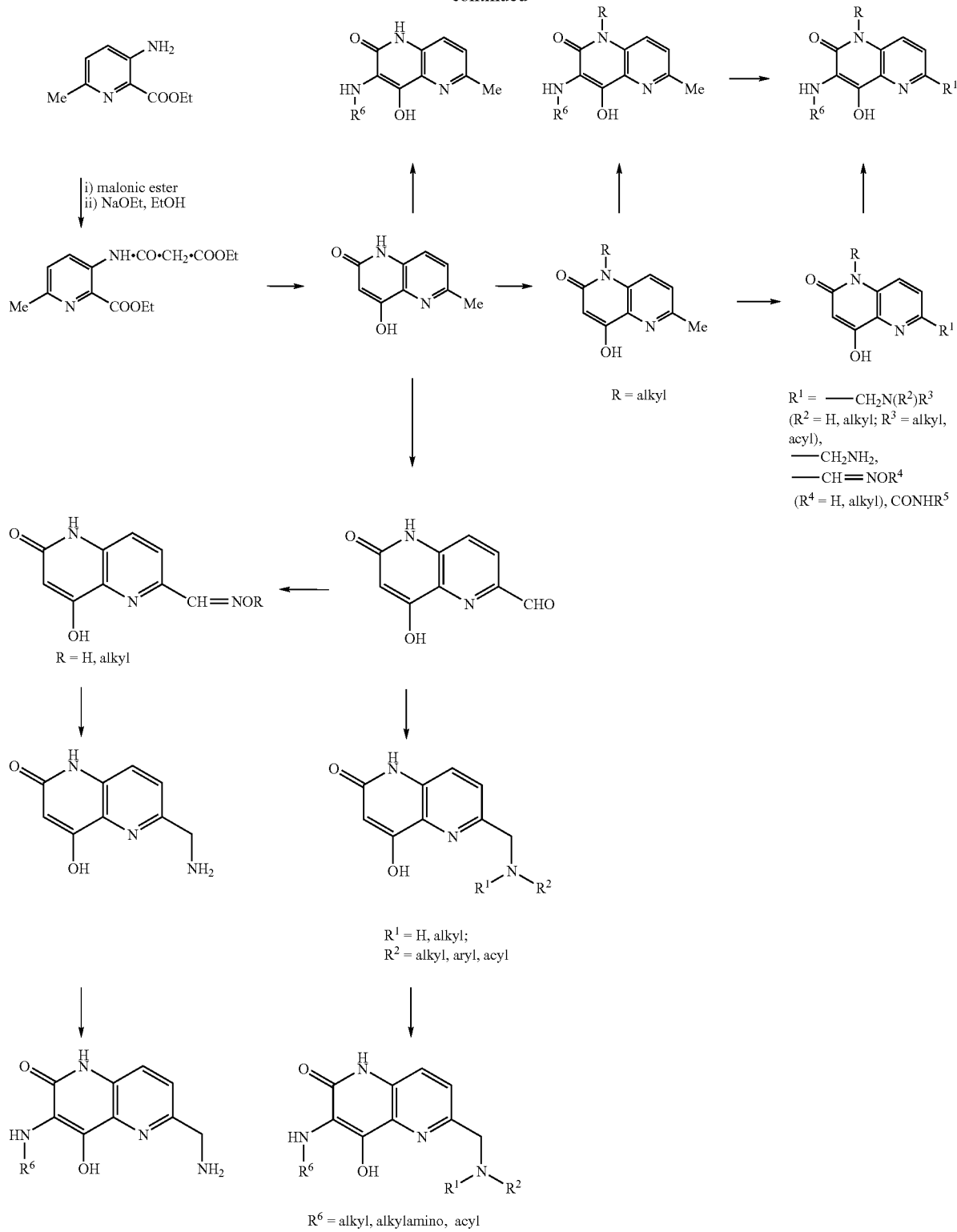
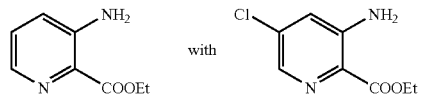
The above reactors were replaced repeated by substituting CHART A4
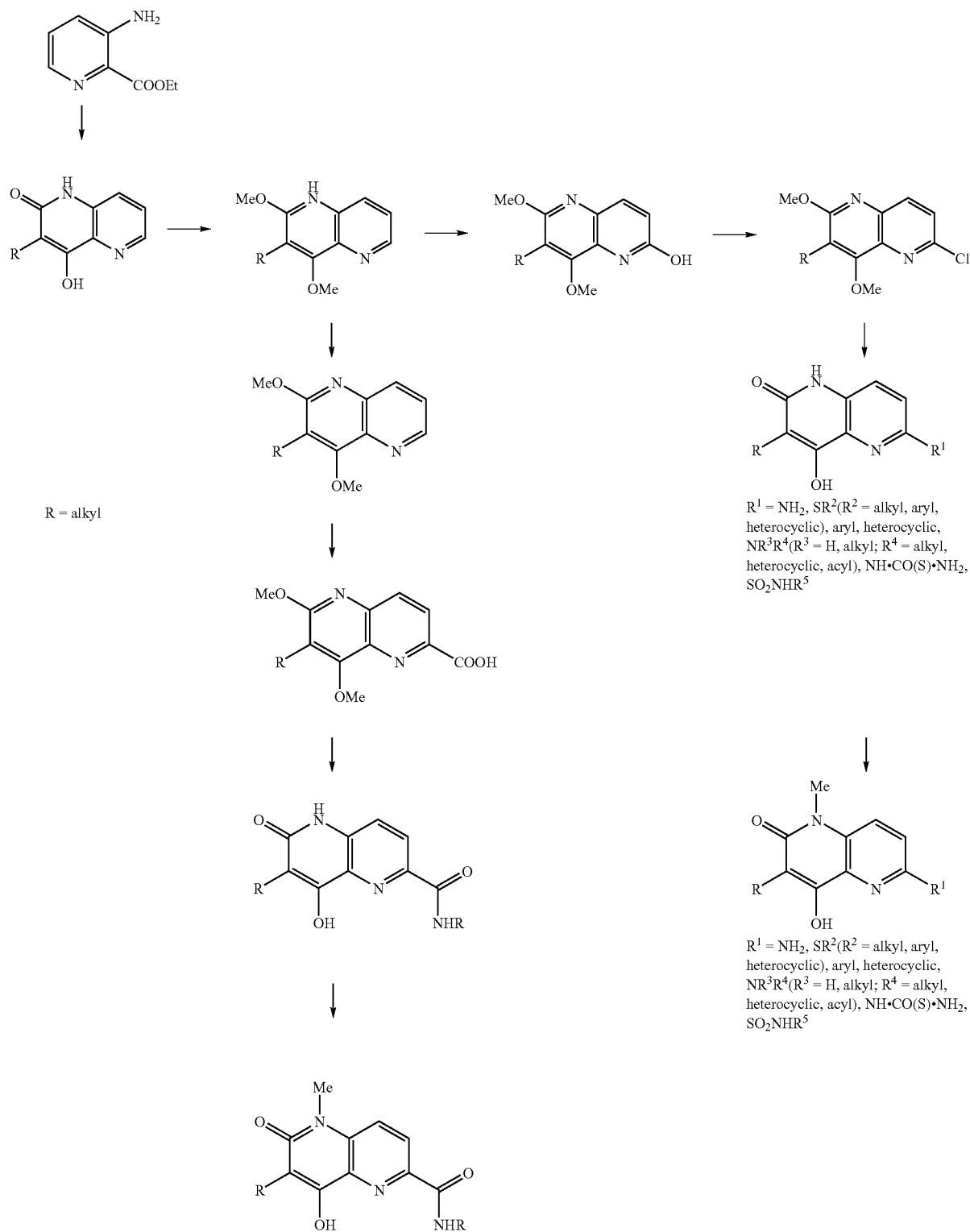
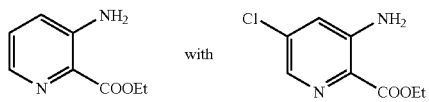
The above reactions were repeated by substituting with CHART B1
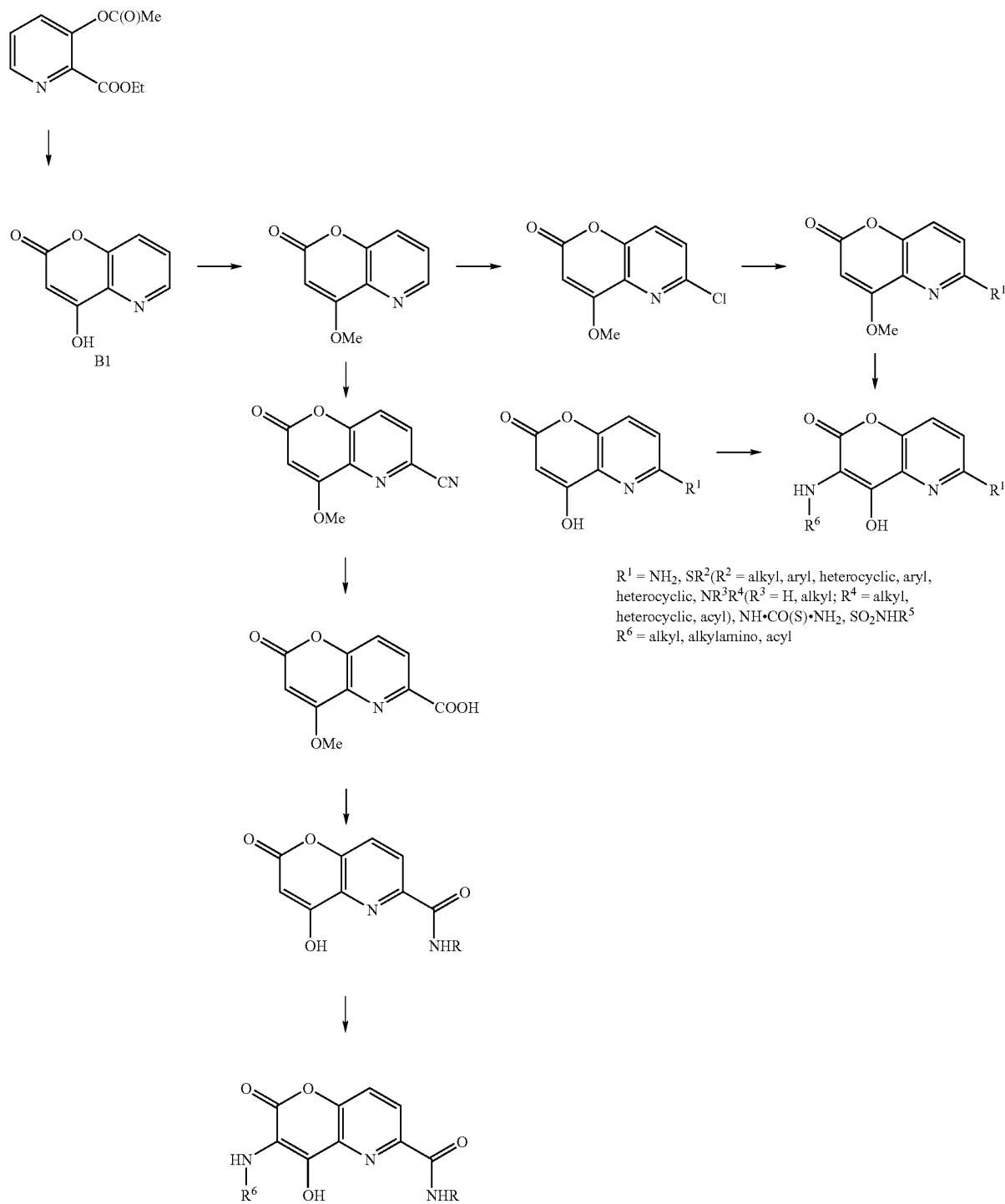
$R^1 = NH_2$, $SR^2$($R^2$ = alkyl, aryl, heterocyclic, aryl, heterocyclic, $NR^3R^4$($R^3$ = H, alkyl; $R^4$ = alkyl, heterocyclic, acyl), NH•CO(S)•NH$_2$, SO$_2$NHR$^5$
$R^6$ = alkyl, alkylamino, acyl
$R^6$ = alkyl, alkylamino, acyl
The above reactions were repeated by substituting
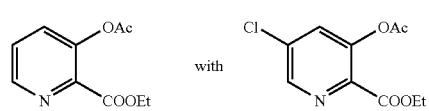
with CHART B2
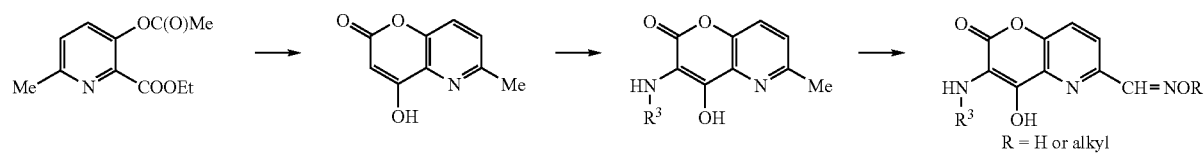
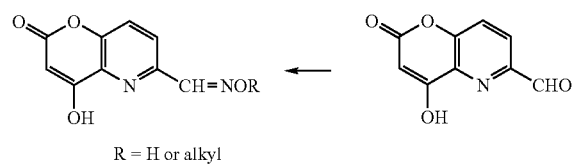
R = H or alkyl
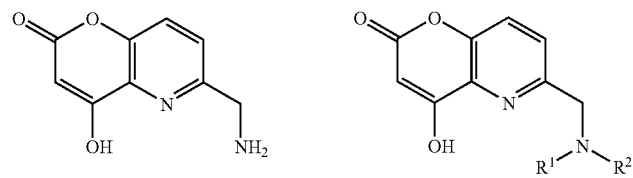
R¹ = H, alkyl;
R² = alkyl, aryl, acyl
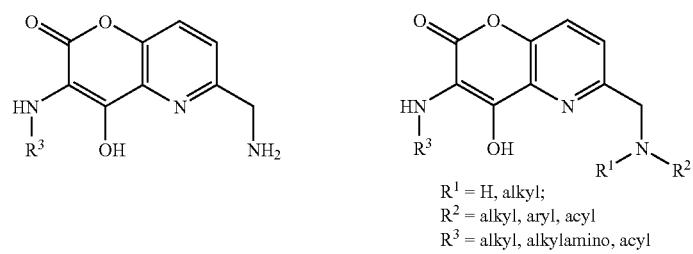
R¹ = H, alkyl;
R² = alkyl, aryl, acyl
R³ = alkyl, alkylamino, acyl
The above reactions were repeated by substituting
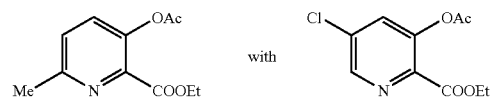
with 145    146
CHART C1
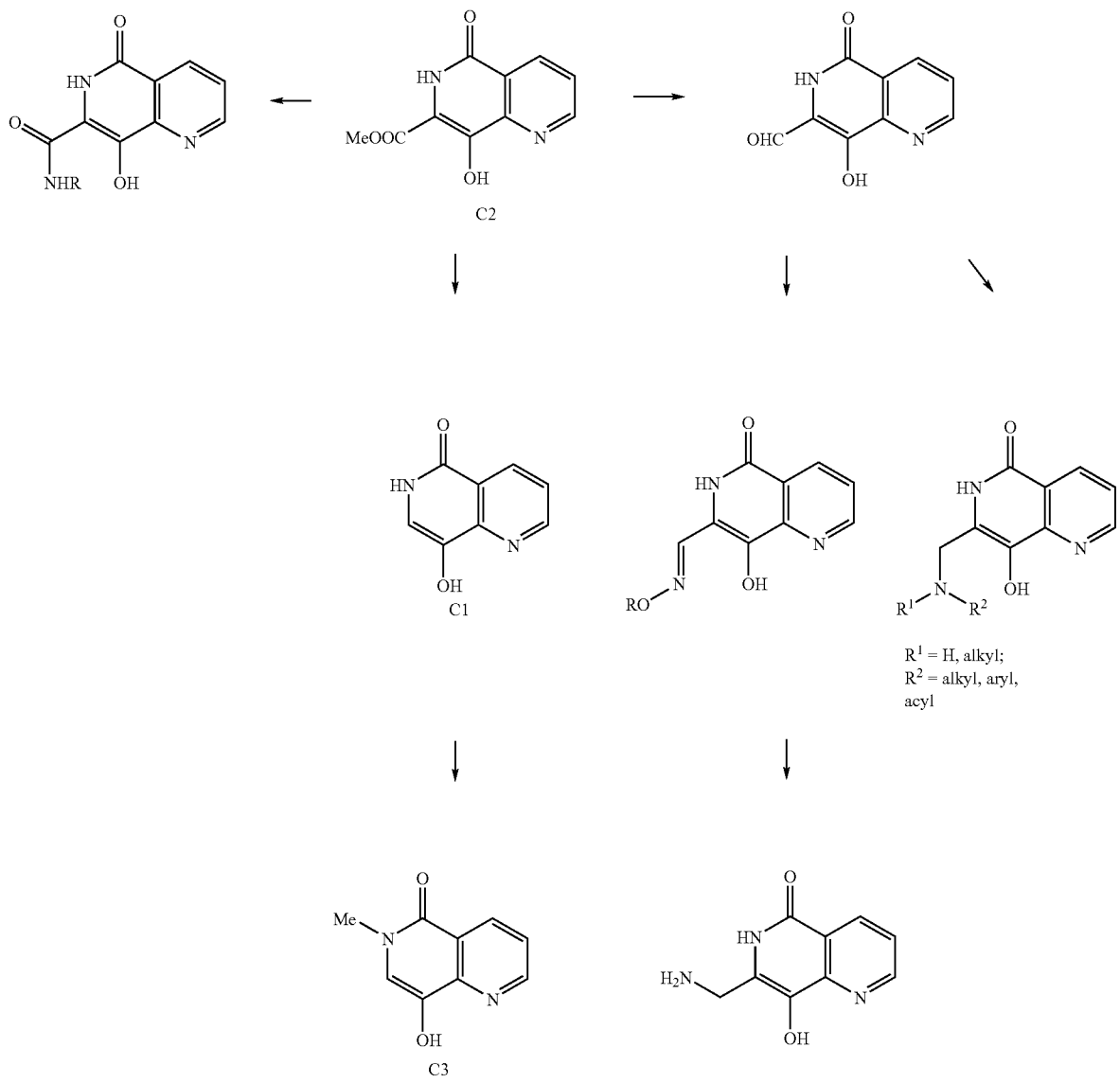
CHART C2
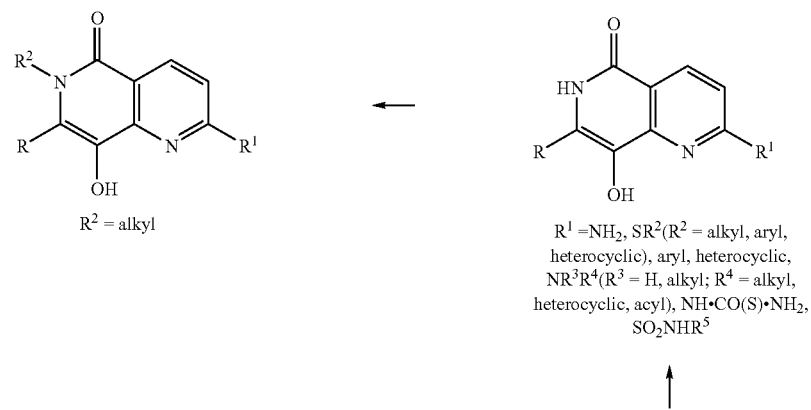

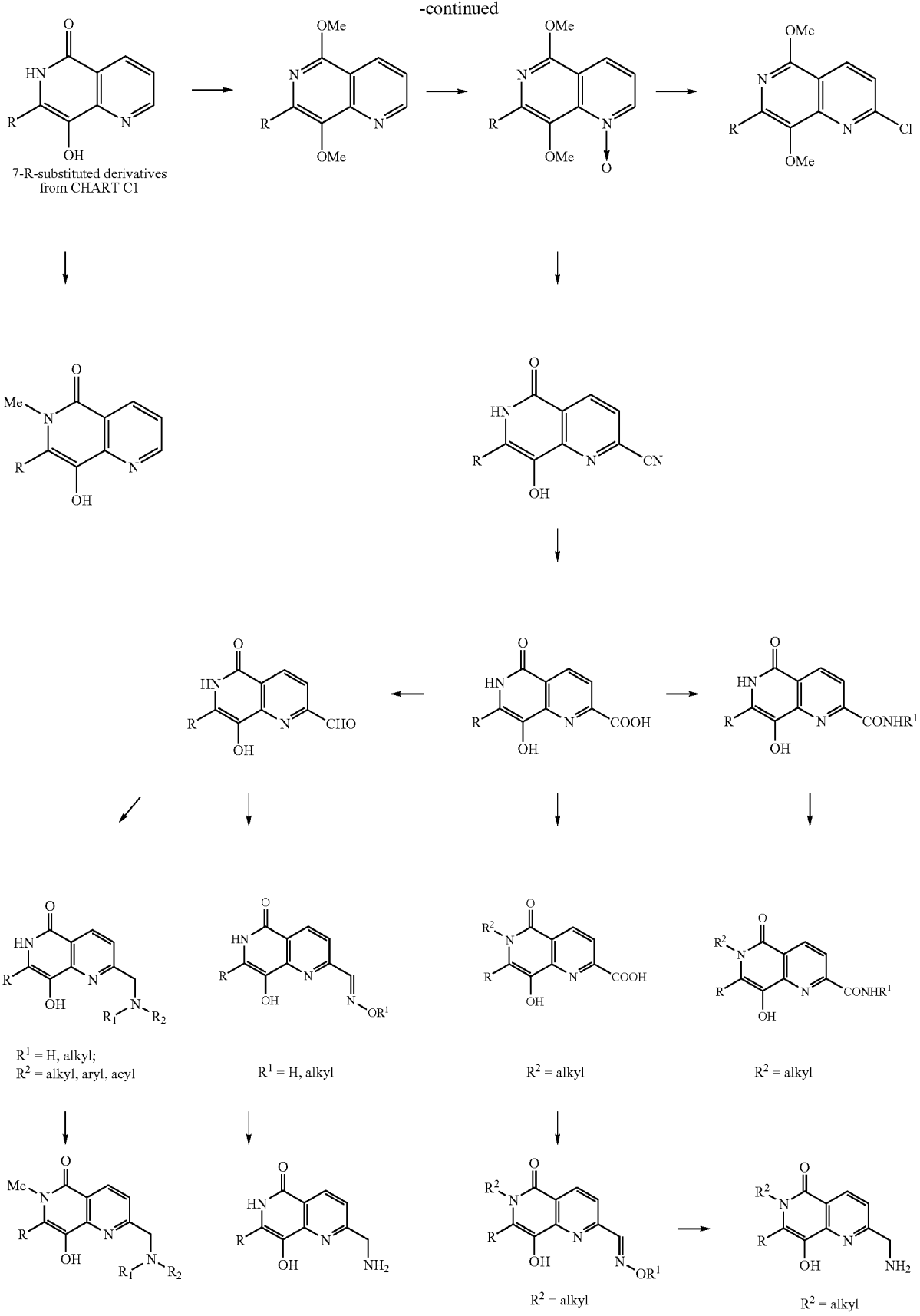

CHART D1
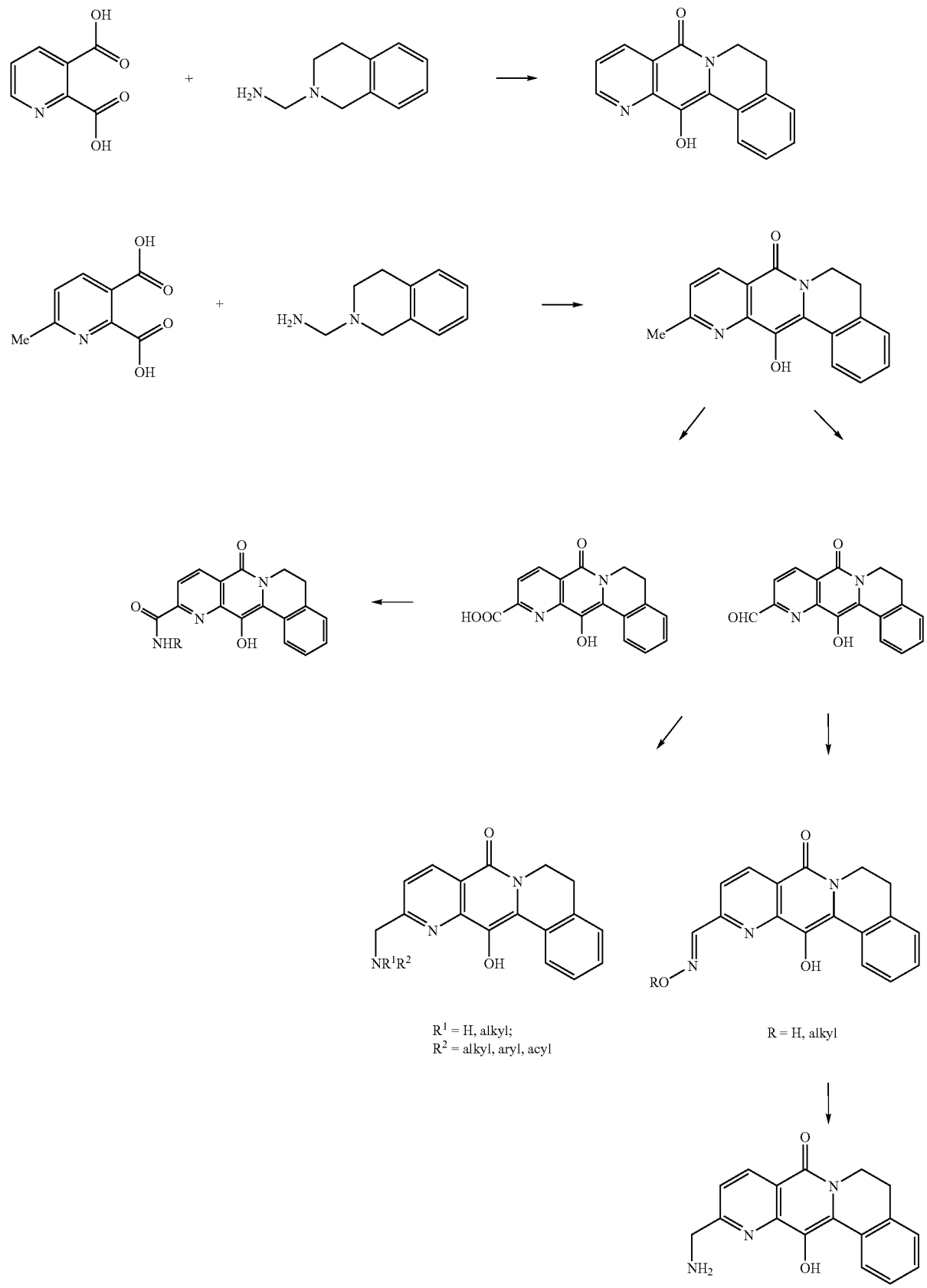
R[1] = H, alkyl;
R[2] = alkyl, aryl, acyl
R = H, alkyl

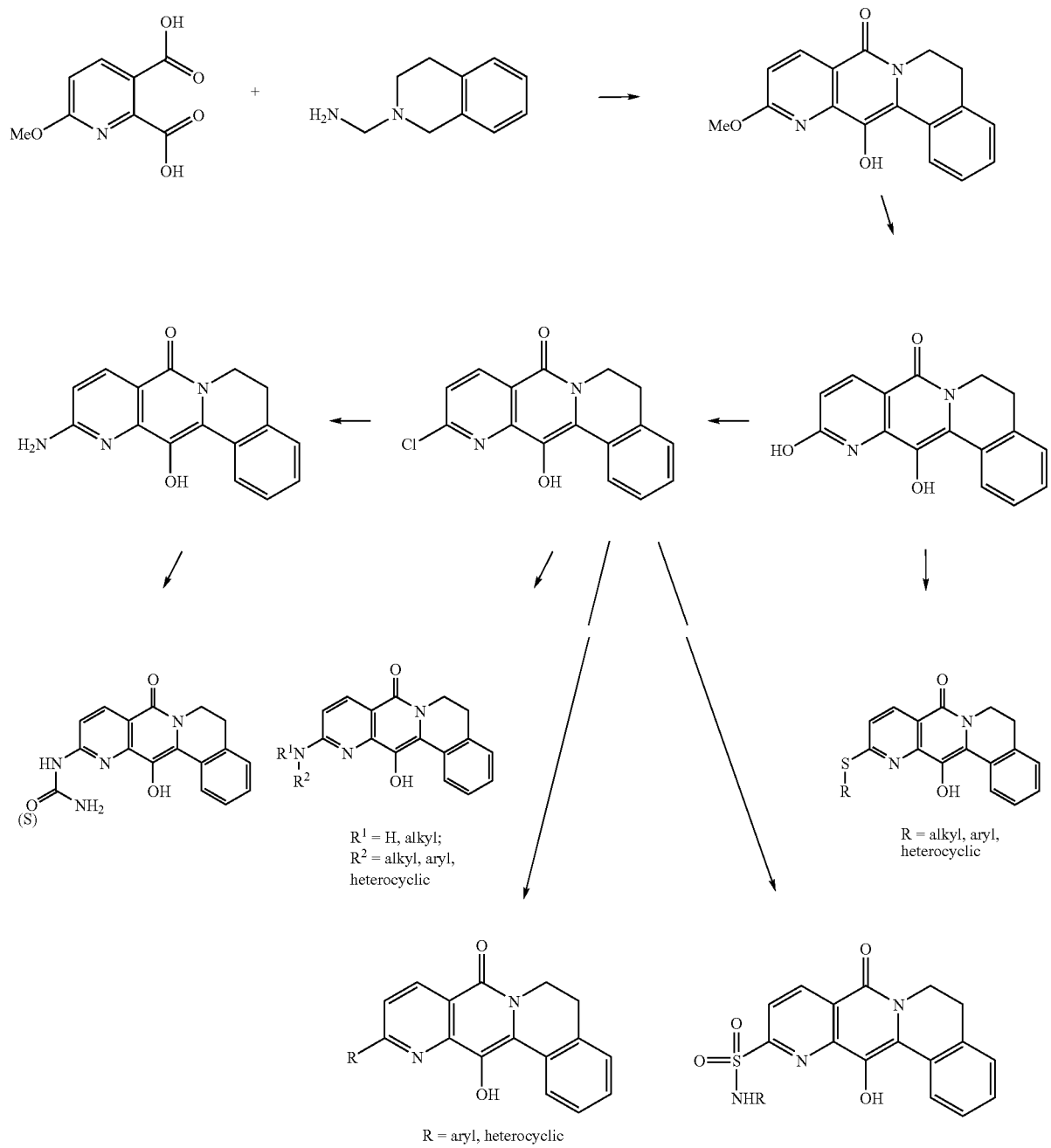
CHART D2
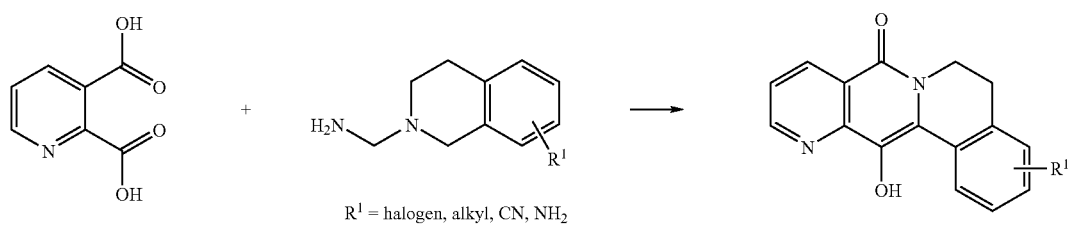
CHART D3

153

-continued

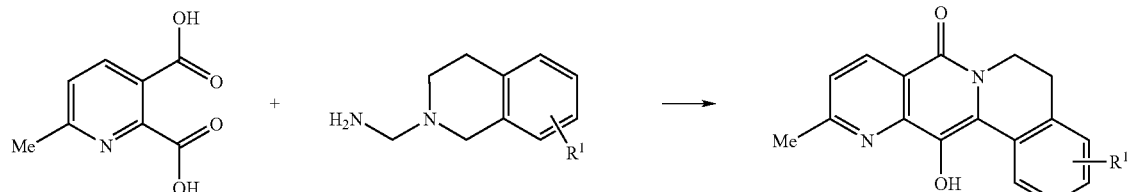

$R^1$ = halogen, alkyl, CN, $NO_2$

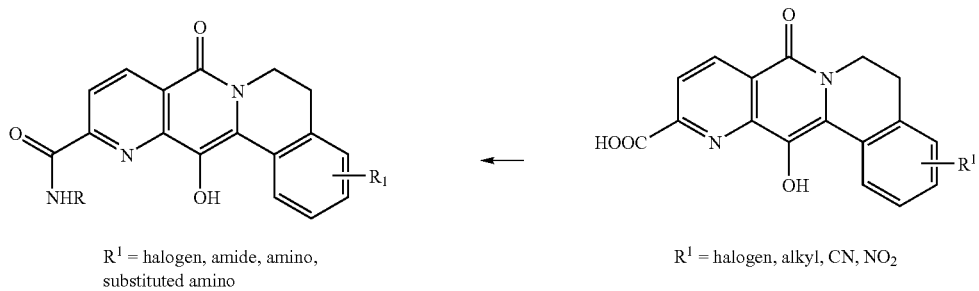

Left structure: $R^1$ = halogen, amide, amino, substituted amino

Right structure: $R^1$ = halogen, alkyl, CN, $NO_2$

154

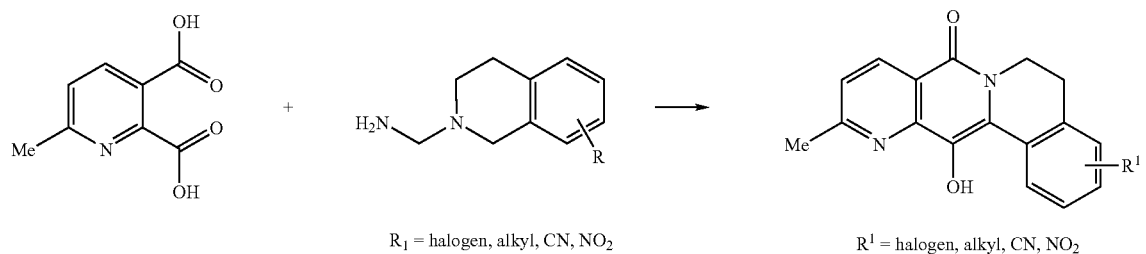

$R_1$ = halogen, alkyl, CN, $NO_2$ (left); $R^1$ = halogen, alkyl, CN, $NO_2$ (right)

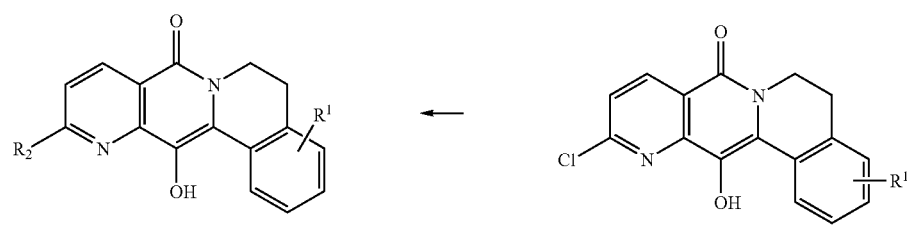

Left structure:
$R^2 = SR^3$ ($R^3$ = alkyl, aryl, heterocyclic), aryl, heterocyclic, $NR^4R^5$($R^4$ = H, alkyl; $R^5$ = alkyl, heteroaryl, acyl), NH•CO(S)•$NH_2$, $SO_2NHR^8$
$R^1$ = halogen, amide, amino, substituted amino Right structure: $R^1$ = halogen, alkyl, CN, $NO_2$ CHART E1
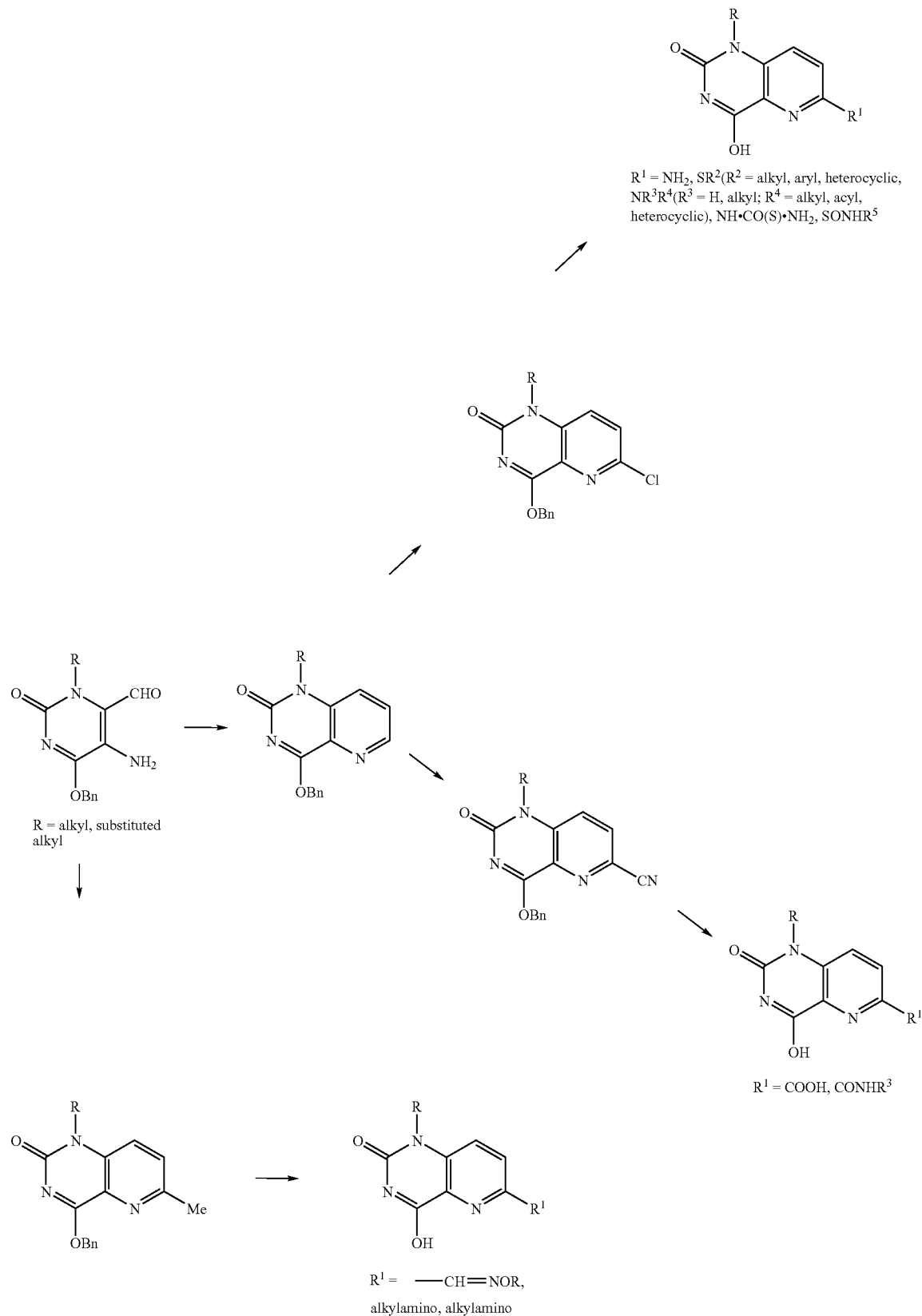

REFERENCES

1. Z.-L. Zhou, J. M. Navratil, S. X. Cai, E. R. Whittemore, S. A. Espitia, J. E. Hawkinson, M. Tran, R. M. Woodward, E. Weber and J. F. W. Keana, *Bioorg. Med. Chem.*, 2001, 9, 2061-2071.
2. M. Blanco, M. G. Lorenzo, I. Perillo and C. B. Schapira, *J. Heterocyclic Chem.*, 1996, 33, 363-366.
3. J. D. Colye, J. F. Challiner, E. J. Haws and G. L. Newport, *J. Chem. Res., M*, 1985, 3748-3747.
4. (a) A. Dondoni, G. Fantin, M. Fogagnolo, A. Medici and P. Pedrini, *Synthesis*, 1987, 998-1001. (b) A. Dondoni, F. L. Merchan, P. Merino, I. Rojo and T. Tejero, *Synthesis*, 1996, 641-646.

(6) PREPARATION OF 9-HYDROXY-PYRIDO[1,2-a]PYRIMIDIN-4-ONE

9-Hydroxypyrido[1,2-a]pyrimidin-4-one itself was synthesised according to a literature procedure (Dennin and coworkers, *J. Heterocyclic Chem.*, 1991, 28, 1287). Derivatives of 9-hydroxypyrido[1,2-a]pyrimidin-4-one can be prepared using known methods (see for example: Yale and coworkers, U.S. Pat. No. 4,022,897). For example, condensation of commercially available 2-amino-3-hydroxypyridine with an appropriate 2-substituted-3-oxo-propionic acid ethyl ester (for methods of preparation, see for example: Marabout and coworkers, Patent FR 2,765,582) produces an intermediate enamine which under dehydrating conditions yields the desired 3-substituted-9-hydroxypyrido[1,2-a]pyrimidin-4-one (Scheme 11). Further elaboration at the 8-position can be achieved using known reported methods (see for example: Smirnov and coworkers, *Chemistry of Heterocyclic Compounds*, 1992, 12, 1425).

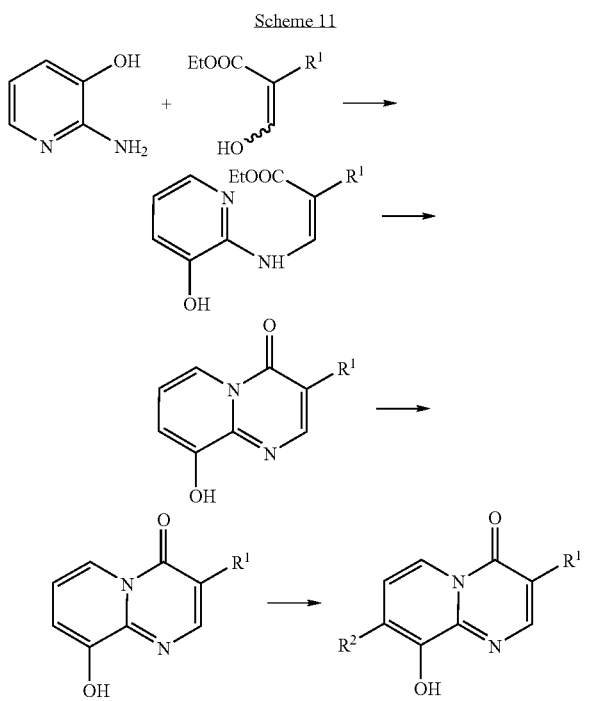

Scheme 11

Scheme 12 shows an alternate route to some functionalised 9-hydroxypyrido[1,2-a]pyrimidin-4-ones where an appropriately substituted 2-amino-3-hydroxypyridine is condensed with a 2-substituted-3-oxo-propionic acid ethyl ester. For example, 2-amino-3-chloro-3-hydroxypyridine (see Gudmundsson and coworkers, *Synthetic Communications*, 1997, 27(5), 861, for preparation) and 2-(4-chlorophenyl)-3-oxo-propionic acid ethyl ester gives an 8-chloro derivative; the latter can be further elaborated using known methods.

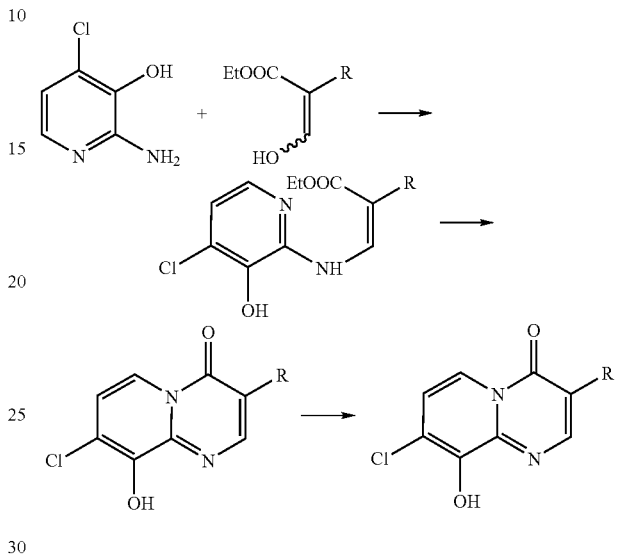

Scheme 12

(7) PREPARATION OF 8-HYDROXY-4(3H)-QUINAZOLINONE, 9-HYDROXYPYRIMIDO[1,6-a]PYRIMIDIN-4-ONE AND 9-HYDROXYPYRIDO[1,2-a]PYRIMIDIN-4-ONE

General

The following compounds/reagents were sourced commercially: amines: ethylamine, histamine, 2-(2-aminoethyl)pyridine, 2-(2-methylaminoethyl)pyridine; aldehydes: 4-imidazolecarboxaldehyde, 2-thiazolecarboxaldehyde and 2-pyridinecarboxaldehyde, azoles: pyrazole, imidazole, methylimidazole and 1H-1,2,3-triazole, boronic acids: phenylboronic acid, 2-(trifluoromethyl)phenylboronic acid, 2-methoxyphenylboronic acid, o-tolylboronic acid, 2-fluorophenylboronic acid, 3-methoxyphenylboronic acid, 4-methoxyphenylboronic acid, m-tolylboronic acid, 3,5-difluorophenylboronic acid, 2,4-difluorophenylboronic acid, 3-thiopheneboronic acid, 3-fluorophenylboronic acid and 4-fluorophenylboronic acid; and organozinc reagents: 2-pyridylzinc bromide, 2-(methylthio)phenylzinc iodide, 2-(ethoxycarbonyl)phenylzinc iodide and 6-methylpyridylzinc bromide (0.5 M solution in THF) (Aldrich). 3-Pyridylboronic acid was purchased from Frontier Scientific. 2-Aminomethylthiazole was prepared according to the literature.[1] Solvents were analytical grade and used as supplied. THF was distilled from sodium and benzophenone under argon. $^1$H NMR spectra (δ, relative to TMS) were recorded on a Varian Unity 300 spectrometer unless otherwise indicated; J-Values are given in hertz. Mass spectral data were recorded on a Micromass Quattro II mass spectrometer.

The synthesis of derivatives of 3 classes of compounds: 8-hydroxy-4(3H)-quinazolinone (A), 9-hydroxypyrimido[1,6-a]pyrimidin-4-one (B) and 9-hydroxypyrido[1,2-a]pyrimidin-4-one (C), is described.

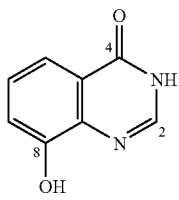

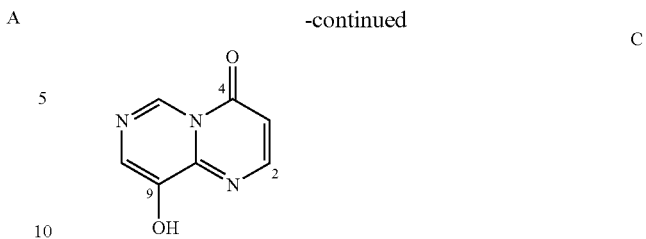

The method[2] of Iyer and coworkers was employed in the synthesis of compounds A1 and A2. Further derivatisation of these compounds to provide a series of 8-hydroxy-4(3H)-quinazolinones employed routes shown in Charts A1-A2. Halogenation of the 5- and/or 7-positions in the 8-hydroxy-4(3H)-quinazolinone system followed methods previously described[3] in the literature for the reactions on 8-hydroxyquinolines. The synthesis of the parent system in classes B and C, compounds B1 and C1, employed the procedure previously reported[4] by Dennin and coworkers. Further derivatisation of B1 and C1 followed routes shown in Charts B1-B2 and C1-C2, respectively.

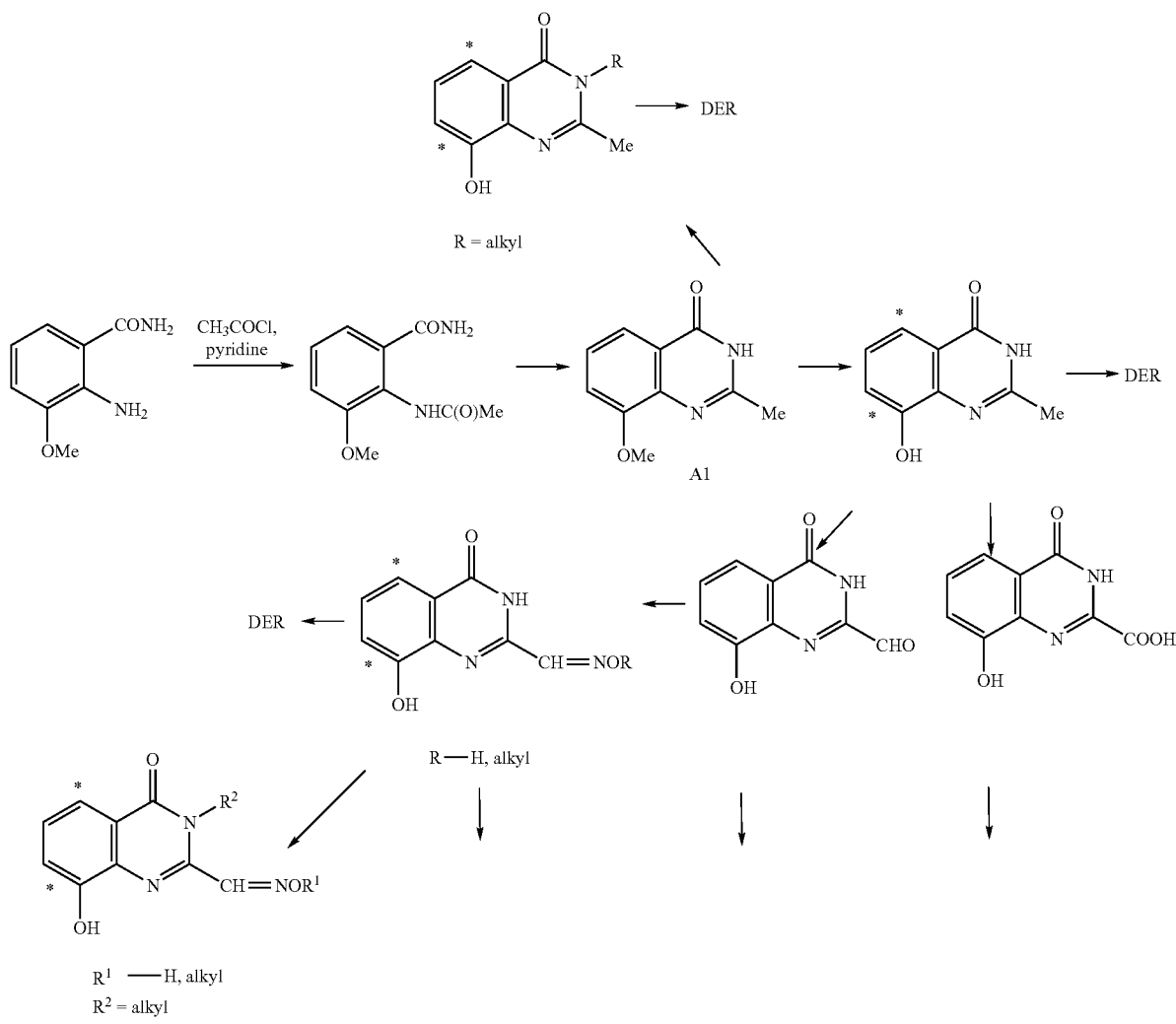

-continued
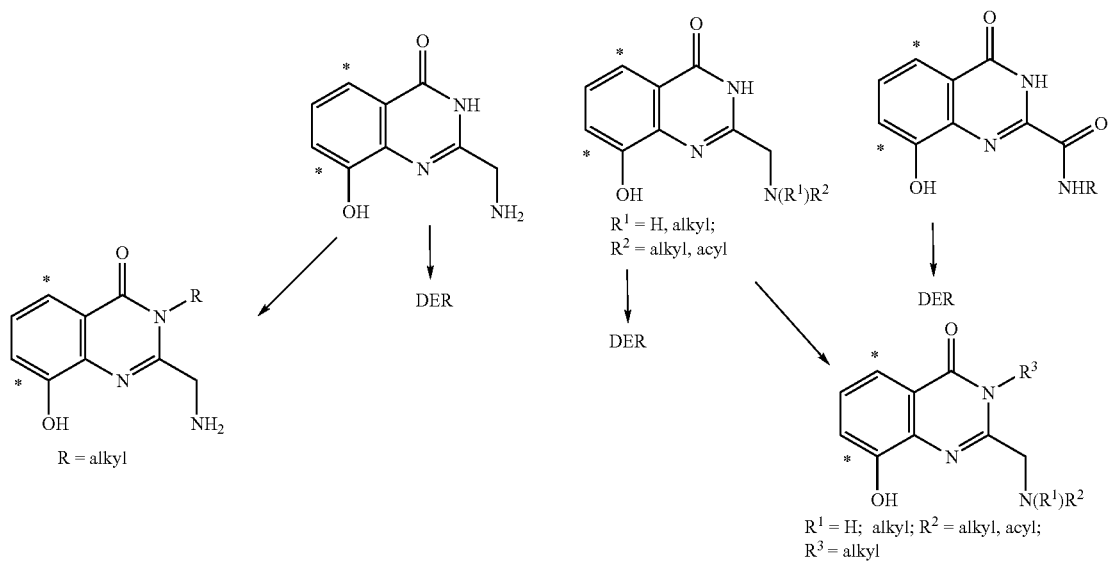
DER: -and derivatives with halogen-substitution, preferably at 5- and/or 7-position(s) indicated by asterik
CHART A2
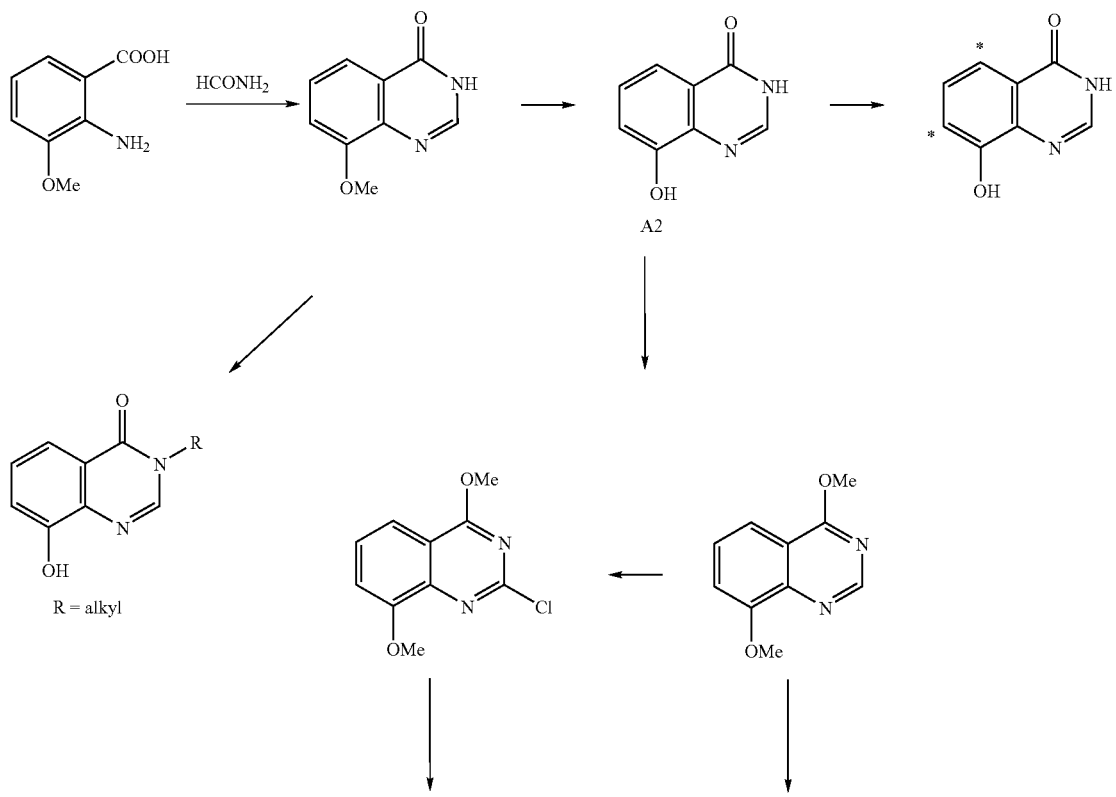

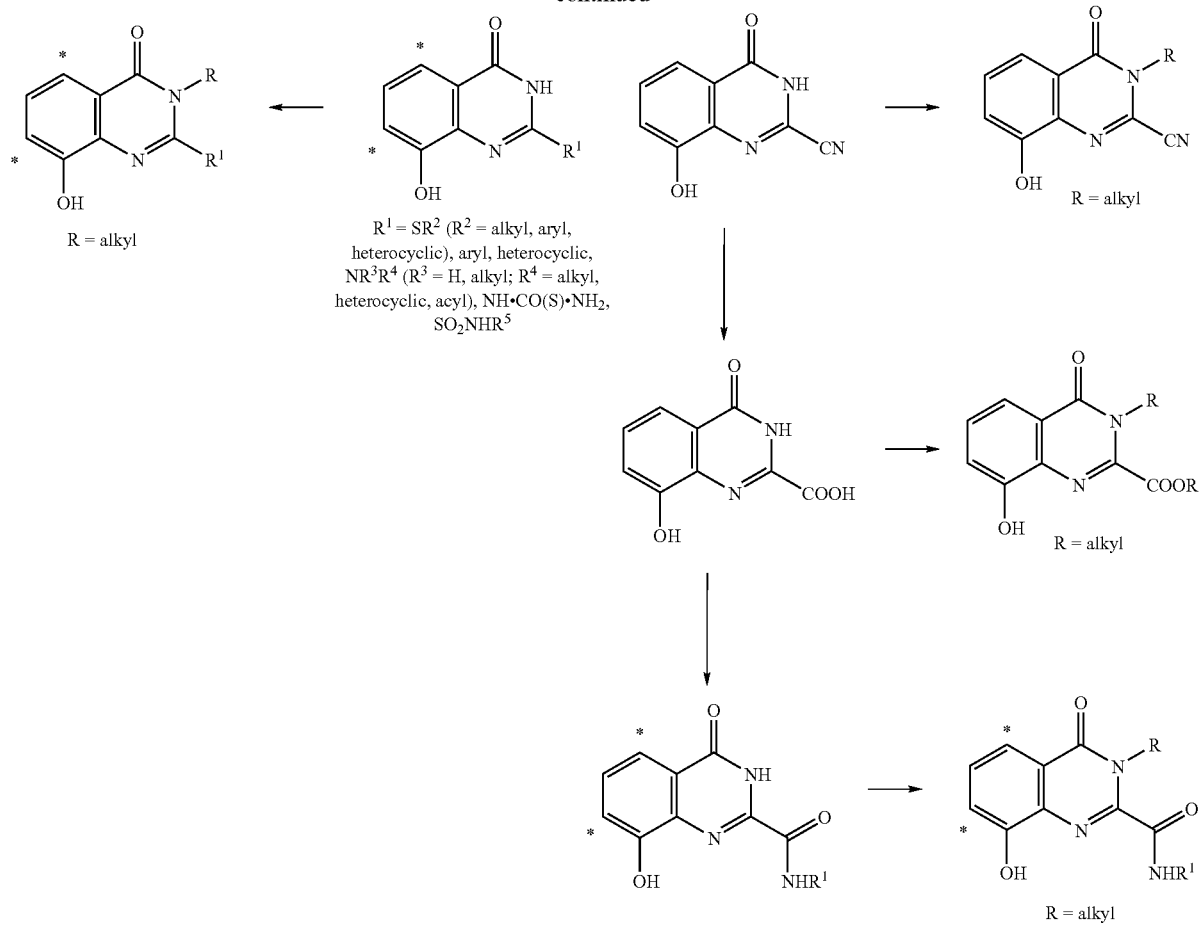
*-and derivatives with halogen-substitution, preferably at the 5-and/or 7-position(s) indicated by asterisk
CHART B1
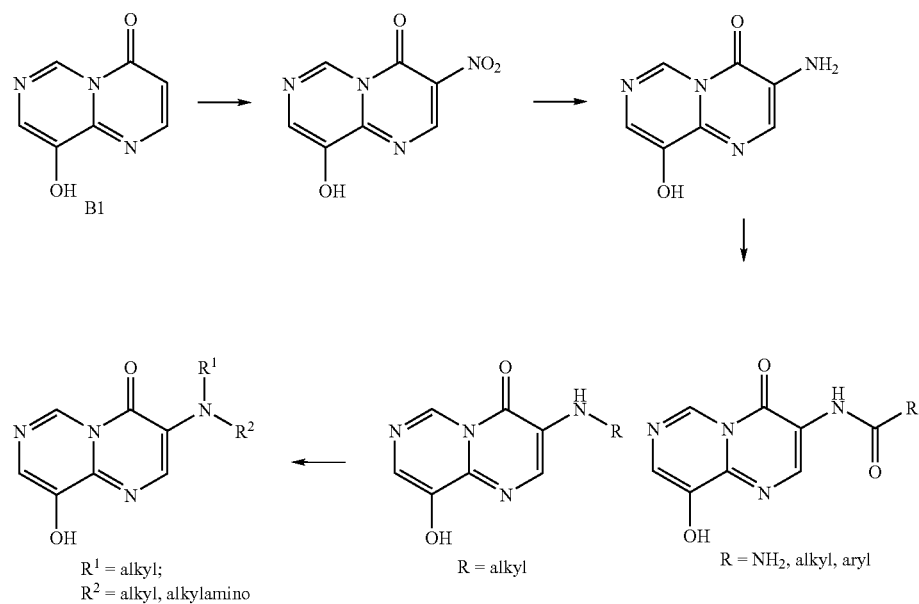

CHART B2
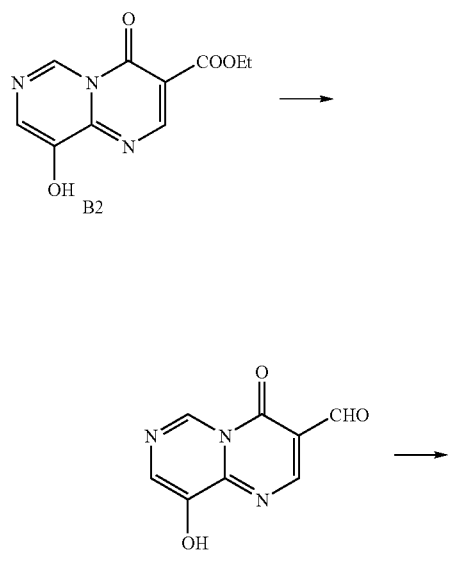
-continued
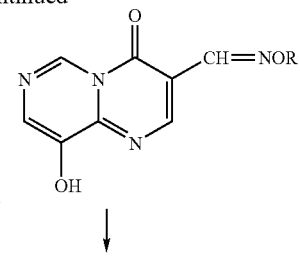
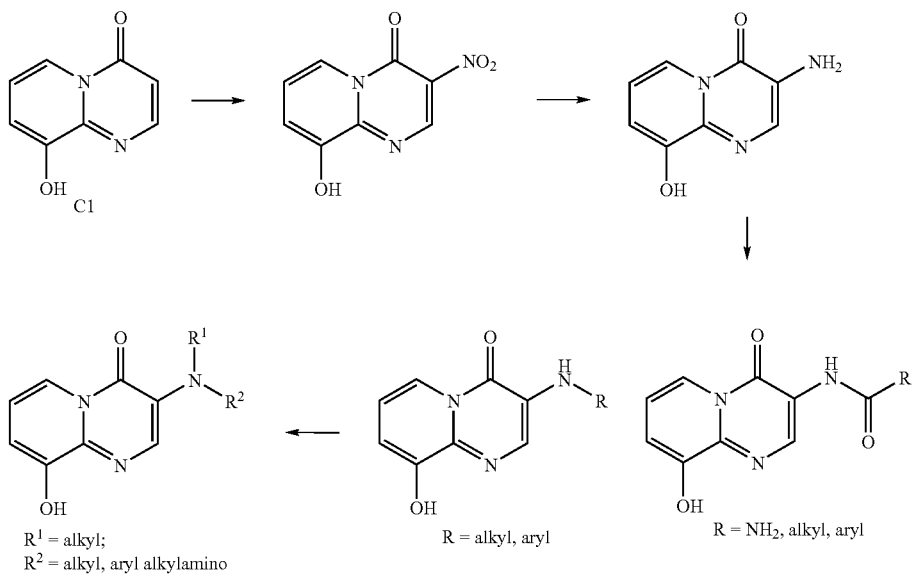
CHART C2
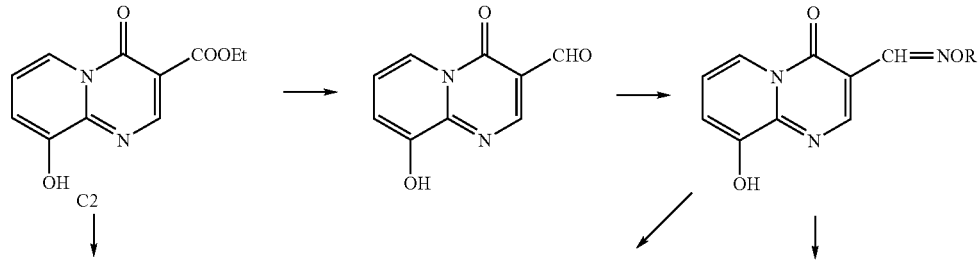

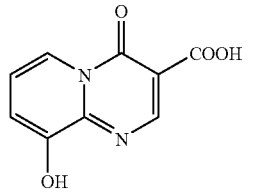
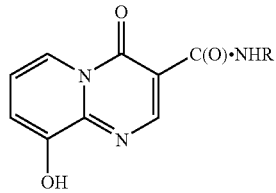

-continued

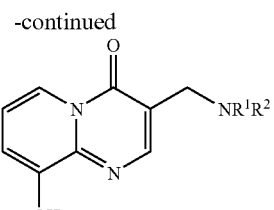

R¹ = H, alkyl;
R² = alkyl, alkylamino, acyl

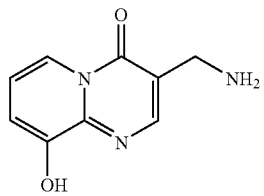

REFERENCES 1. (a) A. Dondoni, G. Fantin, M. Fogagnolo, A. Medici and P. Pedrini, *Synthesis,* 1987, 998-1001. (b) A. Dondoni, F. L. Merchan, P. Merino, I. Rojo and T. Tejero, *Synthesis,* 1996, 641-646.
2. R. N. Iyer, N. Anand and M. L. Dhar, *J. Sci. Ind. Res. A, General,* 1956, 15C, 1-7.
3. H. Gerson, M. W. McNeil, R. Parmegiani and R. K. Godfrey, *J. Med. Chem.,* 1972, 15, 987-989, and references cited therein.
4. F. Dennin, D. Blondeau and H. Sliwa, *J. Heterocyclic Chem.,* 1991, 28, 1287-1291.

General

The following compounds/reagents were sourced commercially: 2,4-dichloroanisole, 2,4-dichlorobenzoic acid, 2,3-pyridine dicarboxylic acid, 6-methyl-2,3-pyridinedicarboxylic acid and 2-amino-3-hydroxypyridine (Aldrich). These compounds were prepared according to literature procedures: 5-chloro-8-hydroxy-[1,6]naphthyridine-7-carboxylic acid methyl ester (PB 1045) from 5,8-dihydroxy-[1,6] naphthyridine-7-carboxylic acid methyl ester (Albert and Hampton, *J. Chem. Soc.,* 1952, 4985; Blanco and coworkers, *J. Heterocyclic Chem.,* 1996, 33, 361); 9-hydroxypyrido[1,2-a]pyrimidin-4-one (PB 1048) (Dennin and coworkers, *J. Heterocyclic Chem.,* 1991, 28, 1287); 8-hydroxy-3H-quinazolin-4-one (PB 1049) (Iyer and Dhar, *J. Sci. Ind. Res.,* 1956, 15C, 1). Solvents were analytical grade and used as supplied. THF was distilled from sodium and benzophenone under argon. ¹H NMR spectra (δ, relative to TMS) were recorded on a Varian Inova 400 spectrometer unless otherwise indicated; J-Values are given in hertz; multiplicity: s=singlet, d=doublet, m=multiplet, sep=septet, t=triplet, q=quartet. Electrospray mass spectral data were recorded on a Micromass Quattro II mass spectrometer.

Example 1

(A) 6,8-Dichloro-3-methylquinoxalin-5-ol (1064) and 6,8-Dichloro-2-methylquinoxalin-5-ol (1065)

Step A: Preparation of 6,8-Dichloro-3-methylquinoxalin-5-ol and 6,8-Dichloro-2-methylquinoxalin-5-ol

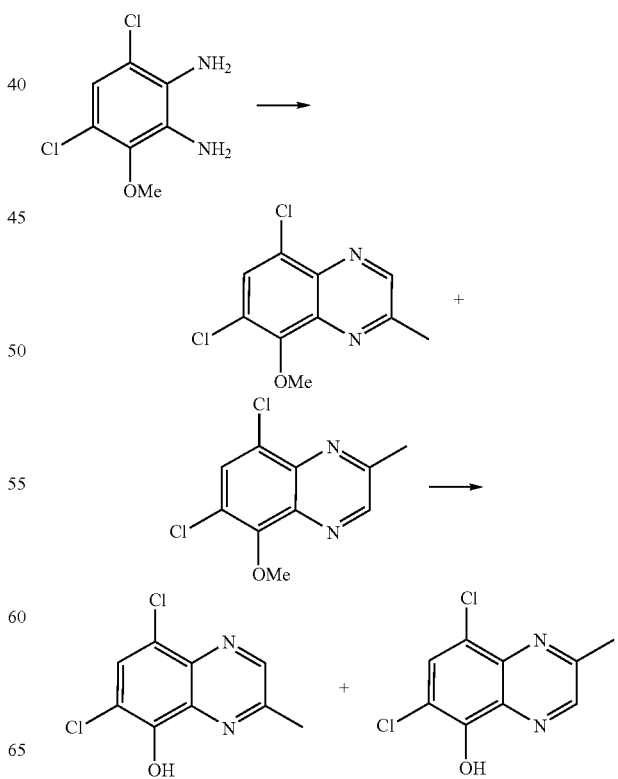

To a stirred suspension of 2,3-diamino-4,6-dichloroanisole (prepared from 2,4-dichloroanisole according to the conditions reported by Philips' Gloeilampenfabrieken, N. V. (1973), Patent GB 1303711) (1.48 g, 7.15 mmol), 2 M AcOH (14.2 mL) and 4 M NaOAc solution (8.8 mL) at 60° C. was added 40% aqueous pyruvic aldehyde solution (1.15 mL). The mixture was then stirred at the same temperature for a further 40 min. The precipitate was isolated via filtration and washed with $H_2O$ (5 mL×2). This solid (1.21 g) was then dissolved in ethyl acetate and the solution was filtered through a short plug of $SiO_2$-gel (ethyl acetate/hexanes, 1:3). This provided a 1:1 mixture of 6,8-dichloro-5-methoxy-2-methylquinoxaline and 6,8-dichloro-5-methoxy-3-methylquinoxaline as a pale pink solid (1.13 g).

To an ice-cooled solution of the mixture of the 2-methyl- and 3-methyl-compounds (2.48 g, 0.01 mol) in dichloromethane (30 mL) was added $BBr_3$ (20.1 mL of a 1 M solution in dichloromethane). The cooling bath was removed after 1 h and the mixture was left to stir at 30° C. for 16 h. MeOH was added and the solution was concentrated. The latter process was repeated four more times. Dichloromethane (20 mL) was added to the remaining residue and the pH of the mixture was adjusted to 7 (conc $NH_4OH$). The organic layer was dried, concentrated, and filtered through a short plug of $SiO_2$-gel (dichloromethane/MeOH, 19:1) to give a 1:1 mixture of 6,8-dichloro-2-methylquinoxalin-5-ol and 6,8-dichloro-3-methylquinoxalin-5-ol as a light yellow solid (1.51 g). A sample of this mixture was extracted with diethyl ether (3×). The ethereal extracts were concentrated and the residue recrystallised from isopropanol to yield 6,8-dichloro-2-methyl-quinoxalin-5-ol as yellow needles. The remaining solid after extraction with diethyl ether was washed with MeOH to give 6,8-dichloro-3-methyl-quinoxalin-5-ol as a pale pink solid.

6,8-Dichloro-3-methylquinoxalin-5-ol: $^1$H NMR ($CDCl_3$): δ 8.88 (s, 1H), 8.01 (br, 1H), 7.79 (s, 1H), 2.83 (s, 3H).

6,8-Dichloro-2-methylquinoxalin-5-ol: $^1$H NMR ($CDCl_3$): δ 8.68 (s, 1H), 7.95 (br, 1H), 7.83 (s, 1H), 2.87 (s, 3H).

Step B: Preparation of 8-Benzyloxy-5,7-dichloro-2-methylquinoxaline

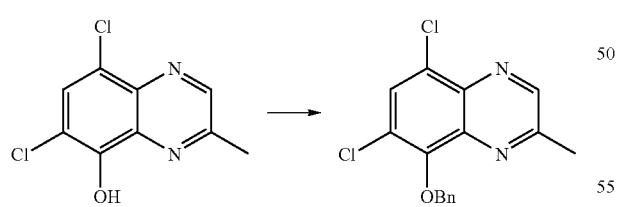

A mixture of 6,8-dichloro-3-methylquinoxalin-5-ol (150 mg, 0.655 mmol), benzyl bromide (0.20 mL, 1.68 mmol), KOH (0.09 g) and EtOH (10 mL) was heated under reflux for 16 h, cooled, and concentrated. Dichloromethane (20 mL) was added and the mixture washed with $H_2O$ (5 mL×2), dried and concentrated. The residue was purified via $SiO_2$-gel chromatography (dichloromethane/MeOH, 1:0-150:1) to give 8-benzyloxy-5,7-dichloro-2-methylquinoxaline (98 mg, 47%).—$^1$H NMR ($CDCl_3$): δ 8.82 (s, 1H), 7.81 (s, 1H), 7.58 (m, 2H), 7.38 (m, 2H), 5.45 (s, 2H), 2.85 (s, 3H).

Step C: Preparation of 8-Benzyloxy-5,7-dichloroquinoxaline-2-carboxaldehyde

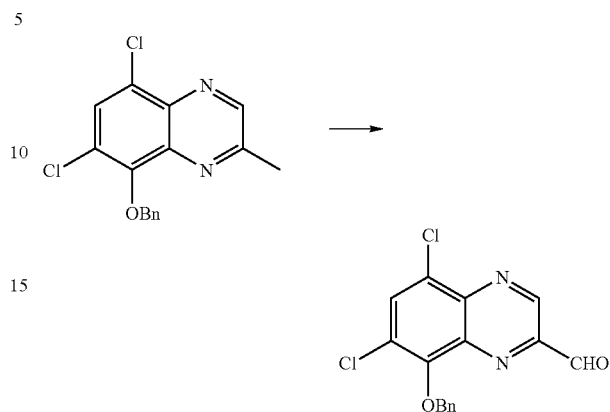

A suspension of the 2-methyl product from Step B (93 mg, 0.291 mmol) and $SeO_2$ (100 mg) in dioxane (4 mL) and $H_2O$ (0.4 mL) was heated under reflux for 3 h. The mixture was cooled, filtered (celite), and concentrated. Dichloromethane was added and the insoluble material was filtered off. The solvent was evaporated and the residue purified by $SiO_2$-gel chromatography (dichloromethane) to yield the desired aldehyde as an off-white solid (57 mg, 59%).

8-Benzyloxy-5,7-dichloroquinoxaline-2-carboxaldehyde: $^1$H NMR ($CDCl_3$): δ 10.31 (s, 1H), 9.48 (s, 1H), 8.06 (s, 1H), 7.58-7.35 (m, 5H), 5.55 (s, 2H).

(B) 6,8-Dichloro-3-(dimethylaminomethyl)quinoxalin-5-ol hydrochloride (1066)

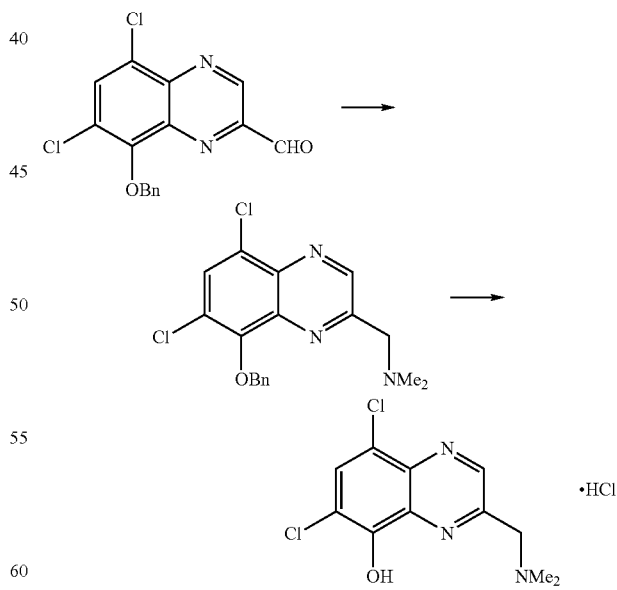

Sodium triacetoxyborohydride (50 mg, 0.236 mmol) was added to a stirred solution of the aldehyde from Step C (57 mg, 0.171 mmol), dimethylamine hydrochloride (15.1 mg, 0.185 mmol) and $Et_3N$ (0.023 mL) in 1,2-dichloroethane (2 mL). After 1 h, dichloromethane (20 mL) was added and the resulting solution was washed with sat'd NaHCO₃ solution (5 mL×2), dried, and concentrated. The residue was purified via SiO₂-gel chromatography (dichloromethane/MeOH, 1:0-75:1) to yield the desired (8-benzyloxy-5,7-dichloro-quinoxalin-2-ylmethyl)dimethylamine as a pale yellow solid (38 mg, 61%).—¹H NMR (CDCl₃): δ 9.11 (s, 1H), 7.84 (s, 1H), 7.58-7.35 (m, 5H), 5.47 (s, 2H).

A solution of (8-benzyloxy-5,7-dichloro-quinoxalin-2-ylmethyl)dimethylamine (38 mg, 0.105 mmol) in conc HCl (2 mL) was stirred at room temperature for 16 h. The orange solution was concentrated to dryness and the remaining residue was washed with diethyl ether (2 mL×3) to give the desired product as a light yellow solid (27 mg, 83%).

6,8-Dichloro-3-(dimethylaminomethyl)quinoxalin-5-ol hydrochloride: ¹H NMR (DMSO-d₆): δ 8.75 (s, 1H), 7.78 (s, 1H), 4.40 (br, 2H), 2.13 (s, 6H); mass spectrum: m/z 272, 274, 276 (M⁺+1, 100%, 66%, 11%).

Example 2

(A) 5,7-Dichloro-3-(4-fluorophenyl)-8-hydroxy-3H-quinazolin-4-one (1055)

Step A: Preparation of 4,6-Dichloro-3-hydroxy-2-nitrobenzoic acid

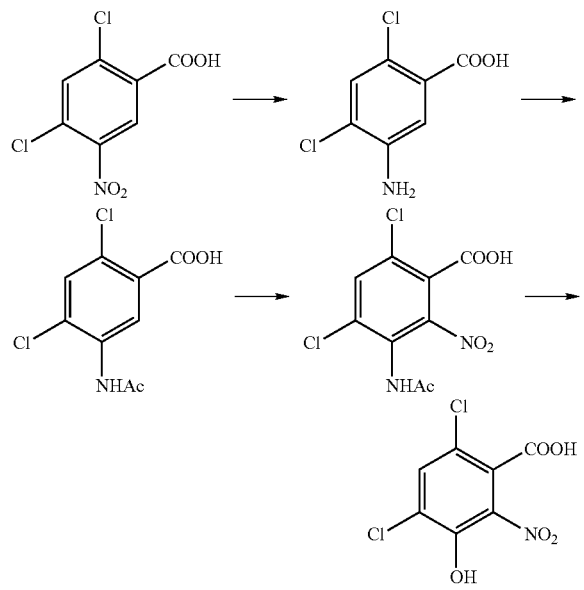

Tin (II) chloride hydrate (50 g, 0.29 mol) was added to a solution of 2,4-dichloro-5-nitrobenzoic acid (prepared according to a reported procedure (Golstein, H. and Schaaf, E., *Helv. Chim. Acta,* 1957, 57(23), 132)) (10.0 g, 0.045 mol) in EtOH (200 mL). The mixture was stirred at 70° C. for 0.5 h, cooled and poured onto ice. The pH of the mixture was adjusted to 8 (sat'd NaHCO₃). The suspension was left to stir at room temperature for 5 h and re-acidified to pH 5 (glacial HOAc). The resulting white suspension was continuously extracted with ethyl acetate, the extracts combined, washed with brine, dried and concentrated to yield the desired amine as an off-white solid (8.8 g, 96%).

5-Amino-2,4-dichlorobenzoic acid: ¹H NMR (CD₃OD): δ 7.30 (s, 1H), 7.27 (s, 1H).

Acetic anhydride (27 mL) was added to 5-amino-2,4-dichlorobenzoic acid (8.0 g, 0.041 mol) in glacial HOAc (150 mL). The solution was stirred at room temperature for 0.5 h and concentrated to yield the desired acetamide as a white solid (9.6 g, 96%).

5-Acetamido-2,4-dichlorobenzoic acid: ¹H NMR (CD₃OD): δ 8.32 (s, 1H), 7.62 (s, 1H), 2.19 (s, 3H).

5-Acetamido-2,4-dichlorobenzoic acid (9.6 g, 0.039 mol) was added in small portions over 30 min to a stirred ice-cooled solution of fuming nitric acid (1.8 mL, 0.043 mol) and conc sulfuric acid (120 mL). After the addition was complete, more fuming nitric acid (17 mL) and conc sulfuric acid (80 mL) were added at 30 min and 60 min intervals. The reaction mixture was then left to stir for an additional 2.5 h at 0° C., allowed to warm to 12-16° C. and left to stir at this temperature until all starting material was consumed (about 3 h). The solution was poured onto ice and extracted with ethyl acetate (3×). The organic extracts were combined, washed with brine, dried, and concentrated to give 3-acetamido-4,6-dichloro-2-nitrobenzoic acid as an orange solid (9.8 g, 86%).

3-Acetamido-4,6-dichloro-2-nitrobenzoic acid: ¹H NMR (CD₃OD): δ 8.01 (s, 1H), 2.13 (s, 3H).

3-Acetamido-4,6-dichloro-2-nitrobenzoic acid (9.7 g, 0.033 mol) was added to a solution of KOH (18.7 g, 0.034 mol) in H₂O (85 mL). The solution was heated under reflux for 18 h and cool to room temperature. Conc HCl was added to adjust the pH to 0. The mixture was diluted with ethyl acetate and H₂O and left to stir at room temperature for 30 min. The layers were separated; the aqueous layer was extracted with ethyl acetate (3×), the extracts combined with the original organic layer, washed with brine, dried and concentrated to yield 4,6-dichloro-3-hydroxy-2-nitrobenzoic acid as a dark red solid (7.4 g, 89%); m.p. 188-189° C. (lit. m.p. (Linderberg, M., Hellberg, S., Bjork, S. et al, *Eur. J. Med. Chem.,* 1999, 34, 729-744): 186° C. (dec)).

4,6-Dichloro-3-hydroxy-2-nitrobenzoic acid: ¹H NMR (CD₃OD): δ 7.79 (s, 1H); mass spectrum: m/z 250, 252, 254 (M⁺−1, 100%, 66%, 11%).

Step B: Preparation of 2-Amino-4,6-dichloro-N-(4-fluorophenyl)-3-hydroxybenzamide

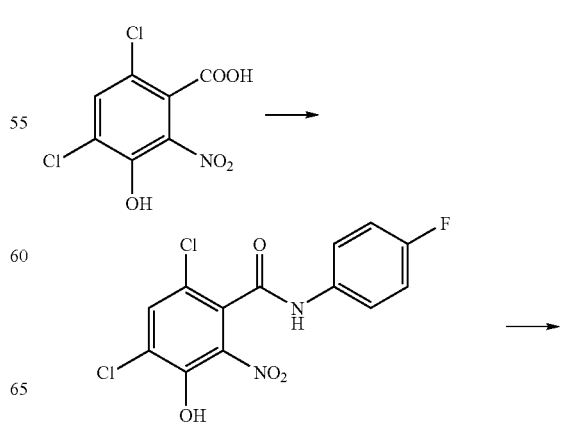

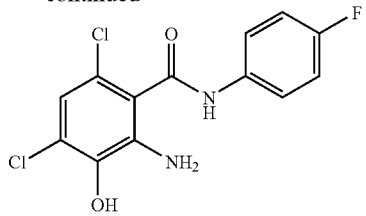

CDI (2.2 g, 0.013 mol) was added to a stirred solution of 4,6-dichloro-3-hydroxy-2-nitrobenzoic acid (3.0 g, 0.012 mol) in anhydrous THF (30 mL) and DMF (2 mL). After 40 min, 4-fluoroaniline (4 mL, 0.042 mol) was added. The solution was heated under reflux overnight, cooled, and concentrated to a dark brown viscous oil. The oil was purified via SiO$_2$-gel chromatography (dichloromethane/methanol, 19:1-9:1) to yield 4,6-dichloro-N-(4-fluorophenyl)-3-hydroxy-2-nitrobenzamide as a light brown oil (2.7 g, 65%).

4,6-Dichloro-N-(4-fluorophenyl)-3-hydroxy-2-nitrobenzamide: $^1$H NMR (CD$_3$OD): δ 7.58 (m, 2H), 7.44 (s, 1H), 7.07 (m, 2H).

A suspension of tin (II) chloride hydrate (8.8 g, 0.039 mol), 4,6-dichloro-N-(4-fluorophenyl)-3-hydroxy-2-nitrobenzamide (2.7 g, 0.008 mol) and EtOH (70 mL) was heated at 70° C. for 1 h and left to cool to room temperature. The mixture was poured onto ice, basified to pH 8 (sat'd NaHCO$_3$), and stirred at room temperature for 1.5 h before re-acidifying to pH 6.5 with glacial HOAc. The suspension was filtered; the filtrate was concentrated to give a beige solid. The beige solid was combined with the filter cake and extracted with hot ethyl acetate (5×). The extracts were combined to provide 2-amino-4,6-dichloro-N-(4-fluorophenyl)-3-hydroxybenzamide as a solid (2.0 g, 79%).

2-Amino-4,6-dichloro-N-(4-fluorophenyl)-3-hydroxybenzamide: $^1$H NMR (CD$_3$OD): δ 7.69 (m, 2H), 7.09 (m, 2H), 6.73 (s, 1H).

Step C: Preparation of 5,7-Dichloro-3-(4-fluorophenyl)-8-hydroxy-3H-quinazolin-4-one (1055)

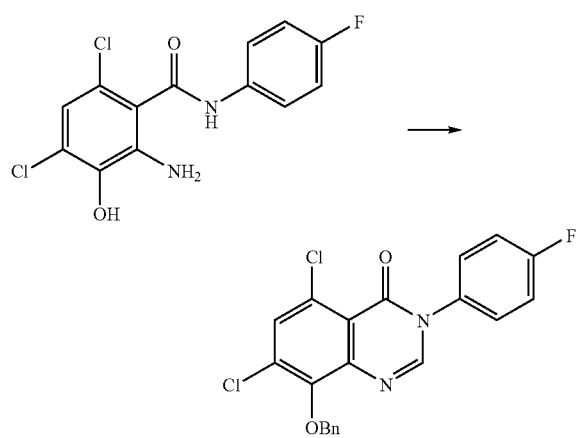

A solution of CDI (0.65 g, 4.0 mmol) and formic acid (0.17 mL, 3.6 mmol) in anhydrous THF (18 mL) and DMF (2 mL) was stirred at room temperature for 4 h. A solution of the amine from Step B (1.01 g, 3.2 mmol) in THF (15 mL) was then added, the solution heated under reflux for 15 h, and concentrated. The resulting brown solid was washed with ethyl acetate to yield the title compound as white needles (0.49 g, 47%).

5,7-Dichloro-3-(4-fluorophenyl)-8-hydroxy-3H-quinazolin-4-one: $^1$H NMR (CDCl$_3$/CD$_3$OD, 9:1): δ 8.10 (br, 1H), 7.50 (s, 1H), 7.36 (m, 2H), 7.21 (m, 2H); mass spectrum: m/z 325, 327, 329 (M$^+$+1, 100%, 66%, 11%).

(B) 5,7-Dichloro-3-cyclopropyl-8-hydroxy-3H-quinazolin-4-one (1061)

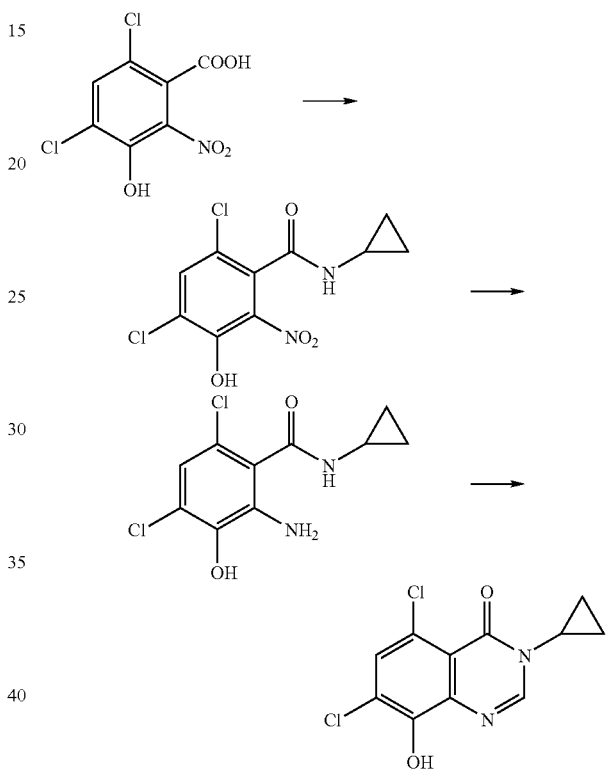

The following compounds were prepared using the methods described in Example 3: thus, replacing 4-fluoroaniline with cyclopropylamine in Step B (reaction was performed in a sealed tube at 70° C.) gave, after SiO$_2$-gel chromatography (dichloromethane/MeOH, 9:1), 4,6-dichloro-N-cyclopropyl-3-hydroxy-2-nitrobenzamide (43%).—$^1$H NMR (CD$_3$OD): δ 7.37 (s, 1H), 2.73 (m, 1H), 0.74 (m, 2H), 0.59 (m, 2H); mass spectrum: m/z 289, 291, 293 (M$^+$−1, 100%, 66%, 11%).

Reduction of 4,6-dichloro-N-cyclopropyl-3-hydroxy-2-nitrobenzamide with tin (II) chloride hydrate using the conditions as described in Step B yielded 2-amino-4,6-dichloro-N-cyclopropyl-3-hydroxybenzamide (93%).—$^1$H NMR (CD$_3$OD): δ 6.67 (s, 1H), 2.86 (m, 1H), 0.79 (m, 2H), 0.62 (m, 2H).

CDI-mediated coupling of formic acid with 2-amino-4,6-dichloro-N-cyclopropyl-3-hydroxybenzamide (as described in Step C) gave, after washing with ethyl acetate and MeOH, 5,7-dichloro-3-cyclopropyl-8-hydroxy-3H-quinazolin-4-one as a white solid (40%).—$^1$H NMR (CDCl$_3$/CD$_3$OD, 9:1): δ 8.30 (s, 1H), 7.46 (s, 1H), 3.22 (m, 1H), 1.21 (m, 2H), 0.94 (m, 2H); mass spectrum: m/z 271, 273, 275 (M$^+$+1, 100%, 66%, 11%).

(C) 5,7-Dichloro-8-hydroxy-3H-quinazolin-4-one (1067)

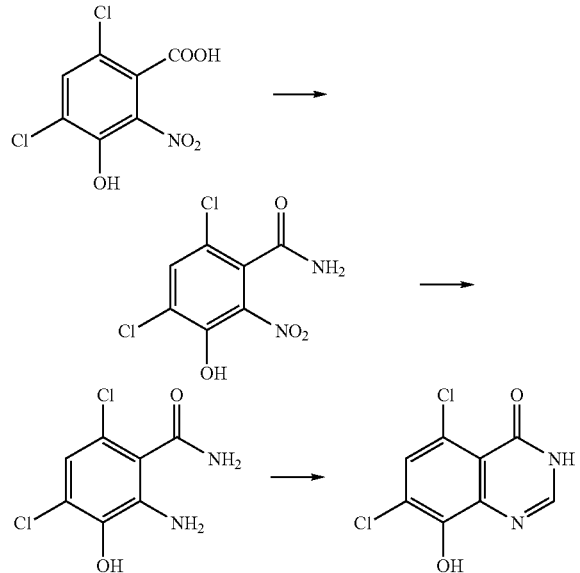

A solution of 2,4-dichloro-5-hydroxy-6-nitrobenzoic acid (Step A) (4.40 g, 17.6 mmol) and thionyl chloride (2 mL, 27 mmol) in toluene (60 mL) was heated under reflux for 1 h and allowed to cool to room temperature. The solution was added to conc NH$_4$OH (40 mL) at 0° C. The cooling bath was removed and the mixture stirred at room temperature for 2 h and then concentrated to give crude 4,6-dichloro-3-hydroxy-2-nitrobenzamide as a brown solid.—$^1$H NMR (CD$_3$OD): δ 7.33 (s, 1H); mass spectrum: m/z 249, 251, 253 (M$^+$−1, 100%, 66%, 11%).

Reduction of 4,6-dichloro-3-hydroxy-2-nitrobenzamide with tin (II) chloride hydrate according to the conditions as described in Step B gave 2-amino-4,6-dichloro-3-hydroxybenzamide as a beige solid (2.5 g, 62% (2 steps)).—$^1$H NMR (CD$_3$OD): δ 6.69 (s, 1H).

According to the procedure described in Step C, 2-amino-4,6-dichloro-3-hydroxybenzamide and formic acid in the presence of CDI gave, after washing the crude product with MeOH, 5,7-dichloro-8-hydroxy-3H-quinazolin-4-one as a white solid (36%).—$^1$H NMR (DMSO-d$_6$): δ 8.12 (s, 1H), 7.55 (s, 1H); mass spectrum: m/z 229, 231, 233 (M$^+$−1, 100%, 66%, 11%).

Example 3

(A) 7-Morpholin-4-yl-[1,6]naphthyridin-8-ol (1053)

Step A: Preparation of 7-Amino-8-isopropoxy-[1,6]naphthyridine

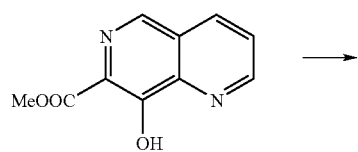

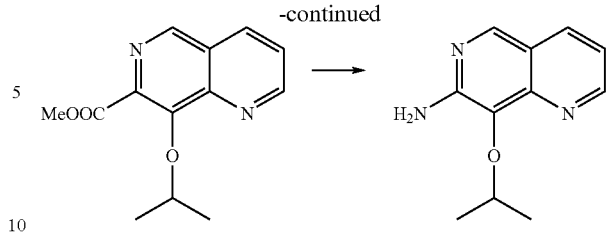

2-Bromopropane (0.9 mL) was added to a stirred mixture of 8-hydroxy-[1,6]naphthyridine-7-carboxylic acid methyl ester (prepared according to Anthony and coworkers, Patent WO 02/30931 A2) (1.00 g, 4.90 mmol), K$_2$CO$_3$ (2.79 g) and DMSO (15 mL). After 40 h at 50° C., sat'd NH$_4$Cl (20 mL) was added and the mixture extracted with dichloromethane (10 mL×3). The extracts were combined and concentrated. Diethyl ether (40 mL) was added to the residue and the resulting mixture washed successively with H$_2$O (5 mL×2) and brine (10 mL), and dried. Solvent removal gave 8-isopropoxy-[1,6]naphthyridine-7-carboxylic acid methyl ester (1.06 g, 88%).—$^1$H NMR (CDCl$_3$): δ 9.16 (dd, J=1.9 and 4.3, 1H), 9.03 (s, 1H), 8.34 (dd, J=1.9 and 8.5, 1 H), 7.63 (dd, J=4.3 and 8.5, 1H), 5.33 (sep, J=6.2, 1H), 4.04 (s, 3H), 1.42 (d, J=6.2, 6H).

A solution of 8-isopropoxy-[1,6]naphthyridine-7-carboxylic acid methyl ester (1.06 g, 4.30 mmol) in MeOH (10 mL) was added dropwise over 5 min into a stirred solution of hydrazine hydrate (2.5 mL), left to stir for a further hour, and concentrated. This provided the desired crude 7-acyl hydrazide as a golden syrup (1.06 g).

8-Isopropoxy-[1,6]naphthyridine-7-carboxylic acid hydrazide: $^1$H NMR (CDCl$_3$): δ 9.16 (dd, J=1.8 and 4.0, 1H), 9.08 (br, 1H), 9.07 (s, 1H), 8.35 (dd, J=1.8 and 8.2, 1H), 7.64 (dd, J=4.0 and 8.2, 1H), 6.02 (br, 1H), 5.39 (sep, J=6.2, 1H), 4.10 (br, 2H), 1.45 (d, J=6.2, 6H).

To a stirring ice-cooled solution of the 7-acyl hydrazide (1.06 g, 4.30 mmol) in 1 M HCl (6 mL) was added a solution of sodium nitrite (334 mg, 4.84 mmol) in H$_2$O (1.5 mL) dropwise at such a rate that the temperature did not rise above 5° C. The mixture was left to stir at 0° C. for a further 20 min and then concentrated in vacuo. HOAc (5 mL) and H$_2$O (5 mL) were added and the resulting orange solution heated at 95° C. for 24 h, cooled, and concentrated. H$_2$O (10 mL) was added, the pH of the mixture was adjusted to 8 (conc NH$_4$OH), extracted with dichloromethane (10 mL×3), and dried. Solvent removal gave the 7-amine as an orange solid (467 mg, 53%).

7-Amino-8-isopropoxy-[1,6]naphthyridine: $^1$H NMR (CDCl$_3$): δ 8.88 (dd, J=1.5 and 4.0, 1H), 8.62 (s, 1H), 8.07 (dd, J=1.5 and 8.2, 1H), 7.15 (dd, J=4.0 and 8.2, 1H), 5.16

(sep, J=6.2, 1H), 4.83 (br, 2H), 1.39 (d, J=6.2, 6H); mass spectrum: m/z 204 (M⁺+1, 100%).

Step B: Preparation of
7-Chloro-8-isopropoxy-[1,6]naphthyridine

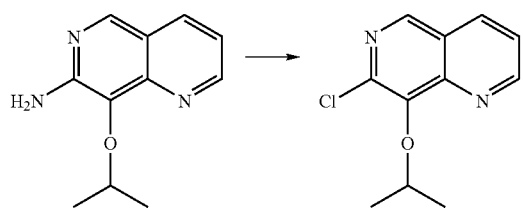

Sodium nitrite (1.8 g, 0.026 mol) was added portionwise into a stirred solution of the amine (1.00 g, 4.92 mmol) in conc HCl (20 mL) at 0-5° C. The mixture was left to stir at this temperature for a further h and then allowed to warm to room temperature over 1 h. Ice was added and the pH of the mixture was adjusted to 8 (conc NH₄OH). The mixture was then extracted with dichloromethane, the extracts washed with brine, dried and concentrated. Purification on SiO₂-gel chromatography (dichloromethane/MeOH, 200:3) provided the desired 7-chloride as a colourless solid (400 mg, 36%).

7-Chloro-8-isopropoxy-[1,6]naphthyridine: ¹H NMR (CDCl₃): δ 9.04 (dd, J=1.8 and 4.2, 1H), 8.76 (s, 1H), 8.23 (dd, J=1.8 and 8.4, 1H), 7.46 (dd, J=4.2 and 8.4, 1H), 5.14 (sep, J=6.2, 1H), 1.38 (d, J=6.2, 6H); mass spectrum: m/z 223, 225 (M⁺+1, 100%, 33%).

Step C: Preparation of 7-Morpholin-4-yl-[1,6]naphthyridin-8-ol (1053)

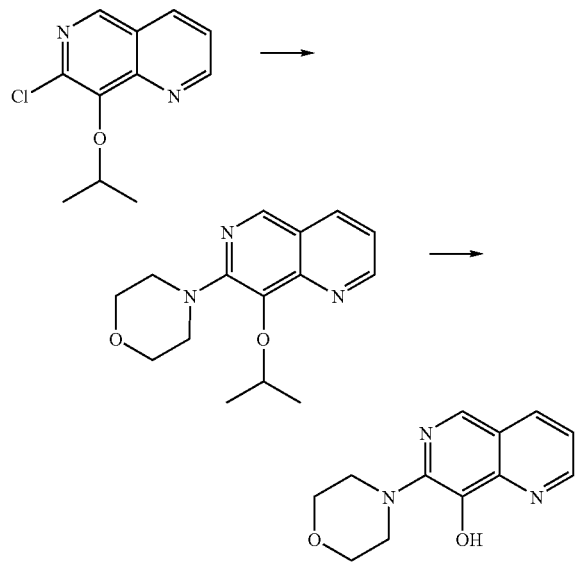

A mixture of the 7-chloride from Step B (100 mg, 0.448 mmol) and morpholine (2 mL) was heated at 180° C. for 20 h and then left to cool to room temperature. The reaction mixture was extracted with MeOH and the extracts concentrated. The residue was purified using SiO₂-gel chromatography (dichloromethane/MeOH, 20:1) to yield the desired product as a yellow solid (78 mg, 64%).

To a stirred solution of 8-isopropoxy-7-morpholin-4-yl-[1,6]naphthyridine (149 mg, 0.545 mmol) in dichloromethane (10 mL) at 0° C. was added BCl₃ (1.5 mL of a 1 M solution in dichloromethane). The dark orange solution was left to stir at room temperature for 24 h. MeOH (10 mL) was added and the mixture concentrated. This process was repeated four times. Further washing of the remaining residue with diethyl ether (5 mL×2) provided 7-morpholin-4-yl-[1,6]naphthyridin-8-ol hydrochloride as a dark red solid (quantitative yield).—¹H NMR (CD₃OD): δ 9.09 (dd, J=1.5 and 5.1, 1H), 9.02 (s, 1H), 8.99 (dd, J=1.5 and 8.2, 1H), 7.79 (dd, J=5.1 and 8.2, 1H), 3.95 (m, 4H), 3.80(m, 4H).

A solution of the 7-morpholin-4-yl-[1,6]naphthyridin-8-ol hydrochloride in dichloromethane (20 mL) was washed with sat'd NaHCO₃ solution (2×), dried, and concentrated. Solvent removal gave, after SiO₂-gel chromatography (dichloromethane/MeOH, 9:1), 7-morpholin-4-yl-[1,6]naphthyridin-8-ol as an orange solid (97 mg, 77%).—¹H NMR (CD₃OD): δ 8.91 (dd, J=1.4 and 4.0, 1H), 8.60 (s, 1H), 8.32 (dd, J=1.4 and 8.2, 1H), 7.41 (dd, J=4.0 and 8.2, 1H), 3.89 (m, 4H), 3.47 (m, 4 H).

(B) 8-Hydroxy-2-methylaminomethyl-[1,6]naphthyridine-7-carboxylic acid (4-fluorophenyl)amide (1070)

Step A: Preparation of
6-Methylpyridine-2,3-dicarboxylic acid 2-isopropyl ester

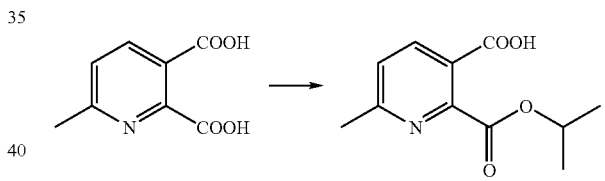

6-Methyl-2,3-pyridinedicarboxylic acid (10.0 g, 0.055 mol) and Ac₂O (50 mL) were heated at 120° C. for 4 h, cooled, and concentrated to a brown oil. Isopropanol was added to the brown oil and the solution heated at 80° C. overnight. The volatiles were removed in vacuo and the residue gave, after washing with diethyl ether, 6-methylpyridine-2,3-dicarboxylic acid 2-isopropyl ester as a straw-coloured solid (8.8 g, 71%).—¹H NMR (CDCl₃): δ 8.24 (d, J=8.2, 1H), 7.34 (d, J=8.2, 1H), 5.34 (sep, J=6.2, 1H), 2.68 (s, 3H), 1.39 (d, J=6.2, 6H).

Step B: Preparation of
3-Hydroxymethyl-6-methylpyridine-2-carboxylic acid isopropyl ester

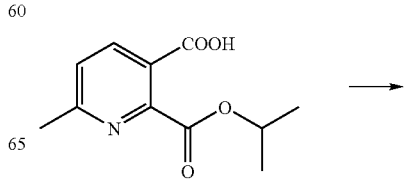

-continued

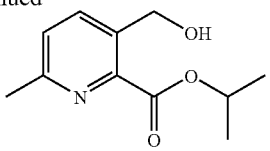

A mixture of 6-methylpyridine-2,3-dicarboxylic acid 2-isopropyl ester (7.31 g, 0.33 mol) and thionyl chloride (65 mL) was heated under reflux for 1 h. The resulting solution was concentrated in vacuo. The residue was washed with anhydrous THF (2×) to give the crude acid chloride as a brown oil. To a stirred ice-cooled solution of the acid chloride in THF (50 mL) was added sodium borohydride (1.26 g, 0.33 mol) in THF (15 mL) dropwise over 20 min. After 1 h at 0° C., the reaction mixture was poured onto ice and extracted with dichloromethane (3×). The extracts were combined, washed with brine, dried and concentrated. The residue gave, after purification via SiO$_2$-gel chromatography (dichloromethane/MeOH, 19:1), 3-hydroxymethyl-6-methylpyridine-2-carboxylic acid isopropyl ester as a light brown solid (3.42 g, 48%).—$^1$H NMR (CDCl$_3$): δ 7.76 (d, J=7.9, 1H), 7.31 (d, J=7.9, 1H), 5.32 (sep, J=6.2, 1H), 4.74 (s, 2H), 1.45 (d, J=6.2, 6H).

Step C: Preparation of 3-[(Benzenesulfonyl(methoxycarbonylmethyl)amino)methyl]-6-methylpyridine-2-carboxylic acid isopropyl ester

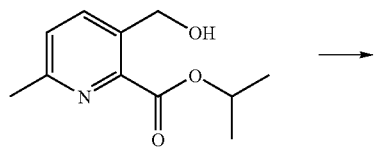

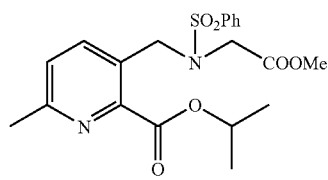

According to the conditions reported by Anthony et al (WO 02/30931 A2) for the preparation of 3-[(benzenesulfonyl(methoxycarbonylmethyl)amino)methyl]pyridine-2-carboxylic acid isopropyl ester, a solution of diisopropyl azodicarboxylate (1.07 g, 5.30 mmol) in THF (5 mL) was added dropwise over 40 min to a stirred solution of 3-hydroxymethyl-6-methyl-pyridine-2-carboxylic acid isopropyl ester (739 mg, 3.53 mmol), N-(phenylsulphonyl)glycine methyl ester (810 mg, 3.53 mmol) and triphenylphosphine (1.39 g, 5.30 mol) in THF (15 mL) The resulting solution was then left to stir at room temperature overnight. The reaction mixture was concentrated to give crude 3-[(benzenesulfonyl(methoxycarbonylmethyl)amino)methyl]-6-methylpyridine-2-carboxylic acid isopropyl ester as a golden syrup. This was used in the subsequent step without further purification.—Selected $^1$H NMR (CDCl$_3$): δ 4.73 (s, 2H), 4.00 (s, 2H), 3.54 (s, 3H), 2.70 (s, 3H).

Step D: Preparation of 8-Hydroxy-2-methyl-[1,6]naphthyridine-7-carboxylic acid methyl ester

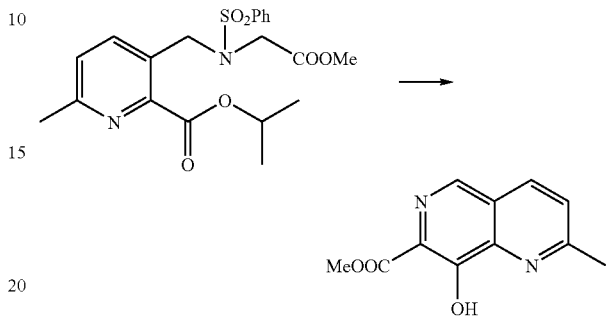

To a stirred solution of crude 3-[(benzenesulfonyl(methoxycarbonylmethyl)amino)methyl]-6-methylpyridine-2-carboxylic acid isopropyl ester (from Step C) in MeOH (20 mL) at 0° C. was added a solution of NaOMe in MeOH (prepared from Na (200 mg) in MeOH (4 mL)) dropwise over 20 min. The resulting solution was left to stir at 0° C. for a further hour and concentrated. Ethyl acetate (50 mL) and ice-H$_2$O (50 mL) were added. The layers were separated; the aqueous layer was extracted with ethyl acetate (2×), the pH adjusted to 6 (5 M HCl) and extracted with dichloromethane (20 mL×3). The extracts were combined, dried, and concentrated to give pure 8-hydroxy-2-methyl-[1,6]naphthyridine-7-carboxylic acid methyl ester as a cream solid (708 mg, 98% (2 steps)).—$^1$H NMR (CDCl$_3$): δ 8.87 (s, 1H), 8.26 (d, J=8.5, 1H), 7.62 (d, J=8.5, 1H), 5.40 (br, 1H), 4.13 (s, 3H), 2.91 (s, 3H).

Step E: Preparation of 8-Hydroxy-2-methyl-[1,6]naphthyridine-7-carboxylic acid (4-fluorophenyl)amide hydrochloride

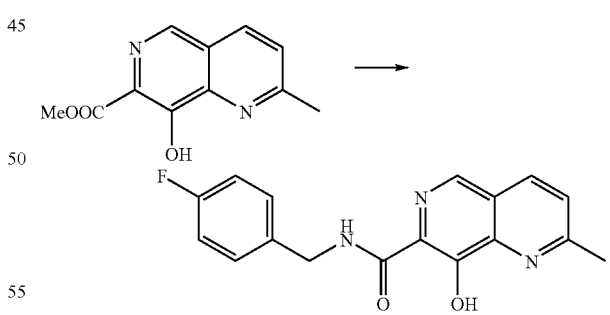

A solution of 8-hydroxy-2-methyl-[1,6]naphthyridine-7-carboxylic acid methyl ester (0.34 g, 1.56 mmol) and 4-fluorobenzylamine (0.5 mL) in toluene (4 mL) was heated under reflux for 16 h and allowed to cool to room temperature. Subsequent solvent removal gave a cream solid which, after washing with diethyl ether, gave 8-hydroxy-2-methyl-[1,6]naphthyridine-7-carboxylic acid (4-fluorophenyl)amide, as an off-white solid (0.40 g, 87%).—$^1$H NMR (CDCl$_3$): δ 8.57 (s, 1H), 8.44 (br, 1H), 8.15 (d, J=8.4, 1H), 7.52 (d, J=8.4, 1H), 7.37 (m, 2H), 7.07 (m, 2H), 4.67 (d, J=6.2, 2H), 2.87 (s, 3H).

Step F: Preparation of 8-Hydroxy-2-(methylamino) methyl-[1, 6]naphthyridine-7-carboxylic acid (4-fluorophenyl)amide hydrochloride (1070)

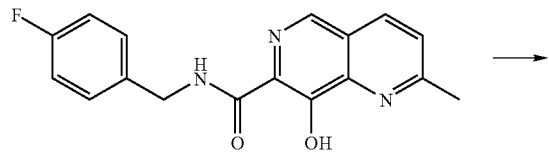

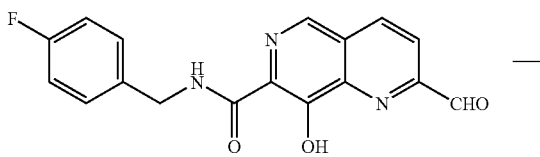

SeO$_2$ (100 mg, 0.901 mmol) was added to a solution of 8-hydroxy-2-methyl-[1,6]naphthyridine-7-carboxylic acid (4-fluorophenyl)amide (150 mg, 0.482 mmol) in 1,4-dioxane (8 mL) and H$_2$O (0.1 mL) and the mixture was heated at 55° C. for 3 h. The mixture was cooled to room temperature and filtered (celite). The filtrate was concentrated to give crude 2-aldehyde as a pale orange solid.—$^1$H NMR (CDCl$_3$): δ 10.37 (s, 1H), 8.75 (s, 1H), 8.46 (d, J=8.4, 1H), 8.45 (br, 1H), 8.26 (d, J=8.6, 1H), 7.40 (m, 2H), 7.30 (br, 1H), 7.08 (m, 2H), 4.70 (d, J=6.0, 2H).

To a stirred solution of the crude 2-aldehyde and methylamine hydrochloride (50 mg, 0.741 mmol) in 1,2-dichloroethane (5 mL) was added Et$_3$N (0.07 mL). Sodium triacetoxyborohydride (102 mg, 0.482 mmol) was then added and the mixture left to stir at room temperature overnight. MeOH was added and the resulting solution was concentrated. Saturated NaHCO$_3$ solution was added and the resulting pale orange solid was isolated via filtration, washed with H$_2$O and dried under vacuum. MeOH (10 mL) was added to the solid and the remaining insoluble material was filtered off. The filtrate was concentrated; conc HCl was added and the solution evaporated to dryness which afforded 8-hydroxy-2-(methylamino) methyl-[1,6]naphthyridine-7-carboxylic acid (4-fluorophenyl)amide hydrochloride (PB 1070) as a pale yellow solid (45 mg, 30%).—$^1$H NMR (CD$_3$OD): δ 8.92 (s, 1H), 8.64 (d, J=8.4, 1H), 7.82 (d, J=8.4, 1H), 7.43 (m, 2H), 7.06 (m, 2H), 4.69 (s, 2H), 4.68 (br, 1H), 4.65 (s, 2H), 2.91 (s, 3H).

Example 4

(A) 3-(4-chlorophenyl)-9-hydroxypyrido[1,2-a]pyrimidin-4-one (1069)

Step A: Preparation of 2-(4-Chlorophenyl)-3-oxo-propanoic acid ethyl ester

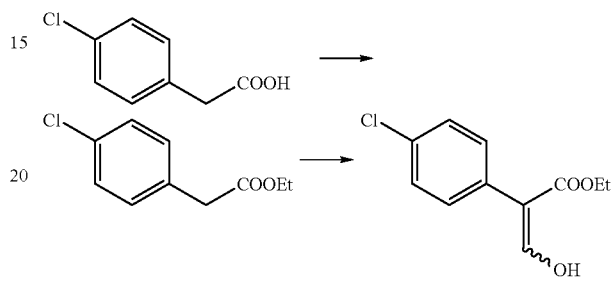

A solution of (4-chlorophenyl)acetic acid (20.0 g, 0.12 mol) and conc sulfuric acid (2 g) in EtOH (150 mL) was heated under reflux for 19 h, cooled, and then concentrated. Diethyl ether (100 mL) was added and the solution was washed with sat'd NaHCO$_3$ solution (40 mL×2), dried, and the volatiles removed. This provided (4-chlorophenyl)acetic acid ethyl ester as an oil (22.3 g, 96%).

Ethyl formate (7.46 g, 0.101 mol) was added dropwise to a stirred ice-cooled suspension of (4-chlorophenyl)acetic acid ethyl ester (20.0 g, 0.101 mol) and NaH (0.131 mol) in diethyl ether (100 mL). The mixture was then allowed to warm to room temperature overnight. The mixture neutralised (1 M HCl); the organic layer was isolated, dried, and the solvent removed to give 2-(4-chlorophenyl)-3-oxo-propanoic acid ethyl ester as a colourless solid (19.8 g, 87%). $^1$H NMR (CDCl$_3$): δ 12.14 (d, J=12.8, 1H), 7.31-7.18 (m, 4H), 4.29 (q, J=7.2, 2H), 1.57 (br, 1H), 1.29 (t, J=7.2, 3H).

Step B: Preparation of 3-(4-Chlorophenyl)-9-hydroxypyrido[1,2-a]pyrimidin-4-one (1069)

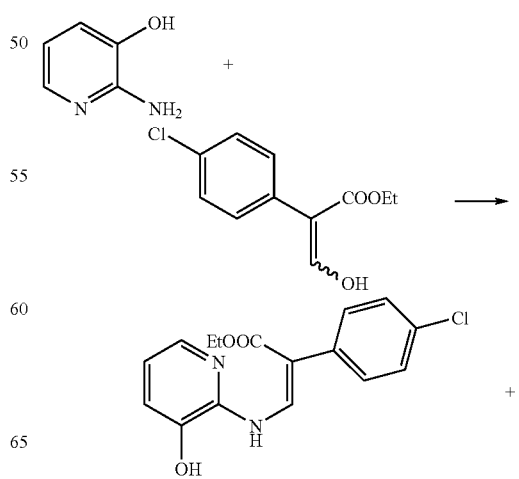

-continued

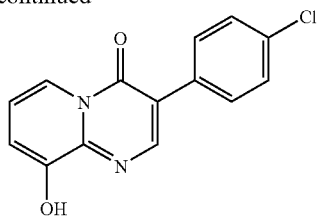

2-Amino-3-hydroxypyridine (5.51 g, 0.05 mol) and 2-(4-chlorophenyl)-3-oxo-propanoic acid ethyl ester (13.6 g, 0.06 mol) in EtOH (100 mL) were heated under reflux for 15 h and then allowed to cool. The precipitate was isolated via filtration to yield a 9:1 mixture of the enamine and the cyclized product (11.1 g).

Enamine: $^1$H NMR (DMSO-$d_6$): δ 10.67 (d, J=12.4, 1H), 8.10 (d, J=12.4, 1H), 7.72 (d, J=4.8, 1H), 7.37 (m, 4H), 7.16 (m, 1H), 6.86 (dd, J=4.8 and 8.0, 1H), 4.16 (q, J=7.2, 2H), 1.18 (t, J=7.2, 3H).

A solution of the mixture of enamine and the cyclized product (11.1 g) in diethylbenzenes (100 mL) was heated at 160° C. for 8 h and cooled. The precipitate was isolated via filtration, washed successively with hexanes and EtOH, and dried. This provided 3-(4-chlorophenyl)-9-hydroxypyrido[1,2-a]pyrimidin-4-one as a straw-coloured solid (7.03 g, 74%).

3-(4-Chlorophenyl)-9-hydroxypyrido[1,2-a]pyrimidin-4-one: $^1$H NMR (DMSO-$d_6$): δ 8.64 (dd, J=2.0 and 6.0, 1H), 8.61 (s, 1H), 7.89 (m, 2H), 7.51 (m, 2H), 7.30 (m, 2H); mass spectrum: m/z 273, 275 (M$^+$+1, 100%, 33%).

(B) 3-(4-Chlorophenyl)-9-hydroxy-8-iodopyrido[1,2-a]pyrimidin-4-one (1063)

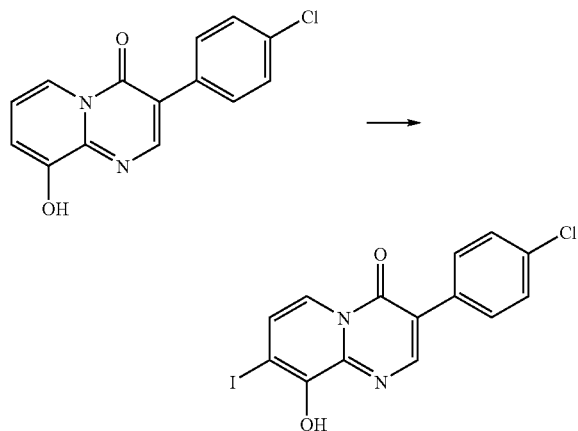

To a stirred suspension of 3-(4-chlorophenyl)-9-hydroxypyrido[1,2-a]pyrimidin-4-one (2.73 g, 0.01 mol) and iodine (2.54 g, 0.01 mol) in EtOH (100 mL) was added hydrogen peroxide (1.94 g of 30% w/v aqueous solution). The mixture was left to stir at room temperature for 6 days. The solid was isolated via filtration, washed with EtOH (20 mL×3), and dried to give a dark green powder (3.56 g). Subsequent recrystallisation from DMF provided 3-(4-chlorophenyl)-9-hydroxy-8-iodopyrido[1,2-a]pyrimidin-4-one as an orange-brown solid (1.80 g).

3-(4-Chlorophenyl)-9-hydroxy-8-iodopyrido[1,2-a]pyrimidin-4-one: $^1$H NMR (DMSO-$d_6$): δ 8.57 (s, 1H), 8.35 (d, J=7.2, 1H), 7.88 (m, 2H), 7.64 (d, J=7.2, 1H), 7.51 (m, 2H); mass spectrum: m/z 399, 401 (M$^+$+1, 100%, 33%).

The following assays are used in the assessment of new compounds according to the invention for suitability for use in the methods of the invention.

Example 5

Assessment of Compounds of Formula I or II

The following Assays were used in the assessment of the compounds of formula I or II for suitability for use in the methods of the invention.

Assay 1. Fluorometric $H_2O_2$ Assay

A fluorometric assay was used to test the ability of a test compound to inhibit hydrogen peroxide generation by Aβ in the presence of copper based on dichlorofluoroscein diacetate (DCF; Molecular Probes, Eugene Oreg.). The DCF solution (5 mM) in 100% dimethyl sulphoxide (previously purged with argon for 1 hr at 20° C.) was deacetylated in the presence of 0.025M NaOH for 30 min and neutralised at pH 7.4 to a final concentration of 1 mM. Horseradish peroxidase (HARPY) stock solution was prepared to 1 μM at pH 7.4. The reactions were carried out in PBS, pH 7.4 in a 96 well plate (total volume=250 μl/well). The reaction solutions contained Aβ 1-42 at concentrations in the range of 50 nM to 1 μM, copper-glycine chelate (Cu-Gly), was prepared by adding $CuCl_2$ to glycine in the ratio of 1:6 and added to the Aβ in the proportion 2Cu-Gly: 1Aβ), reducing agents including dopamine (5 μM) or ascorbic acid, deacetylated DCF 100 μM, and HRP, 0.1 μM. 1-10 μM EDTA or another chelator may also be present as a control for free copper, but was not required for the assay to function. The reaction mixture was incubated at 37 C for 60 min. Catalase (4000 units/ml) and $H_2O_2$ (1-2.5 μM) standards in PBS pH 7.4 may be included as positive controls. Fluorescence was recorded using a plate reader with excitation and emission filters at 485 nM and 530 nM respectively. $H_2O_2$ concentration may be established by comparing fluorescence with the $H_2O_2$ standards. Inhibition of Aβ $H_2O_2$ production was assayed by including a given concentration of test compound(s) in the test wells.

Assay 2. Neurotoxicity Assays

Primary Cortical Neuronal Cultures

Cortical cultures were prepared as previously described (White et al., 1998). Embryonic day 14 BL6Jx129sv mouse cortices were removed, dissected free of meninges and dissociated in 0.025% (wt/vol) trypsin. Dissociated cells were plated in 48 well culture plates at a density of 2×10$^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% $CO_2$. Prior to experimentation, the culture medium was replaced with Neurobasal media and B27 minus antioxidants (Invitrogen Life Technologies).

Primary Cerebellar Granule Neuronal Cultures

Cerebella from post-natal day 5-6 (P5-6) mice were removed and dissected free of meninges and dissociated in 0.025% trypsin. Cerebellar granule neurons (CGN) were plated in 24 well culture plates at 350 000 cells/cm$^2$ in BME (Invitrogen Life Technologies) supplemented with 10% Fetal Calf Serum (FCS), 2 mM glutamine and 25 mM KCl. Gentamycin sulphate (100 μg/mL) was added to all plating media and cultures were maintained at 37° C. in 5% $CO_2$.

Assay 3. Assays for Cell Viability (a) MTS Assay for Cell Viability

Cell viability is determined using the MTS assay. Culture medium is replaced with fresh neurobasal medium plus B27 supplements minus antioxidants. 1/10th volume MTS solution (Cell Titre 96 Aqueous One, Promega Corporation) and incubated at at 37° C., 2 hrs. 200 microliter aliquots are measured with a spectrophotometer at 560 nm.

(b) LDH Assay for Cell Viability

Cell death is determined from culture supernatants free of serum and cell debris using the lactate dehydrogenase (LDH) Cytotoxicity Detection Kit (Boehringer Ingelheim) according to the manufacturer's instructions.

(c) Assay for Aβ Neurotoxicity and Aβ Neuroprotection

Neuronal cortical cells were cultured for five days as per Assay 2. On day six the neurobasal (NB) media (Invitrogen Life Technologies) and B27 supplement (Invitrogen Life Technologies) were replaced with NB media and B27 supplement (no antioxidants). On day six, test compounds were individually added to the neuronal cell cultures:

The test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM.

Aβ Preparation:

Aβ was initially dissolved in 20 mM NaOH to a concentration of 1 mM and sonicated for 5 minutes. The peptide was then diluted in $H_2O$ and 10×PBS to a final concentration of 200 uM Aβ in 1×PBS. The peptide was again sonicated for 5 minutes and then spun at 14000 rpm for 5 min and transferred to a fresh tube.

The test compounds were dissolved in 100% DMSO to a concentration of 2.5 mM (10 mM if excess compound was weighed out per vial—then diluted to 2.5 mM). 2.5 mM stock solution was serially diluted 1 in 10 [in NB media and B27 (no antioxidants)] to give working solutions of 250 uM, 25 uM, 2.5 uM. Test compounds were not added directly to cells, instead they were added to a 48 well 'Drug Plate' as comprised below:

Preparation of "Drug Plate":

To a 48 well plate add:
Well 1: 515 ul NB+B27(no antioxidant)*+24 ul 25 uM test compound+60 ul Aβ diluent**
Well 2: 515 ul NB+B27(no antioxidant)+24 ul 250 uM test compound+60 ul Aβ diluent
Well 3: 515 ul NB+B27(no antioxidant)+24 ul test compound diluent***+60 ul Aβ1-42
Well 4: 515 ul NB+B27(no antioxidant)+24 ul 2.5 uM test compound+60 ul Aβ1-42
Well 5: 515 ul NB+B27(no antioxidant)+24 ul 25 uM test compound+60 ul Aβ1-42
Well 6: 515 ul NB+B27(no antioxidant)+24 ul 250 uM test compound+60 ul Aβ1-42 diluent
Well 7: 515 ul NB+B27(no antioxidant)+24 ul test compound diluent+60 ul Aβ1-42 diluent
Well 8: 600 ul NB+B27(no antioxidant)
N.B. 60 ul Aβ1-42 equals 20 ul Aβ1-42 per well equals 20 uM Aβ1-42

The Drug Plate was incubated at 37° C. for 15 mins. 200 ul of each well was added in triplicate to the corresponding cell plate. The cell plate was incubated at 37 C, for 4 days.
* NB media+B27 (no antioxidants),
** Aβ diluent 2 mM NaOH, 1×PBS
*** PBT diluent 10% DMSO in NB+B27(no antioxidant)

Completion of the Assay:

On the $4^{th}$ day after treating the cells the assay is completed by adding MTS to the cells.

(d) Assay for Test Compound Cytoxicity

Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM. Test compounds were not added directly to cells, instead they were added to a 48 well 'Drug Plate' as comprised below:

Preparation of "Drug Plate":

To a 48 well plate add:
Well 1: 576 ul NB+B27(no antioxidant)*+24 ul 2.5 uM test compound
Well 2: 576 ul NB+B27(no antioxidant)+24 ul 25 uM test compound
Well 3: 576 ul NB+B27(no antioxidant)+24 ul 250 uM test compound
Well 4: 576 ul NB+B27(no antioxidant)+24 ul 2.5 uM test compound
Well 5: 576 ul NB+B27(no antioxidant)+24 ul 25 uM test compound
Well 6: 576 ul NB+B27(no antioxidant)+24 ul 250 uM test compound
Well 7: 576 ul NB+B27(no antioxidant)+24 ul test compound diluent**
Well 8: 600 ul NB+B27(no antioxidant)

The Drug Plate was incubated at 37° C. for 15 mins. 200 ul of each well was added in triplicate to the corresponding cell plate. The cell plate was incubated at 37 C, for 4 days, (2 compounds are tested on each plate of cells).
* NB media and B27 (no antioxidants),
** PBT diluent 10% DMSO in NB+B27 (no antioxidants)

On completion of the assay, 1/10 volume MTS was added per well of plate (ie 25 ul/250 ul). The plates were incubated at 37 C for 2 hrs, and then absorbance was read at 560 nm.

Assay 4. Caspase Assay

To measure caspase activity in neuronal cultures, growth medium is removed, cells are washed twice with control salt solution (pH 7.4) and ice-cold cell extraction buffer is added directly to the cultures. The extraction buffer consists of 20 mM Tris (pH 7.4), 1 mM sucrose, 0.25 mM EDTA, 1 mM dithiothreitol (DTT), 0.5 mM PMSF, 1% Triton X-100 (Tx-100) and 1 μg/mL of pepstatin and aprotinin. After incubation for 15 min on ice, the extraction buffer is removed, centrifuged for 5 min at 4° C. in a microcentrifuge and 100 μL of supernatant is added to each well of a 96 well plate. 100 μL of 200 μM substrate (either DEVD-pNA, VEID-pNA or IETD-pNA for caspases 3, 6 and 8 respectively) is added to each well to give a final concentration of 100 μM substrate. Plates are incubated at 37° C. for 2, 4, 6 or 24 hr and the absorbance is determined at a wavelength of 415 nm (Abs415). The absorbance reading is compared to a known standard of pNA alone.

Assay 5. Annexin V Assay

To determine the level of annexin V binding to cells, cultures are washed twice with control salt solution (pH 7.4) followed by the addition of annexin V-FITC at a concentration of approximately 0.5 μg/mL in control salt solution (pH 7.4). Propidium iodide (10 μg/mL) is also added to the cultures at the same time. Cells are incubated in the dark for 30 min at ambient temperature and subsequently washed three times with fresh control salt solution. Analysis of FITC fluorescence (ex. 488 nm, em. 510 nm) is determined using a Leica DMIRB microscope. Photographs are taken with a Leica MPS 60 camera attachment using ASA400 colour film, and negatives are scanned into Adobe Photoshop v2.0.1.

Assay 6. Lipoprotein Oxidation Assay

Two different assays of metal-mediated lipid peroxidation can be utilized. The first assay involves measuring the oxidative activity of metallated proteins. This is determined by mixing dialyzed metallated or native protein (at designated concentrations) with 0.5 mg/mL LDL for 24 hr (37° C.). Lipid peroxidation (LPO) is measured using a lipid peroxidation assay kit (LPO 486, Oxis International Inc. Portland, Oreg.) as per kit instructions. The level of LPO is determined by comparing absorbance (486 nm) with LDL alone (100% LPO). The second assay is used to measure the LPO activity of native proteins in the presence of free, non-protein-bound Cu. This involves adding non-metallated peptides (140 μM) to 0.5 mg/mL LDL together with 20 μM Cu-gly and assaying for LPO as for the metallated proteins. The level of LPO is determined by comparing the absorbance (486 nm) with LDL+Cu-gly (100% LPO). As a negative control, LDL is also exposed to dialysed Cu-gly solutions comparable to those used to Cu-metallate the proteins.

Assay 7. Cytotoxicity Induced by Cu-Metallated Proteins

Proteins or synthetic peptides are mixed with metal-glycine solutions at equimolar or two-fold metal to protein concentration. Metal-protein mixtures are incubated overnight at 37° C. and then extensively dialysed (24 hr against two changes of $dH_2O$ (3 L/change) at room temperature) using mini-dialysis cups with a 3,500 kilodalton cut-off (Pierce, Rockford, Ill.). Dialysis of proteins against PBS pH 7.4 resulted in metallated proteins with identical activity to $dH_2O$ dialysis. To determine their neurotoxic effects, metallated proteins, native proteins or peptides are added to two day-old primary cortical neuronal cultures. The cultures are also exposed to Cu-gly (5 or 10 μM) or LDL. Positive control cultures are treated with Cu-gly+LDL or the LPO product, 4-hydroxy-nonenol (HNE, Sigma Chemicals). Cultures are assayed for cell death using the lactate dehydrogenase (LDH) assay kit (Roche Molecular Biochemicals, Nunawading, Australia) according to the manufacturer's instructions.

Assay 8. Acridine Orange Assay for Aβ-Mediated Loss of Lysosomal Acidification

Cultured mouse cortical neurons are treated with Aβ1-42 (20 μM) for 16 h and then stained with 5 mg/ml acridine orange (AO) for 5 min at 37° C. 15 min at 37° C. The AO-induced fluorescence is measured with a red filter on a fluorescence microscope. AO is a lysosomotropic weak base which accumulates in the endosomal/lysosomal compartments and displays orange fluorescence during incubation. AO is sequestered inside the lysosomes as long as there is a substantial proton gradient over the lysosomal membranes. Treatment of cells with Aβ1-42 disrupts the lysosomal membrane proton gradient and relocalises AO into the cytosol, as indicated by the loss of orange fluorescence within 16-24 hr.

Assay 9. Human Brain Amyloid Solubilisation Assay

This assay was performed in order to assess the ability of a test compound to mobilise Aβ from the insoluble to the soluble phase of an extract of tissue from post mortem human AD brain.

Up to 0.5 g of plaque-bearing cortex without meninges was homogenized using a DIAX 900 homogenizer (Heudolph and Co, Kelheim, Germany) or other suitable device for three 30-second periods at full speed in up to 2 ml of ice-cold phosphate-buffered saline, pH 7.4. To obtain the phosphate-buffered saline-extractable fraction, the homogenate was centrifuged at 100,000×g for 30 min and the supernatant removed. Alternatively, the tissue was freeze dried then pulverised to form a powder which was then weighed out into aliquots for extraction as above. A 101 aliquot of supernatant was removed after centrifugation and mixed with an equal volume of 2×Tris-Ticene SDS sample buffer, pH 8.3, containing 8% SDS, 10% 2-mercaptoethanol. Samples were then heated for 10 mins at 90° C. and separated by gel electrophoresis. The insoluble fraction of the cortical samples was obtained by resuspending the initial pelleted sample in 1 ml of phosphate-buffered saline. A 50-μl aliquot of this suspension was then boiled in 200 ml of sample buffer as above.

Tris-Tricine polyacrylamide gel electrophoresis was performed by loading appropriately diluted samples on to 10% to 20% gradient gels (Novex, San Diego, Calif.) followed by transfer on to 0.2-μm nitrocellulose membrane (Bio-Rad, Hercules, Calif.). Aβ was detected by using monoclonal antibody W02, which detects residues 5 through 8, 17 (or another suitable antibody) in conjunction with horseradish peroxidase-conjugated rabbit anti-mouse IgG (Dako, Denmark), and visualized by using enhanced chemiluminescence (eg ECL; Amersham Life Science, Buckinghamshire, UK). Each gel included three lanes containing 0.5, 1, and 2 ng of synthetic $Aβ_{40}$ (Keck Laboratory, Yale University, New Haven, Conn.) as reference standards.

Blot films were scanned by using a suitable imaging system such as the UVP gel documentation system, and densitometry performed using suitable software, eg UVP Labworks. The dynamic range of the film/scanner was determined by using a step tablet (No. 911ST600, Kodak, Rochester N.Y.), a calibrated film exposed by the manufacturer to provided steps of known increasing intensity. The quantifiable range of signal intensity for densitometric analysis of the mono- and dimeric Aβ bands was based on the comparison with a curve obtained by scanning and densitometry of the step tablet. Samples in which the signal intensity is low after preliminary assay may be re-assayed by using synthetic standards of lower or higher concentration.

All samples were analysed several times, and gel loadings and dilutions were adjusted to fit within the quantifiable region of the standard curve. The insoluble Aβ being comprised of the pelletable fraction derived from the insoluble amyloid plaque from the above cortical samples and the soluble fraction comprising monomeric and/or oligomeric soluble Aβ.

Several gels were run per test compound with a PBS control included on each gel. Each gel containing varying concentrations of the test compound. A student's 't test' was used to compare the mean of the highest value obtained by the test compound for each gel at any concentration, to the mean of the PBS values taken from the multiple gels. Accordingly a determination can be made of whether the average increase in solubilisation obtained by any test compound is significant compared with PBS alone. Test compounds with a (+) score are compounds which achieved a statistically significant increase in plaque solubilisation over that of PBS alone. A test compound with a (−) score is a compound which does not achieve a statistically significant increase in plaque solubilisation over that of PBS alone Assay 10. Metal Partitioning To assay effects upon the partitioning of various metals, including zinc and copper, following extraction of brain tissue in the presence of a test compound, soluble and insoluble fractions from an extract of human brain tissue are prepared as for the amyloid solubilisation assay. Metals in the two fractions are analysed by inductively-coupled plasma mass spectrometry, following appropriate pretreatment with nitric acid and/or hydrogen peroxide where necessary.

Assay 11. Effect of Administration of Test Compounds on Aβ Deposits in Transgenic Animals Transgenic mouse models are available for a number of neurological disorders, including Alzheimer's disease (Games et al., 1995; Hsiao et al., 1996); Parkinson's disease (Masliah et al., 2000); familial amyotrophic lateral sclerosis (ALS) (Gurney et al., 1994); Huntington's disease (Reddy et al., 1998); and Creutzfeld-Jakob disease (CJD) (Telling et al., 1994). We have found that one of the transgenic models for Alzheimer's disease, the APP2576 transgenic mouse (Hsiao et al., 1996) also has a high incidence of cataract. These animal models are suitable for testing the methods of the invention.

Transgenic mice of the strain APP2576 (Hsiao et al 1996) are used. Eight to nine month old female mice are selected and divided into groups for treatment.

Mice are sacrificed at intervals, and their brains examined to determine whether the treatment with test compounds decreased brain amyloid formation, and the identification of the most effective administration protocol. The levels of soluble and insoluble Aβ in the brain and serum are determined using calibrated Western blots as per the methodology described for Assay 9. Brain Amyloid Solubilisation Assay.

Other mice in each group are tested over a period of up to eight months for cognitive performance, using a Morris water maze according to standard methods. The general health and well-being of the animals is also measured every day by a blinded operator, using a five point integer scale which subjectively rates a combination of features, including motor activity, alertness and general health signs.

Assay 12. Physiochemical Properties

Polar Surface Area Calculations (PSA)

Polar surface area values were calculated using the web-based program available through "Molinspiration", a package for calculation of molecular properties.

Turbidimetric Solubility Measurements

The solubility estimate was measured at both pH 2.0 and pH 6.5. This is within the pH range that can be anticipated along the proximal gastrointestinal tract in humans.

The compounds were dissolved in DMSO to appropriate concentrations and then spiked into either 0.01M HCl (approx. pH=2.0) or pH 6.5 isotonic phosphate buffer, the final DMSO concentration being 1%. Samples were then analysed via Nephelometry to determine a solubility range. [as per D. Bevan and R. S. Lloyd, Anal. Chem. 2000, 72, 1781-1787].

cLog P Values

Theoretical Log P values were determined using the ACD Log P software. The values quoted have been calculated from an untrained database and refer to the unionised species.

Assay 13. Blood Brain Barrier Penetration

The test compounds were dissolved in DMSO and phosphate buffered saline (PBS) was added to obtain solutions at a concentration of 50 µM in PBS containing 1.25-2.5% DMSO. A trace amount of $^{14}$C-sucrose was added to each stock infusion solution (approx 0.01 µCi/mL) to act as Blood-Brain Barrier (BBB)-impermeable marker in order to assess the integrity of the BBB during each perfusion and to estimate the volume of the residual vascular space (RVS) in samples of brain tissue (ie: the volume of fluid remaining inside the lumen of blood vessels at the end of each perfusion).

Adult male Spague Dawley rats (180-190 g) were anaesthetized with intraperitoneal injections of Urethane (25% w/v) at a dose of 1.0 mL/100 g body weight. The right common carotid artery was surgically exposed and cannulated for perfusion of the cerebral circulation. The right external carotid artery (which supplies tissues outside the skull) was then ligated distal to its bifurcation from the right common carotid artery so that all of the infusion solution would pass into the brain via the remaining right internal carotid artery. The heart was then exposed and transected immediately prior to the commencement of the infusion. The rate of the infusion was controlled by a pump set to deliver at 3.2 mL/min (approx. 85% of the normal blood supply to the brain for this size of rat). The infusion cannula initially contained a 0.5 mL pre-wash of heparinised PBS (10 IU/ml) that acts to flush blood vessels and to prevent blood from clotting and blocking small vessels.

After 1.5 minutes, the infusion pump automatically stopped, the cannula was withdrawn from the carotid artery and a sample of the infusion solution (1-1.5 mL) was then collected from the tip of the infusion cannula. The brain was then dissected free and divided into 3 parts; the right hemisphere together with the right midbrain, the left hemisphere together with the left midbrain and the hindbrain (cerebellum, pons and brainstem). Only the right part of the brain was used for subsequent measurements because perfusion via the right internal carotid artery preferentially supplies the right hemisphere and right midbrain (the left hemisphere and hindbrain receive a variable collateral perfusion). The brain tissue samples from each animal were frozen at −30° C., homogenized and weighed aliquots analysed by LC-MS to give total brain concentration. The analysis was carried out using the Micromass Triple Quad instrument. The mobile phase consisted of an acetonitrile/water gradient (containing 0.05% Formic acid) and the column was a Phenomenex Luna CN.

Small aliquots from each brain tissue sample and the corresponding infusion solution were analysed by liquid scintillation counting to determine the level of $^{14}$C-sucrose. The residual vascular space (RVS) in each brain tissue sample was calculated by dividing the measured concentration of sucrose in brain tissue (dpm/mg) by its concentration in the corresponding infusion solution (dpm/µL). This is the volume of fluid that remains inside blood vessels at the end of each perfusion. Multiplying this RVS by the concentration of the test compound in the infusion solution gives the total residual amount of the test compound that is present inside blood vessels in each brain tissue sample (ie: that which has not crossed the BBB). Subtracting this from the total brain concentration gives the amount of drug in each brain tissue sample that is outside the blood vessels (ie: which has crossed the BBB). Dividing this RVS-corrected brain concentration gives the brain uptake ratio (Equation. 1).

$$\text{Brain Uptake Ratio} = \frac{[\text{brain } ng.mg^{-1}] - [RVS\ ng.\mu l^{-1}]}{[\text{infusion solution } ng.\mu L^{-1}]}. \quad \text{Equation 1}$$

A total of 5-6 brain perfusion experiments were performed for each of the test compounds and mean brain uptake ratios were calculated.

Ratios of greater than 50% indicate compounds that enter the brain extremely rapidly; ratios between 10 and 50% indicate compounds that enter the brain well; ratios less than 10% (not observed) would indicate compounds that enter the brain very slowly and would not be suitable for therapeutic administration; ratios less than 1% (not observed) would indicate compounds that are effectively excluded from the brain.

Assay 14. Transgenic Mouse Brain Immunohistochemistry

The APP2576 transgenic mouse (Hsiao et al., 1996) as referred to in Assay 11 is utilized in this assay. The contralateral formalin-fixed mouse brain tissue is coronally cut. Sections (10 µm) are taken from the corresponding sites and treated with 80% formic acid for antigen retrieval. The primary antibody used is monoclonal antibody 1E8, which recognizes epitopes between residues 18 and 22 of Aβ (Smith-Kline Beecham, UK). Immunoreactivity is developed with secondary antibody linked to horseradish peroxidase (using a 3,39-diaminobenzidinechromagen) (Dako) and alkaline phosphatase (using 5-bromo-4-chloro 3-indoxyl phosphate and nitroblue tetrazolium chloride chromagen) (Dako). Plaque abundance per section is assessed by two operators blinded to treatment according to the following scale:

0=no plaques apparent
1=plaques present but very sparse
2=several plaques present
3=numerous plaques visible in restricted areas
4=plaques abundant and not restricted to any particular area.

Intermediate values eg 2.5 are assigned where applicable.

Students' t' test is used for comparisons between groups.

Assay 15 Pharmacokinetic Profile
 Intravenous infusion of test compound; 2 mg/Kg in a suitable vehicle is administered to 2 rats and arterial blood is sampled up to 24 hours.
 Oral administration of test compound; 30 mg/Kg in a suitable vehicle is administered via oral gavage to 2 rats and arterial blood is sampled up to 24 hours.
 Plasma concentrations of test compound are determined by suitable analytical method.
 Calculations:

$$CL_{total} = \frac{Dose_{IV}}{AUC_{IV}}$$

$$V_{d\beta} = \frac{CL_{total}}{\beta}$$

$$BA(\%) = \frac{AUC_{oral} * Dose_{IV}}{AUC_{IV} * Dose_{oral}}$$

$CL_{total}$=total plasma clearance after IV administration
$V_{d\beta}$=volume of distribution during the elimination phase after IV administration
BA=oral bioavailability
$AUC_{IV}$=area under the plasma concentration versus time profile from time zero to infinity after IV administration
$AUC_{oral}$=area under the plasma concentration versus time profile from time zero to infinity after oral administration
β=terminal elimination rate constant after IV administration Assay 16 Determination of Mouse Plasma Levels of Test Compounds

PBT 1061

Oral administration of PBT 1061 at 30 mg/kg, as a suspension in Na-Carboxymethyl Cellulose (CMC) was administered by oral gavage to four mice. Two mice were sacrificed 30 minutes after administration and two mice were sacrificed 60 minutes after administration. Blood was obtained by cardiac puncture and plasma separated by centrifugation.

The concentration of PBT1061 was determined by LC/MS using the ZQ instrument. The mobile phase consisted of an acetonitrile (ACN)/water gradient (containing 0.05% Formic acid) and the column was a Phenomenex Polar-RP 4 µM 80A (50×2 mm) column.

The mouse plasma samples were directly injected following a protein precipitation with ACN. The analytical method in plasma was linear in the range of 125 to 10,000 ng/ml ($R^2$=0.9992). Diazepam was used as the internal standard. Recovery of PBT1061 from plasma was ~100%.

The concentration of PBT1061 in mouse plasma after dosing orally at 30 mg/kg is given in Table 1.

TABLE 1

Concentrations of PBT1061 in Mouse Plasma after Oral Dosing at 30 mg/kg

| Mouse ID | Dose (mg/Kg) | Time (min) | Conc. (ng/ml) |
|---|---|---|---|
| 2703 | 30 | 30 | 1826.61 |
| 2743 | 30 | 30 | 5475.88 |
| 2740 | 30 | 60 | 1115.24 |
| 2801 | 30 | 60 | 2417.55 |

PBT 1063

Oral administration of PBT 1063 at 30 mg/kg, as a suspension in Na-Carboxymethyl Cellulose (CMC) was administered by oral gavage to four mice. Two mice were sacrificed 30 minutes after administration and two mice were sacrificed 60 minutes after administration. Blood was obtained by cardiac puncture and plasma separated by centrifugation.

The concentration of PBT1063 was determined by LC/MS using the single quadrupole instrument. The mobile phase consisted of an acetonitrile (ACN)/water gradient (containing 0.05% Formic acid) and the column was a Phenomenex C8 4 µm 80A (50×2 mm) column.

The supplied acute toxicity mouse plasma samples (delivered Feb. 9, 2003) were directly injected following a protein precipitation with ACN. Concentrations were determined by comparison to a calibration curve prepared in rat plasma. The analytical method in plasma was linear in the range of 312 to 10,000 ng/ml ($R^2$=0.9976). Diazepam was used as the internal standard. Recovery of PBT1063 from plasma was ~42.9%.

The concentrations of PBT1063 in the mouse plasma samples are given in Table 2.

TABLE 2

Concentrations of PBT1063 in Mouse Plasma after Oral Dosing at 30 mg/kg

| Exp. No. | Time (min) | Conc. (ng/ml) |
|---|---|---|
| 2835 | 30 | 412.81 |
| 2843 | 30 | 279.39 |
| 2814 | 60 | 439.49 |
| 2677 | 60 | 330.66 |

TABLE 3

| Assay | Assay 1 Peroxide IC$_{50}$ (µM) | Assay 9 Brain amyloid solubilisation $^a$ | Assay 3(d) Cytotoxicity (% viable at 1 and 10 uM) | Assay 3(c) Neuroprotection (% inhibition of Abeta toxicity) | Assay 12 clogP | Assay 12 Polar surface area (PSA) |
|---|---|---|---|---|---|---|
| PBT-1053 | 0.63 | (+) | 104, 98 | 11 | 1.99 | 58.5 |
| PBT-1055 | 0.75 |  | 98, 67 | 29 | 3.33 | 52.9 |
| PBT-1061 | 0.45 | (+) | 91, 77 | 16 | 2.11 | 52.9 |
| PBT-1063 | 0.62 |  | 41, 33 | 3 | 3.41 | 52.9 |
| PBT-1045 | 0.90 |  | 85, 82 | 12 | 2.209 |  |
| PBT-1048 | 0.35 |  | 93, 91 | 22 |  |  |
| PBT-1049 | 1.60 |  | 92, 87 | 11 | 0.49 |  |
| PBT-1066 |  |  | 92, 95 |  | 2.52 | 49.3 |
| PBT-1067 | 0.95 |  | 103, 89 |  | 1.12 | 61.7 |
| PBT-1069 | 0.60 |  | 97, 42 |  | 2.62 |  |
| PBT-1070 | 1.14 |  |  |  |  |  |
| PBT 1064 |  |  | 86, 83 | 29 |  |  |
| PBT-1065 |  |  | 99, 76 | 7 |  |  |

| Assay | Assay 12 Solubility at pH 6.5 | Assay 12 Solubility in 0.01 M HCl, pH 2.0 | Assay 16 Mice plasma concentration | Assay 13 Rat brain perfusion |
|---|---|---|---|---|
| PBT-1053 | >200 µg/mL | 50-100 µg/mL |  | Between 10 and 50% |
| PBT-1055 | 3-6.3 µg/mL | 3-6.3 µg/mL |  | Between 10 and 50% |
| PBT-1061 | 12.5-25 µg/mL | 3.1-6.2 µg/mL | Refer to Table 1 | >50% |
| PBT-1063 | <5 µg/mL | <10 µg/mL | Refer to Table 2 |  |
| PBT-1045 |  |  |  |  |
| PBT-1048 |  |  |  |  |
| PBT-1049 |  |  |  |  |
| PBT-1066 | >100 µg/mL | >100 µg/mL |  |  |
| PBT-1067 | 25-50 µg/mL | 12.5-25 µg/mL |  |  |
| PBT-1069 |  |  |  |  |
| PBT-1070 |  |  |  |  |
| PBT 1064 |  |  |  |  |
| PBT-1065 |  |  |  |  |

$^a$ (+) = effective at solubilising plaques at more than 1 concentration relative to PBS, (−) = not effective at solubilising plaques relative to PBS.

Example 6

Clinical Trial of Compound of Formula I or II for the Treatment of Alzheimer's Disease A Phase II clinical trial of the compound of formula I or II for the treatment of AD was undertaken to study the effects of oral PBT-1 treatment in a randomised, double-blind, placebo-controlled pilot phase 2 clinical trial of moderately severe AD patients. Thirty-six subjects were randomized [18 placebo and 18 PBT-1, with 32 completions], and stratified into more- and less-severely affected groups. The effect of treatment was statistically significant in preventing cognitive deterioration over 36 weeks in the more-severely affected patients (baseline ADAS-cog≧25). The performance of the less-severely affected group (ADAS-cog<25) deteriorated negligibly over this interval, so cognitive changes could not be discriminated in this stratum. Plasma Aβ42 declined in the PBT-1 group but increased in the placebo group (p<0.001). Plasma Zn levels rose significantly (≈30%) in the PBT-1 group.

Dosage

Several considerations drove the choice of dose. In previous studies on transgenic mice, doses of 20-30 mg/kg of PBT-1 orally daily for five days per week were markedly effective at inhibiting Aβ accumulation after 2-3 months of treatment. The human equivalent dose of 1500-2250 mg/day is close to the prescribed antibiotic dose of PBT-1 (600 mg po qid). However, this magnitude of dose, administered for months, would raise concerns about SMON toxicity.

The starting dose of 3.3 mg/kg/day, assuming 75 kg average weight, is within the same order of magnitude of the effective dose in the transgenic mouse model, but only about one tenth of the antibiotic dose.

Since there is no data from the transgenic mouse study of the effectiveness of doses less than 20 mg/kg/day, we reasoned that a beneficial effect might require a longer period of treatment than the 9-12 week duration of the mouse study (Cherny et al., 2001). Therefore a trial length of 36 weeks at an average dose which is approximately one-third of what is effective in the transgenic mice is chosen. The final dose of 10 mg/kg/day is half of an effective dose in mice.

The starting dose of 3.3 mg/kg/day was within the same order of magnitude of the effective dose in the transgenic mouse model, but only about one tenth of the anti-infective dose. The study was powered to detect biochemical effects on metal and Aβ levels that would be in the same magnitude as those seen in the transgenic study.

Experimental Procedures

Ethical issues: In compliance with Australian laws concerning consent from individuals whose cognitive function may be impaired to the extent of being unable to make informed judgements or decisions, "Consent to Special Procedures" administered by the Victorian Civil and Administrative Tribunal was obtained for each participant not able to consent on their own behalf. In addition, third party consent was obtained from all carers. All subjects were stabilized on donepezil prior to commencement of the study. The study was approved by the Royal Melbourne Hospital Research Foundation's Clinical Research and Ethics Committee.

Study population: The study took place at the AD clinical trials unit, Mental Health Research Institute of Victoria and at the Royal Melbourne Hospital. Criteria for inclusion in the study were: informed consent; a diagnosis of probable AD by NINCDS-ADRDA criteria (McKhann et al., 1984); AD Assessment Scale-cognitive (ADAS-cog) (Rosen et al., 1984) score of 18-45; Mini Mental State Examination (MMSE) (Folstein et al., 1975) score of 10-24; on donepezil 5 mg or 10 mg for at least 6 months; relative or carer willing and able to support the trial; able to complete trial examinations; primary sensorial functions intact.

Patients were excluded if they had a history or clinical evidence of peripheral or optic neuropathy or had co-existing illnesses or past history that may have affected cognitive function, nerve conduction or illnesses that may have confounded the adverse event profile.

The following factors were obtained at baseline to determine if they correlated with outcome measures: age, sex, premorbid IQ [estimated from the National Adult Reading Test (NART)], years of education, and apolipoprotein E (ApoE) allotype.

Study design: The study was a double blind, placebo-controlled, parallel group randomized design. Thirty-six patients and their carers were recruited to participate, with patients randomized at a 1:1 ratio to receive either PBT-1 or placebo. The duration of the study was 36 weeks. PBT-1 oral dosage was 125 mg bid from weeks 0-12, increased to 250 mg bid from weeks 13-24, and finally, 375 mg bid from weeks 25-36.

Study procedures: Screening procedures consisted of a complete medical history, physical, neurological and ophthalmic examination, blood and urine tests and psychometric tests (ADAS-cog, MMSE). Nerve conduction tests and visual evoked responses were conducted between the screening and baseline visits to provide a baseline measurement. Blood was collected for ApoE allotyping, baseline plasma levels of metals and Aβ prior to randomization. All patients continued their study entry dose of donepezil and all patients received 100 mg vitamin $B_{12}$ intramuscularly every four weeks.

Blood samples were collected by antecubital venepuncture except on weeks 12, 24 and 36 when they were collected by an indwelling catheter. The procedural change did not affect biochemical readouts except for Zn levels which were found to be consistently ~10% depressed (probably as a result of differences in platelet activation). Zn data from these intervals were therefore omitted from analysis.

Outcome measures: The primary clinical efficacy variable was a change from baseline score on the ADAS-cog conducted at baseline and at weeks 4, 12, 24 and 36. This measure was chosen to allow comparability of treatment effects with current therapeutics such as donepezil, where efficacy trials also used ADAS-cog as their primary outcome measure (Rogers et al., 1998). Although numerous neuropsychological tests could be considered as secondary measures, it was necessary to avoid fatiguing the subjects at review. Therefore the only other cognitive test was the Mini-Mental State Exam (MMSE). The CIBIC+ (clinician interview based impression of change incorporating caregiver information), a subjective observational index was also conducted. Plasma Aβ, and plasma zinc and copper were all taken every four weeks.

Double antibody capture enzyme-linked immunosorbent assay (ELISA) for Aβ detection: Polystyrene plates were coated with mAb G210 (for Aβ40) or mAb G211 (for Aβ42). Plates were washed and biotinylated mAb WO2 was added. Bound antibody was detected with streptavidin-labelled Europium (Perkin Elmer, Vic Australia). The values obtained from triplicated wells were calculated based on standard curves generated on each plate. Plasma samples supplemented with synthetic Aβ1-40 and Aβ1-42 were also assayed to confirm measurement reliability across the concentration range of interest.

Metal levels: Metals were measured by inductively coupled plasma mass spectrometry as previously described (Cherny et al., 2001).

Therapeutic drug monitoring: At weeks 12, 24 and 36, PBT-1 blood levels were assayed by HPLC with appropriate validation studies (Centre for Pharmaceutical Research, University of South Australia).

Safety measures: Standard adverse event reporting was conducted and biochemical tests, renal and liver function, complete blood examination, serum vitamin $B_{12}$ and folate levels were documented at each visit. To assess for peripheral and optic neuropathy a neurological examination was conducted at each visit, and visual evoked responses, nerve conduction studies and ophthalmic examination were conducted at screening, week 16 and prior to the final trial visit. An ECG was done at screening and weeks 12, 24 and 36.

Data preparation and statistical analysis: Data monitoring and management were undertaken by independent contractors (Kendle International and Health Research Solutions, Melbourne). Evidence for efficacy was indicated by a significant difference in change from baseline between treatment arms. Analysis of variance was the principal method of evaluating statistical significance with the treatment arm illness severity at baseline being the primary design factor. Potentially significant covariates were introduced as necessary. Differences between groups on categorical measures were analysed using exact statistical methods in order to maximise power. Based on the assumption of a correlation of 0.60 between measurement occasions, power to detect an effect of one standard deviation difference in change between groups from baseline to week 36 would have been approximately 80% if 15 subjects were recruited per group. Since an attrition rate of 15% has been observed in similar populations, 18 patients were recruited into each arm.

Results

Subject recruitment and demographics: Thirty-six subjects were recruited over a 12 month period commencing April 2000 (FIG. 1). Of these, 32 had sufficient data for per protocol analysis. Two subjects were lost from each arm.

The baseline illness severity factor was created, as planned, by division of the sample into two groups at the median ADAS-cog score at baseline (values <25, ≧25), yielding less-severely and more-severely affected groups (n=8 and 8 in the treatment arm and n=7 and 9 in the placebo arm, respectively).

The groups did not differ across demographic, biological and clinical parameters at baseline (Table 4), other than the treatment arm having a higher mean premorbid IQ than the placebo group as estimated using the NART (111.4 compared to 104.9; t(30)=2.27, p=0.031) and a lower level of thyroid stimulating hormone (TSH) (1.14 compared to 2.00 mU/L; t(30)=4.400, p<0.001). The NART and TSH were subsequently provisionally entered into analyses as co-variates but were found to be not significant in any analysis.

Figure 2:
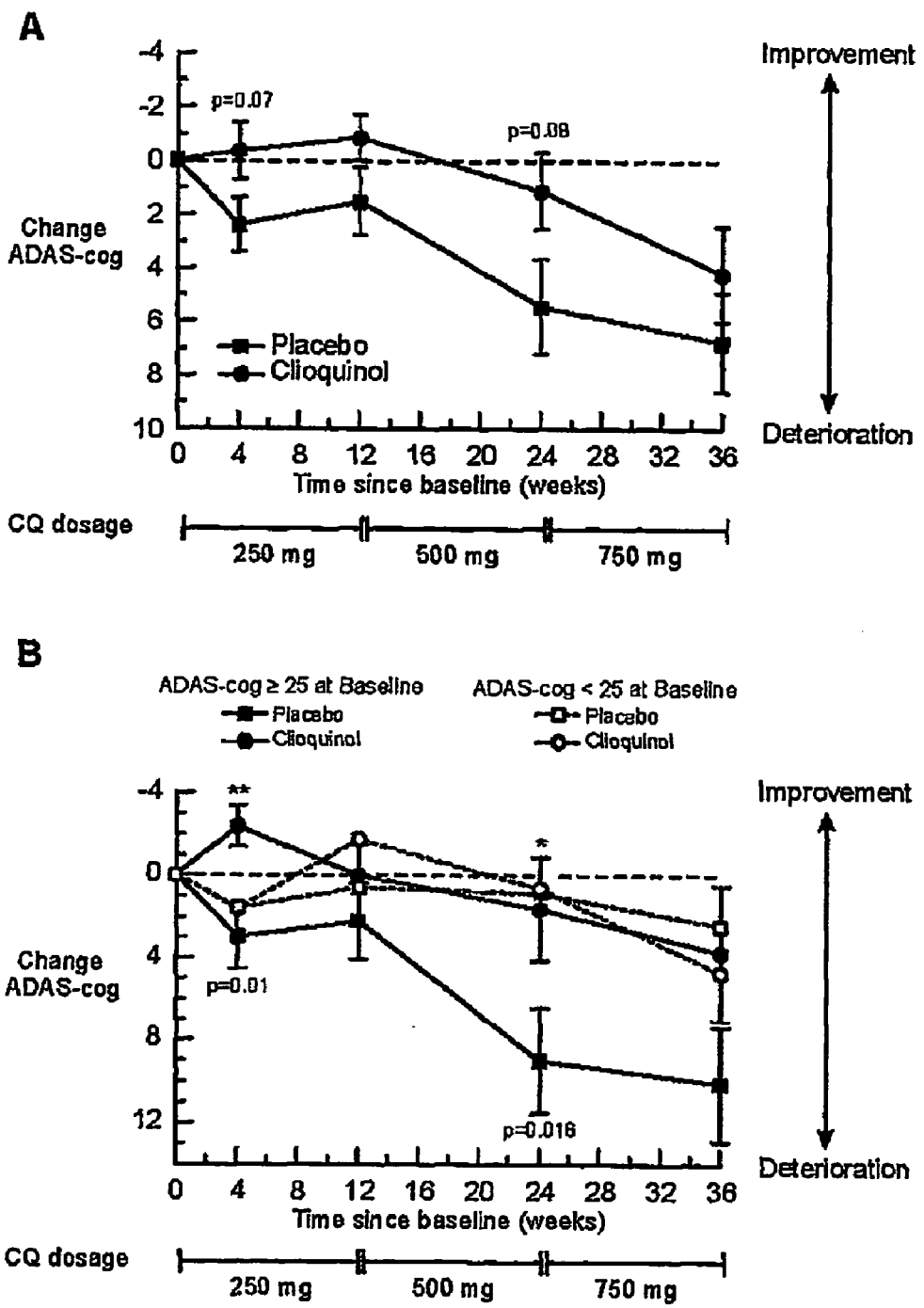
FIG. 2 are graphs showing mean change (±SE) over time from baseline in cognitive abilities (as assessed with ADAS-cog) in (A) two arms of CQ vs placebo and (B) stratification by severity within treatment arms [less-severely affected (ADAS-cog<25), more-severely affected (ADAS-cog≧25) (*p≦0.05; **p≦0.01)

Clinical effects: Changes in the ADAS-cog score at weeks 4, 12, 24 and 36 from baseline were subject to two-way analysis of variance with factors of treatment arm and baseline illness severity. The means of the changes in ADAS-cog score showed greater deterioration in the placebo treated group at each examination interval, compared to the PBT-1-treated group (FIG. 2A). This trend came close to statistical significance at week 4 [F(1,28)=3.55, p=0.070] and week 24 [(F(1,28)=3.31, p=0.080] (FIG. 2A). As planned in the protocol, the effect of severity of illness was examined by stratification of the sample into subjects less- or more-severely affected (baseline ADAS-cog values <25, ≧25). Simple effects tests within level of severity showed the trend in the pooled groups to be separable into non-significant results for the less-severe stratum on all weeks and significant differences in the more-severe stratum at weeks 4 [F(1,28)=7.73, p=0.010] and week 24 [F(1,28)=6.63, p=0.016] (FIG. 2B). This trend was maintained at week 36 but narrowly escaped statistical significance [F(1,28)=3.62, p=0.068]. In the more-severely affected groups, the difference in mean change from baseline ADAS-cog score of PBT-1 over placebo at weeks 24 and 36 was a difference of 7.37 (95% CI: 1.51-13.24) and 6.36 (95% CI: −0.50-13.23) respectively (FIG. 2B).

Figure 3:
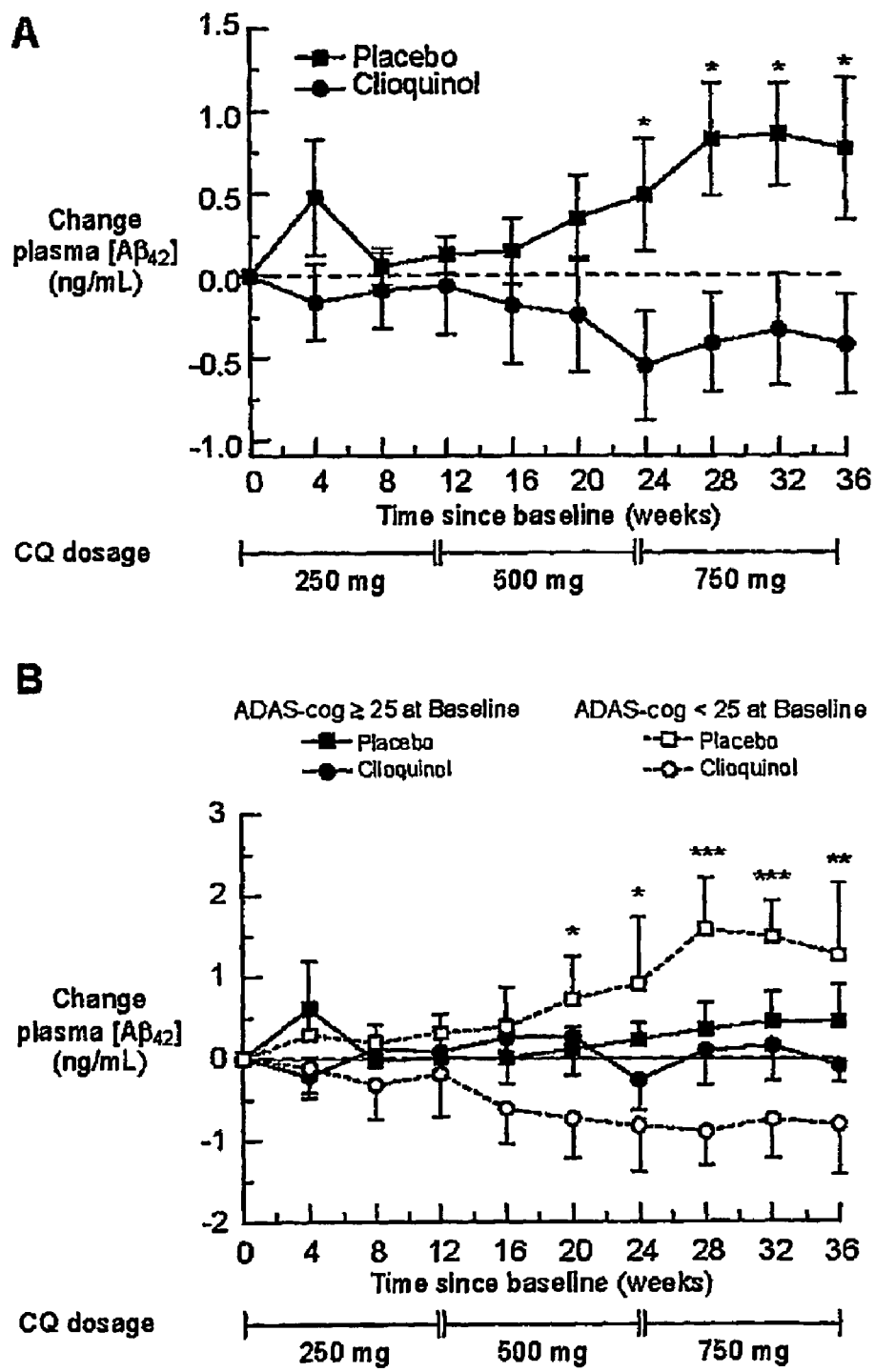
FIG. 3 are graphs showing mean change (±SE) over time from baseline in plasma $A\beta_{42}$ levels in (A) the arms of CQ vs placebo and (B) stratification by severity as in FIG. 8. (***p≦0.001)

Effects on plasma Aβ, Zn and Cu: At baseline, there were no significant differences in plasma $A\beta_{42}$ levels between treatment arms or severity strata. The variance in individual levels at baseline in plasma $A\beta_{40/42}$ was large and led to reduced power of the study to detect any significant differences in mean changes between groups. However, reference of individual Aβ levels to baseline reference levels markedly decreased variance, and revealed significant treatment effects. Plasma $A\beta_{42}$ showed a significant decline from baseline in the PBT-1-treated group from week 20 onwards; over the same time, plasma $A\beta_{42}$ in the placebo group increased (FIG. 3A). Stratification by illness severity as above demonstrated that changes were evident only in the less-severely affected (FIG. 3B).

Figure 4:
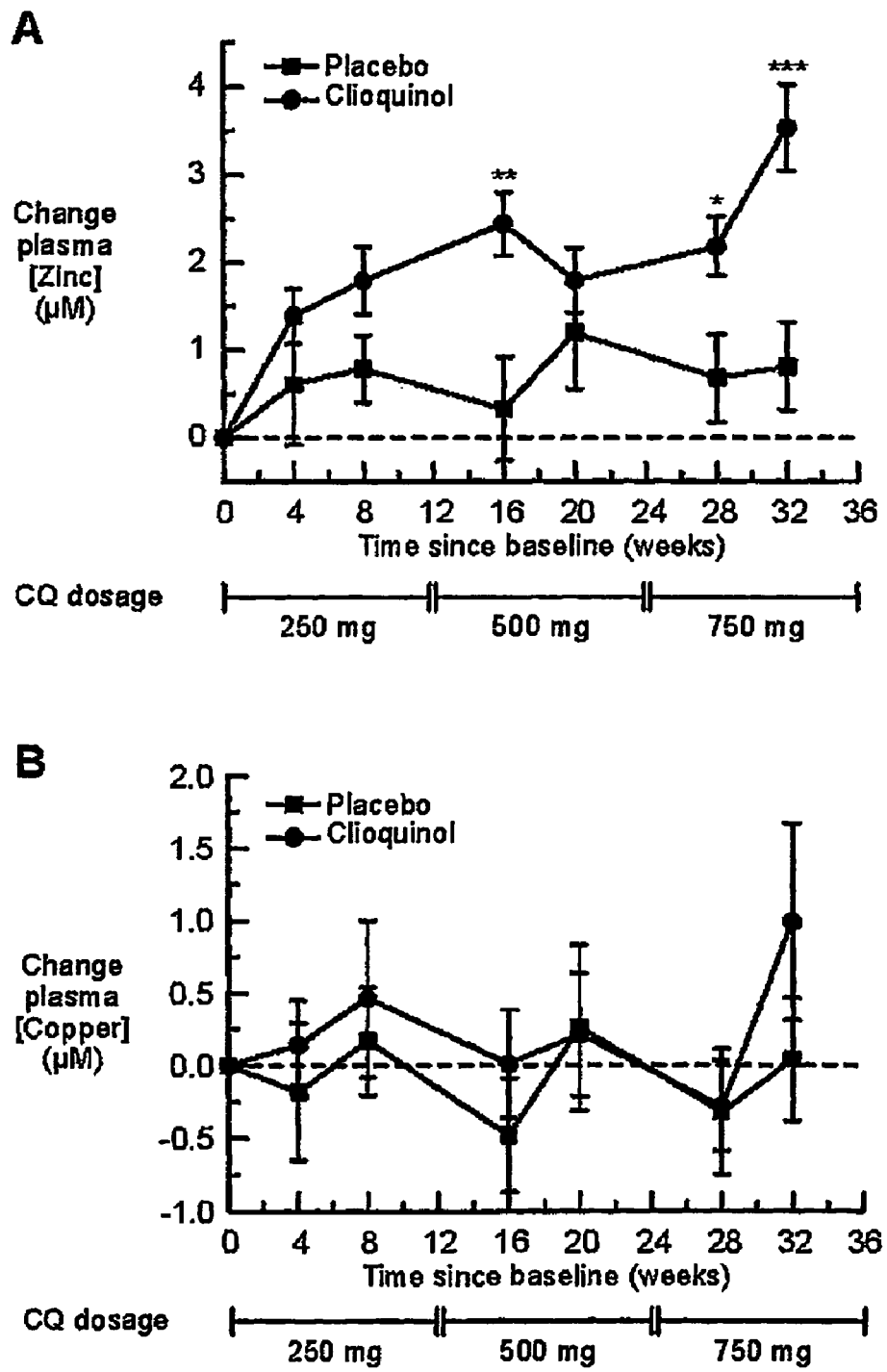
FIG. 4 are graphs showing mean change (±SE) over time from baseline in (A) plasma Zn (B) plasma Cu in the two arms of CQ vs placebo.
Figure 5:
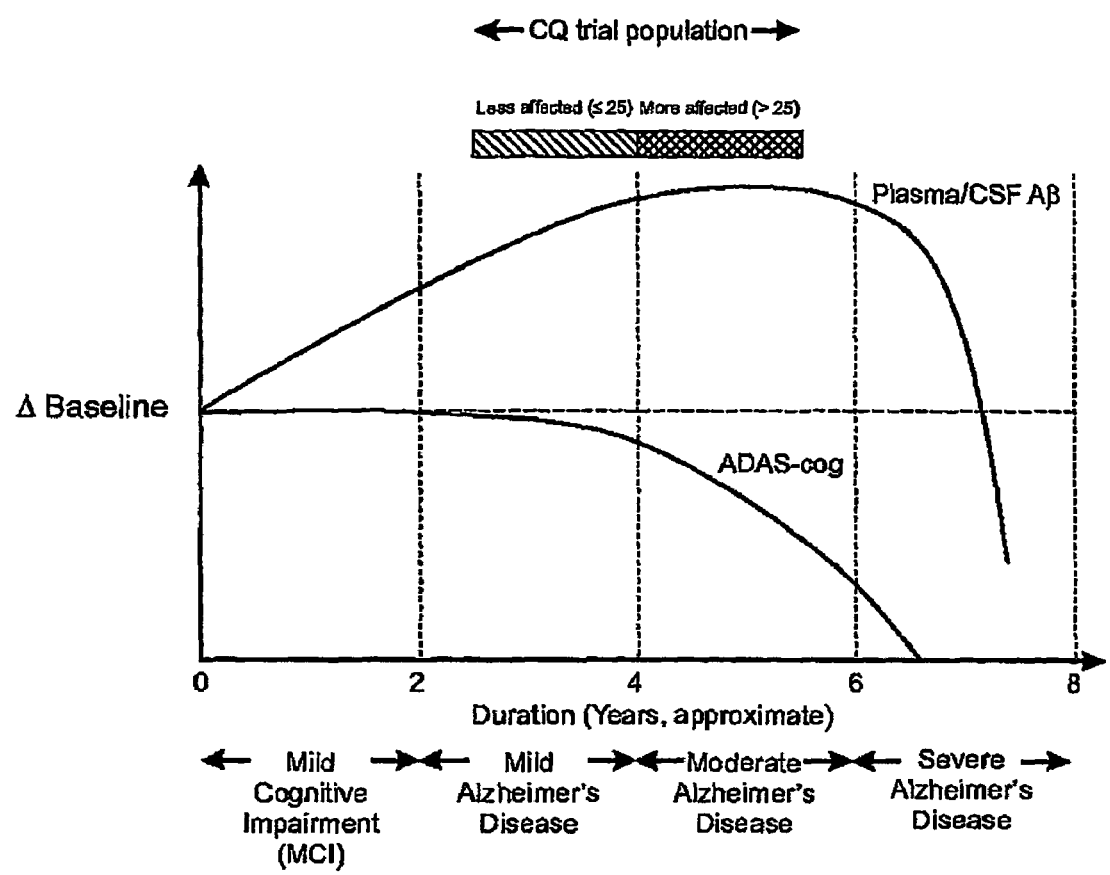
FIG. 5 is a graph showing relative changes in behavioral (ADAS-cog) and biochemical (plasma/CSF Aβ) levels over the course of AD.

Administration of PBT-1 was associated with a significant elevation (≈30%) of total plasma Zn (FIG. 4A) but with no effect on plasma Cu (FIG. 4B). Mean baseline levels of Zn (9.4 μM) in the pooled AD groups were below age-related normative values (Wood and Zheng, 1997). The increase in plasma Zn induced by PBT-1 treatment therefore represented a normalization of levels. In contrast, mean baseline levels of Cu (13.1 μM) were within the age-related normative range (Rahil-Khazen et al., 2000). Correlation of plasma $A\beta_{42/40}$ levels with Zn/Cu levels assayed on the same or subsequent occasions showed no significant associations.

An important result of treatment of AD subjects with PBT-1 is the paradoxical elevation in plasma Zn (FIG. 4A), which is consistent with a restoration in the ZnT3-mediated communication of synaptic zinc with the blood. This also indicates that, in contrast to a typical metal chelator such as desferrioxamine, the mechanism of action of PBT-1 at this dose is not that of a gross tissue chelator. The relatively weak affinity of PBT-1 for the metals appears to be insufficient to cause marked systemic metal depletion in the presence of a re-established equilibrium of metal homeostasis.

Blood levels of PBT-1: Steady state pre-dose levels of PBT-1 at total daily dosages of 250, 500 and 750 mg were 4.03±2.10, 6.74±3.70, 7.60±2.15 μg/ml, respectively, and did not show significant correlations with ADAS-cog, metal or Aβ levels assayed on the same or subsequent occasions.

TABLE 4

Baseline demographics and key clinical variables

| Variable | Total Sample (n = 32) | Group Clioquinol (n = 16) | Placebo (n = 16) | P Value |
|---|---|---|---|---|
| Age mean (SD; min-max) | 72.50 (8.37; 56-87) | 73.19 (8.61; 58-87) | 71.81 (8.35; 56-87) | P = 0.65[†] |
| Sex (n; % male) | 17 (53.1%) | 8 (47.1%) | 9 (52.9%) | P = 1.00[‡] |
| ApoE status ApoE4 heterozygote n (%) | 15 (46.9%) | 7 (43.8%) | 8 (50.0%) | P = 1.00[‡] |
| ApoE4 homozygote n (%) | 3 (9.4%) | 2 (12.5%) | 1 (6.3%) | |
| Estimated premorbid IQ NART mean, (SD; min-max) | 108.1 (8.86; 91-124) | 111.4 (8.04; 94-121) | 104.9 (8.26; 91-124) | P = 0.03[†] |
| ADAS-Cog | 26.31 (7.27; 15-46) | 25.56 (7.67; 15-46) | 27.06 (7.01; 19-41) | P = 0.57[†] |
| Age of first diagnosis mean, (SD; min-max) | 70.09 (7.98; 54-83) | 70.88 (8.50; 57-83) | 69.31 (7.61; 54-83) | P = 0.59[†] |
| Duration of illness (years) mean (SD; min-max) | 2.41 (1.19; 1-5) | 2.31 (1.08; 1-4) | 2.56 (1.32; 1-5) | P = 0.66[†] |

[†]Independent sample t-test (all tests 30 df)
[‡]Exact, two-tailed test.

References cited in the description and examples are listed on the following pages, and are incorporated herein by this reference.

REFERENCES

Abe, Y., Kayakiri, H., Satoh, S. et al, *J. Med. Chem.,* 1998, 41, 4062-4079.
Albert, A. and Hampton, A., *J. Chem. Soc.,* 1952, 4985-4993.
Anthony, N. J., Gomez, R. P., Young, S. D. et al, (2002) Patent WO 02/30931 A2.
Antoniotti, S. and Dunach, E., *Tetrahedron Letters,* 2002, 4, 3971-3973.
Ariga, T., Kobayashi, K., Hasegawa, A., Kiso, M., Ishida, H., and Miyatake, T. (2001) Characterization of high-affinity binding between gangliosides and amyloid β-protein. Arch. Biochem. Biophys. 388, 225-230.
Atwood et al., J. Biol. Chem., 1998, 273(21), 12817-12826.
Beyreuther K, Christen Y, Masters C L (eds) Neurodegenerative Disorders: Loss of Function Through Gain of Function. Springer. Berlin. 2001. 189 pp.

Blanco, M., Lorenzo, M. G., Perillo, I. and Schapira, C. B., *J. Heterocyclic Chem.*, 1996, 33, 361-366.

Brower V. Harnessing the immune system to battle Alzheimer's: Some of the most promising approaches to fight Alzheimer's diseases aim to develop vaccines. EMBO Rep 2002; 3:207-9.

Bush A I, Masters C L. Clioquinol's return. Science 2001; 292:2251-2252.

Bush A I. Therapeutic targets in the biology of Alzheimer's disease. Current Opinion in Psychiatry 2001; 14:341-348.

Cherny R A, Atwood C S, Xilinas M E et al. Treatment with a copper-zinc chelator markedly and rapidly inhibits β-amyloid accumulation in Alzheimer's disease transgenic mice. Neuron 2001; 30:665-676.

Corder, E. H., Saunders, A. M., Strittmatter, W. J., Schmechel, D. E., Gaskell, P. C., Small, G. W., Haines, J. L., and Pericak-Vance, M. A. (1993) Gene dose of apolipoprotein E type 4 allele and the risk of Alzheimer's disease in the late onset familial disease. Science 261, 921-923.

Curtain, C. C., Ali, F., Volitakis, I., Cherny, R. A., Norton, R. S., Beyreuther, K., Barrow, C. J., Masters, C. L., Bush, A. I., and Barnham, K. J. (2001) Alzheimer's disease amyloid β binds copper and zinc to generate an allosterically ordered membrane-penetrating structure containing superoxide dismutase-like subunits. J. Biol. Chem. 276, 20466-20473.

Czech, C., Forstl, H., Hentschel, F., Monning, U., Besthorn, C., Geigerkabisch, C., Sattel, H., Masters, C., and Beyruether, K. (1994) Apolipoprotein E-4 gene dose in clinically diagnosed Alzheimer's disease: prevalence, plasma cholesterol levels and cerebrovascular change. Eur. Arch. Psychiatry Clin. Neurosci. 243, 291-292.

Dennin, F., Blondeau, D. and Sliwa, H., *J. Heterocyclic Chem.*, 1991, 28, 1287-1291.

Fassbender, K., Simons, M., Bergmann, C., Stroick, M., Lutjohann, D., Keller. P., Runz, H., Kuhl, S., Bertsch, T., von Bergmann. K., Hennerici, M., Beyreuther, K., and Hartmann, T. (2001) Simvastatin strongly reduces levels of Alzheimer's disease β-amyloid peptides Aβ 42 and Aβ 40 in vitro and in vivo. Proc. Natl. Acad. Sci. USA. 98, 5856-5861.

Folstein M F, Folstein S E, McHugh P R. Mini-mental state: a practical method for grading the cognitive state of patients for the clinician. J. Psychiatr. Res. 1975; 12:189-198.

Frears, E. R., Stephens, D. J., Walters, C. E., Davies, H., and Austen, B. M. (1999) The role of cholesterol in the biosynthesis of b-amyloid. NeuroReport 10, 1699-1705.

Friedhoff, L. T., Cullen, E. I., Geoghagen, N. S., and Buxbaum, J. D. (2001) Treatment with controlled-release lovastatin decreases serum concentrations of human β-amyloid (Aβ) peptide. Int. J. Neuropsychopharmacol. 4, 127-130.

Games D., Adams D., Alessandrini R., Barbour R., Berthelette P., Blackwell C., Carr T., Clemens J., Donaldson T., Gillespie F., Guido T., Hagopian S., Johnsonwood K., Khan K., Lee M., Leibowitz P., Lieberburg I., Little S., Masliah E., Mcconlogue L., Montoyazavala M., Mucke L., Paganini L., Penniman E., Power M., Schenk D., Seubert P., Snyder B., Soriano F., Tan H., Vitale J., Wadsworth S., Wolozin B., Zhao J., NATURE, 1995, 373 (6514): 523-527.

Gilgun-Sherki Y., Melamed E., Offen D., Neuropharmacology, 2001, 40 (8): 959-975.

Golstein, H. and Schaaf, E., *Helv. Chim. Acta*, 1957, 57(23), 132.

Gudmundsson, K. J., Hinkley, J. M., Brieger, M. S., Drach, J. C. and Townsend, L. B., *Synthetic Communications*, 1997, 27(5), 861-870.

Gurney M. E., Pu H. F., Chiu A. Y., Dalcanto M. C., Polchow C. Y., Alexander D. D., Caliendo J., Hentati A., Kwon Y. W., Deng H. X., Chen W. J., Zhai P., Sufit R. L., Siddique T., SCIENCE, 1994, 264 (5166): 1772-1775.

Hartmann, T. (2001) Cholesterol, Aβ and Alzheimer's disease. Trends Neurosci. 24, S45-S48.

Hertel, C., Terzi, E., Hauser, N., Jakob-Rotne, R., Seelig, J., and Kemp, J. A. (1997) Inhibition of the electrostatic interaction between β-amyloid peptide and membranes prevents β-amyloid-induced toxicity. Proc. Natl. Acad. Sci. USA. 94, 9412-9416.

Hsiao, K., Chapman, P., Nilsen, S., Eckman, C., Harigaya, Y., Younkin, S., Yang, F., Cole, G. (1996) Correlative memory deficits, Aβ elevation, and amyloid plaques in transgenic mice SCIENCE; 274(5284):99-102.

Huang X, Atwood C S, Hartshorn M A et al. The Aβ peptide of Alzheimer's disease directly produces hydrogen peroxide through metal ion reduction. Biochemistry 1999; 38:7609-7616.

Iyer, R. N. and Dhar, M. L., *J. Sci. Ind. Res.*, 1956, 15C, 1-7.

Ji, S. R., Wu, Y., and Sui, S. F. (2002) Cholesterol is an important factor affecting the membrane insertion of β-amyloid peptide (Aβ 1-40), which may potentially inhibit the fibril formation. J. Biol. Chem. 277, 6273-6279.

Karbownik M., Lewinski A., Reiter R. J., Int. J. Biochemistry & Cell Biology, 2001, 33 (8): 735-753.

Lee J-Y, Cole T B, Palmiter R D, Suh S W, Koh J-Y. Contribution by synaptic zinc to the gender-disparate plaque formation in human Swedish mutant APP transgenic mice. Proc Natl Acad Sci USA 2002: Early edition.

Lee, S. J., Konishi, Y., Yu, D. T. et al, *J. Med. Chem.*, 1995, 38, 3547-3557.

Linderberg, M., Hellberg, S., Bjork, S. et al, *Eur. J. Med. Chem.*, 1999, 34, 729-744.

Manfredini S, Pavan B, Vertuani S, Scaglianti M, Compagnone D, Biondi C, Scatturin A, Tanganelli S, Ferraro L, Prasad P, Dalpiaz A, JOURNAL OF MEDICINAL CHEMISTRY, 45 (3): 559-562 Jan. 31, 2002

Marabout, B., Sevrin, M. and Estenne, B. G., (1999) Patent FR 2,765,582.

Masliah E., Rockenstein E., Veinbergs I., Mallory M., Hashimoto M., Takeda A., Sagara Y., Sisk A., Mucke L., SCIENCE, 2000, 287 (5456): 1265-1269.

McKhann G, Drachman D, Folstein M F, Katzman R, Price D, Stadlen E. Clinical diagnosis of Alzheimer's disease: Report of the NINCDS-ADRDA work group under the auspices of the Department of Health and Human Services Task Force on Alzheimer's Disease. Neurology 1984; 34:939-944.

Nunan, J., and Small, D. H. (2000) Regulation of APP cleavage by α-, β- and δ-secretases. FEBS Lett. 483, 6-10.

Philips' Gloeilampenfabrieken, N. V., (1973) Patent GB 1303711

Petersen, R. C, Stevenas, J. C., Ganguli, M., Tangalos, E. G., Cummings, J. L., and DeKosky, S. T. Practice parameter: Early detection of dementia: Mild cognitive impairment Neurology 2001 56 1133-1142.

Reddy P. H., Williams M., Charles V., Garrett L., Pike-Buchanan L., Whetsell W. O., Miller G., Tagle D. A., NATURE GENETICS, 1998, 20 (2): 198-202.

Rogers S L, Farlow M R, Doody R S, Mohs R, Friedhoff L T. A 24-week, double-blind, placebo-controlled trial of donepezil in patients with Alzheimer's disease. Donepezil Study Group. Neurology 1998; 50:136-45.

Rosen W G, Mohs R C, Davis K L. A new rating scale for Alzheimer's disease. Am J Psychiatry 1984; 141:1356-64.

Sakaeda T, Tada Y, Sugawara T, Ryu T, Hirose F, Yoshikawa T, Hirano K, Kupczyk-Subotkowska L, Siahaan T J, Audus K L, Stella V J, JOURNAL OF DRUG TARGETING, 9 (1): 23-37 2001.

Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieberburg, I., Motter, R., Mutter, L., Soriano, F., Shopp, G., Vasquez, N., Vandervert, C., Walker, S., Wogulis, M., Yednock, T., Games, D., and Seubert, P. (1999) Immunization with amyloid-β attenuates Alzheimer's disease like pathology in the PDAPP mouse. Nature 400, 173-177.

Selkoe, D. J. Alzheimer's disease: genes, proteins and therapy. Physiol Rev 81 (2): 741-766.

Shearman M S, Beher D, Clarke E E et al. L-685,458, an aspartyl protease transition state mimic, is a potent inhibitor of amyloid β-protein precursor β-secretase activity. Biochemistry 2000; 29:8698-704.

Shiraki, H. The neuropathology of subacute myelo-opticoneuropathy (SMON) in the humans: With special reference to the quinoform intoxication. Jpn J Med Sci Biol 1975; 28 (suppl): 101-164.

Simons M, Schwärzler F, Lütjohann D et al. Treatment with simvastatin in normocholesterolemic patients with Alzheimer's disease: a 26-week randomised, placebo-controlled, double-blind trial. Ann of Neurol In Press.

Sinha S, Anderson J P, Barbour R et al. Purification and cloning of amyloid precursor protein β-secretase from human brain. Nature 1999; 402:537-40.

Smirnov, L. D., Nikitin, S. V., Chernyshev, A. I., Sorokin, A. A., Lezina, V. P., Zabrodnyaya, V. G. and Kaganskii, M. M., *Chemistry of Heterocyclic Compounds*, 1992, 12, 1425-1431.

St George-Hyslop, P. H. (2000) Molecular genetics of Alzheimer's disease. *Biol. Psychiatry* 47, 183-199.

T. C. Wang, Y. L. Chen, K. H. Lee and C. C. Tzeng, *Tetrahedron Lett.*, 1996, 37, 6369-6370.

Telling G. C., Scott M., Hsiao K. K., Foster D., Yang S. L., Torchia M., Sidle K. C. L., Collinge J., Dearmond S. J., Prusiner S. B., PROCEEDINGS OF THE NATIONAL ACADEMY OF SCIENCES OF THE UNITED STATES OF AMERICA, 11 Oct. 1994, 91 (21): 9936-9940.

Tani, J., Yamada, Y., Oine, T. et al, *J. Med. Chem.*, 1979, 22, 95-99.

Valdez-Gonzalez, T., Inagawa, J., and Ido, T. (2001) Neuropeptides interact with glycolipid receptors: a surface plasmon resonance study. Peptides 22; 1099-1106.

Wepplo, P. J., (1984) U.S. Pat. No. 4,460,776.

White et al., J Neuroscience, (1998) 18, 6207-6217.

Wright, J. S. Johnson, E. R. and DiLabio, G. A. *J. Am. Chem. Soc* 2001 123 1173-1183.

Yale, H. L. and Sheehan, J. T. (1977) U.S. Pat. No. 4,022,897.

Yassin M S, Ekblom J, Xilinas M, Gottfries C G, Oreland L. Changes in uptake of vitamin B(12) and trace metals in brains of mice treated with clioquinol. J Neurol Sci 2000; 173:40-44.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A compound of Formula Ia

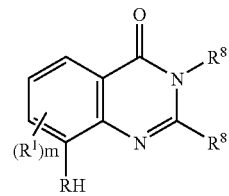

in which

R is O or S;

each $R^1$ is independently halo;

each $R^8$ is independently selected from H, optionally substituted alkyl, optionally substituted alkenyl; optionally substituted alkynyl; optionally substituted aryl; optionally substituted heterocyclyl; CN; halo; $CF_3$; $SO_3H$; $OR^2$, $SR^7$, $SOR^2$, $SO_2R^2$, $NR^2R^3$, $(CH_2)_nNR^2R^3$, $HCNOR^2$, $HCNNR^2R^3$, $CONR^2R^3$, $CSNR^2R^3$, $NCOR^2$, $NCSR^2$, $COR^2$, $CO_2R^2$, $CSR^2$ and $SO_2NR^2R^3$, in which $R^2$ and $R^3$ are independently selected from H, optionally substituted alkyl, optionally substituted alkenyl, optionally substituted alkynyl, optionally substituted aryl, or optionally substituted heterocyclyl, and n is an integer of 1 to 10;

$R^7$ is optionally substituted alkyl, optionally substituted alkenyl, optionally substituted alkynyl, optionally substituted aryl or optionally substituted heterocyclyl;

n is an integer of 1 to 10 and m is 1 or 2;

or pharmaceutically acceptable salts thereof or tautomers of compounds of Formula Ia, wherein aryl is a 5 or 6-membered aryl group; heterocyclyl is a saturated or unsaturated 3 to 6-membered heterocyclyl containing at least one heteroatom selected from N, O and S, and the optional substituent is $C_{1-6}$ alkyl, $CF_3$, F, Cl, I, cyano, $C_{1-6}$ alkoxy, aryl, heterocyclyl, amino or $C_{1-6}$ alkylamino, with the provisos that:

(1) when R is O, m is 2 and $R^1$ is

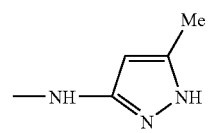

at position 3, then $R^1$ at position 2 is not

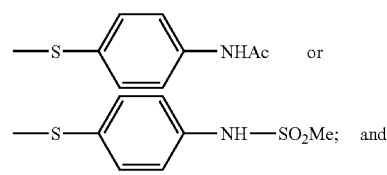

(2) $R^1$ is located at position 5 or 7 or both positions 5 and 7 of the ring.

2. A pharmaceutical or veterinary composition comprising the compound of formula Ia according to claim 1 and a pharmaceutically or veterinarily acceptable carrier.

3. The compound according to claim 1 in which R is O.

4. The compound according to claim 1 in which $R^8$ is halo, optionally substituted aryl, optionally substituted heterocyclyl, optionally substituted alkyl, $OR^2$, $SR^4$, $(CH_2)_nNR^2R^3$, $CONR^2R^3$ or $NCOR^2$.

5. The compound according to claim 1 in which $R^8$ is F, I, Cl, optionally substituted phenyl, an optionally substituted unsaturated 3 to 6-membered heteromonocyclic group containing 1 to 4 nitrogen atoms, an optionally substituted saturated 3 to 6-membered heteromonocyclic group containing 1 to 4 nitrogen atoms, an optionally substituted saturated 3 to 6-membered heteromonocyclic group containing 1 to 2 oxygen atoms and 1 to 3 nitrogen atoms, optionally substituted $C_{1-4}$ alkyl, optionally substituted $C_{3-6}$ cycloalkyl, optionally substituted $C_{1-6}$ alkoxy, optionally substituted thio, $CH_2NR^4R^5$ in which $R^4$ and $R^5$ are independently selected from H and $C_{1-4}$ alkyl or $CONH(CH_2)_2R^6$ in which $R^6$ is optionally substituted heterocyclyl.

6. The compound according to claim 1 wherein $R^8$ is independently selected from halo, optionally substituted heterocyclyl, optionally substituted alkyl, or $(CH_2)_nNR^2R^3$.

7. The compound according to claim 1, wherein $R^8$ is chlorine, optionally substituted phenyl, $C_{2-6}$ cycloalkyl, $(CH_2)NR^4R^5$, wherein $R^4R^5$ are independently selected from H and $C_{1-4}$ alkyl.

8. The compound according to claim 1 having the formula:

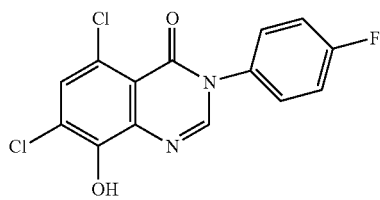

1055

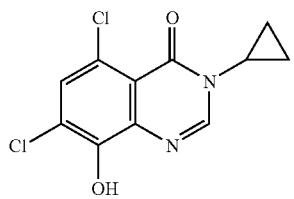

1061

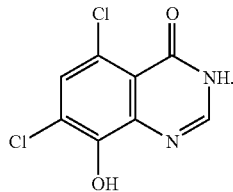

1067

9. The compound according to claim 1 wherein Cl is at position 5 or 7 of the ring.

10. The compound according to claim 1 in which halo is at positions 5 and 7 of the ring.

11. The compound according to claim 1 wherein Cl is at position 5 and 7 of the ring.

\* \* \* \* \*